(12) United States Patent
Yofu et al.

(10) Patent No.: US 9,349,965 B2
(45) Date of Patent: May 24, 2016

(54) PHOTOELECTRIC CONVERSION MATERIAL, FILM CONTAINING THE MATERIAL, PHOTOELECTRIC CONVERSION DEVICE, METHOD FOR PREPARING PHOTOELECTRIC CONVERSION DEVICE, METHOD FOR USING PHOTOELECTRIC CONVERSION DEVICE, PHOTOSENSOR AND IMAGING DEVICE

(71) Applicant: FUJIFILM CORPORATION, Tokyo (JP)

(72) Inventors: Katsuyuki Yofu, Kanagawa (JP); Kimiatsu Nomura, Kanagawa (JP); Eiji Fukuzaki, Kanagawa (JP); Yuki Hirai, Kanagawa (JP); Mitsumasa Hamano, Kanagawa (JP); Tetsuro Mitsui, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 173 days.

(21) Appl. No.: 13/789,537

(22) Filed: Mar. 7, 2013

(65) Prior Publication Data

US 2013/0181202 A1 Jul. 18, 2013

Related U.S. Application Data

(63) Continuation of application No. PCT/JP2011/069849, filed on Aug. 31, 2011.

(30) Foreign Application Priority Data

Sep. 8, 2010 (JP) ................. 2010-201491
Apr. 5, 2011 (JP) ................. 2011-084012

(51) Int. Cl.
| | | |
|---|---|---|
| C07D 221/18 | (2006.01) |
| C07D 221/22 | (2006.01) |
| C07D 223/14 | (2006.01) |
| H01L 51/00 | (2006.01) |
| C07D 219/02 | (2006.01) |
| C07D 455/03 | (2006.01) |
| C07D 455/06 | (2006.01) |
| C07D 471/14 | (2006.01) |
| C07D 471/16 | (2006.01) |
| C07C 225/22 | (2006.01) |
| H01L 51/42 | (2006.01) |

(52) U.S. Cl.
CPC .......... *H01L 51/0072* (2013.01); *C07C 225/22* (2013.01); *C07D 219/02* (2013.01); *C07D 221/18* (2013.01); *C07D 455/03* (2013.01); *C07D 455/06* (2013.01); *C07D 471/14* (2013.01); *C07D 471/16* (2013.01); *H01L 51/0052* (2013.01); *H01L 51/0059* (2013.01); *H01L 51/0058* (2013.01); *H01L 51/0094* (2013.01); *H01L 51/4206* (2013.01); *H01L 51/4273* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 4,241,157 A | 12/1980 | Webster et al. | |
| 4,395,473 A | 7/1983 | Horie et al. | |
| 5,670,090 A | 9/1997 | Marder et al. | |
| 5,965,875 A | 10/1999 | Merrill | |
| 7,264,891 B2 | 9/2007 | Lin et al. | |
| 2003/0209651 A1 | 11/2003 | Iwasaki | |
| 2009/0223566 A1* | 9/2009 | Mitsui ............... | B82Y 10/00 136/263 |
| 2010/0308311 A1 | 12/2010 | Mitsui et al. | |
| 2010/0308372 A1* | 12/2010 | Mitsui ............... | B82Y 10/00 257/184 |
| 2011/0056562 A1 | 3/2011 | Hamano et al. | |
| 2011/0063485 A1 | 3/2011 | Nomura et al. | |
| 2011/0204208 A1 | 8/2011 | Mitsui et al. | |
| 2012/0080585 A1 | 4/2012 | Fukuzaki et al. | |
| 2013/0015435 A1 | 1/2013 | Sawaki et al. | |
| 2013/0020566 A1 | 1/2013 | Suzuki | |
| 2013/0122276 A1 | 5/2013 | Nomura et al. | |

FOREIGN PATENT DOCUMENTS

| | | | |
|---|---|---|---|
| JP | S54-24628 A | 2/1979 |
| JP | S57-119355 A | 7/1982 |
| JP | H07-281436 A | 10/1995 |
| JP | H08-314139 A | 11/1996 |
| JP | 2003-332551 A | 11/2003 |
| JP | 2005-209682 A | 8/2005 |
| JP | 2007-123707 A | 5/2007 |
| JP | 2010-103457 A | 5/2010 |
| JP | 2010-168511 A | 8/2010 |
| JP | 4699561 B1 | 3/2011 |

(Continued)

OTHER PUBLICATIONS

Carey, FA. Organic Chemistry 6th Ed. McGraw Hill. 2006, chapter 1, p. 9.*

(Continued)

*Primary Examiner* — Janet L Andres
*Assistant Examiner* — Ben S Michelson
(74) *Attorney, Agent, or Firm* — Studebaker & Brackett PC

(57) ABSTRACT

There is provided a compound represented by a specific formula, which has an absorption maximum at 400 nm or more and less than 720 nm in a UV-visible absorption spectrum, wherein a molar extinction coefficient is 10,000 mol$^{-1}$·l·cm$^{-1}$ or more at the absorption maximum wavelength, and a difference between a melting point and a deposition temperature (a melting point−a deposition temperature) is 31° C. or more.

6 Claims, 2 Drawing Sheets

(56) References Cited

FOREIGN PATENT DOCUMENTS

| JP | 2011-213706 A | 10/2011 |
|---|---|---|
| JP | 5124620 B2 | 11/2012 |
| JP | 5520647 B2 | 4/2014 |
| JP | 5557663 B2 | 6/2014 |
| JP | 5651507 B2 | 11/2014 |
| WO | 2011-118578 A1 | 9/2011 |
| WO | 2011/125526 A1 | 10/2011 |

OTHER PUBLICATIONS

The Written Opinion of the International Searching Authority mailed Nov. 29, 2011, which corresponds to International Application No. PCT/JP2011/069849 and is related to U.S. Appl. No. 13/789,537 with translation.

International Search Report; PCT/JP2011/069849; Nov. 29, 2011.

An Office Action issued by the Taiwanese Patent Office on Feb. 6, 2015, which corresponds to Taiwanese Patent Application No. 100132422 and is related to U.S. Appl. No. 13/789,537; with English language translation.

An Office Action; "Notice of Reasons for Rejection," issued by the Japanese Patent Office on Jan. 27, 2015, which corresponds to Japanese Patent Application No. 2011-084012 and is related to U.S. Appl. No. 13/789,537; with English language partial translation.

An Office Action; "Decision of Rejection," issued by the Japanese Patent Office on Oct. 6, 2015, which corresponds to Japanese Patent Application No. 2011-084012 and is related to U.S. Appl. No. 13/789,537; with English language partial translation.

An Office Action; "Notice of Grounds for Rejection," issued by the Korean Patent Office on Oct. 14, 2015, which corresponds to Korean Patent Application No. 2013-7005963 and is related to U.S. Appl. No. 13/789,537; with English language partial translation.

* cited by examiner

PHOTOELECTRIC CONVERSION MATERIAL, FILM CONTAINING THE MATERIAL, PHOTOELECTRIC CONVERSION DEVICE, METHOD FOR PREPARING PHOTOELECTRIC CONVERSION DEVICE, METHOD FOR USING PHOTOELECTRIC CONVERSION DEVICE, PHOTOSENSOR AND IMAGING DEVICE

TECHNICAL FIELD

The present invention relates to a compound useful for a photoelectric conversion device material, a photoelectric conversion material, a film containing the material, photoelectric conversion device, a method for preparing a photoelectric conversion device, a method for using a photoelectric conversion device, a photosensor and an imaging device.

BACKGROUND ART

As a conventional photosensor, a device fabricated by forming a photodiode (PD) on a semiconductor substrate such as silicon (Si) is general. As for a solid-state imaging device, a flat solid-state imaging device is widely used, in which PDs are two-dimensionally arranged in a semiconductor substrate and a signal according to a signal charge generated by photoelectric conversion in each PD is read out through a CCD or CMOS circuit.

As a method for achieving a color solid-state imaging device, a structure in which a color filter transmitting only light at a specific wavelength for a color separation is disposed on the light incident surface side of the flat solid-state imaging device is common. In particular, a single-plate solid-state imaging device in which color filters transmitting blue (B) light, green (G) light and red (R) light, respectively, are regularly disposed on each of the two-dimensionally arranged PDs, is well known as a system widely used presently in a digital camera.

In this single-plate solid-state imaging device, since the color filter transmits only light at a limited wavelength, light not transmitted through the color filter is not utilized and the light utilization efficiency tends to be low. In addition, in recent years, manufacturing of a multipixel device is in progress, and the pixel size becomes smaller. As a result, the area of a photodiode part becomes smaller and problems such as the reduction in the aperture ratio and the reduction in the light collection efficiency arise.

In order to solve the disadvantages, a method is suggested stacking photoelectric conversion units capable of detecting light waves having different length in a longitudinal direction. For such a method, when limited to visible light, there is disclosed, for example, a method of forming a longitudinally laminated structure using a wavelength dependence on the absorption coefficient of Si, and separating colors by the difference in each depth (Patent Document 1), or a method of forming a first light receiving unit using an organic semiconductor, and second and third light receiving units composed of Si (Patent Document 2).

However, in these methods, there are disadvantages in that the color separation is insufficient because the absorption range in each light receiving unit has an overlapped portion in the depth direction of Si, and thus, spectral characteristics are poor. Further, as other solutions, a structure forming a photoelectric conversion film by amorphous silicon or an organic photoelectric conversion film on a substrate for reading-out signals is known as a means for raising aperture ratio.

Further, there are several publicly known examples for a photoelectric conversion using an organic photoelectric conversion film, an imaging device, a photosensor and a solar cell. The photoelectric conversion device using an organic photoelectric conversion film has a problem that needs to be resolved to enhance a photoelectric conversion efficiency or to reduce a dark current. Several methods have been disclosed for an improvement including introduction of a p-n junction or introduction of a bulk hetero-structure in the former case, and introduction of a blocking layer in the latter case.

In the case of making the photoelectric conversion efficiency high by the introduction of a p-n junction or a bulk hetero-structure, increase in dark current often becomes problematic. Further, since the degree of improvement in photoelectric conversion efficiency is different depending on the combination of materials, the ratio of optical signal amount to dark noise may not be increased compared to the ratio before introduction of these structures in some cases. When using these means, it is important which materials are combined, and in particular, when considering reduction in dark noise, it is difficult to achieve the reduction in dark noise with combination of materials which have already been reported.

Further, the kind of materials to be used and the film structure are main factors of a photoelectric conversion efficiency (exciton dissociation efficiency and charge transportability) and a dark current (carrier amount during a dark state and the like), as well as dominant factors of a signal response although it is not mentioned in the reports so far achieved. When using as a solid-state imaging device, it is necessary to satisfy all of a high photoelectric conversion efficiency, a low dark current and a high response speed, but, the organic photoelectric conversion materials and device structure of the kind have not been described in detail.

Although a photoelectric conversion film containing fullerenes is described in Patent Document 3, it is impossible to satisfy all of a high photoelectric conversion efficiency, a low dark current and a high response speed as described above with only fullerenes. Further, Patent Document 4 describes a device including a bulk hetero film composed of an organic matter having a specific structure and fullerenes as an organic photoelectric conversion film, but there has been no description about thermal stability and chemical stability of photoelectric conversion materials when fabricating the photoelectric conversion film.

PRIOR ART DOCUMENTS

Patent Document

Patent Document 1: U.S. Pat. No. 5,965,875
Patent Document 2: Japanese Patent Application Laid-Open No. 2003-332551
Patent Document 3: Japanese Patent Application Laid-Open No. 2007-123707
Patent Document 4: Japanese Patent Application Laid-Open No. 2010-103457

DISCLOSURE OF INVENTION

Problems to be Solved by the Invention

In the organic photoelectric conversion device, in order to implement high photoelectric conversion efficiency, low dark current property and high speed response property, it is required that the organic photoelectric conversion film to be used satisfies following requirements.

1. With respect to the high efficiency and the high speed response, it is required that a signal charge can be rapidly transferred to both electrodes without loss after an exciton is dissociated. It is required that the number of sites trapping carriers is small, mobility is high, and electric charge transportability is high.

2. With respect to the high photoelectric conversion efficiency, it is preferred that stabilization energy of the exciton is low, and the exciton can be rapidly dissociated (high exciton dissociation efficiency) by an electric field applied from the outside, or an electric field generated in the inside by a pn-junction.

3. In order to decrease the carriers generated in the inside during a dark state as much as possible, it is preferred to select a film structure and a material having a small amount of impurities which are one of the factors of an intermediate level of the inside.

4. In the case where a plurality of layers is laminated, it is required to match energy levels of adjacent layers, and thus, the electric charge transporting is obstructed if an energy barrier is formed.

5. In consideration of an application to a manufacturing process having a heating process, such as installation of a color filter, building of a protective film and soldering of a device, or an improvement of a preservation property, there is a need for a material for a photoelectric conversion device to have a high heat resistance.

In the case where an organic photoelectric conversion film is formed, a deposition method is preferred in that thermal decomposition is suppressed during the deposition as a decomposition temperature is increased compared to a deposition feasible temperature. An application coating method is preferred in that a film is formed without a limitation by the decomposition as described above, and a low cost can be realized. However, since uniform film formation is facilitated and a possibility of introducing impurities is reduced, the film formation by the deposition method is more preferred.

Although a high molecular weight material having a high van der Waals force is generally selected as a material having a high heat resistance, high molecular weight molecules have a high deposition feasible temperature, and the material is prone to be subjected to a thermal decomposition during deposition. If the material is decomposed, the decomposed products are deposited in a photoelectric conversion film, and acts as an excitation inhibitor or a carrier trap site, thereby causing the deterioration of the device performance. Furthermore, in the case of a manufacturing process, since the material is heated for a long period of time without changing a crucible, more decomposed products may be produced. In order to satisfy the above-mentioned requirements at a high level and to make the materials suitable for manufacturing, it is necessary to find a compound that does not cause decomposition during deposition.

The present invention has been made in order to improve the problems as described above, and an object is to provide a compound which can contribute to providing a photoelectric conversion device exhibiting high photoelectric conversion efficiency, low dark current property and high speed response property, and which does not cause decomposition during deposition.

Means for Solving the Problems

The present inventor has extensively examined, and found out that the above-mentioned object is achieved by using a compound having specific properties and structure.

That is, the above-mentioned problems may be solved by the following means.

[1] A compound represented by the following Formula (I), which has an absorption maximum at 400 nm or more and less than 720 nm in a UV-visible absorption spectrum,
wherein a molar extinction coefficient is 10,000 $mol^{-1} \cdot l \cdot cm^{-1}$ or more at the absorption maximum wavelength, and a difference between a melting point and a deposition temperature (a melting point–a deposition temperature) is 31° C. or more:

Formula (I)

[Chem. 1]

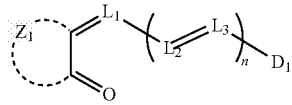

in Formula (I), $Z_1$ is a ring containing at least two carbon atoms, and represents a 5-membered ring, a 6-membered ring, or a condensed ring containing at least one of a 5-membered ring and a 6-membered ring,
each of $L_1$, $L_2$ and $L_3$ independently represents an unsubstituted methine group or a substituted methine group,
$D_1$ represents an atomic group,
n represents an integer of 0 or more.

[2] The compound as described in [1],
wherein $D_1$ is represented by the following Formula (II):

Formula (II)

[Chem. 2]

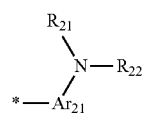

in Formula (II), each of $R_{21}$ and $R_{22}$ independently represents a hydrogen atom or a substituent,
$Ar_{21}$ represents an aromatic hydrocarbon ring group or an aromatic heterocyclic group,
* represents a bonding position to $L_1$ or $L_3$ in Formula (I),
each of $Ar_{21}$ and $R_{21}$, $Ar_{21}$ and $R_{22}$, and $R_{21}$ and $R_{22}$ may be bound to each other to form a ring.

[3] The compound as described in [1] or [2] above,
wherein $D_1$ is represented by the following Formula (III):

Formula (III)

[Chem. 3]

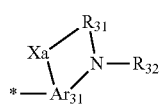

in Formula (III), $R_{31}$ represents a single bond or a divalent linking group,
$R_{32}$ represents a hydrogen atom or a substituent,
$Ar_{31}$ represents an aromatic hydrocarbon ring group or an aromatic heterocyclic group,
* represents a bonding position to $L_1$ or $L_3$ in Formula (I),
Xa represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent,
each of $Ar_{31}$ and $R_{32}$, and $R_{31}$ and $R_{32}$ may be bound to each other to form a ring.

[4] The compound as described in [3] above,
wherein $R_{31}$ in Formula (III) is a substituted or unsubstituted arylene group, and
$R_{32}$ is a substituted or unsubstituted aryl group.

[5] The compound as described in any one of [1] to [3] above,
wherein the compound represented by Formula (I) is represented by the following Formula (IV):

Formula (IV)

[Chem. 4]

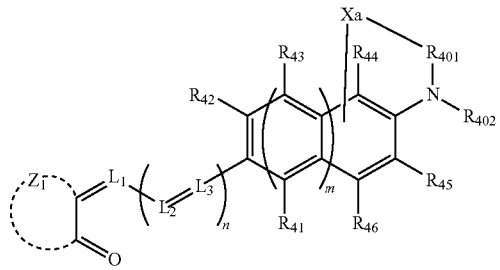

in Formula (IV), $Z_1$ is a ring containing at least two carbon atoms, and represents a 5-membered ring, a 6-membered ring, a condensed ring containing at least one of a 5-membered ring and a 6-membered ring, each of $L_1$, $L_2$ and $L_3$ independently represents an unsubstituted methine group or a substituted methine group, n represents an integer of 0 or more, m represents 0 or 1, each of $R_{41}$ to $R_{46}$ independently represents a hydrogen atom or a substituent, each of $R_{42}$ and $R_{43}$, $R_{43}$ and $R_{44}$, $R_{45}$ and $R_{46}$, and $R_{41}$ and $R_{46}$ may be bound to each other to form a ring, $R_{401}$ represents a single bond or a divalent linking group, $R_{402}$ represents a hydrogen atom or a substituent, Xa represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent, and are linked as any one of $R_{41}$ to $R_{46}$, each of $R_{401}$ and $R_{402}$, and $R_{402}$ and $R_{41}$ to $R_{46}$ may be bound to each other to form a ring.

[6] The compound as described in any one of [1] to [3] above,
wherein the compound represented by Formula (I) is represented by the following Formula (V):

Formula (V)

[Chem. 5]

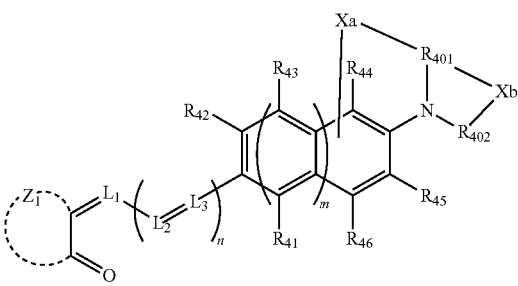

in Formula (V), $Z_1$ is a ring containing at least two carbon atoms, and represents a 5-membered ring, a 6-membered ring or a condensed ring containing at least one of a 5-membered ring and a 6-membered ring, each of $L_1$, $L_2$ and $L_3$ independently represents an unsubstituted methine group or a substituted methine group, n represents an integer of 0 or more, m represents 0 or 1, each of $R_{41}$ to $R_{46}$ independently represents a hydrogen atom or a substituent, each of $R_{42}$ and $R_{43}$, $R_{43}$ and $R_{44}$, $R_{45}$ and $R_{46}$, and $R_{41}$ and $R_{46}$ may be bound to each other to form a ring, $R_{401}$ represents a trivalent linking group, $R_{402}$ represents a single bond or a divalent linking group, each of Xa and Xb independently represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent, Xa is linked as any one of $R_{41}$ to $R_{46}$, each of $R_{402}$ and $R_{41}$ to $R_{46}$ may be bound to each other to form a ring.

[7] The compound as desried in any one of [1] to [3] above,
wherein the compound represented by Formula (I) is represented by the following Formula (VI):

Formula (VI)

[Chem. 6]

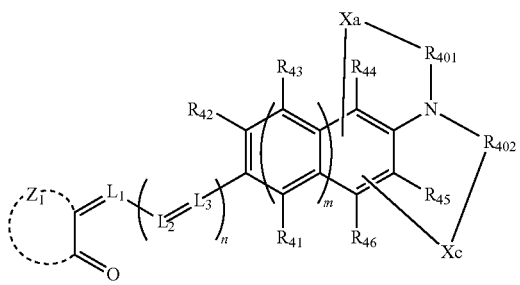

in Formula (VI), $Z_1$ is a ring containing at least two carbon atoms, and represents a 5-membered ring, a 6-membered ring or a condensed ring containing at least one of a 5-membered ring and a 6-membered ring, each of $L_1$, $L_2$ and $L_3$ independently represents an unsubstituted methine group or a substituted methine group, n represents an integer of 0 or more, m represents 0 or 1, each of $R_{41}$ to $R_{46}$ independently represents a hydrogen atom or a substituent, each of $R_{42}$ and $R_{43}$, $R_{43}$ and $R_{44}$, $R_{45}$ and $R_{46}$, and $R_{41}$ and $R_{46}$ may be bound to each other to form a ring, $R_{401}$ represents a single bond or a divalent linking group, $R_{402}$ represents a single bond or a divalent linking group, each of Xa and Xc independently represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent, and are linked as any one of $R_{41}$ to $R_{46}$, and $R_{401}$ and $R_{402}$ may be bound to each other to form a ring.

[8] The compound as described in any one of [1] to [3] above,
wherein the compound represented by Formula (I) is represented by Formula (VII):

Formula (VII)

[Chem. 7]

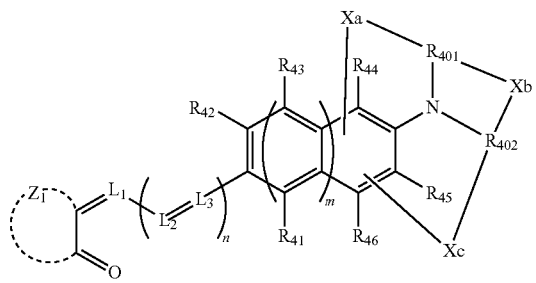

in Formula (VII), $Z_1$ is a ring containing at least two carbon atoms, and represents a 5-membered ring, a 6-membered ring or a condensed ring containing at least one of a 5-membered ring and a 6-membered ring, each of $L_1$, $L_2$ and $L_3$ independently represents an unsubstituted methine group or a substituted methine group, n represents an integer of 0 or more, m represents 0 or 1, each of $R_{41}$ to $R_{46}$ independently represents a hydrogen atom or a substituent, each of $R_{42}$ and $R_{43}$, $R_{43}$ and $R_{44}$, $R_{45}$ and $R_{46}$, and $R_{41}$ and $R_{46}$ may be bound to each other to form a ring, $R_{401}$ represents a trivalent linking group, $R_{402}$ represents a trivalent linking group, each of Xa, Xb and Xc independently represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent, and each of Xa and Xc are linked as any one of $R_{41}$ to $R_{46}$.

[9] The compound as described in any one of [5] to [8] above,
wherein each of Xa, Xb and Xc in Formulas (IV) to (VII) is independently a single bond, an oxygen atom, an alkylene group or a silylene group.

[10] The compound as described in any one of [5] to [8] above,
wherein each of Xa, Xb and Xc in Formulas (IV) to (VII) is an alkylene group.

[11] The compound as described in any one of [1] to [10] above,
wherein the structure formed by $Z_1$ and an oxygen atom is represented by the following Formula (VIII) or the following Formula (IX):

Formula (VIII)

[Chem. 8]

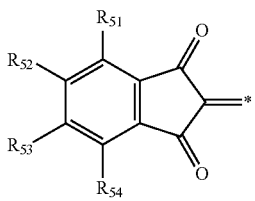

in Formula (VIII), each of $R_{51}$ to $R_{54}$ independently represents a hydrogen atom or a substituent, any adjacent two of $R_{51}$ to $R_{54}$ may be bound to each other to form a ring, and

* represents a bonding position to $L_1$:

Formula (IX)

[Chem. 9]

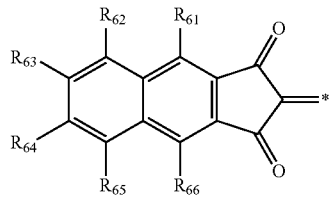

in Formula (IX), each of $R_{61}$ to $R_{66}$ independently represents a hydrogen atom or a substituent, any adjacent two of $R_{61}$ to $R_{66}$ may be bound to each other to form a ring, and

* represents a bonding position to $L_1$.

[12] The compound as described in any one of [1] to [11] above,
wherein $L_1$, $L_2$ and $L_3$ are an unsubstituted methine group.

[13] The compound as described in any one of [1] to [12] above,
wherein n is 0.

[14] A photoelectric conversion device containing:
a conductive film,
an organic photoelectric conversion film and
a transparent conductive film,
wherein the organic photoelectric conversion film contains the compound as described in any one of [1] to [13] above and a fullerene or a fullerene derivative.

[15] The photoelectric conversion device as described in [14] above, which contains the conductive film, the organic photoelectric conversion film and the transparent conductive film in this order.

[16] The photoelectric conversion device as described in [14] or [15] above,
wherein the fullerene or the fullerene derivative is $C_{60}$.

[17] The photoelectric conversion device as described in any one of [14] to [16] above,
wherein the organic photoelectric conversion film has a bulk hetero structure formed in the state where the compound as described in any one of [1] to [13] above and the fullerene or the fullerene derivative are mixed.

[18] The photoelectric conversion device as described in [17] above,
wherein the ratio (molar ratio) of (the fullerene or the fullerene derivative)/(the compound as described in any one of [1] to [13] above) is 0.5 or more.

[19] The photoelectric conversion device as described in any one of [14] to [18] above,
wherein the transparent conductive film is an electrode membrane, and light is incident from the top of the electrode membrane to the photoelectric conversion film.

[20] An imaging device which contains:
the photoelectric conversion device as described in any one of [14] to [19] above.

Advantage of the Invention

According to the present invention, a film can be formed by deposition at a high temperature without causing materials to be decomposed, and thus, it is possible to provide a compound capable of providing a photoelectric conversion device having high charge collection efficiency, high speed response property, low dark current property and high heat resistance, and suitable for manufacturing (able to endure thermal evaporation for a long period of time). Further, it is possible to provide the photoelectric conversion device and an imaging device including the photoelectric conversion device.

EMBODIMENTS FOR CARRYING OUT THE INVENTION

Figure 1A:
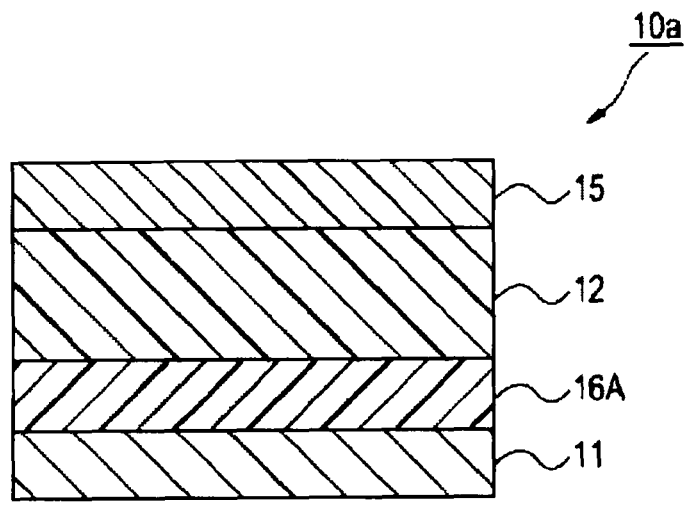
FIG. 1A and FIG. 1B are cross-sectional schematic diagrams illustrating an example of a configuration of a photoelectric conversion device according to the present invention, respectively.

The compound in the present invention is a compound which has an absorption maximum at 400 nm or more and less than 720 nm in a UV-visible absorption spectrum, wherein a molar extinction coefficient is 10,000 $mol^{-1}·l·cm^{-1}$ or more at the absorption maximum wavelength, and a difference between a melting point and a deposition temperature (a melting point–a deposition temperature) is 31° C. or more.

Conventionally, a photoelectric conversion dye material has a structure including a donor moiety (for example, a triarylamine structure) and an acceptor moiety (for example, an indandione structure), and has a high charge collection efficiency, a high speed response property and a low dark current property. However, since decomposition occurred during film forming by deposition, the device performance was deteriorated in some cases. In order to suppress the decomposition of the dye material, the deposition temperature is generally lowered. However, since the material having a low deposition temperature is usually a low molecular weight material having a low van der Waals force (intermolecular force), the heal resistance of the device is prone to be lowered, and thus, it is difficult to make the heat stability and chemical stability of the dye material and the heat resistance of the device compatible during deposition.

However, in the present invention, by using a compound (dye) in which the difference between the melting point and the deposition temperature (the melting point–the deposition temperature) is 31° C. or more, a film can be formed by deposition at a high temperature without causing materials to be decomposed, and thus, it is possible to fabricate a device having a high charge collection efficiency, a high speed response property, a low dark current property and a high heat resistance, and suitable for manufacturing (able to endure thermal evaporation for a long period of time).

Since the compound in which the difference between the melting point and the deposition temperature (the melting point–the deposition temperature) is 31° C. or more is not melt in a crucible during deposition, molecular collision between dyes and collision between the impurity molecules contained in the material and the dye molecules do not occur, and it is difficult for decomposition reaction to proceed. Accordingly, it is assumed that the decomposition of the dye material does not occur during deposition. Further, since a material which causes melting during deposition is prone to be subjected to bumping and the deposition speed is prone to be fluctuated, a material which does not cause melting during the fabrication of the device is preferred.

The present invention relates to a compound which has an absorption maximum at 400 nm or more and less than 720 nm in a UV-visible absorption spectrum, wherein a molar extinction coefficient is 10,000 $mol^{-1}·l·cm^{-1}$ or more at the absorption maximum wavelength, and a difference between a melting point and a deposition temperature (a melting point–a deposition temperature) is 31° C. or more.

The compound in the present invention has an absorption maximum at 400 nm or more and less than 720 nm in the UV-visible absorption spectrum. The peak wavelength of the absorption spectrum (absorption maximum wavelength) is preferably 450 nm to 700 nm, more preferably 480 nm to 700 nm, and still more preferably 510 nm to 680 nm from the viewpoint of absorbing light widely in the visible region.

The absorption maximum wavelength of the compound may be measured with a chloroform solution of the compound by using UV-2550 manufactured by Shimadzu Corporation. The concentration of the chloroform solution is preferably $1×10^{-7}$ mol/l to $5×10^{-5}$ mol/l, more preferably $2×10^{-6}$ mol/l to $3×10^{-5}$ mol/l, and particularly preferably $5×10^{-6}$ mol/l to $2×10^{-5}$ mol/l.

The compound in the present invention has an absorption maximum at 400 nm or more and less than 720 nm in the UV-visible absorption spectrum and the molar extinction coefficient is 10,000 $mol^{-1}·l·cm^{-1}$ or more at the absorption maximum wavelength, but in order to make a device having a high charge collection efficiency and a high speed response property by thinning the film thickness of the photoelectric conversion layer, a material having a high molar extinction coefficient is preferred. The molar extinction coefficient of the compound in the present invention is preferably 30,000 $mol^{-1}·l·cm^{-1}$ or more, more preferably 50,000 $mol^{-1}·l·cm^{-1}$ or more, still more preferably 60,000 $mol^{-1}·l·cm^{-1}$ or more, and particularly preferably 70,000 $mol^{-1}·l·cm^{-1}$ or more. The molar extinction coefficient of the compound in the present invention is measured with a chloroform solution.

As the difference between the melting point and the deposition temperature (the melting point–the deposition temperature) is increased, the compound in the present invention is hardly decomposed during deposition. Thus, the deposition speed may be increased by applying a high temperature. Further, the difference between the melting point and the deposition temperature (the melting point–the deposition temperature) is preferably 40° C. or more, more preferably 50° C. or more, and still more preferably 60° C. or more.

The melting point of the compound of the present invention is preferably 200° C. or more, more preferably 220° C. or more, and still more preferably 240° C. or more. When the melting point is 200° C. or more, it is preferred in that melting rarely occurs before deposition to form a film stably, and additionally that decomposed products of the compound are hardly generated and thus it is difficult for the photoelectric conversion performance to be deteriorated.

The deposition temperature of the compound is defined as a temperature at which the deposition speed reaches 0.4 Å/s ($0.4×10^{-10}$ m/s) when heating in a degree of vacuum of $4×10^{-4}$ Pa or less. During deposition, the distance between an opening of a crucible and a substrate was set to 30 cm, and Thermoball Cell (bottom of crucible: 15 mmΦ) manufactured by Choshu Industry was used as a crucible.

The molecular weight of the above-mentioned compound is preferably 300 to 1,500, more preferably 500 to 1,000, and particularly preferably 500 to 900. When the molecular weight of the compound is 1,500 or less, the deposition temperature is not high, and thus, decomposition of the compound hardly occurs. When the molecular weight of the compound is 300 or more, the glass transition temperature of the deposited film does not decrease, and thus, the heat resistance of the device is hardly deteriorated.

The glass transition temperature (Tg) of the above-mentioned compound is preferably 95° C. or more, more preferably 110° C. or more, still more preferably 135° C. or more, and particularly preferably 150° C. or more, and particularly preferably 160° C. or more. When the glass transition temperature is increased, it is preferred in that the heat resistance of the device is enhanced.

In the compound which has an absorption maximum at 400 nm or more and less than 720 nm in a UV-visible absorption spectrum, wherein a molar extinction coefficient is 10,000 $mol^{-1} \cdot l \cdot cm^{-1}$ or more at the absorption maximum wavelength, and a difference between a melting point and a deposition temperature (a melting point–a deposition temperature) is 31° C. or more, one preferred aspect is a donor-acceptor type compound. The donor-acceptor compound as used herein refers to a molecule in which both of the atomic group (donor) containing an electron donating substituent and the atomic group (acceptor) containing an electron withdrawing substituent are inserted into a conjugated system.

In the present specification, the donor indicates an atomic group having 1 to 30 carbon atoms that contains an electron donating group having a Hammett value σ within a range of $0 \geq \sigma \geq -0.83$.

The acceptor indicates an atomic group having 1 to 30 carbon atoms that contains an electron withdrawing group having a Hammett value σ within a range of $0 < \sigma < 0.8$. Such a substituent is not particularly limited, but may be exemplified by substituents as described in, for example, Chemical Review, 1991, 91, 165-195. The electron donating group contained as a donor is preferably an arylamino group, a dimethylamino group, an amino group, a hydroxyl group, an aryloxy group such as a phenoxy group, an alkyloxy group such as a methoxy group, a straight-chained alkyl group such as a methyl group, an ethyl group, an n-propyl group and an n-butyl group, a secondary alkyl group such as an isopropyl group, a sec-butyl group and a sec-amyl group, a tertiary alkyl group such as a tert-butyl group and a tert-amyl group, a cycloalkyl group such as a cyclohexyl group and an adamantyl group, an aryl group, a thioalkyl group or a thioaryl group, more preferably an arylamino group, a dimethylamino group, an amino group, a hydroxyl group, an aryloxy group, an alkyloxy group, a thioalkyl group or a thioaryl group, and particularly preferably an arylamino group, a dimethylamino group, aryloxy group, alkyloxy group, a thioalkyl group or a thioaryl group.

The electron withdrawing group contained as an acceptor is preferably a cyano group, a nitro group, a heterocyclic group, a carboxyl group, an acyloxy group, an alkoxycarbonyloxy group, an aryloxycarbonyloxy group, an ammonio group, an acylamino group, an aminocarbonylamino group, an alkoxycarbonylamino group, an aryloxycarbonylamino group, a sulfamoylamino group, an alkyl or arylsulfonylamino group, a sulfamoyl group, a sulfo group, an alkyl or arylsulfinyl group, an alkyl or arylsulfonyl group, an acyl group, an aryloxycarbonyl group, an alkoxycarbonyl group, a carbamoyl group, an aryl and heterocyclic azo group, an imide group, a phosphino group, a phosphinyl group, a phosphinyloxy group, a phosphinylamino group, a phospho group, an ureido group or the like, more preferably a cyano group, a nitro group, a heterocyclic group, carboxyl group, a sulfo group or a phospho group, and particularly preferably a cyano group, a nitro group, a heterocyclic group or carboxyl group.

The donor-acceptor type compound is preferred in that both of the donor and the acceptor are linked by a p-conjugated linking group (for example, a single bond, an alkenyl group, an alkynyl group, an aryl group, a heterocyclic group, carboxyl group, aryloxy group, a heterocyclic oxy group, amino group, an arylthio group or a heterocyclic thio group) and inserted in the conjugated system, thereby making the polarization in the molecule strong and, in turn, making the molar extinction coefficient (e) of the molecule high.

In the compound which has an absorption maximum at 400 nm or more and less than 720 nm in a UV-visible absorption spectrum, wherein a molar extinction coefficient is 10,000 $mol^{-1} \cdot l \cdot cm^{-1}$ or more at the absorption maximum wavelength, and a difference between a melting point and a deposition temperature (a melting point–a deposition temperature) is 31° C. or more, one preferred aspect is a compound represented by the following Formula (I).

Formula (I)

[Chem. 10]

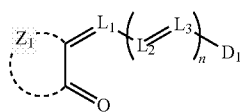

In Formula (I), $Z_1$ represents an atomic group necessary for forming a 5- or 6-membered ring. Each of $L_1$, $L_2$ and $L_3$ independently represents an unsubstituted methine group or a substituted methine group. $D_1$ represents an atomic group. n represents an integer of 0 or more.

In Formula (I), $Z_1$ is a ring containing at least two carbon atoms, and represents a 5-membered ring, a 6-membered ring or a condensed ring containing at least one of a 5-membered ring and a 6-membered ring. The 5-membered ring, the 6-membered ring, or the condensed ring containing at least one of the 5-membered ring and the 6-membered ring are preferably one commonly used as an acidic nucleus in a merocyanine dye, and specific examples thereof may include the followings.

(a) a 1,3-dicarbonyl neucleus: for example, a 1,3-indandione neucleus, 1,3-cyclohexanedione, 5,5-dimethyl-1,3-cyclohexanedione, 1,3-dioxan-4,6-dione and the like.
(b) a pyrazolinone neucleus: for example, 1-phenyl-2-pyrazolin-5-one, 3-methyl-1-phenyl-2-pyrazolin-5-one, 1-(2-benzothiazoyl)-3-methyl-2-pyrazolin-5-one and the like.
(c) an isoxazolinone neucleus: for example, 3-phenyl-2-isoxazolin-5-one, 3-methyl-2-isoxazolin-5-one and the like.
(d) an oxindole neucleus: for example, 1-alkyl-2,3-dihydro-2-oxindole and the like.
(e) 2,4,6-triketohexahydropyrimidine neucleus: for example, barbituric acid or 2-thiobarbituric acid, a derivative thereof and the like. Examples of the derivative include a 1-alkyl form such as 1-methyl and 1-ethyl, a 1,3-dialkyl form such as 1,3-dimethyl, 1,3-diethyl and 1,3-dibutyl, a 1,3-diaryl form such as 1,3-diphenyl, 1,3-di(p-chlorophenyl) and 1,3-di(p-ethoxycarbonylphenyl), a 1-alkyl-1-aryl form such as 1-ethyl-3-phenyl, a 1,3-diheterocyclic substitution form such as 1,3-di(2-pyridyl).
(f) a 2-thio-2,4-thiazolidinedione neucleus: for example, rhodanine, a derivative thereof and the like. Examples of the derivative include 3-allylrhodanine such as 3-methylrhodanine, 3-ethylrhodanine and 3-allylrhodanine, 3-arylrhodanine such as 3-phenylrhodanine, 3-heterocyclic ring-substituted rhodanine such as 3-(2-pyridyl)rhodanine.
(g) a 2-thio-2,4-oxazolidinedione (2-thio-2,4-(3H,5H)-oxazoledione) neucleus: for example, 3-ethyl-2-thio-2,4-oxazolidinedione and the like.

(h) a thianaphthenone nucleus: for example, 3(2H)-thianaphthenone-1,1-dioxide and the like.
(i) a 2-thio-2,5-thiazolidinedione nucleus: for example, 3-ethyl-2-thio-2,5-thiazolidinedione and the like.
(j) a 2,4-thiazolidinedione nucleus: for example, 2,4-thiazolidinedione, 3-ethyl-2,4-thiazolidinedione, 3-phenyl-2,4-thiazolidinedione and the like.
(k) a thiazoline-4-one nucleus: for example, 4-thiazolidone, 2-ethyl-4-thiazolidone and the like.
(l) a 2,4-imidazolidinedione (hydantoin) nucleus: for example, 2,4-imidazolidinedione, 3-ethyl-2,4-imidazolidinedione and the like.
(m) a 2-thio-2,4-imidazolidinedione (2-thiohydantoin) nucleus: for example, 2-thio-2,4-imidazolidinedione, 3-ethyl-2-thio-2,4-imidazolidinedione and the like.
(n) an imidazoline-5-one nucleus: for example, 2-propylmercapto-2-imidazoline-5-one and the like.
(o) a 3,5-pyrazolidinedione nucleus: for example, 1,2-diphenyl-3,5-pyrazolidinedione, 1,2-dimethyl-3,5-pyrazolidinedione and the like.
(p) a benzothiophene-3-one nucleus: for example, benzothiophene-3-one, oxobenzothiophene-3-one, dioxobenzothiophene-3-one and the like.
(q) an indanone nucleus: for example, 1-indanone, 3-phenyl-1-indanone, 3-methyl-1-indanone, 3,3-diphenyl-indanone, 3,3-dimethyl-1-indanone and the like.

The ring represented by $Z_1$ is preferably a 1,3-dicarbonyl nucleus, a pyrazolinone nucleus, a 2,4,6-triketohexahydropyrimidine nucleus (including a thioketone form, for example, a barbituric acid nucleus and a 2-thiobarbituric acid nucleus), a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, a 2-imidazoline-5-one nucleus, a 3,5-pyrazolidinedione nucleus, a benzothiophene-3-one nucleus and an indanone nucleus, and more preferably a 1,3-dicarbonyl nucleus, a 2,4,6-triketohexahydropyrimidine nucleus (including a thioketone form, for example, a barbituric acid nucleus, and a 2-thiobarbituric acid nucleus), a 3,5-pyrazolidinedione nucleus, a benzothiophene-3-one nucleus, and an indanone nucleus, more preferably a 1,3-dicarbonyl nucleus, a 2,4,6-triketohexahydropyrimidine nucleus (including a thioketone form, for example, a barbituric acid nucleus, and a 2-thiobarbituric acid nucleus), and particularly preferably a 1,3-indandione nucleus, a barbituric acid nucleus, a 2-thiobarbituric acid nucleus and a derivative thereof.

The ring represented by $Z_1$ is preferably represented by the following Formula (Z1).

Formula (Z1)

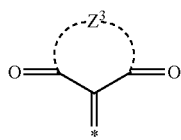

[Chem. 11]

$Z^3$ is a ring containing at least three carbon atoms, and represents a 5-membered ring, a 6-membered ring or a condensed ring containing at least one of a 5-membered ring and a 6-membered ring. * represents a bonding position to $L_1$ in Formula (I).

$Z^3$ may be selected from the rings formed by $Z_1$, and is preferably a 1,3-dicarbonyl neucleus, a 2,4,6-triketohexahydropyrimidine neucleus (also including a thioketone form), and particularly preferably a 1,3-indandione neucleus, a barbituric acid neucleus, a 2-thiobarbituric acid neucleus and a derivative thereof.

In Formula (I), the ring represented by $Z_1$ functions as an acceptor portion in some cases, but the present inventors has found out that a high hole transporting property can be exhibited by controlling the interaction between acceptor portions when used as a co-deposited film with fullerene $C_{60}$. It is possible to control the interaction by introduction of a substituent that is a structure of the acceptor portion and steric hinderance. In the case of a barbituric acid neucleus and a 2-thiobarbituric acid neucleus, it is possible to control the intermolecular interaction by substituting preferably all of two hydrogen atoms at the N-positions with substituents, and the substituent may be exemplified by Substituent W as described below, but is more preferably an alkyl group, and still more preferably a methyl group, an ethyl group, a propyl group or a butyl group.

When the ring represented by $Z_1$ is a 1,3-indandione neucleus, a group represented by the following Formula (VIII) or a group represented by the following Formula (IX) is preferred.

Formula (VIII)

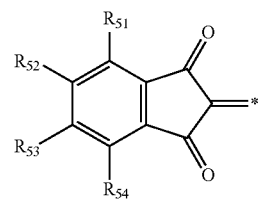

[Chem. 12]

In Formula (VIII), each of $R_{51}$ to $R_{54}$ independently represents a hydrogen atom or a substituent. Any adjacent two of $R_{51}$ to $R_{54}$ may be bound to each other to form a ring. * represents a bonding position to $L_1$.

Formula (IX)

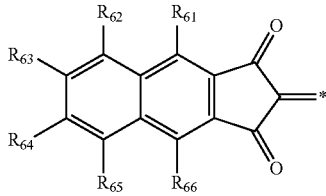

[Chem. 13]

In Formula (IX), each of $R_{61}$ to $R_{66}$ independently represents a hydrogen atom or a substituent. Any adjacent two of $R_{61}$ to $R_{66}$ may be bound to each other to form a ring. * represents a bonding position to $L_1$.

In the group represented by Formula (VIII), each $R_{51}$ to $R_{54}$ independently represents a hydrogen atom or a substituent. The substituent may be, for example, those exemplified by Substituent W as described below, and is preferably an alkyl group, and more preferably an alkyl group having 1 to 6 carbon atoms. Further, any adjacent two of $R_{51}$ to $R_{54}$ may be bound to each other to form a ring. When forming a ring, it is preferred that $R_{52}$ and $R_{53}$ are boned to each other to form a ring (for example, a benzene ring, a pyridine ring, a pyrazine ring).

It is preferred that all of $R_{51}$ to $R_{54}$ are a hydrogen atom.

In Formula (IX), each of $R_{61}$ to $R_{66}$ independently represents a hydrogen atom or a substituent. The substituent may be those exemplified by Substituent W as described below, and is preferably an alkyl group, and more preferably an alkyl group having 1 to 6 carbon atoms. It is preferred that all of $R_{61}$ to $R_{66}$ are a hydrogen atom.

When the ring represented by $Z_1$ is a 2,4,6-triketohexahydropyrimidine neucleus (also including a thioketone form), the group represented by Formula (X) is preferred.

Formula (X)

[Chem. 14]

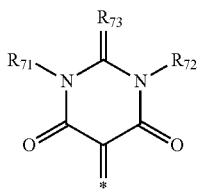

In Formula (X), each of $R_{71}$ and $R_{72}$ independently represents a hydrogen atom or a substituent. $R_{73}$ represents an oxygen atom, a sulfur atom or a substituent. * represents a bonding position to $L_1$.

In Formula (X), each of $R_{71}$ and $R_{72}$ independently represents a hydrogen atom or a substituent. The substituent may be, for example, those exemplified by Substituent W as described below. Each of $R_{71}$ and $R_{72}$ independently represents preferably an alkyl group, an aryl group or a heterocyclic group (preferably 2-pyridyl and the like), and more preferably an alkyl group having 1 to 6 carbon atoms (for example, methyl, ethyl, n-propyl and t-butyl).

$R_{73}$ represents an oxygen atom, a sulfur atom or a substituent, but it is preferred that $R_{73}$ represents an oxygen atom or a sulfur atom. As the substituent, a substituent whose bonding portion is a nitrogen atom or a carbon atom is preferred. In the case of a nitrogen atom, an alkyl group (having 1 to 12 carbon atoms) or an aryl group (having 6 to 12 carbon atoms) is preferred, and specific examples thereof include a methylamino group, an ethylamino group, a butylamino group, a hexylamino group, a phenylamino group or a naphthylamino group. In the case of a carbon atom, it is preferred to be further substituted with at least one electron withdrawing group, and examples of the electron withdrawing group include a carbonyl group, a cyano group, a sulfoxide group, a sulfonyl group or a phosphoryl group, which may further have a substituent. This substituent may be exemplified by Substituent W as described below. $R_{73}$ is preferably a group forming 5-membered ring or 6-membered ring containing the carbon atom, and specific examples thereof include the following structures.

[Chem. 15]

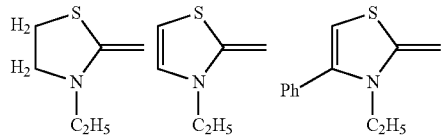

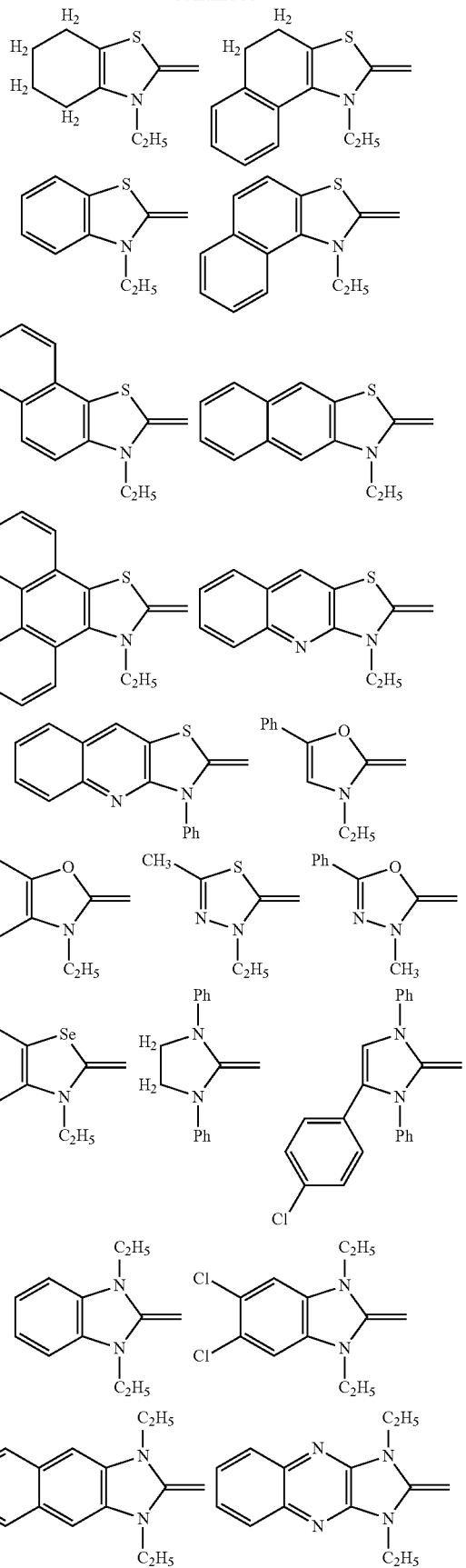

-continued
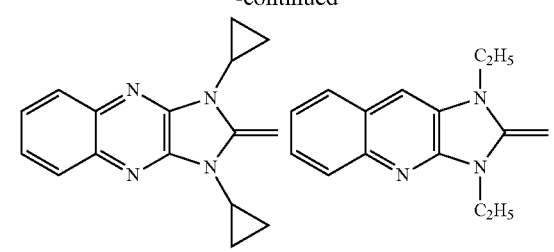
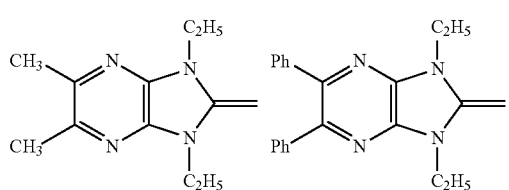
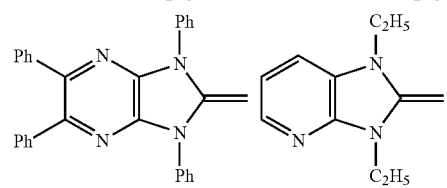
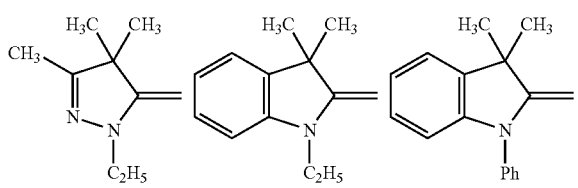
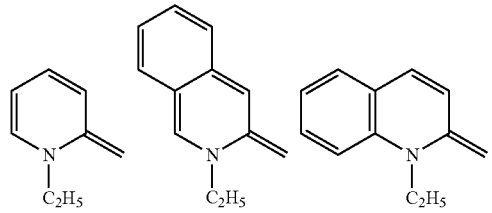
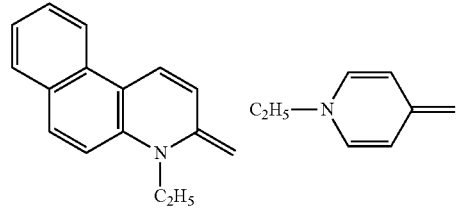
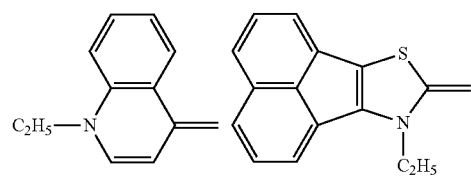
[Chem. 16]
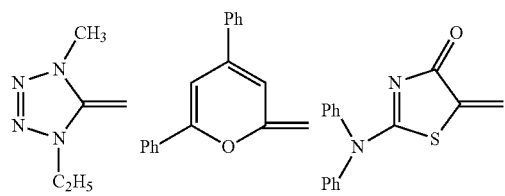
-continued
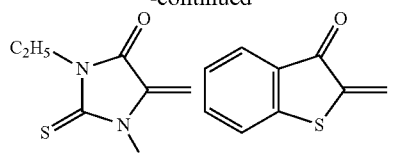
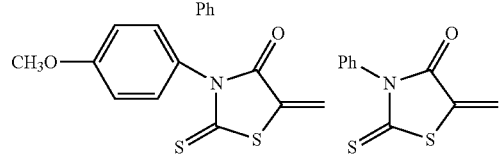
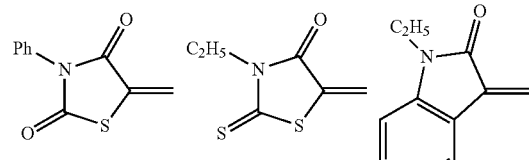
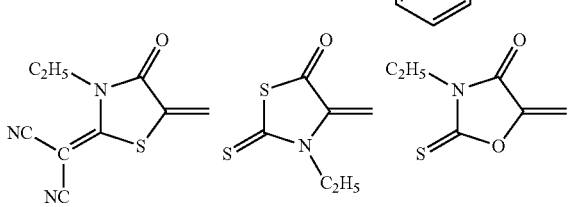
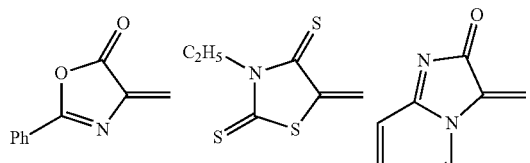
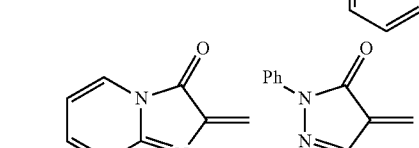
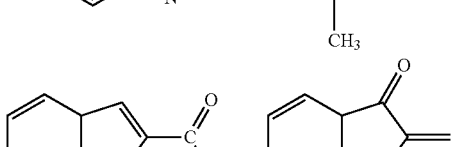
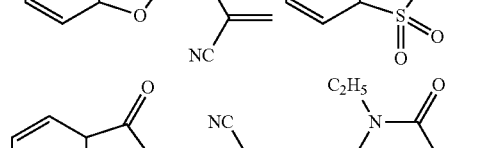
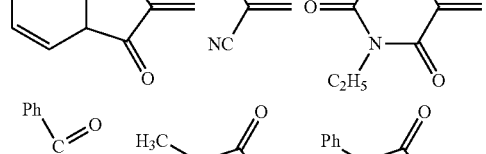
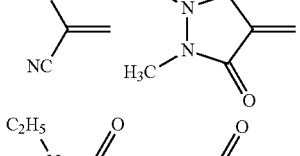
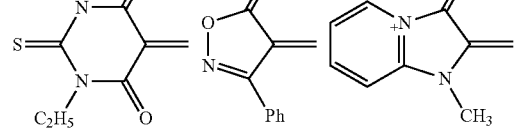

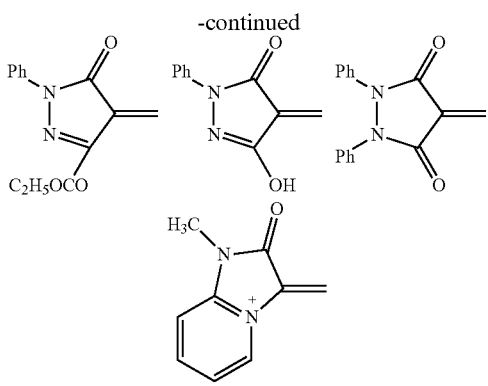

In the above groups, Ph represents a phenyl group.

In Formula (I), each of $L_1$, $L_2$ and $L_3$ independently represents an unsubstituted methine group or a substituted methine group. Substituted methine groups may be bound to each other to form a ring. Examples of the ring include a 6-membered ring (for example, a benzene ring and the like). The substituent of the substituted methine group may be exemplified by Substituent W as described below, but it is preferred that all of $L_1$, $L_2$ and $L_3$ are an unsubstituted methine group.

In Formula (I), n represents an integer of 0 or more, preferably an integer of 0 to 3, and more preferably 0. In the case where n is increased, the absorption wavelength region may be a long wavelength, but a decomposition temperature by heat is decreased. n is preferably 0 in that appropriate absorption is provided in a visible ray region and heat decomposition is suppressed during film formation by deposition.

In Formula (I), $D_1$ represents an atomic group. $D_1$ is preferably a group containing $-NR^a(R^b)$, and further, $D_1$ preferably represents an aryl group (preferably a phenyl group or a naphthyl group, which may have a substituent) substituted with $-NR^a(R^b)$. Each of $R^a$ and $R^b$ independently represents a hydrogen atom or a substituent, and the substituent may be exemplified by Substituent W as described below, and is preferably an aliphatic hydrocarbon group (preferably an alkyl group or an alkenyl group, which may have a substituent), an aryl group or a heterocyclic group.

The heterocyclic ring is preferably a 5-membered ring such as a furan ring, a thiophene ring, a pyrrole ring or an oxadiazole ring.

When $R^a$ and $R^b$ are a substituent (preferably an aryl group, an alkyl group or an alkenyl group), these substituents may be bound to a hydrogen atom or a substituent of the aromatic ring (preferably a benzene ring or a naphthalene ring) skeleton of the aryl group substituted with $-NR^a(R^b)$ to form a ring (preferably a 6-membered ring).

$R^a$ and $R^b$ may be bound to each substituent to for a ring (preferably a 5-membered or 6-membered ring, and more preferably a 6-membered ring), and further, each of $R^a$ and $R^b$ may be bound to a substituent of L (referred to as any of $L_1$, $L_2$ and $L_3$) to form a ring (preferably a 5-membered or 6-membered ring, and more preferably a 6-membered ring).

$D_1$ is preferably an aryl group (preferably a phenyl group or a naphthyl group) substituted with an amino group at the para-position. The substituent of this amino group may be exemplified by Substituent W as described below, but is preferably an aliphatic hydrocarbon group (preferably an alkyl group which may be substituted), an aryl group (preferably a phenyl group or a naphthyl group, which may be substituted) or a heterocyclic group. The amino group is preferably a so-called diaryl group-substituted amino group, which is substituted with two aryl groups. Furthermore, the substituent (preferably an alkyl group or an alkenyl group, which may be substituted) of the amino group may be bound to a hydrogen atom or a substituent of the aromatic ring (preferably a benzene ring or a naphthyl group) skeleton of the amino group to form a ring (preferably a 6-membered ring).

The substituent in the case where $R^a$ and $R^b$ is an aliphatic hydrocarbon group, aryl group or a heterocyclic ring is preferably an alkyl group, an alkenyl group, an aryl group, an alkoxy group, an aryloxy group, an acyl group, an alkoxycarbonyl group, an aryloxycarbonyl group, an acylamino group, a sulfonylamino group, a sulfonyl group, a silyl group, an aromatic heterocyclic group, more preferably an alkyl group, an alkenyl group, an aryl group, an alkoxy group, an aryloxy group, a silyl group, an aromatic heterocyclic group, and still more preferably an alkyl group, an aryl group, an alkoxy group, an aryloxy group, a silyl group, an aromatic heterocyclic group. Specific examples may include those exemplified by Substituent W as described below.

$R^a$ and $R^b$ are preferably an alkyl group, an aryl group or an aromatic heterocyclic group. $R^a$ and $R^b$ are particularly preferably an alkyl group, an alkylene group which is linked with L to form a ring or an aryl group, more preferably an alkyl group having 1 to 8 carbon atoms, or an alkylene group which is linked with L to for a 5- to 6-membered ring or a substituted or unsubstituted aryl group, still more preferably an alkyl group having 1 to 8 carbon atoms or a substituted or unsubstituted aryl group, and particularly preferably a substituted or unsubstituted phenyl group or naphthyl group.

It is also preferred that $D_1$ is represented by the following Formula (II).

Formula (II)

[Chem. 17]

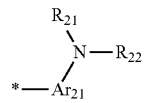

In Formula (II), each of $R_{21}$ and $R_{22}$ independently represents a hydrogen atom or a substituent. $Ar_{21}$ represents an aromatic hydrocarbon ring group or an aromatic heterocyclic group. * represents a bonding position to $L_1$ or $L_3$ in Formula (I). Each of $Ar_{21}$ and $R_{21}$, $Ar_{21}$ and $R_{22}$, and $R_{21}$ and $R_{22}$ may be bound to each other to form a ring.

Each of $R_{21}$ and $R_{22}$ independently represents a hydrogen atom or a substituent, and the substituent may be exemplified by Substituent W as described below. These may further have a substituent. Specific examples of the further substituent include Substituent W as described below, preferably a halogen atom, an alkyl group, an aryl group, a heterocyclic group, a hydroxyl group, amino group or a mercapto group, more preferably a halogen atom, an alkyl group, an aryl group or a heterocyclic group, still more preferably a fluorine atom, an alkyl group or an aryl group, particularly preferably an alkyl group, an aryl group, and most preferably an alkyl group. The alkyl group is preferably a straight-chained or branched structure, and has preferably 1 to 20 carbon atoms, more preferably 1 to 10 carbon atoms, and still more preferably 1 to 5 carbon atoms.

$R_{21}$ and $R_{22}$ are preferably an alkyl group, an alkenyl group, an aryl group, an alkoxy group, an aryloxy group, an acyl group, an alkoxycarbonyl group, an aryloxycarbonyl group, an acylamino group, a sulfonylamino group, a sulfonyl group, a silyl group, an aromatic heterocyclic group; more preferably an alkyl group, an aryl group, an alkoxy group, an aryloxy group, a silyl group, an aromatic heterocyclic group (preferably a furan ring, a thiophene ring, a pyridine ring, a pyridazine ring, a pyrimidine ring, a pyrazine ring, an oxadiazole ring, a triazole ring, an imidazole ring, a pyrazole ring or a thiazole ring), still more preferably an alkyl group, an aryl group or an aromatic heterocyclic group (preferably a furan ring, a thiophene ring, a pyridine ring, an oxadiazole ring, an imidazole ring, a pyrazole ring or a thiazole ring), particularly preferably an alkyl group or an aryl group, and among them, preferably an alkyl group having 1 to 8 carbon atoms or a phenyl group, an alkyl-substituted phenyl group, a phenyl-substituted phenyl group, a naphthyl group, a phenanthryl group, an anthryl group or a fluorenyl group (preferably a 9,9'-dimethyl-2-fluorenyl group), particularly preferably a substituted or unsubstituted aryl group, and most preferably a substituted or unsubstituted a phenyl group or a naphthyl group. Further, a plurality of substituents described above may be bound to each other to form a ring.

$Ar_{21}$ represents an aromatic hydrocarbon ring or an aromatic heterocyclic group, and the substituent which these may have is exemplified by Substituent W as described below. $Ar_{21}$ is preferably a benzene ring, a naphthalene ring, an indane ring, an anthracene ring, a fluorene ring, a pyrene ring, a phenanthrene ring, a perylene ring, a pyridine ring, a quinoline ring, an isoquinoline ring, a phenanthridine ring, a pyrimidine ring, a pyrazine ring, a pyridazine ring, a triazine ring, a cinnoline ring, an acridine ring, a phthalazine ring, a quinazoline ring, a quinoxaline ring, a naphthyridine ring, a pteridine ring, a pyrrole ring, a pyrazole ring, a triazole ring, an indole ring, a carbazole ring, an indazole ring, a benzimidazole ring, an oxazole ring, a thiazole ring, an oxadiazole ring, a thiadiazole ring, a benzoxazole ring, a benzothiazole ring, an imidazopyridine ring, a thiophene ring, a benzothiophene ring, a furan ring, a benzofuran ring, a phosphor ring, a phosphinine ring or silole ring, more preferably a benzene ring, a naphthalene ring, a fluorene ring, an indane ring, an anthracene ring, a pyrene ring, a phenanthrene ring, a perylene ring, a pyrrole ring, an indole ring, a carbazole ring, an indazole ring, a thiophene ring, a benzothiophene ring, a furan ring or a benzofuran ring, still more preferably a benzene ring, a naphthalene ring, a fluorene ring, an indane ring, an indole ring, a carbazole ring or an indazole ring, particularly preferably a benzene ring, a naphthalene ring, a fluorene ring, an indane ring or an anthracene ring, and among them, preferably a benzene ring, a naphthalene ring or a fluorene ring, and most preferably a benzene ring or a naphthalene ring.

$Ar_{21}$ may further have a substituent. Specific examples of the further substituent may be exemplified by Substituent W as described below, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably an alkyl group.

In the case where the compound (dye) having a structure in which $D_1$ in Formula (I) is represented by Formula (II) has a triarylamine structure in the donor portion represented by $D_1$, if using a combination with fullerenes, it is possible to realize the high charge collection efficiency and the high speed response, particularly while maintaining the heat resistance of the device.

One preferred aspect of Formula (II) is Formula (II-a).

Formula (II-a)

[Chem. 18]

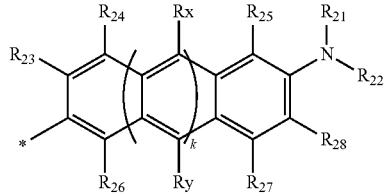

In Formula (II-a), each of $R_{21}$ and $R_{22}$ independently represents a hydrogen atom or a substituent. Each of $R_{23}$ to $R_{28}$ independently represents a hydrogen atom or a substituent. k represents an integer of 0 or more. Each of Rx and Ry independently represents a hydrogen atom or a substituent. When k is 2 or more, each of Rx and Ry may be the same as or different from every other Rx and Ry. Further, each of $R_{23}$ and $R_{24}$, $R_{24}$ and Rx, Rx and $R_{25}$, $R_{25}$ and $R_{21}$, $R_{26}$ and Ry, Ry and $R_{27}$, $R_{27}$ and $R_{28}$, $R_{28}$ and $R_{22}$, and $R_{21}$ and $R_{22}$ may be bound to each other to form a ring. * represents a bonding position to $L_1$ or $L_3$ in Formula (I).

In Formula (II-a), k is preferably 0 or 1, and more preferably 0.

$R_{21}$ and $R_{22}$ have the same meaning as $R_{21}$ and $R_{22}$ in Formula (II), and preferred ranges thereof are also the same.

When $R_{23}$ to $R_{28}$, Rx and Ry represent a substituent, the substituent may be exemplified by Substituent W as described below. These may further have a substituent. Specific examples of the further substituent may be exemplified by Substituent W as described below, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably an alkyl group.

It is preferred that all of $R_{23}$ to $R_{28}$ are a hydrogen atom. Further, it is preferred that both of Rx and Ry are a hydrogen atom.

It is more preferred that $R_{23}$ to $R_{28}$ are a hydrogen atom, and Rx and Ry are also a hydrogen atom.

It is also preferred that $D_1$ is a group represented by the following Formula (II-b) or Formula (II-c).

Formula (II-b)

[Chem. 19]

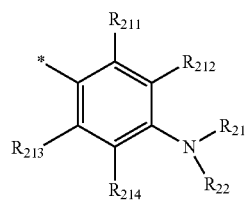

In Formula (II), each of $R_{21}$ and $R_{22}$ independently represents a hydrogen atom or a substituent. Each of $R_{211}$ to $R_{214}$ independently represents a hydrogen atom or a substituent. Each of $R_{211}$ and $R_{212}$, $R_{213}$ and $R_{214}$, $R_{21}$ and $R_{22}$, $R_{212}$ and $R_{21}$, and $R_{214}$ and $R_{22}$ may be bound to each other to form a ring. * represents a bonding position to $L_1$ or $L_3$ in Formula (I).

$R_{21}$ and $R_{22}$ have the same meaning as $R_{21}$ and $R_{22}$ in Formula (II), and preferred ranges are also the same.

When $R_{211}$ to $R_{214}$ represents a substituent, the substituent may be exemplified by Substituent W as describe below, but it is preferred that $R_{211}$ to $R_{214}$ are a hydrogen atom or $R_{212}$ and $R_{21}$ or $R_{214}$ and $R_{22}$ form a 5-membered ring or a 6-membered ring, and it is more preferred that any of $R_{211}$ to $R_{214}$ is a hydrogen atom.

When each of $R_{211}$ and $R_{212}$, $R_{213}$ and $R_{214}$, $R_{21}$ and $R_{22}$, $R_{212}$ and $R_{21}$, and $R_{214}$ and $R_{22}$ are bound to each other to form a ring, the ring to be formed may be exemplified by Ring R as described below. A benzene ring, a naphthalene ring, an anthracene ring, a pyridine ring, a pyrimidine ring and the like are preferred.

Formula (II-c)

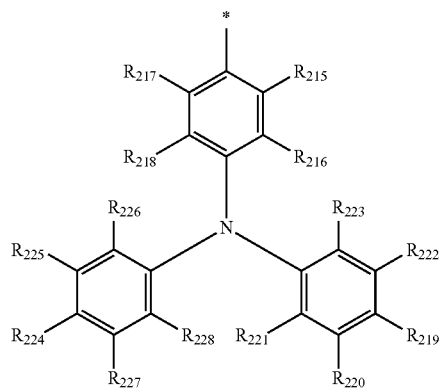

[Chem. 20]

In Formula (II-c), each of $R_{215}$ to $R_{218}$, $R_{219}$ to $R_{223}$ and $R_{224}$ to $R_{228}$ independently represents a hydrogen atom or a substituent. Each of $R_{215}$ and $R_{216}$, $R_{217}$ and $R_{218}$, $R_{223}$ and $R_{222}$, $R_{222}$ and $R_{219}$, $R_{219}$ and $R_{220}$, $R_{220}$ and $R_{221}$, $R_{228}$ and $R_{227}$, $R_{227}$ and $R_{224}$, $R_{224}$ and $R_{225}$, and $R_{225}$ and $R_{226}$ may be bound to each other to form a ring. * represents a bonding position to $L_1$ or $L_3$ in Formula (I).

Each of $R_{215}$ and $R_{216}$, $R_{217}$ and $R_{218}$, $R_{223}$ and $R_{222}$, $R_{222}$ and $R_{219}$, $R_{219}$ and $R_{220}$, $R_{220}$ and $R_{221}$, $R_{228}$ and $R_{227}$, $R_{227}$ and $R_{224}$, $R_{224}$ and $R_{225}$, and $R_{225}$ and $R_{226}$ may be bound to each other to form a ring, and the ring to be formed may be exemplified by Ring R as described below. A benzene ring, a naphthalene ring, an anthracene ring, a pyridine ring, a pyrimidine ring and the like are preferred.

Each of $R_{216}$ and $R_{223}$, $R_{218}$ and $R_{226}$, and $R_{228}$ and $R_{221}$ may be linked. $R_{216}$ and $R_{223}$, $R_{218}$ and $R_{226}$, and $R_{228}$ and $R_{221}$ may be bound together with an N atom to form a 5 to 10-membered ring (preferably a 5 to 6-membered ring), and the linkage of $R_{216}$ and $R_{223}$, $R_{218}$ and $R_{226}$, and $R_{228}$ and $R_{221}$ may be a single bond.

When $R_{215}$ to $R_{218}$, $R_{219}$ to $R_{223}$, and $R_{224}$ to $R_{228}$ represents a substituent, the substituent may be exemplified by Substituent W as describe below. $R_{215}$ to $R_{218}$, $R_{219}$ to $R_{223}$, and $R_{224}$ to $R_{228}$ are preferably a hydrogen atom, a halogen atom, an alkyl group having 1 to 18 carbon atoms, an aryl group having 6 to 18 carbon atoms or a heterocyclic group having 4 to 16 carbon atoms, more preferably a hydrogen atom, an alkyl group having 1 to 12 carbon atoms, an aryl group having 6 to 14 carbon atoms or a fluorine atom, still more preferably a hydrogen atom, an alkyl group having 1 to 6 carbon atoms or an aryl group having 6 to 10 carbon atoms, and among them, preferably a hydrogen atom, a fluorine atom, a methyl group, an ethyl group, a propyl group, a butyl group, a hexyl group, a cyclohexyl group, a phenyl group or a naphthyl group, and particularly preferably a hydrogen atom, a methyl group, a butyl group, a hexyl group or a phenyl group. The alkyl group may be branched.

These may further have a substituent. Specific examples of the further substituent may be exemplified by Substituent W as described below, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably an alkyl group.

Formula (I) is preferably the following Formula (II-d).

Formula (II-d)

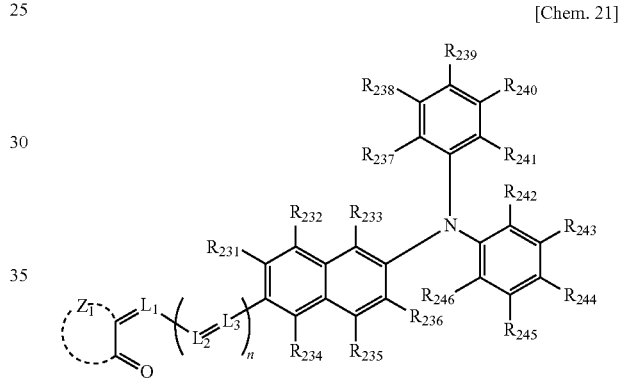

[Chem. 21]

In Formula (II-d), $Z_1$ represents an atomic group necessary for forming a 5- or 6-membered ring. Each of $L_1$, $L_2$ and $L_3$ independently represents an unsubstituted methine group or a substituted methine group. Each of $R_{231}$ to $R_{236}$ independently represents a hydrogen atom or a substituent. Further, each of $R_{231}$ and $R_{232}$, $R_{232}$ and $R_{233}$, $R_{234}$ and $R_{235}$, and $R_{235}$ and $R_{236}$ may be bound to each other to form a ring. Each of $R_{237}$ to $R_{241}$ and $R_{242}$ to $R_{246}$ independently represents a hydrogen atom or a substituent. Further, any adjacent groups among $R_{237}$ to $R_{241}$ and $R_{242}$ to $R_{246}$ may be bound to each other to form a ring. Each of $R_{233}$ and $R_{237}$, and $R_{236}$ and $R_{246}$ may be independently bound to form a ring.

In Formula (II-d), $Z_1$, $L_1$, $L_2$ and $L_3$ have the same meaning as $Z_1$, $L_1$, $L_2$ and $L_3$ in Formula (I), and preferred ranges thereof are also the same.

When $R_{231}$ to $R_{236}$ represent a substituent, the substituent may be exemplified by Substituent W as describe below. $R_{231}$ to $R_{236}$ are preferably a hydrogen atom, a halogen atom, an alkyl group having 1 to 18 carbon atoms, an aryl group having 6 to 18 carbon atoms or a heterocyclic group having 4 to 16 carbon atoms, more preferably a hydrogen atom, an alkyl group having 1 to 12 carbon atoms, an aryl group having 6 to 14 carbon atoms or a fluorine atom, still more preferably a hydrogen atom, an alkyl group having 1 to 6 carbon atoms or an aryl group having 6 to 10 carbon atoms, and among them, preferably a hydrogen atom, a fluorine atom, a methyl group, an ethyl group, a propyl group, a butyl group, a hexyl group, a cyclohexyl group, a phenyl group or a naphthyl group, and particularly a hydrogen atom, a methyl group, a butyl group, a hexyl group or a phenyl group. The alkyl group may be branched.

These may further have a substituent. Specific examples of the further substituent may be exemplified by Substituent W as described below, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably alkyl group.

Each of $R_{231}$ and $R_{232}$, $R_{232}$ and $R_{233}$, $R_{234}$ and $R_{235}$, and $R_{235}$ and $R_{236}$ may be bound to each other to form a ring. The ring to be formed may be exemplified by Ring R as describe below. A benzene ring, a naphthalene ring, an anthracene ring, a pyridine ring, a pyrimidine ring and the like are preferred.

Each of $R_{237}$ to $R_{241}$, $R_{242}$ to $R_{246}$ independently represents a hydrogen atom or a substituent. When $R_{237}$ to $R_{241}$ and $R_{242}$ to $R_{246}$ represent a substituent, the substituent may be exemplified by Substituent W as describe below. $R_{237}$ to $R_{241}$ and $R_{242}$ to $R_{246}$ are preferably a hydrogen atom, a halogen atom, an alkyl group having 1 to 18 carbon atoms, an aryl group having 6 to 18 carbon atoms or a heterocyclic group having 4 to 16 carbon atoms, more preferably a hydrogen atom, an alkyl group having 1 to 12 carbon atoms, an aryl group having 6 to 14 carbon atoms or a fluorine atom, still more preferably a hydrogen atom, an alkyl group having 1 to 6 carbon atoms or an aryl group having 6 to 10 carbon atoms, and among them, preferably a hydrogen atom, a fluorine atom, a methyl group, an ethyl group, a propyl group, a butyl group, a hexyl group, a cyclohexyl group, a phenyl group or a naphthyl group, and particularly preferably a hydrogen atom, a methyl group, a butyl group, a hexyl group or a phenyl group. The alkyl group may be branched.

These may further have a substituent. Specific examples of the further substituent may be exemplified by Substituent W as described below, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably an alkyl group.

Further, any adjacent groups among $R_{237}$ to $R_{241}$ and $R_{242}$ to $R_{246}$ may be bound to each other to form a ring. The ring to be formed may be exemplified by Ring R as described below. The ring to be formed is preferably a benzene ring, a naphthalene ring, an anthracene ring, a pyridine ring, a pyrimidine ring or the like.

Further, each of $R_{233}$ and $R_{237}$, and $R_{236}$ and $R_{246}$ may be linked. When $R_{233}$ and $R_{237}$ or $R_{236}$ and $R_{246}$ are linked, these groups forms a condensed ring formed of 4 or more rings containing a naphthylene group and a phenyl group. The linkage of $R_{233}$ and $R_{237}$ or $R_{236}$ and $R_{246}$ may be a single bond.

One preferred aspect of $D_1$ in Formula (I) is the following Formula (III).

Formula (III)

[Chem. 22]

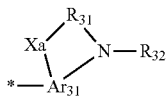

In Formula (III), $R_{31}$ represents a single bond or a divalent linking group, and $R_{32}$ represents a hydrogen atom or a substituent. $Ar_{31}$ represents an aromatic hydrocarbon ring group or an aromatic heterocyclic group. * represents a bonding position to $L_1$ or $L_3$ in Formula (I). Xa represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent. Each of $Ar_{31}$ and $R_{32}$, and $R_{31}$ and $R_{32}$ may be bound to each other to form a ring.

$R_{32}$ and $Ar_{32}$ have the same meaning as $R_{22}$ and $Ar_{21}$ in Formula (II), and preferred ranges thereof are also the same.

$R_{31}$ represents a single bond or a divalent linking group.

$R_{31}$ is preferably an alkylene group, an alkenylene group, an arylene group, an oxygen atom, a sulfur atom, an alkyleneoxy group, an aryleneoxy group, a carbonyl group, a carbonylalkylene group, a carbonylarylene group, an alkyleneoxycarbonyl group, aryleneoxycarbonyl group, a divalent acylamino group, a divalent sulfonylamino group, a sulfonylene group, a silylene group or a divalent aromatic heterocyclic group, more preferably an alkylene group, an arylene group, an alkyleneoxy group, an aryleneoxy group, a silylene group or a divalent aromatic heterocyclic group (preferably a furan ring, a thiophene ring, a pyridine ring, a pyridazine ring, a pyrimidine ring, a pyrazine ring, an oxadiazole ring, a triazole ring, an imidazole ring, a pyrazole ring or a thiazole ring), still more preferably an alkylene group, an arylene group or a divalent aromatic heterocyclic group (preferably a furan ring, a thiophene ring, a pyridine ring, an oxadiazole ring, an imidazole ring, a pyrazole ring or a thiazole ring), particularly preferably an alkylene group or an arylene group, and among them, preferably an alkylene group having 1 to 8 carbon atoms or a substituted or unsubstituted arylene group, and most preferably a substituted or unsubstituted phenylene group or naphthylene group.

Further, these linking groups may have a substituent. Specific examples of the substituent may be exemplified by Substituent W as described below, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably an alkyl group.

Xa represents a single bond, an oxygen atom, a sulfur atom, an alkylene group, a silylene group, an alkenylene group, a cycloalkylene group, a cycloalkenylene group, an arylene group, a divalent heterocyclic group or an imino group, and links $R_{32}$ and $Ar_{32}$. These may further have a substituent. Specific examples of the further substituent may be exemplified by Substituent W, and include preferably an alkyl group or an aryl group.

From the viewpoint of chemical stability and heat resistance, Xa is preferably a single bond, an oxygen atom, an alkylene group or a silylene group, and more preferably an alkylene group.

Xa is preferably a single bond, an alkylene group having 1 to 12 carbon atoms, an alkenylene group having 2 to 12 carbon atoms, an arylene group having 6 to 14 carbon atoms, a heterocyclic group having 4 to 13 carbon atoms, an oxygen atom, a sulfur atom, an imino group (for example, a phenylimino group, a methylimino group or a t-butylimino group) having a hydrocarbon group having 1 to 12 carbon atoms (preferably an aryl group or an alkyl group) or a silylene group, more preferably a single bond, an oxygen atom, an alkylene group having 1 to 6 carbon atoms (for example, a methylene group, a 1,2-ethylene group, a 1,1-dimethylmethylene group), an alkenylene group having 2 carbon atoms (for example, —CH$_2$=CH$_2$—), an arylene group having 6 to 10 carbon atoms (for example, 1,2-phenylene group, 2,3-naphthylene group) or a silylene group, still more preferably a single bond, an oxygen atom or an alkylene group having 1 to 6 carbon atoms (for example, methylene group, a 1,2-ethylene group, a 1,1-dimethylmethylene group), particularly preferably a single bond, an oxygen atom, a methylene group or a 1,2-ethylene group, and most preferably a methylene group.

Since the compound (dye) in which $D_1$ in Formula (I) is a structure represented by Formula (III) having a condensed ring structure has a small entropic change (ΔS) when melting and the melting point is likely to increase, the difference between the melting point and the deposition temperature (the melting point–the deposition temperature) becomes larger, and thus, decomposition hardly occurs during deposition. Further, since the molecular thermal motion is suppressed to extend the lifetime of excitons, it is more preferred in that the exciton dissociation efficiency of the dye is enhanced and the photoelectric conversion efficiency (sensitivity) of the device becomes higher. Especially, the compound represented by Formula (III) has a longer conjugation length by the condensed ring structure and thus the absorption wavelength become longer, thereby enhancing the sensitivity in the region of 500 nm to 750 nm (red). It is thought that, since the thermal motion of the dye is suppressed, the heat inactivation hardly occurs and thus the fluorescence intensity becomes higher. Accordingly, a dye having a high fluorescence intensity is expected to have a high photoelectric conversion efficiency (sensitivity) of a device.

One preferred aspect of the compound represented by Formula (I) is a compound represented by the following Formula (IV).

Formula (IV)

[Chem. 23]

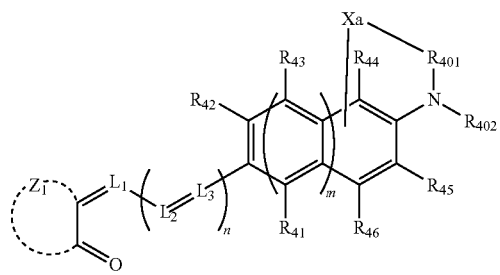

In Formula (IV), $Z_1$ is a ring containing at least two carbon atoms, and represents a 5-membered ring, a 6-membered ring or a condensed ring containing at least one of a 5-membered ring and a 6-membered ring. Each of $L_1$, $L_2$ and $L_3$ independently represents an unsubstituted methine group or a substituted methine group. n represents an integer of 0 or more. m represents 0 or 1. Each of $R_{41}$ to $R_{46}$ independently represents a hydrogen atom or a substituent. Each of $R_{42}$ and $R_{43}$, $R_{43}$ and $R_{44}$, $R_{45}$ and $R_{46}$, and $R_{41}$ and $R_{46}$ may be bound to each other to form a ring. $R_{401}$ represents a single bond or a divalent linking group, and $R_{402}$ represents a hydrogen atom or a substituent. Xa represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent, and are linked as any one of $R_{41}$ to $R_{46}$. Each of $R_{401}$ and $R_{402}$, and $R_{402}$ and $R_{41}$ to $R_{46}$ may be bound to each other to form a ring.

When $R_{41}$ to $R_{46}$ represent a substituent, the substituent may be exemplified by Substituent W as described below, and specific examples and preferred ranges thereof are the same as the specific examples and preferred ranges in the case where $R_{231}$ to $R_{236}$ in Formula (II-d) represent a substituent. These may further have a substituent. Specific examples of the further substituent may be exemplified by Substituent W as described below, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably an alkyl group.

It is preferred that all of $R_{41}$ to $R_{46}$ are a hydrogen atom.

$R_{401}$ represents a single bond or a divalent linking group, $R_{402}$ represents a hydrogen atom or a substituent. Each of $R_{401}$ and $R_{402}$ has the same meaning as $R_{31}$ and $R_{32}$ in Formula (III) respectively, and preferred ranges thereof are also the same.

In Formula (IV), $Z_1$, $L_1$, $L_2$, $L_3$ and n have the same meaning as $Z_1$, $L_1$, $L_2$, $L_3$ and n in Formula (I), and preferred ranges thereof are also the same.

In Formula (IV), Xa has the same meaning as Xa in Formula (III), and preferred ranges thereof are also the same.

Xa is preferably linked as one of $R_{44}$ or $R_{45}$.

One preferred aspect of Formula (IV) is the following Formula (IV-a).

Formula (IV-a)

[Chem. 24]

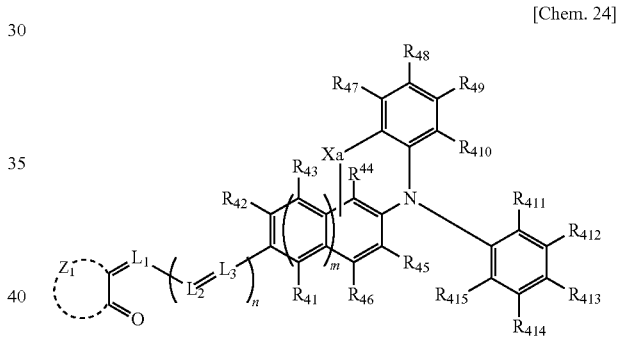

In Formula (IV-a), $Z_1$ is a ring containing at least two carbon atoms, and represents a 5-membered ring, a 6-membered ring or a condensed ring containing any one of a 5-membered ring and a 6-membered ring. Each of $L_1$, $L_2$ and $L_3$ independently represents an unsubstituted methine group or a substituted methine group. n represents an integer of 0 or more. m represents 0 or 1. Each of $R_{41}$ to $R_{46}$ independently represents a hydrogen atom or a substituent. Each of $R_{42}$ and $R_{43}$, $R_{43}$ and $R_{44}$, $R_{45}$ and $R_{46}$, and $R_{41}$ and $R_{46}$ may be bound to each other to form a ring. Xa represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent, and linked as any one of $R_{41}$ to $R_{46}$. Each of $R_{47}$ to $R_{410}$ and $R_{411}$ to $R_{415}$ independently represents a hydrogen atom or a substituent. Further, any adjacent groups among $R_{47}$ to $R_{410}$ and $R_{411}$ to $R_{415}$ may be bound to each other to form a ring. Each of $R_{410}$ and $R_{411}$, and $R_{415}$ and $R_{41}$ to $R_{46}$ may be bound to each other to form a ring.

In Formula (IV-a), $Z_1$, $L_1$, $L_2$, $L_3$, n, $R_{41}$ to $R_{46}$ and m have the same meaning as $Z_1$, $L_1$, $L_2$, $L_3$, n, $R_{41}$ to $R_{46}$ and m in Formula (IV), and preferred ranges thereof are also the same.

Preferred ranges of Xa in Formula (IV-a) are the same as Xa in Formula (III).

When m=0, Xa is preferably linked as one of $R_{44}$ or $R_{45}$. When m=1, Xa is preferably linked to one of $R_{44}$ or $R_{45}$.

Xa is preferably linked as $R_{44}$.

Each of $R_{47}$ to $R_{410}$ and $R_{411}$ to $R_{415}$ independently represents a hydrogen atom or a substituent. When $R_{47}$ to $R_{410}$ and $R_{411}$ to $R_{415}$ represents a substituent, the substituent may be exemplified by Substituent W as describe below, but is preferably a hydrogen atom, a halogen atom, an alkyl group having 1 to 18 carbon atoms, an aryl group having 6 to 18 carbon atoms or a heterocyclic group having 4 to 16 carbon atoms, more preferably a hydrogen atom, an alkyl group having 1 to 12 carbon atoms, an aryl group having 6 to 14 carbon atoms or a fluorine atom, still more preferably a hydrogen atom, an alkyl group having 1 to 6 carbon atoms or an aryl group having 6 to 10 carbon atoms, and among them, preferably a hydrogen atom, a fluorine atom, a methyl group, an ethyl group, a propyl group, a butyl group, a hexyl group, a cyclohexyl group, a phenyl group or a naphthyl group, and particularly preferably a hydrogen atom, a methyl group, a butyl group, a hexyl group or a phenyl group. The alkyl group may be branched.

These may further have a substituent. Specific examples of the further substituent may be exemplified by Substituent W as described below, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably an alkyl group.

Further, any adjacent groups among $R_{47}$ to $R_{410}$ and $R_{411}$ to $R_{415}$ may be bound to each other to form a ring. The ring to be formed may be exemplified by Ring R as described below. The ring to be formed is preferably an aromatic ring or an aromatic heterocyclic ring, particularly a benzene ring, a naphthalene ring, an anthracene ring, a pyridine ring, a pyrimidine ring, a fluorene ring (formed including a benzene ring to which $R_{47}$ to $R_{410}$ and $R_{411}$ to $R_{415}$ are bound) or the like.

Furthermore, each of $R_{410}$ and $R_{411}$, and $R_{415}$ and $R_{45}$ may be linked. Preferred ranges of the linking group when linked are the same as the preferred ranges of Xa in Formula (III), and particularly, it is preferred to link with an alkylene group. When $R_{410}$ and $R_{411}$, and $R_{415}$ and $R_{45}$ are linked, these groups, together with an N atom, may form a 5- to 10-membered ring (preferably a 5- to 6-membered ring, and more preferably a 6-membered ring). Further, the linkage of $R_{410}$ and $R_{411}$, and $R_{415}$ and $R_{45}$ may be a single bond.

It is also preferred that the compound represented by Formula (I) is represented by the following Formula (V).

Formula (V)

[Chem. 25]

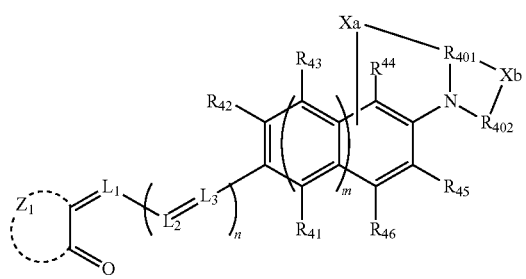

In Formula (V), $Z_1$ is a ring containing at least two carbon atoms, and represents a 5-membered ring, a 6-membered ring or a condensed ring containing at least one of a 5-membered ring and a 6-membered ring. Each of $L_1$, $L_2$ and $L_3$ independently represents an unsubstituted methine group or a substituted methine group. n represents an integer of 0 or more. m represents 0 or 1. Each of $R_{41}$ to $R_{46}$ independently represents a hydrogen atom or a substituent. Each of $R_{42}$ and $R_{43}$, $R_{43}$ and $R_{44}$, $R_{45}$ and $R_{46}$, and $R_{41}$ and $R_{46}$ may be bound to each other to form a ring. $R_{401}$ represents a trivalent linking group, and $R_{402}$ represents a single bond or a divalent linking group. Each of Xa and Xb independently represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent. Xa is linked as any one of $R_{41}$ to $R_{46}$. Each of $R_{402}$ and $R_{41}$ to $R_{46}$ may be bound to each other to form a ring.

In Formula (V), $Z_1$, $L_1$, $L_2$, $L_3$, n, $R_{41}$ to $R_{46}$, m, Xa, $R_{401}$ and $R_{402}$ have the same meaning as $Z_1$, $L_1$, $L_2$, $L_3$, n, $R_{41}$ to $R_{46}$, m, Xa, $R_{401}$ and $R_{402}$ in Formula (IV), and preferred ranges thereof are also the same. In addition, the valence number of $R_{401}$ and $R_{402}$ is increased by one with respect to $R_{401}$ and $R_{402}$ in Formula (IV).

In Formula (V), Xb has the same meaning as Xa, and preferred ranges thereof are also the same.

Xa is preferably linked as one of $R_{44}$ or $R_{45}$.

It is also preferred that the compound represented by Formula (I) is represented by the following Formula (VI).

Formula (VI)

[Chem. 26]

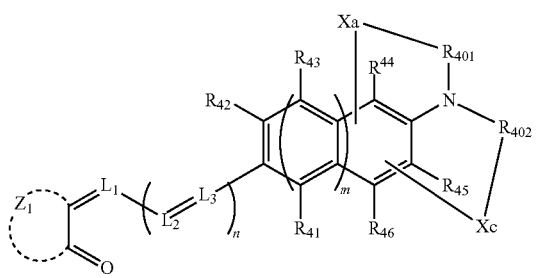

In Formula (VI), $Z_1$ is a ring containing at least two carbon atoms, and represents a 5-membered ring, a 6-membered ring or a condensed ring containing at least one of a 5-membered ring and a 6-membered ring. Each of $L_1$, $L_2$ and $L_3$ independently represents an unsubstituted methine group or a substituted methine group. n represents an integer of 0 or more. m represents 0 or 1. Each of $R_{41}$ to $R_{46}$ independently represents a hydrogen atom or a substituent. Each of $R_{42}$ and $R_{43}$, $R_{43}$ and $R_{44}$, $R_{45}$ and $R_{46}$, and $R_{41}$ and $R_{46}$ may be bound to each other to form a ring. $R_{401}$ represents a single bond or a divalent linking group, and $R_{402}$ represents a single bond or a divalent linking group. Each of Xa and Xc independently represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent, and are linked as any one of $R_{41}$ to $R_{46}$. $R_{401}$ and $R_{402}$ may be bound to each other to form a ring.

In Formula (VI), $Z_1$, $L_1$, $L_2$, $L_3$, n, $R_{41}$ to $R_{46}$, m, Xa, $R_{401}$ and $R_{402}$ have the same meaning as $Z_1$, $L_1$, $L_2$, $L_3$, n, $R_{44}$ to $R_{46}$, m, Xa, $R_{401}$ and $R_{402}$ in Formula (IV), and preferred ranges thereof are also the same. In addition, the valence number of $R_{402}$ is increased by one with respect to $R_{402}$ in Formula (IV).

In Formula (VI), Xc has the same meaning as Xa, and preferred ranges thereof are also the same.

Xa is preferably linked as $R_{44}$. Xc is preferably linked as $R_{45}$.

It is also preferred that the compound represented by Formula (I) is represented by the following Formula (VII).

Formula (VII)

[Chem. 27]

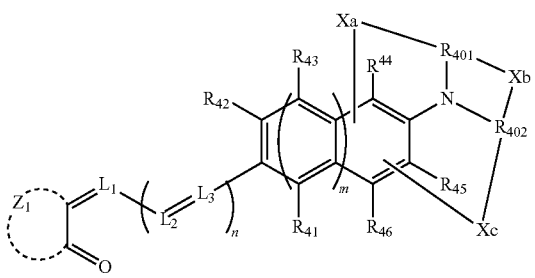

In Formula (VII), $Z_1$ is a ring containing at least two carbon atoms, and represents a 5-membered ring, a 6-membered ring or a condensed ring containing at least one of a 5-membered ring and a 6-membered ring. Each of $L_1$, $L_2$ and $L_3$ independently represents an unsubstituted methine group or a substituted methine group. n represents an integer of 0 or more. m represents 0 or 1. Each of $R_{41}$ to $R_{46}$ independently represents a hydrogen atom or a substituent. Each of $R_{42}$ and $R_{43}$, $R_{43}$ and $R_{44}$, $R_{45}$ and $R_{46}$, and $R_{41}$ and $R_{46}$ may be bound to each other to form a ring. $R_{401}$ represents a trivalent linking group, and $R_{402}$ represents a trivalent linking group. Each of Xa, Xb and Xc independently represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent. Each of Xa and Xc are linked as any one of $R_{41}$ to $R_{46}$.

In Formula (VII), $Z_1$, $L_1$, $L_2$, $L_3$, n, $R_{41}$ to $R_{46}$, m, Xa, $R_{401}$ and $R_{402}$ have the same meaning as $Z_1$, $L_1$, $L_2$, $L_3$, n, $R_{41}$ to $R_{46}$, m, Xa, $R_{401}$ and $R_{402}$ in Formula (IV), and preferred ranges thereof are also the same. In addition, the valence number of $R_{401}$ and $R_{402}$ is increased by one with respect to $R_{401}$ and $R_{402}$ in Formula (IV).

In Formula (VII), Xb and Xc have the same meaning as Xa, and preferred ranges thereof are also the same.

Xa is preferably linked as $R_{44}$. Xc is preferably linked as $R_{45}$.

[Substituent W]

Substituent W in the present specification will be described.

Examples of Substituent W include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group (may be also referred to as hetero ring group), a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, acylamino group, an aminocarbonylamino group, an alkoxycarbonylamino group, an aryloxycarbonylamino group, a sulfamoylamino group, an alkyl- and arylsulfonylamino group, a mercapto group, an alkylthio group, an arylthio group, a heterocyclic thio group, a sulfamoyl group, a sulfo group, an alkyl- and arylsulfinyl group, an alkyl- and arylsulfonyl group, an acyl group, an aryloxycarbonyl group, an alkoxycarbonyl group, a carbamoyl group, an aryl- and heterocyclic azo group, an imide group, a phosphino group, a phosphinyl group, a phosphinyloxy group, a phosphinylamino group, a phosphono group, a silyl group, a hydrazino group, an ureido group, a borate group ($—B(OH)_2$), a phosphate group ($—OPO(OH)_2$), a sulfato group ($—OSO_3H$), and other known substituents.

More particularly, Substituent W represents the following (1) to (48).

(1) Halogen Atom:

For example, a fluorine atom, a chlorine atom, a bromine atom and an iodine atom (2) Alkyl Group:

Straight-chained, branched or cyclic substituted or unsubstituted alkyl groups are included. These include (2-a) to (2-e).

(2-a) Alkyl Group:

Preferably an alkyl group having 1 to 30 carbon atoms (for example, methyl, ethyl, n-propyl, isopropyl, t-butyl, n-octyl, eicosyl, 2-chloroethyl, 2-cyanoethyl and 2-ethylhexyl)

(2-b) Cycloalkyl Group:

Preferably a substituted or unsubstituted cycloalkyl group having 3 to 30 carbon atoms (for example, cyclohexyl, cyclopentyl and 4-n-dodecylcyclohexyl)

(2-c) Bicycloalkyl Group:

Preferably a substituted or unsubstituted bicycloalkyl group having 5 to 30 carbon atoms (for example, bicyclo[1,2,2]heptan-2-yl and bicyclo[2,2,2]octan-3-yl)

(2-d) Tricycloalkyl Group:

Preferably a substituted or unsubstituted tricycloalkyl group having 7 to 30 carbon atoms (for example, 1-adamantyl)

(2-e) Polycyclic Cycloalkyl Group Having Many Ring Structures:

Meanwhile, the alkyl group in the substituents as described below (for example, the alkyl group in an alkylthio group) represents an alkyl group of such a concept, but also include an alkenyl group and an alkynyl group.

(3) Alkenyl Group:

Straight-chained, branched or cyclic substituted or unsubstituted alkenyl groups are included. These include (3-a) to (3-c).

(3-a) Alkenyl Group:

Preferably a substituted or unsubstituted alkenyl group having 2 to 30 carbon atoms (for example, vinyl, allyl, prenyl, geranyl and oleyl)

(3-b) Cycloalkenyl Group:

Preferably a substituted or unsubstituted cycloalkenyl group having 3 to 30 carbon atoms (for example, 2-cyclopenten-1-yl and 2-cyclohexen-1-yl)

(3-c) Bicycloalkenyl Group:

A substituted or unsubstituted bicycloalkenyl group, preferably a substituted or unsubstituted bicycloalkenyl group having 5 to 30 carbon atoms (for example, bicyclo[2,2,1]hept-2-en-1-yl and bicyclo[2,2,2]oct-2-en-4-yl)

(4) Alkynyl Group:

Preferably a substituted or unsubstituted alkynyl group having 2 to 30 carbon atoms (for example, an ethynyl, propargyl and trimethylsilylethynyl group)

(5) Aryl Group:

Preferably a substituted or unsubstituted aryl group having 6 to 30 carbon atoms (for example, phenyl, p-tolyl, naphthyl, m-chlorophenyl, o-hexadecanoylaminophenyl and ferrocenyl)

(6) Heterocyclic Group:

Preferably a monovalent group formed by removing one hydrogen atom from a 5- or 6-membered, substituted or unsubstituted, aromatic or non-aromatic heterocyclic compound, still more preferably a 5- or 6-membered aromatic heterocyclic group having 2 to 50 carbon atoms (for example, 2-furyl, 2-thienyl, 2-pyrimidinyl and 2-beznothiazolyl. Meanwhile, a cationic heterocyclic group such as 1-methyl-2-pyridinio and 1-methyl-2-quinolinio may be used)

(7) Cyano Group:

(8) Hydroxyl Group:

(9) Nitro Group:

(10) Carboxyl Group:

(11) Alkoxy Group:

Preferably a substituted or unsubstituted alkoxy group having 1 to 30 carbon atoms (for example, methoxy, ethoxy, isopropoxy, t-butoxy, n-octyloxy and 2-methoxyethoxy)

(12) Aryloxy Group:

Preferably a substituted or unsubstituted aryloxy group having 6 to 30 carbon atoms (for example, phenoxy, 2-methylphenoxy, 4-t-butylphenoxy, 3-nitrophenoxy and 2-tetradecanoylaminophenoxy)

(13) Silyloxy Group:

Preferably a silyloxy group having 3 to 20 carbon atoms (for example, trimethylsilyloxy and t-butyldimethylsilyloxy)

(14) Heterocyclic Oxy Group:

Preferably a substituted or unsubstituted a heterocyclic oxy group having 2 to 30 carbon atoms (for example, 1-phenyltetrazol-5-oxy and 2-tetrahydropyranyloxy)

(15) Acyloxy Group:

Preferably a formyloxy group, a substituted or unsubstituted alkylcarbonyloxy group having 2 to 30 carbon atoms and a substituted or unsubstituted arylcarbonyloxy group having 6 to 30 carbon atoms (for example, formyloxy, acetyloxy, pivaloyloxy, stearoyloxy, benzoyloxy and p-methoxyphenylcarbonyloxy)

(16) Carbamoyloxy Group:

Preferably a substituted or unsubstituted carbamoyloxy group having 1 to 30 carbon atoms (for example, N,N-dimethylcarbamoyloxy, N,N-diethylcarbamoyloxy, morpholinocarbonyloxy, N,N-di-n-octylaminocarbonyloxy and N-n-octylcarbamoyloxy)

(17) Alkoxycarbonyloxy Group:

Preferably a substituted or unsubstituted alkoxycarbonyloxy group having 2 to 30 carbon atoms (for example, methoxycarbonyloxy, ethoxycarbonyloxy, t-butoxycarbonyloxy and n-octylcarbonyloxy)

(18) Aryloxycarbonyloxy Group:

Preferably a substituted or unsubstituted aryloxycarbonyloxy group having 7 to 30 carbon atoms (for example, phenoxycarbonyloxy, p-methoxyphenoxycarbonyloxy, p-n-hexadecyloxyphenoxycarbonyloxy)

(19) Amino Group:

Preferably an amino group, a substituted or unsubstituted alkylamino group having 1 to 30 carbon atoms, a substituted or unsubstituted anilino group having 6 to 30 carbon atoms (for example, amino, methylamino, dimethylamino, anilino, N-methyl-anilino and diphenylamino)

(20) Ammonio Group:

Preferably an ammonio group and an ammonio group substituted with a substituted or unsubstituted alkyl, aryl or heterocycle having 1 to 30 carbon atoms (for example, trimethylammonio, triethylammonio and diphenylmethylammonio)

(21) Acylamino Group:

Preferably a formylamino group, a substituted or unsubstituted alkylcarbonylamino group having 1 to 30 carbon atoms and a substituted or unsubstituted arylcarbonylamino group having 6 to 30 carbon atoms (for example, formylamino, acetylamino, pivaloylamino, lauroylamino, benzoylamino and 3,4,5-tri-n-octyloxyphenylcarbonylamino)

(22) Aminocarbonylamino Group:

Preferably a substituted or unsubstituted aminocarbonylamino group having 1 to 30 carbon atoms (for example, carbamoylamino, N,N-dimethylaminocarbonylamino, N,N-diethylaminocarbonylamino and morpholinocarbonylamino)

(23) Alkoxycarbonylamino Group:

Preferably a substituted or unsubstituted alkoxycarbonylamino group having 2 to 30 carbon atoms (for example, methoxycarbonylamino, ethoxycarbonylamino, t-butoxycarbonylamino, n-octadecyloxycarbonylamino and N-methyl-methoxycarbonylamino)

(24) Aryloxycarbonylamino Group:

Preferably a substituted or unsubstituted aryloxycarbonylamino group having 7 to 30 carbon atoms (for example, phenoxycarbonylamino, p-chlorophenoxycarbonylamino and m-n-octyloxyphenoxycarbonylamino)

(25) Sulfamoylamino Group:

Preferably a substituted or unsubstituted sulfamoylamino group having 0 to 30 carbon atoms (for example, sulfamoylamino, N,N-dimethylaminosulfonylamino and N-n-octylaminosulfonylamino)

(26) Alkyl- or arylsulfonylamino Group:

Preferably a substituted or unsubstituted alkylsulfonylamino having 1 to 30 carbon atoms, a substituted or unsubstituted arylsulfonylamino group having 6 to 30 carbon atoms (for example, methylsulfonylamino, butylsulfonylamino, phenylsulfonylamino, 2,3,5-trichlorophenylsulfonylamino and p-methylphenylsulfonylamino)

(27) Mercapto Group:

(28) Alkylthio Group:

Preferably a substituted or unsubstituted alkylthio group having 1 to 30 carbon atoms (for example, methylthio, ethylthio and n-hexadecylthio)

(29) Arylthio Group:

Preferably a substituted or unsubstituted arylthio having 6 to 30 carbon atoms (for example, phenylthio, p-chlorophenylthio, m-methoxyphenylthio)

(30) Heterocyclic Thio Group:

Preferably a substituted or unsubstituted heterocyclic thio group having 2 to 30 carbon atoms (for example, 2-benzothiazolylthio, 1-phenyltetrazol-5-ylthio)

(31) Sulfamoyl Group:

Preferably a substituted or unsubstituted sulfamoyl group having 0 to 30 carbon atoms (for example, N-ethylsulfamoyl, N-(3-dodecyloxypropyl)sulfamoyl, N,N-dimethylsulfamoyl, N-acetylsulfamoyl, N-benzoylsulfamoyl and N—(N'-phenylcarbamoyl)sulfamoyl)

(32) Sulfo Group:

(33) Alkyl- or Arylsulfinyl Group:

Preferably a substituted or unsubstituted alkylsulfinyl group having 1 to 30 carbon atoms, a substituted or unsubstituted arylsulfinyl group having 6 to 30 carbon atoms (for example, methylsulfinyl, ethylsulfinyl, phenylsulfinyl and p-methylphenylsulfinyl)

(34) Alkyl- or Aryl Sulfonyl Group:

Preferably a substituted or unsubstituted alkyl sulfonyl group having 1 to 30 carbon atoms, a substituted or unsubstituted arylsulfonyl group having 6 to 30 carbon atoms (for example, methylsulfonyl, ethylsulfonyl, phenylsulfonyl and p-methylphenylsulfonyl)

(35) Acyl Group:
Preferably a formyl group, a substituted or unsubstituted alkylcarbonyl group having 2 to 30 carbon atoms, a substituted or unsubstituted arylcarbonyl group having 7 to 30 carbon atoms, a substituted or unsubstituted heterocyclic carbonyl group having 4 to 30 carbon atoms which is linked via a carbon atom to a carbonyl group (for example, acetyl, pivaloyl, 2-chloroacetyl, stearoyl, benzoyl, p-n-octyloxyphenylcarbonyl, 2-pyridylcarbonyl and 2-furylcarbonyl)

(36) Aryloxycarbonyl Group:
Preferably a substituted or unsubstituted aryloxycarbonyl group having 7 to 30 carbon atoms (for example, phenoxycarbonyl, o-chlorophenoxycarbonyl, m-nitrophenoxycarbonyl and p-t-butylphenoxycarbonyl)

(37) Alkoxycarbonyl Group:
Preferably a substituted or unsubstituted alkoxycarbonyl group having 2 to 30 carbon atoms (for example, methoxycarbonyl, ethoxycarbonyl, t-butoxycarbonyl and n-octadecyloxycarbonyl)

(38) Carbamoyl Group:
Preferably a substituted or unsubstituted carbamoyl having 1 to 30 carbon atoms (for example, carbamoyl, N-methylcarbamoyl, N,N-dimethylcarbamoyl, N,N-di-n-octylcarbamoyl and N-(methylsulfonyl)carbamoyl)

(39) Aryl- and Heterocyclic Azo Group:
Preferably a substituted or unsubstituted arylazo group having 6 to 30 carbon atoms, a substituted or unsubstituted heterocyclic azo group having 3 to 30 carbon atoms (for example, phenylazo, p-chlorophenylazo and 5-ethylthio-1,3,4-thiadiazol-2-ylazo)

(40) Imide Group:
Preferably N-succinimide or N-phthalimide

(41) Phosphino Group:
Preferably a substituted or unsubstituted phosphino group having 2 to 30 carbon atoms (for example, dimethylphosphino, diphenylphosphino and methylphenoxyphosphino)

(42) Phosphinyl Group:
Preferably a substituted or unsubstituted phosphinyl group having 2 to 30 carbon atoms (for example, phosphinyl, dioctyloxyphosphinyl and diethoxyphosphinyl)

(43) Phosphinyloxy Group:
Preferably a substituted or unsubstituted phosphinyloxy group having 2 to 30 carbon atoms (for example, diphenoxyphosphinyloxy and dioctyloxyphosphinyloxy)

(44) Phosphinylamino Group:
Preferably a substituted or unsubstituted phosphinylamino group having 2 to 30 carbon atoms (for example, dimethoxyphosphinylamino, dimethylaminophosphinylamino)

(45) Phospho Group:
(46) Silyl Group:
Preferably a substituted or unsubstituted silyl group having 3 to 30 carbon atoms (for example, trimethylsilyl, triethylsilyl, triisopropylsilyl, t-butyldimethylsilyl, phenyldimethylsilyl)

(47) Hydrazino Group:
Preferably a substituted or unsubstituted hydrazino group having 0 to 30 carbon atoms (for example, trimethylhydrazino)

(48) Ureido Group:
Preferably a substituted or unsubstituted ureido group having 0 to 30 carbon atoms (for example, N,N-dimethylureido)

Further, two Substituents W may jointly form a ring. Examples of such a ring include an aromatic or non-aromatic hydrocarbon ring or heterocyclic ring, or a polycyclic condensed ring formed in combination thereof. Examples thereof include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring and a phenazine ring.

Among the above-mentioned Substituents W, a substituent having a hydrogen atom may be further substituted with the above-mentioned substituent in place of the hydrogen atom. Examples of such a substituent include a —CONHSO$_2$— group (sulfonylcarbamoyl group or carbonylsulfamoyl group), a —CONHCO— group (carbonylcarbamoyl group) and a —SO$_2$NHSO$_2$— group (sulfonylsulfamoyl group). More particularly, examples thereof include an alkylcarbonylaminosulfonyl group (for example, acetylaminosulfonyl), an arylcarbonylaminosulfonyl group (for example, a benzoylaminosulfonyl group), an alkylsulfonylaminocarbonyl group (for example, methylsulfonylaminocarbonyl) and an arylsulfonylaminocarbonyl group (for example, p-methylphenylsulfonylaminocarbonyl).

[Ring R]
Ring R in the present specification may include an aromatic or non-aromatic hydrocarbon ring or heterocyclic ring, or a polycyclic condensed ring formed in combination thereof. Examples thereof include a benzene ring, a naphthalene ring, an anthracene ring, a phenanthrene ring, a fluorene ring, a triphenylene ring, a naphthacene ring, biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthenes ring, a phenoxathiin ring, a phenothiazine ring and a phenazine ring.

The compound represented by Formula (I) may be prepared in accordance with a synthesis as described in Japanese Patent Application Laid-Open No. 2000-297068.

Hereinafter, specific examples of the compound represented by Formula (I) will be shown, but the present invention is not limited thereto. Meanwhile, in the following specific examples, $R_{101}$ and $R_{102}$ represent a hydrogen atom, an alkyl group or an aryl group.

[Chem. 28]

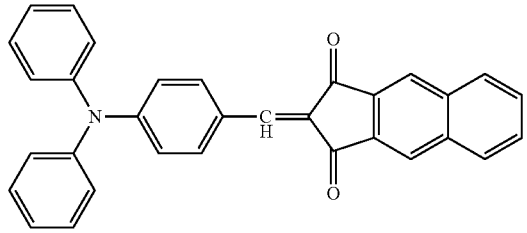

-continued
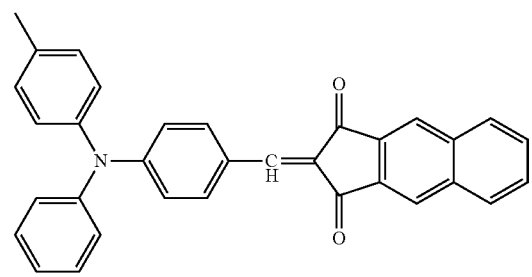
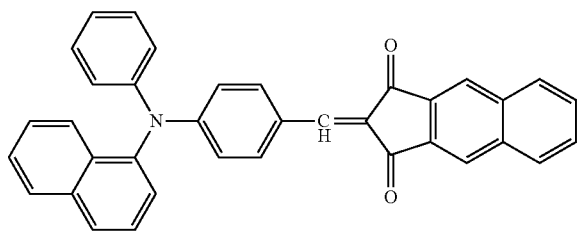
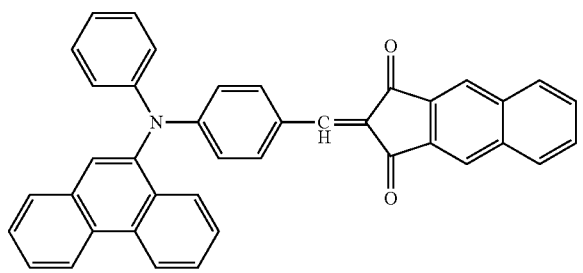
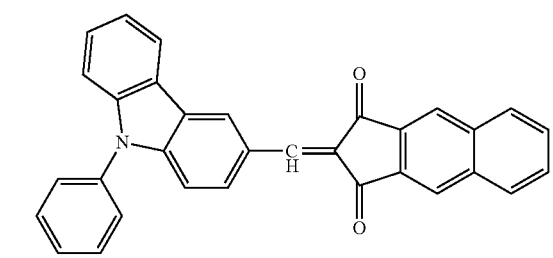
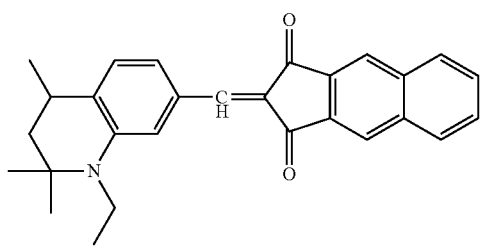
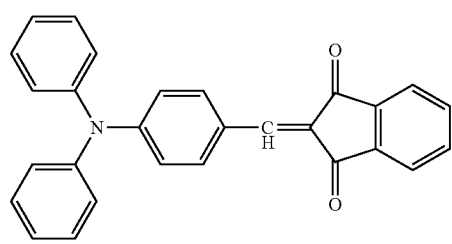
-continued
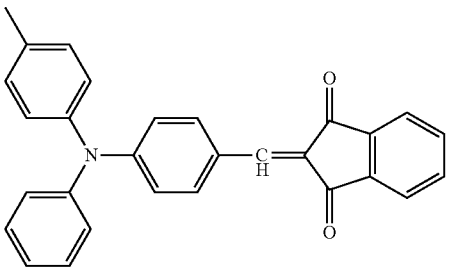
[Chem. 29]
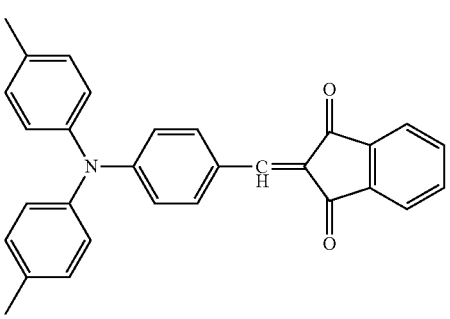
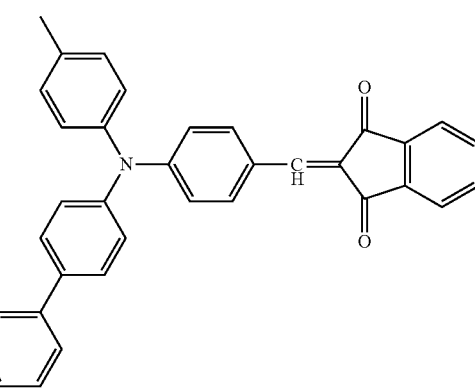
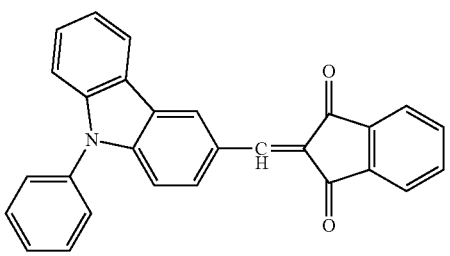
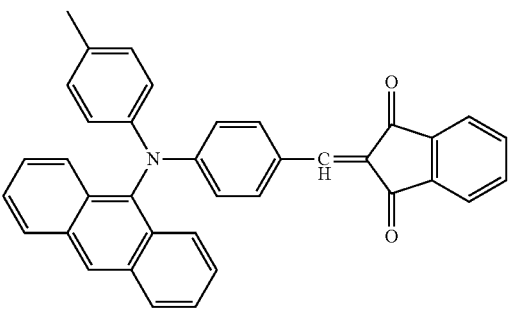

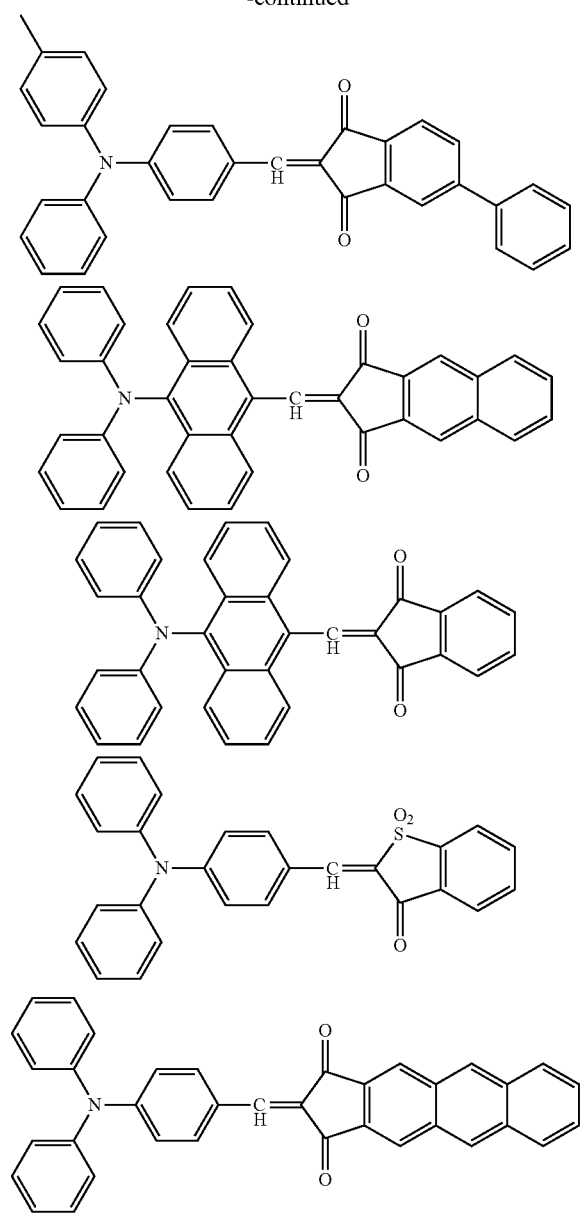
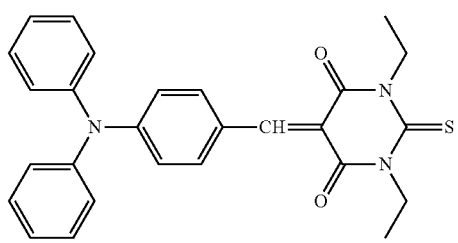
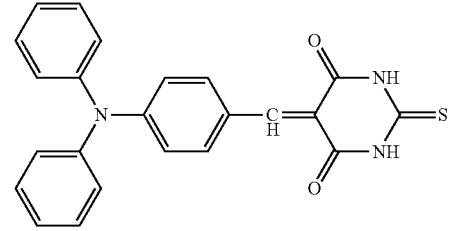
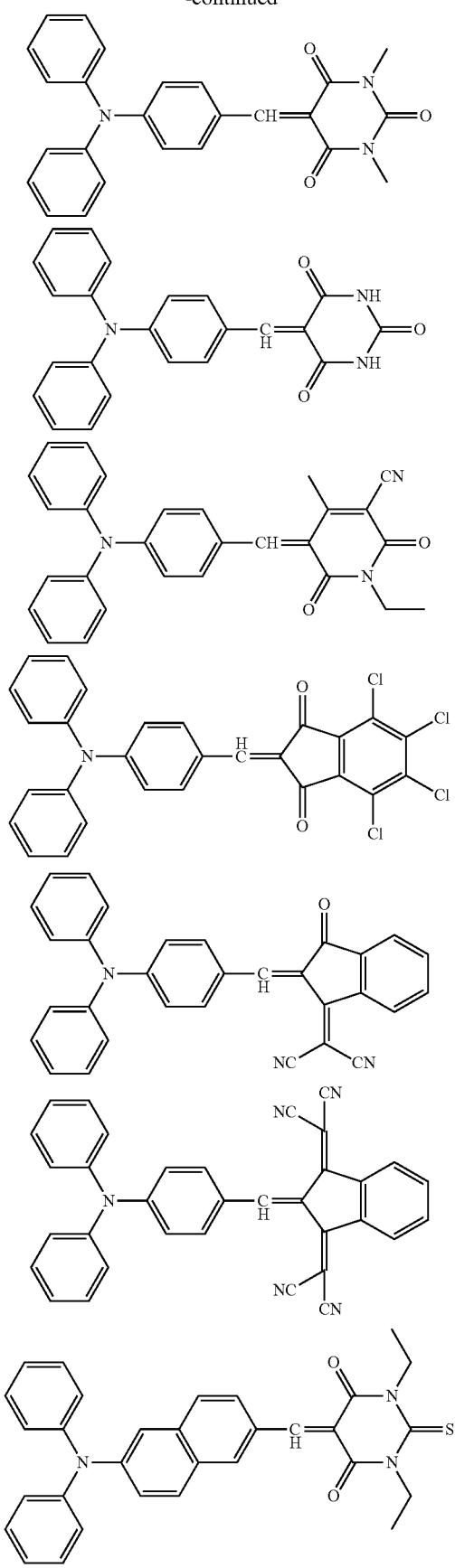

41
-continued
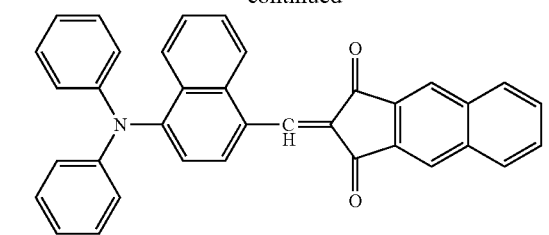
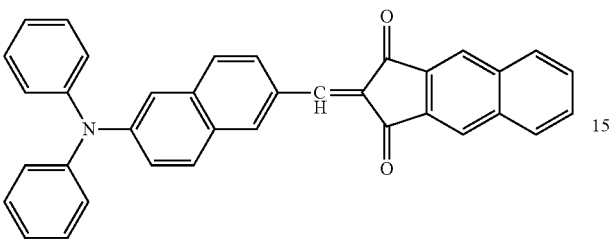
[Chem. 31]
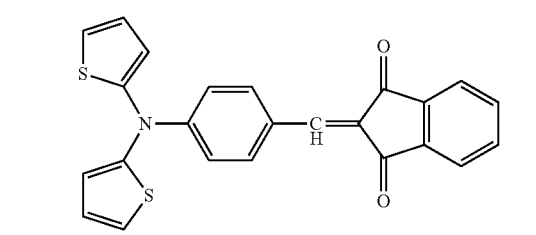
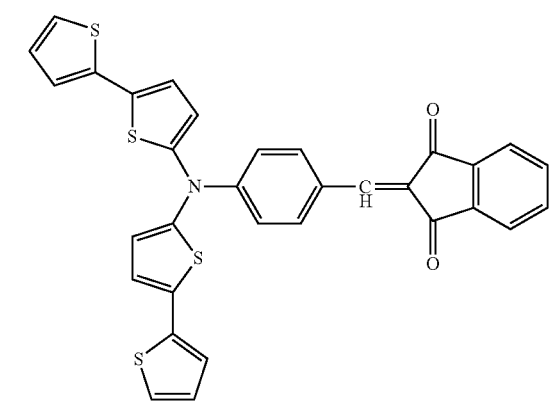
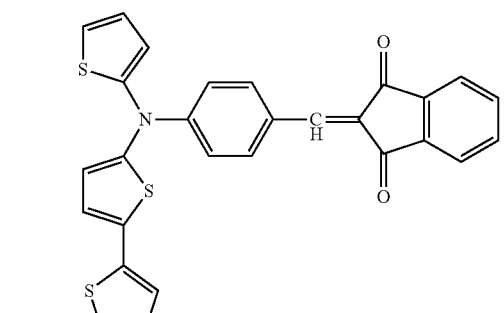
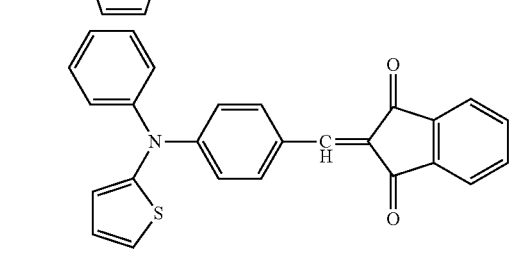
42
-continued
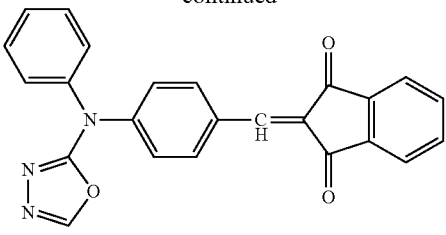
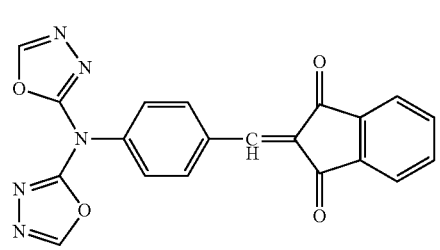
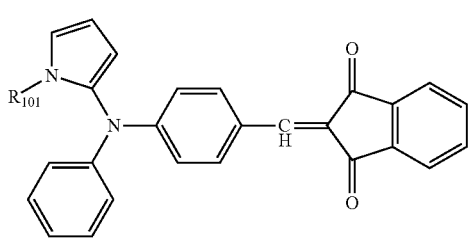
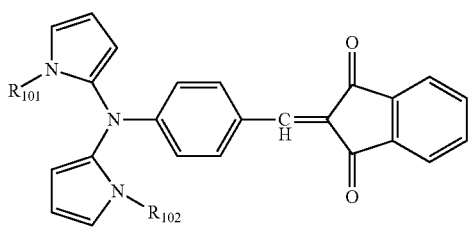
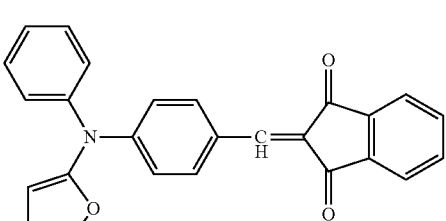
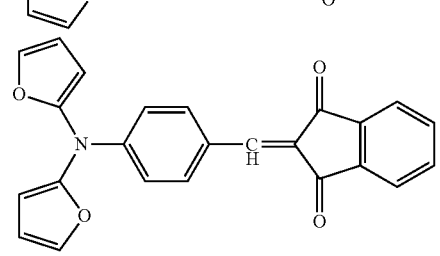
[Chem. 32]
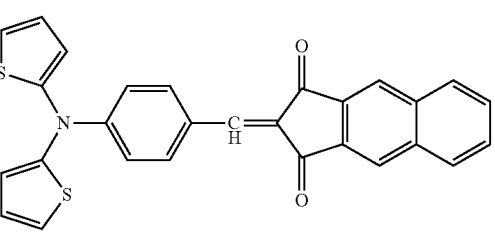

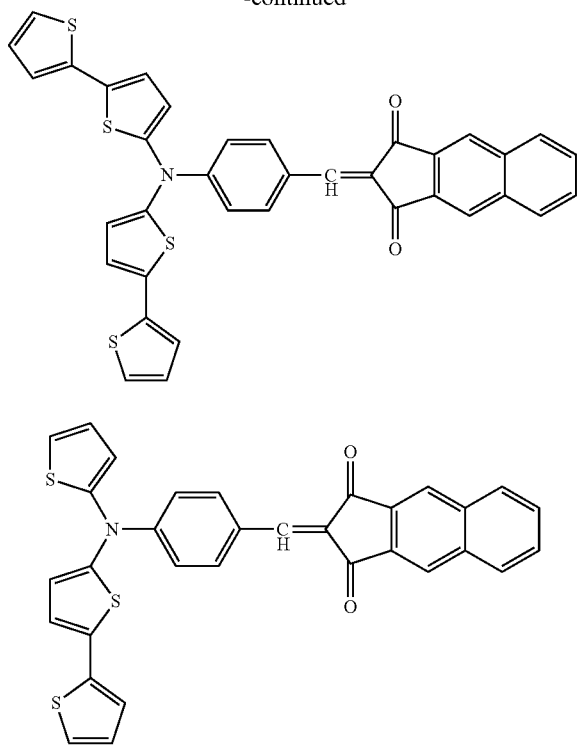
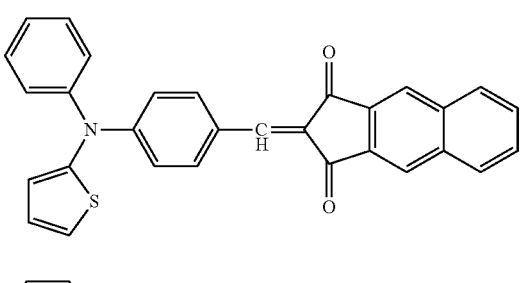
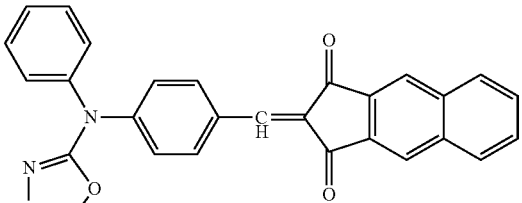
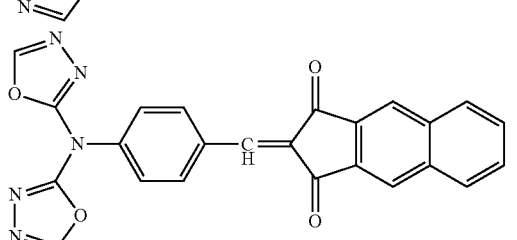
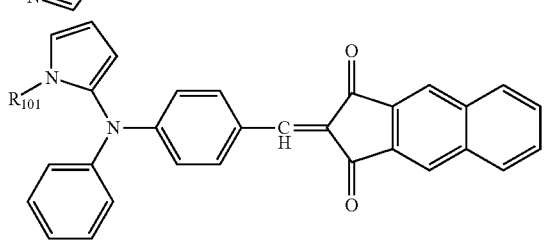
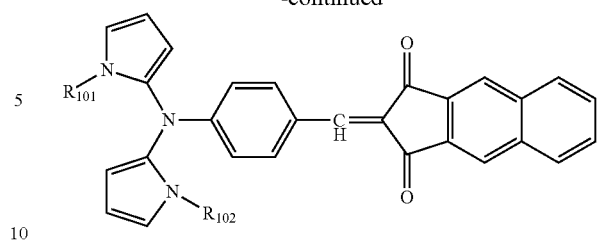
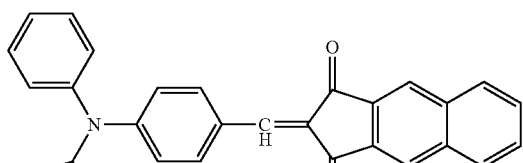
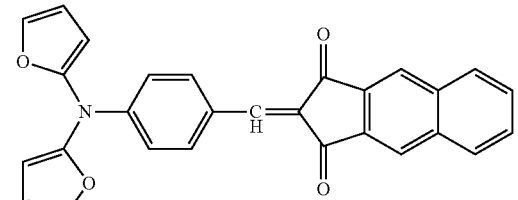
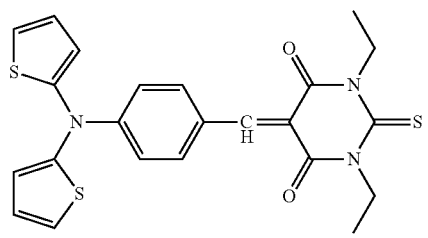
[Chem. 33]
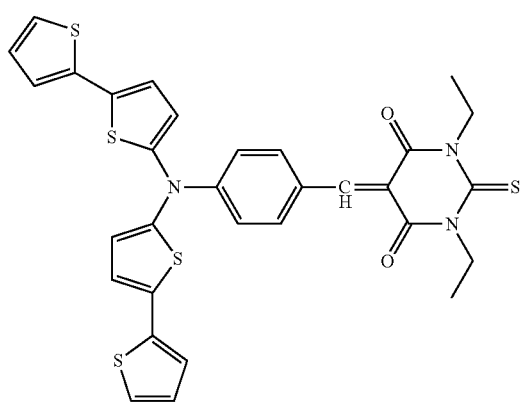
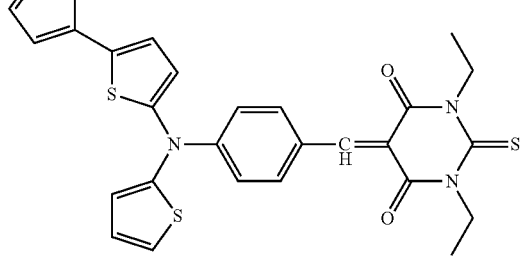

[Chem. 34]
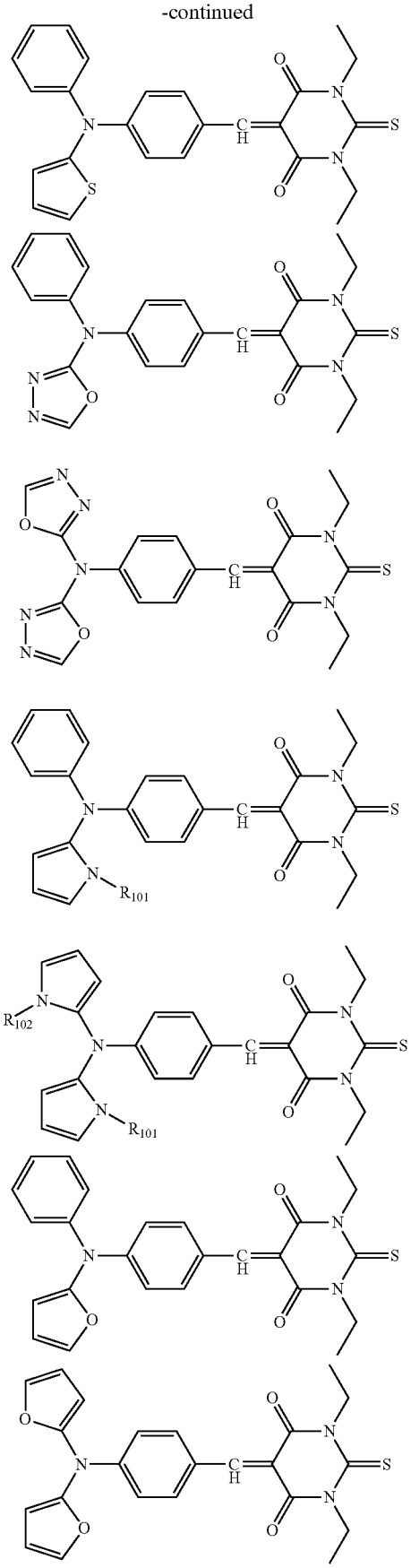
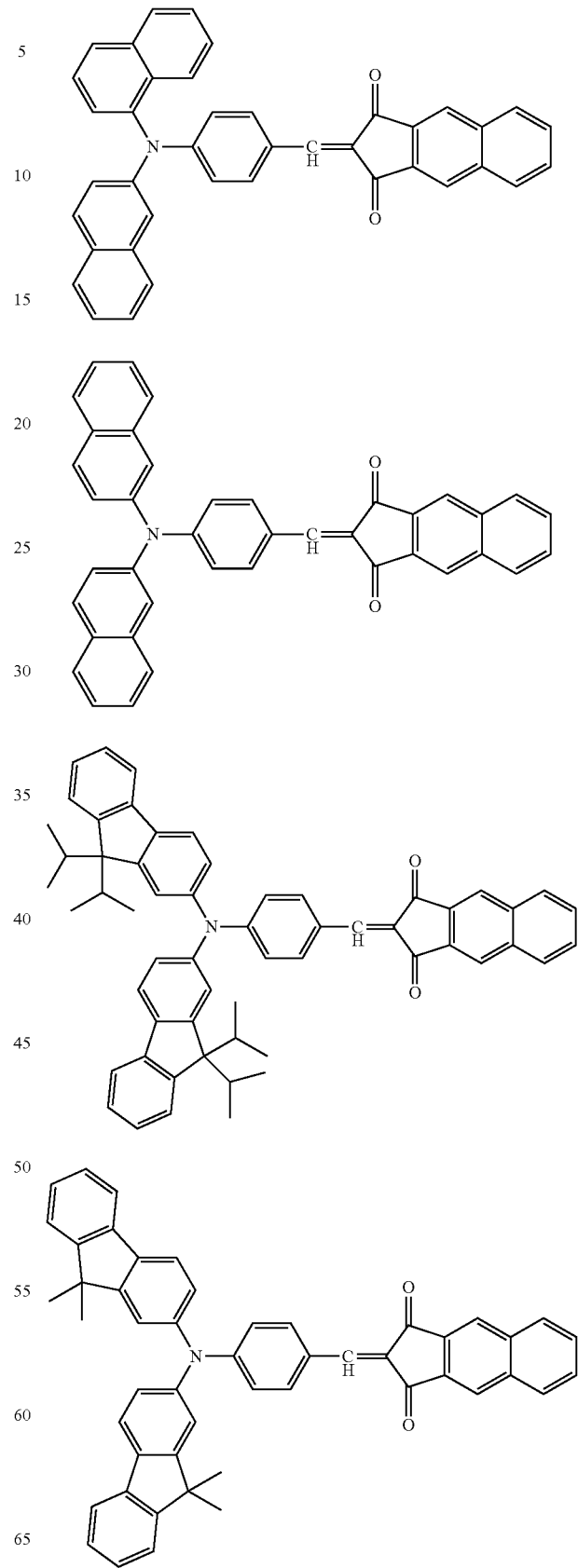

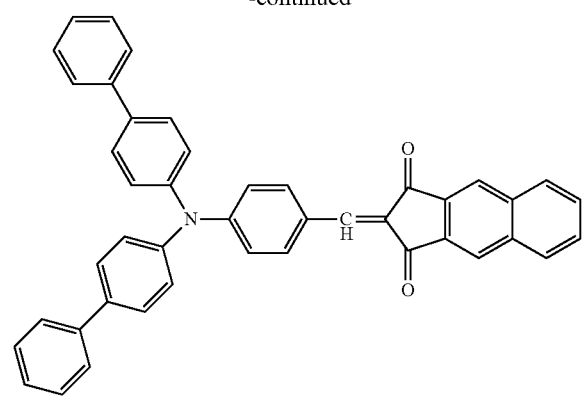
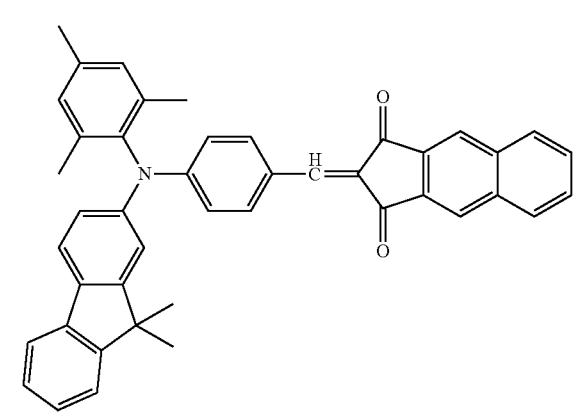
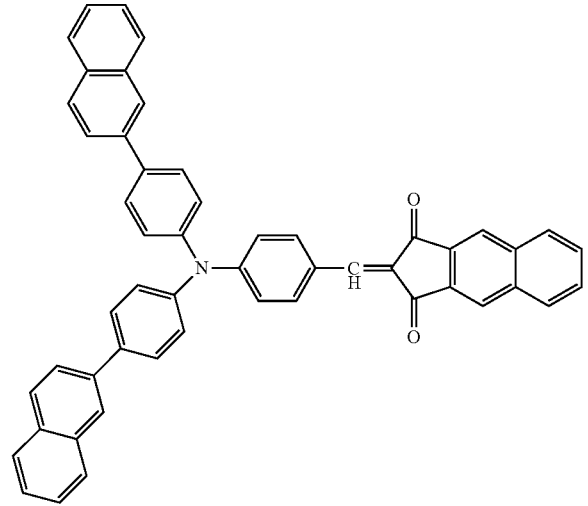
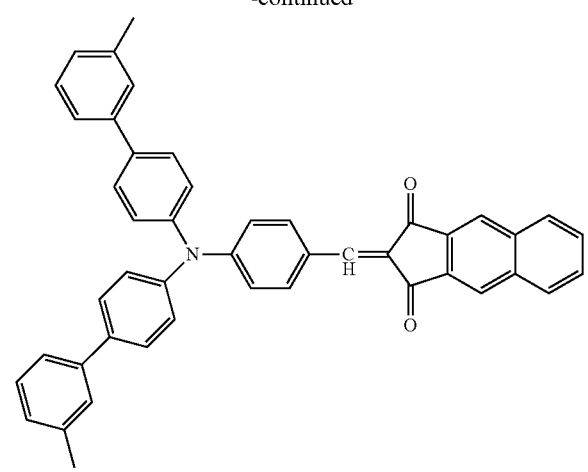
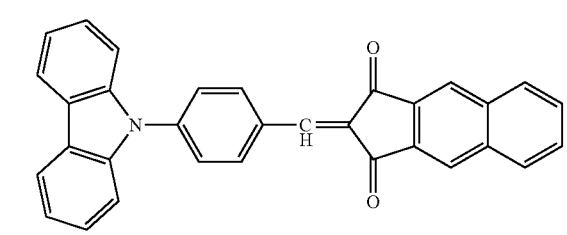
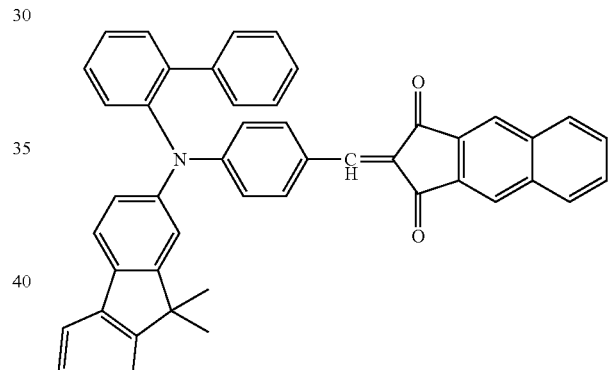
[Chem. 35]
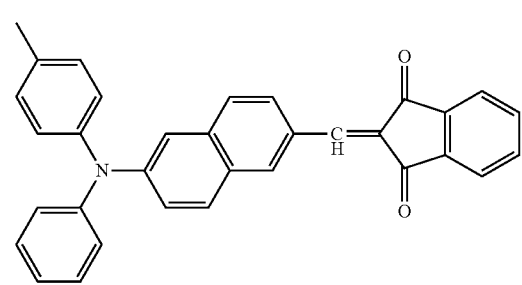

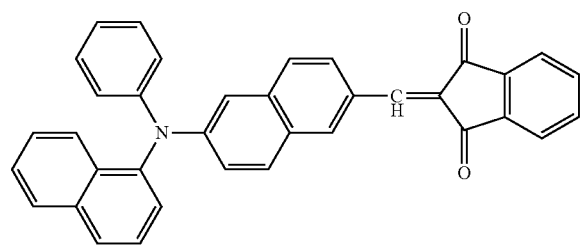
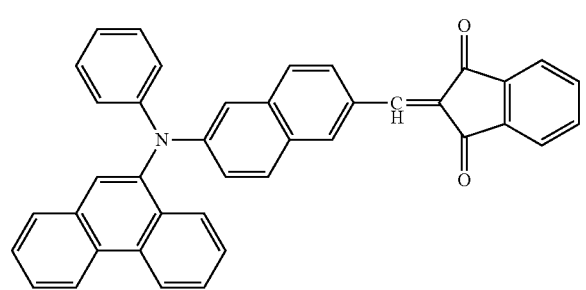
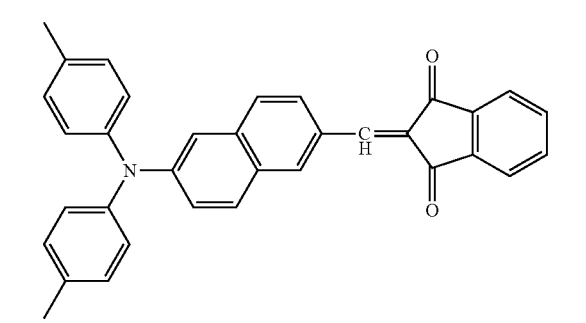
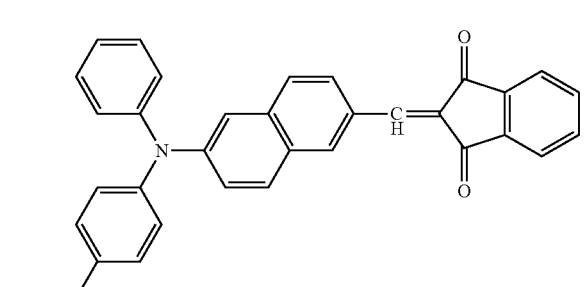
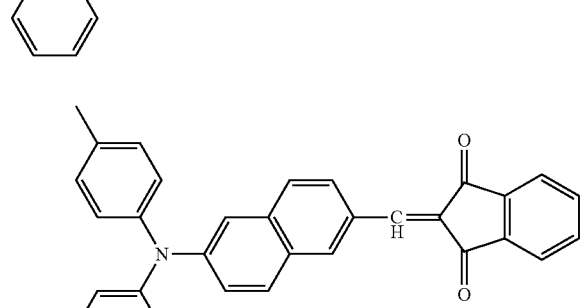
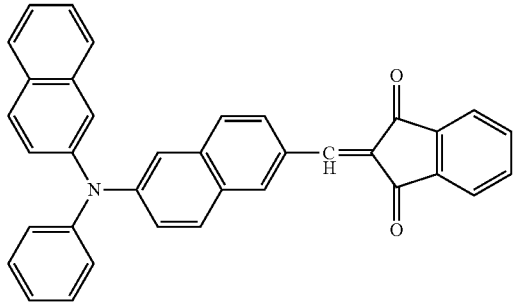
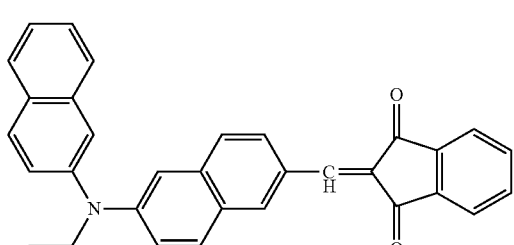
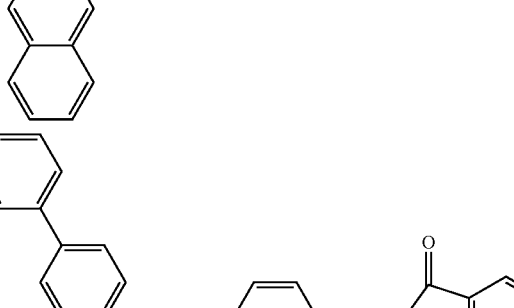
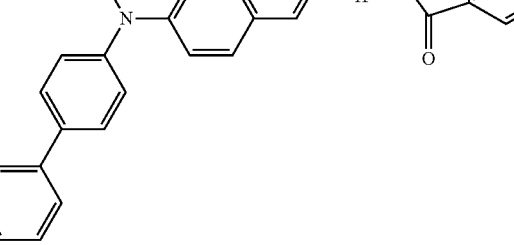
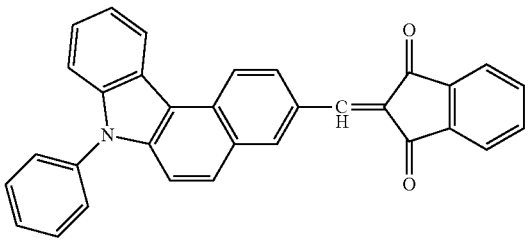
[Chem. 36]
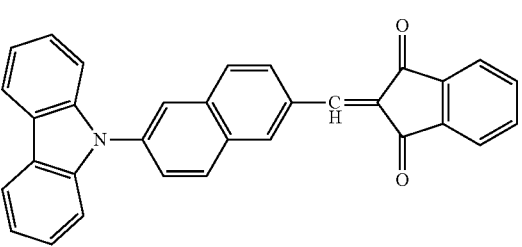

51
-continued
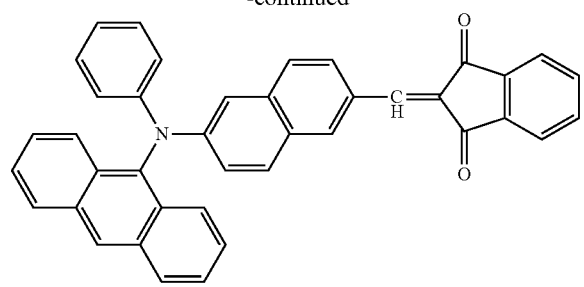
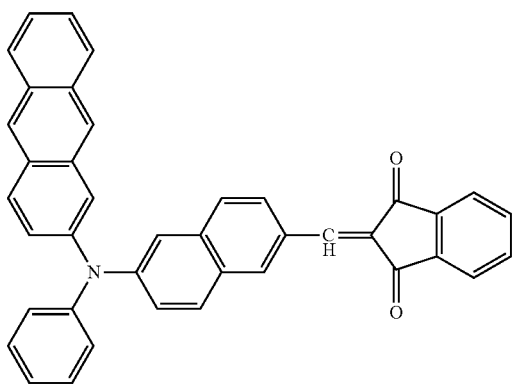
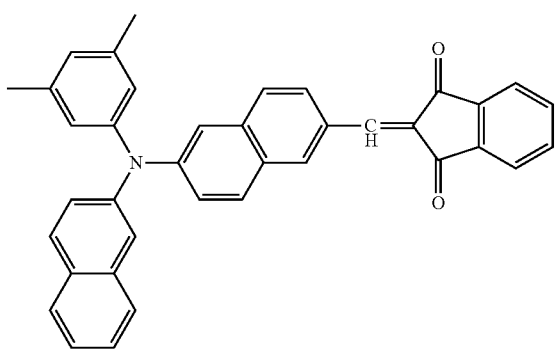
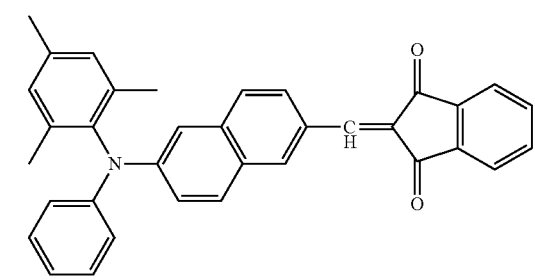
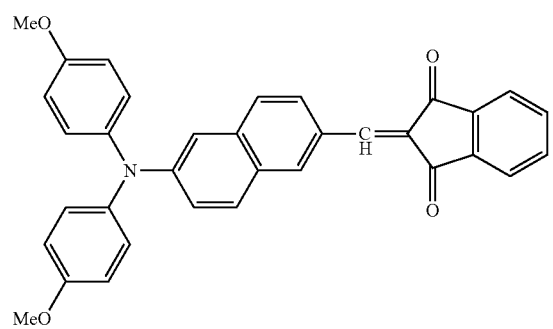
52
-continued
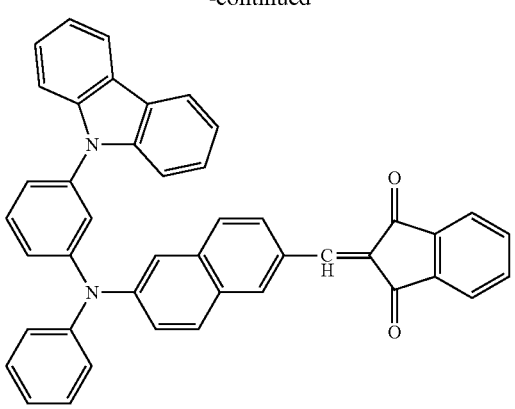
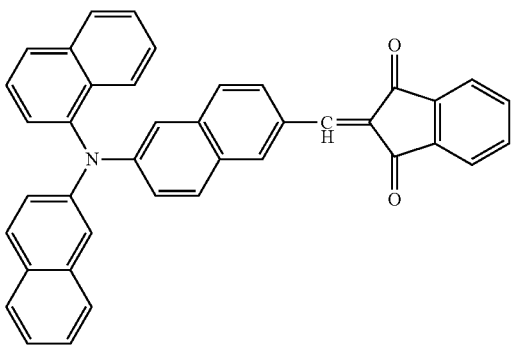
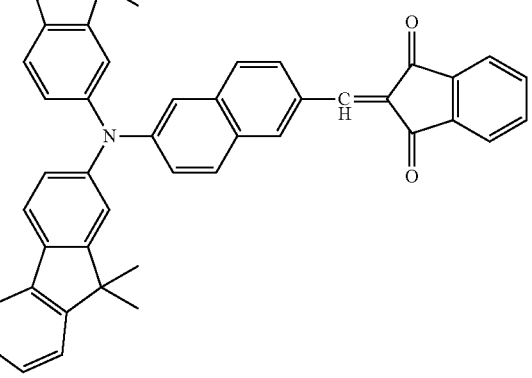

53
-continued
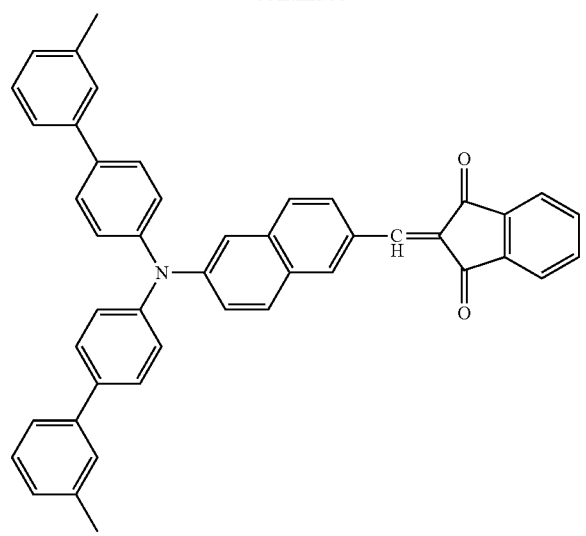
54
-continued
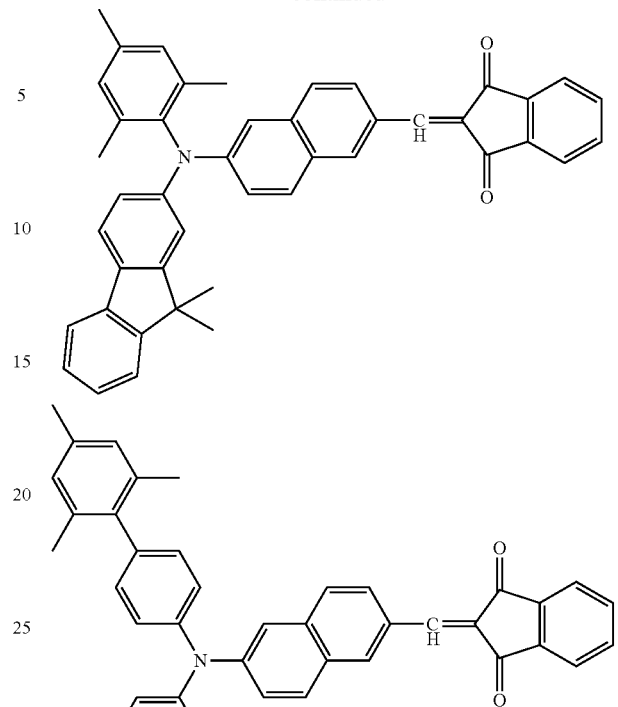
[Chem. 37]
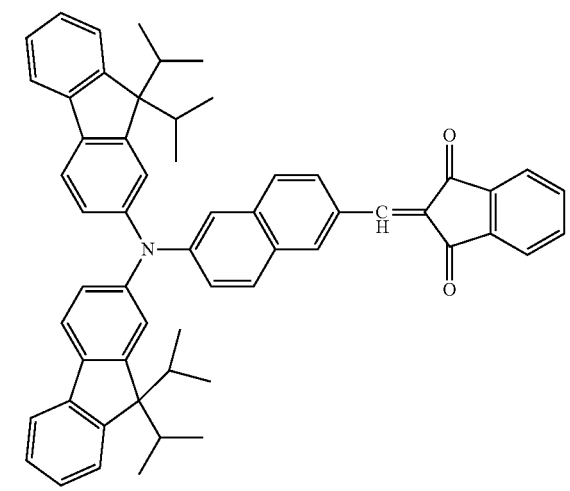
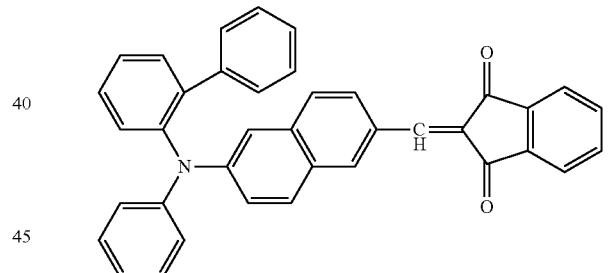
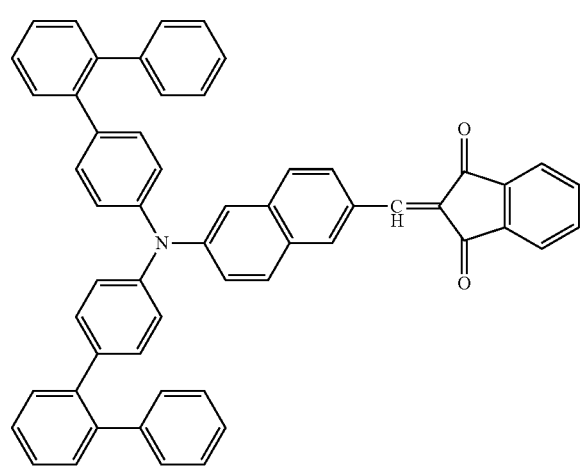
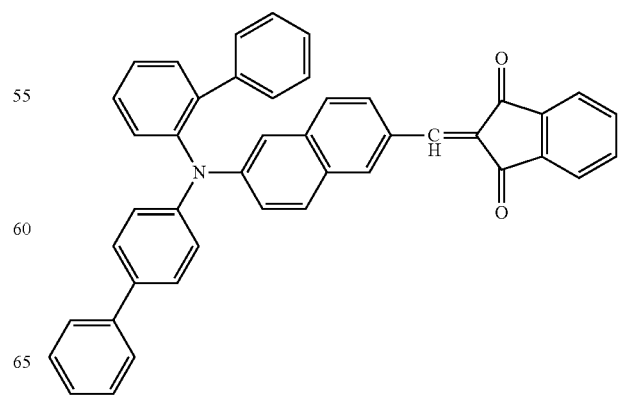

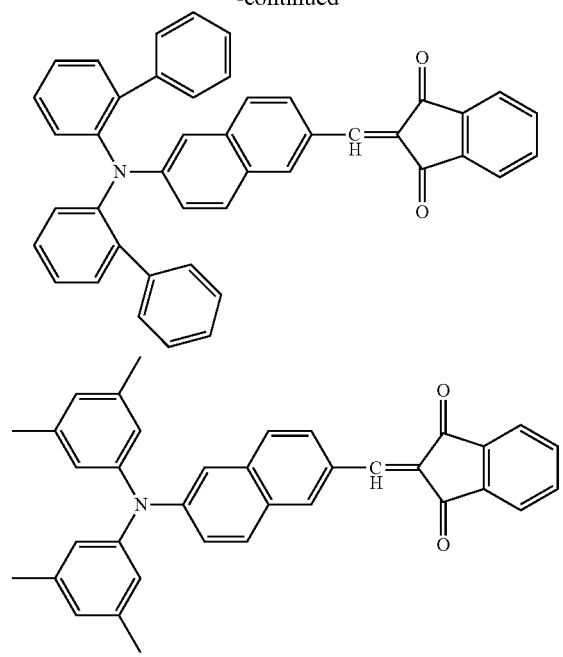
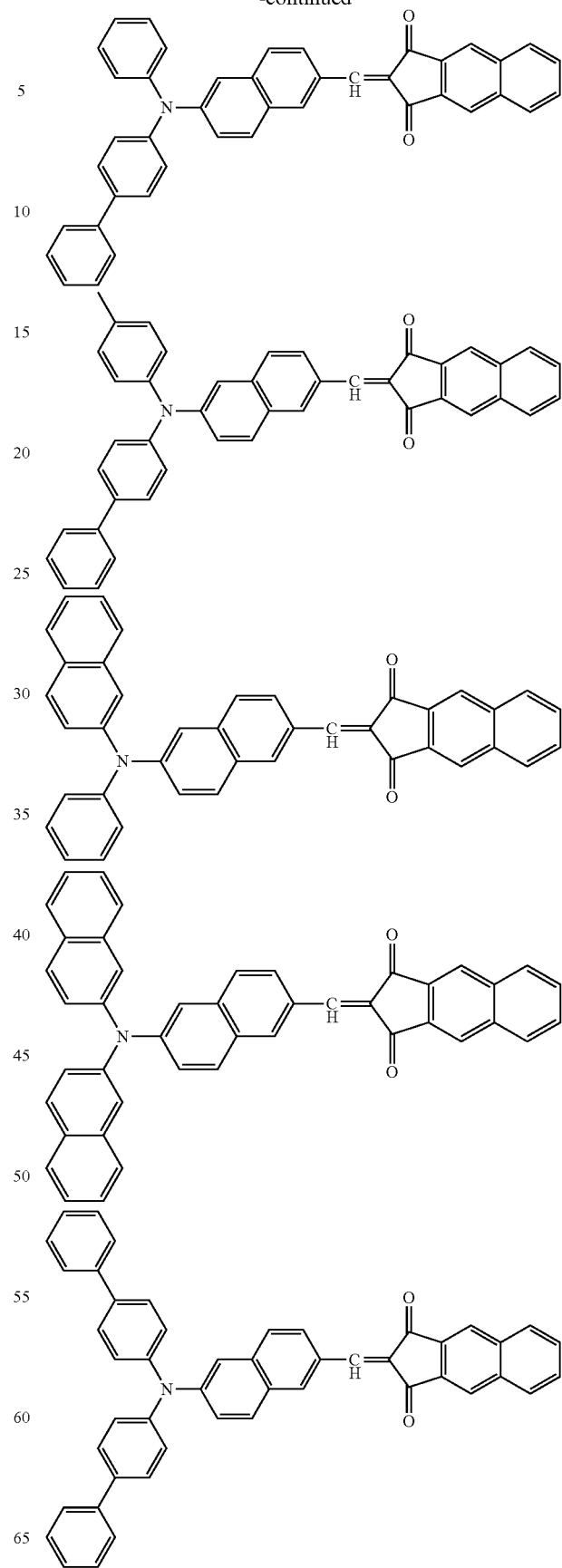

[Chem. 39]
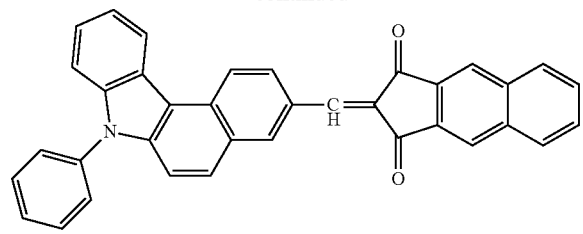
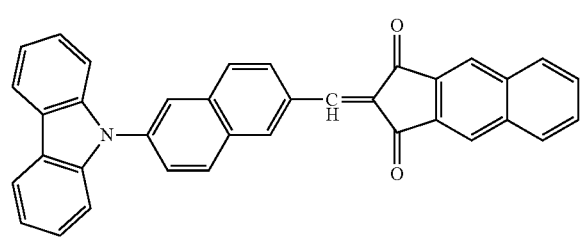
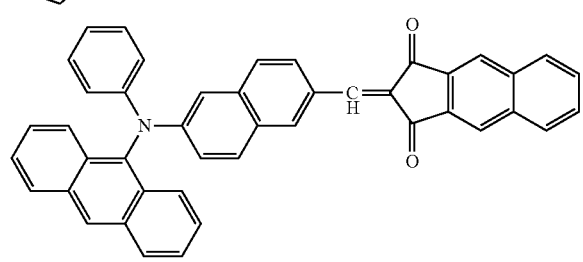
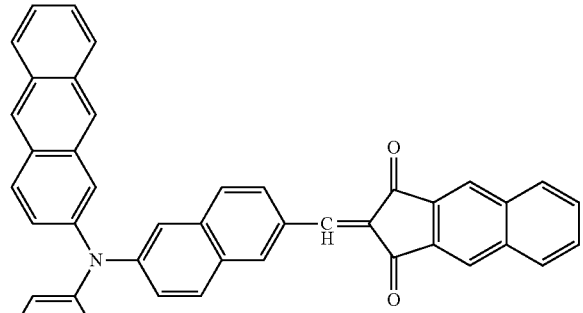
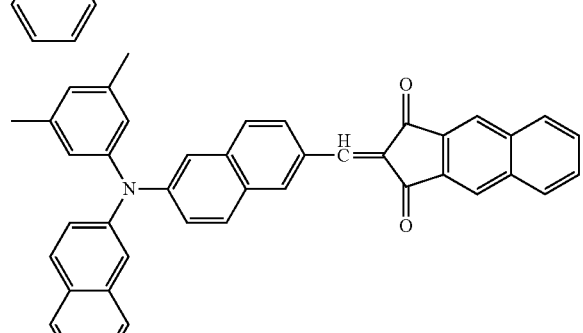
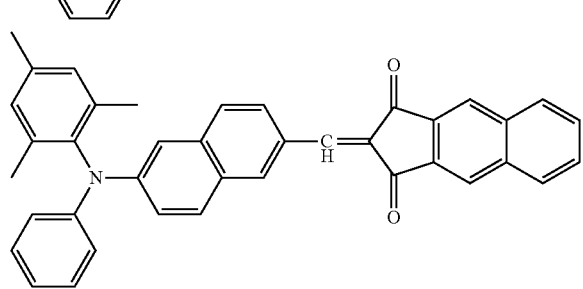
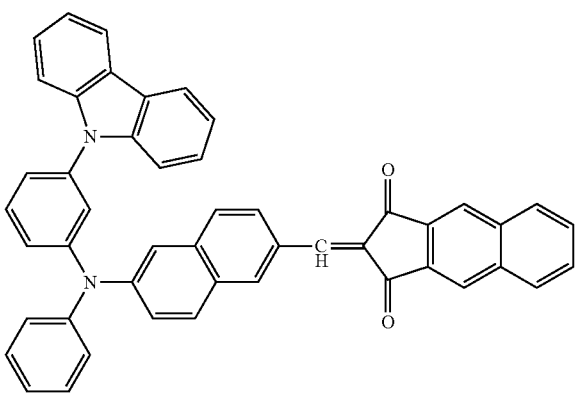
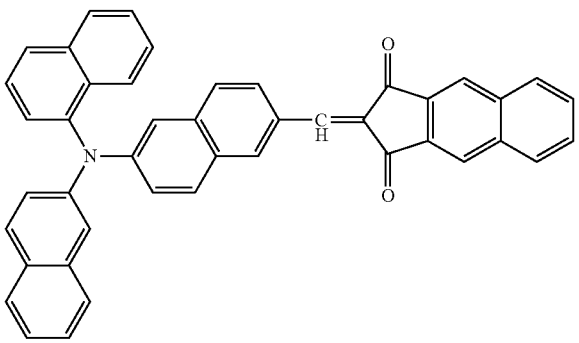
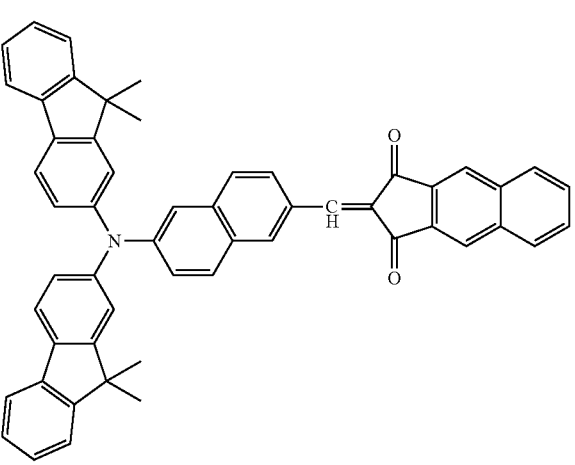

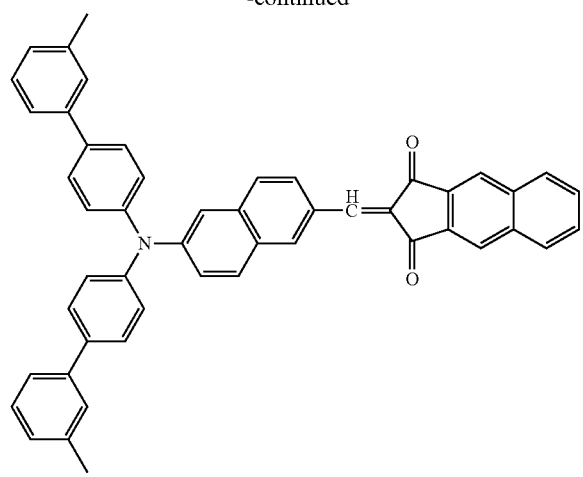
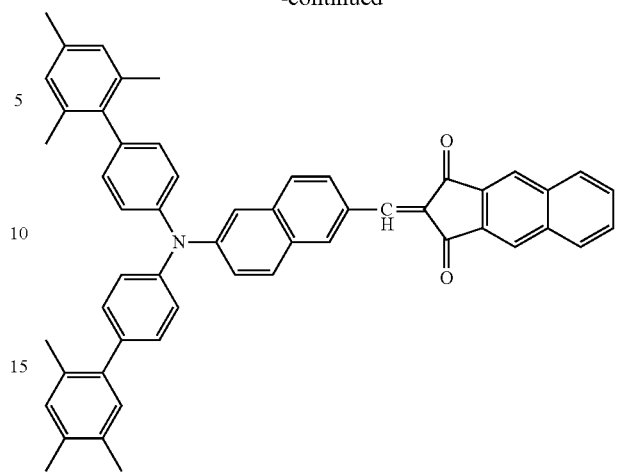
[Chem. 40]
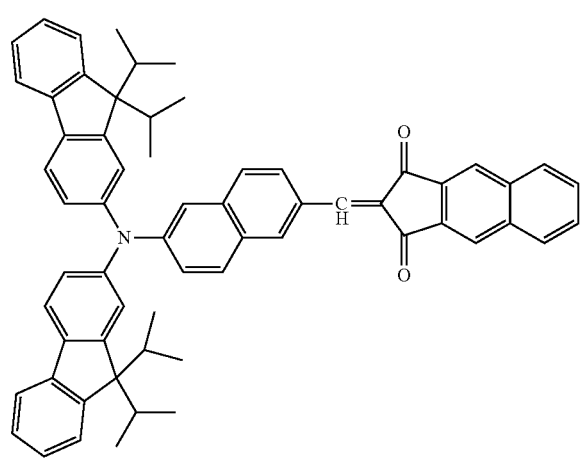
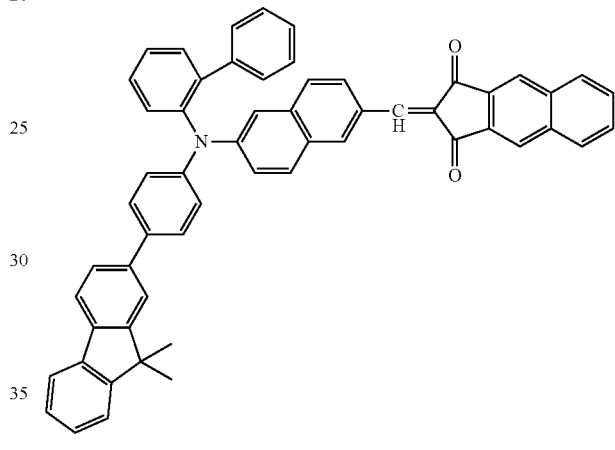
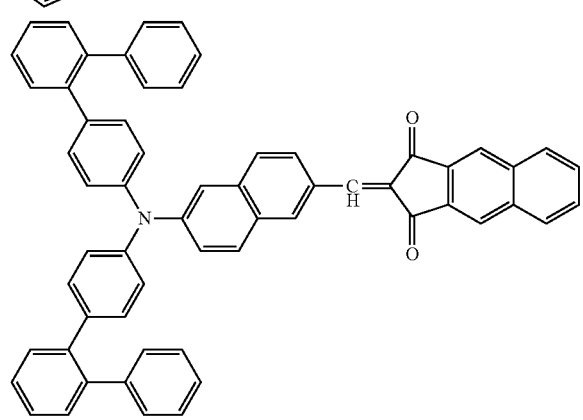
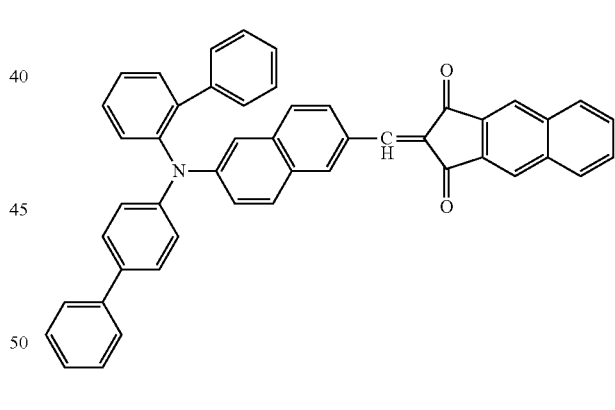
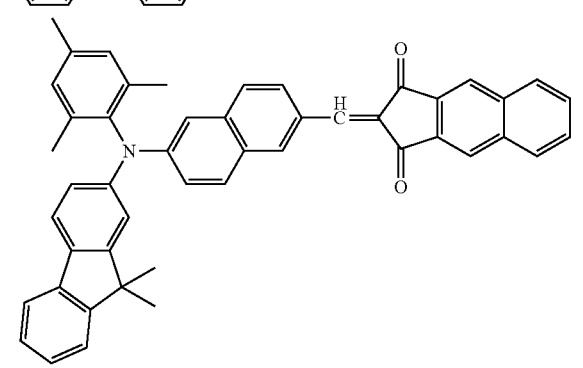
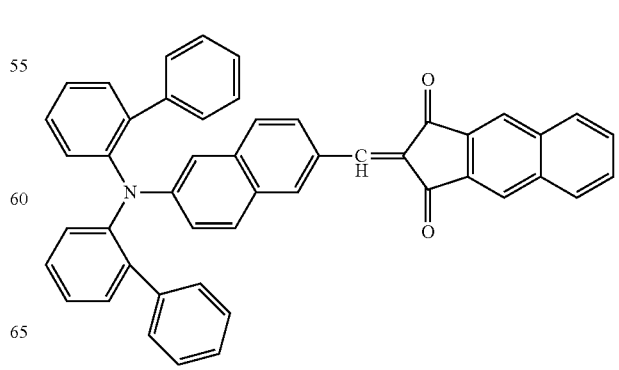

61
-continued
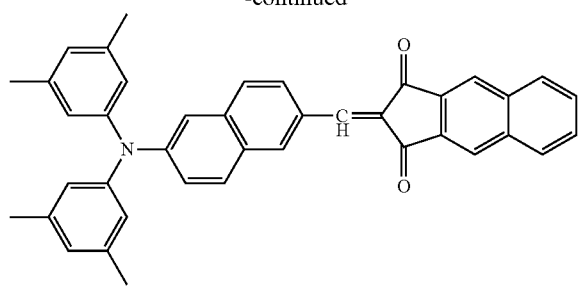
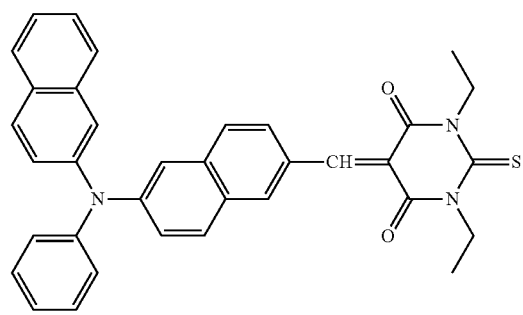
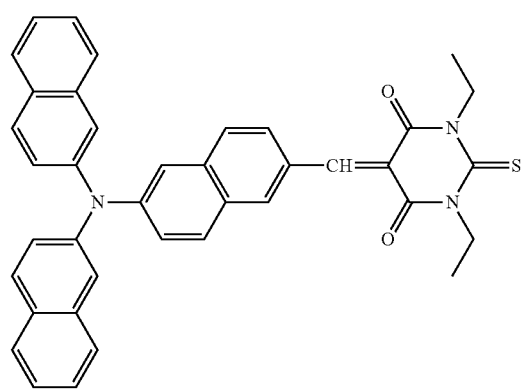
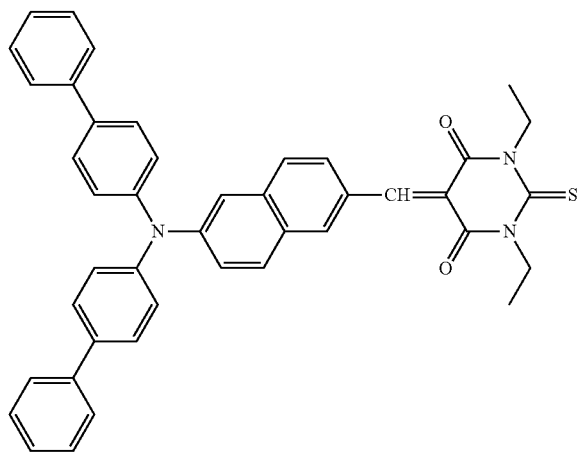
62
-continued
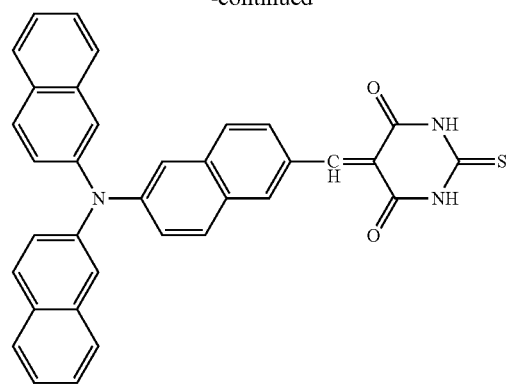
[Chem. 41]
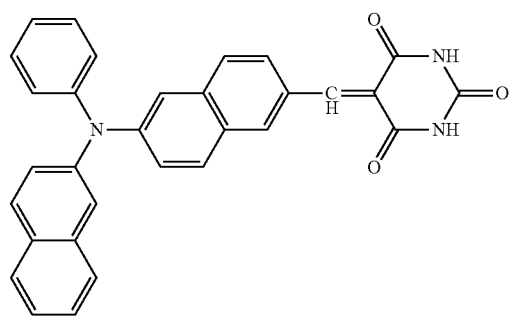
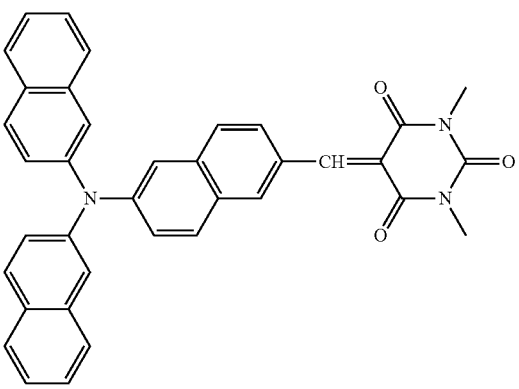
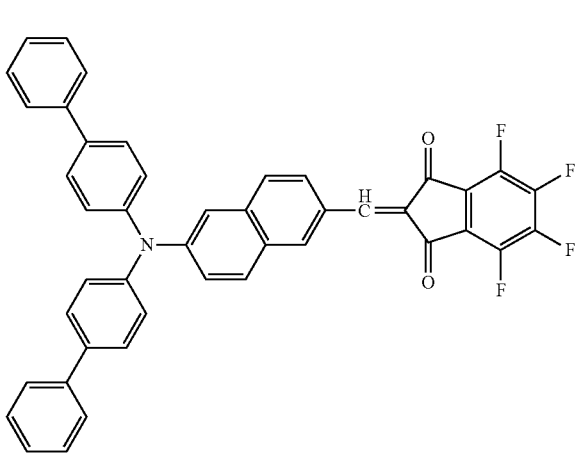

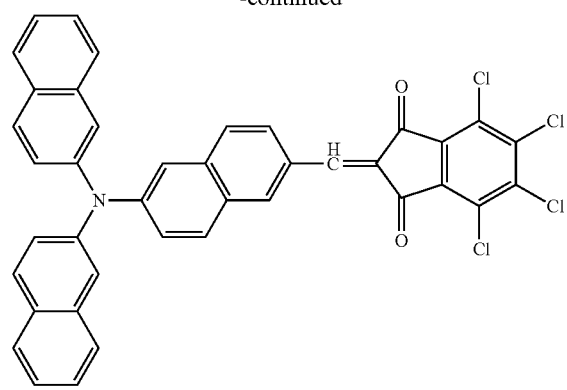
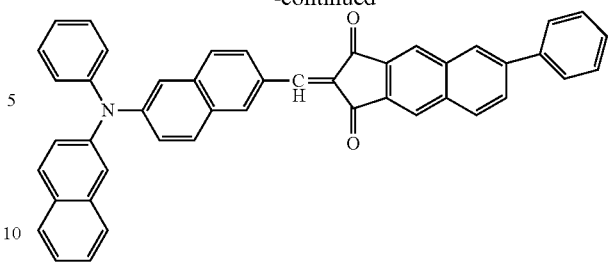
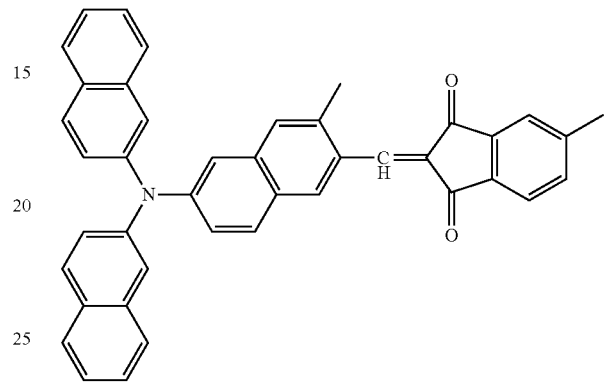
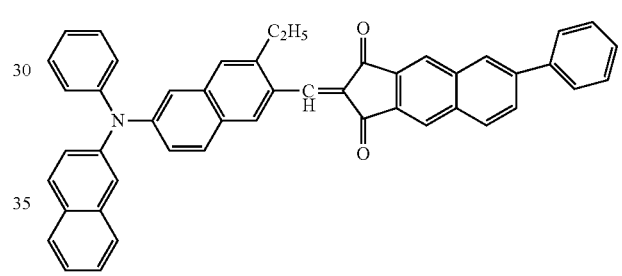
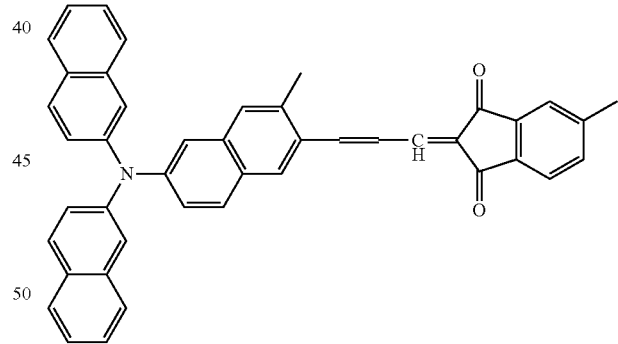
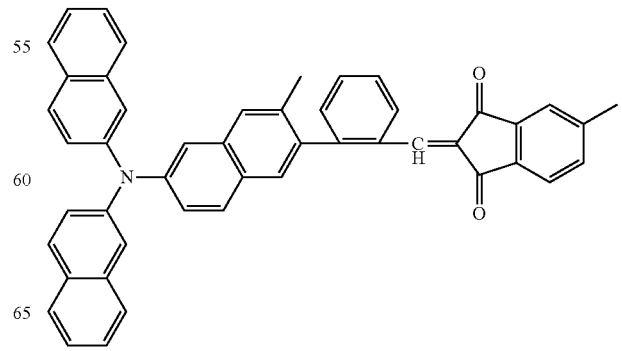
[Chem. 42]

-continued
[Chem. 43]
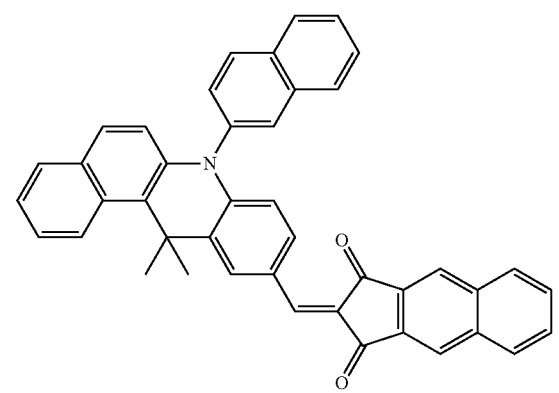
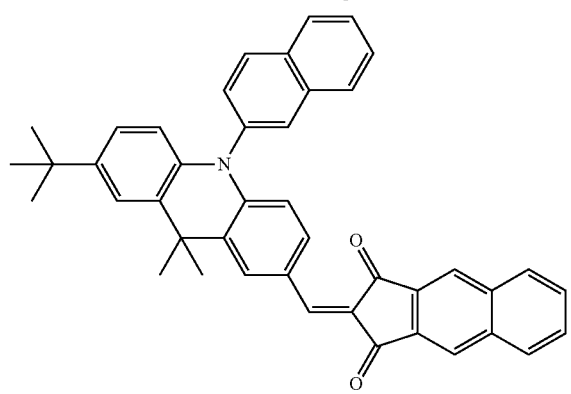
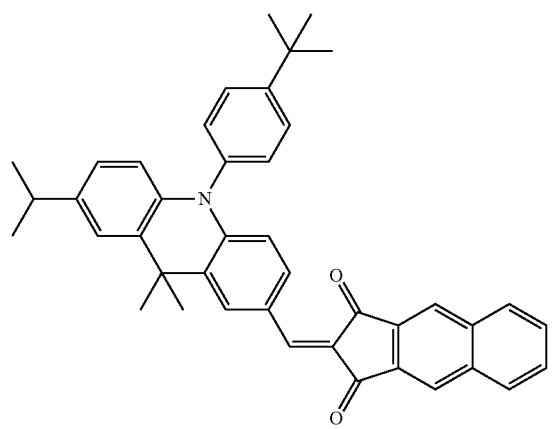
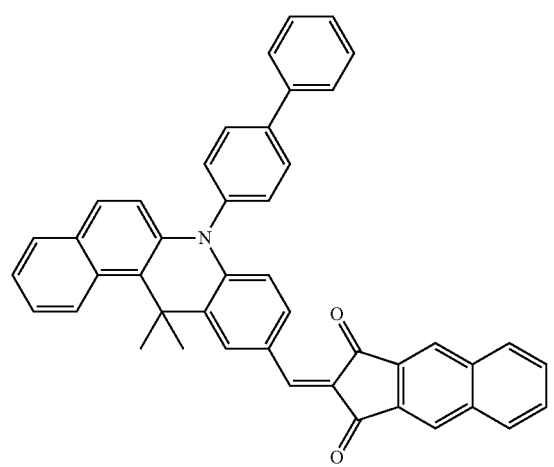
-continued
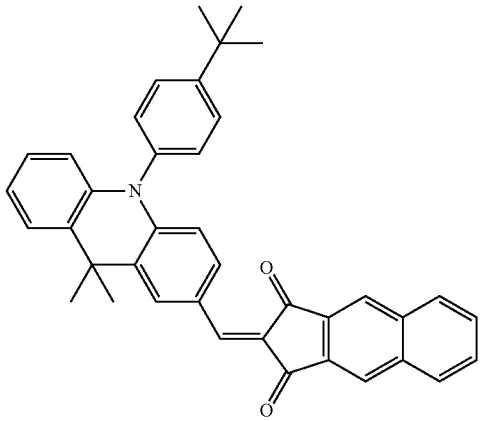
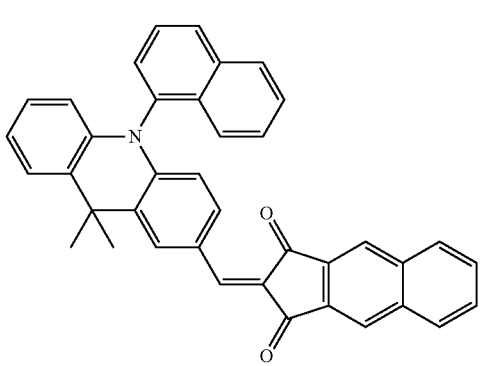
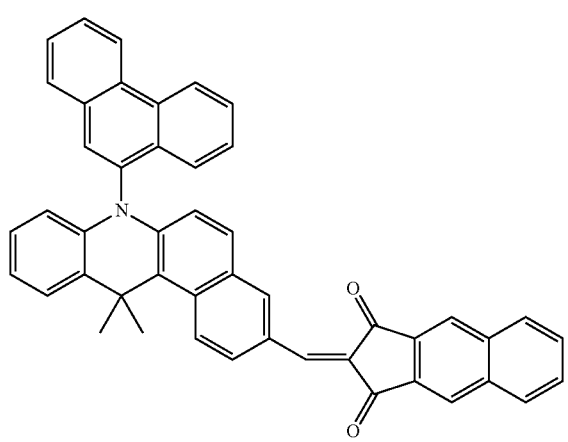
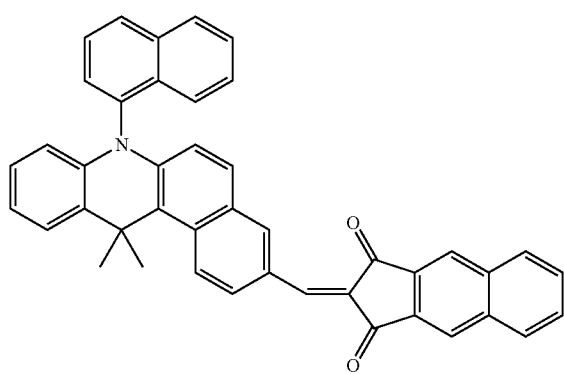

[Chem. 44]
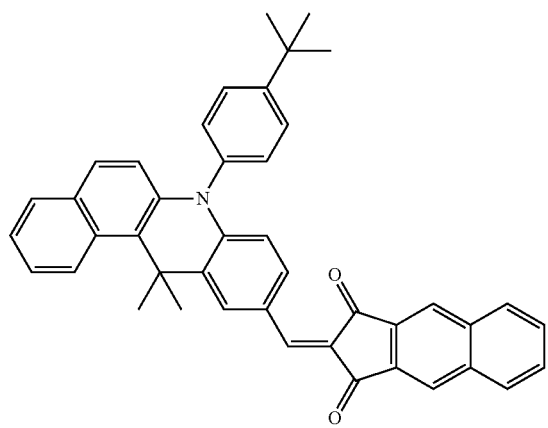
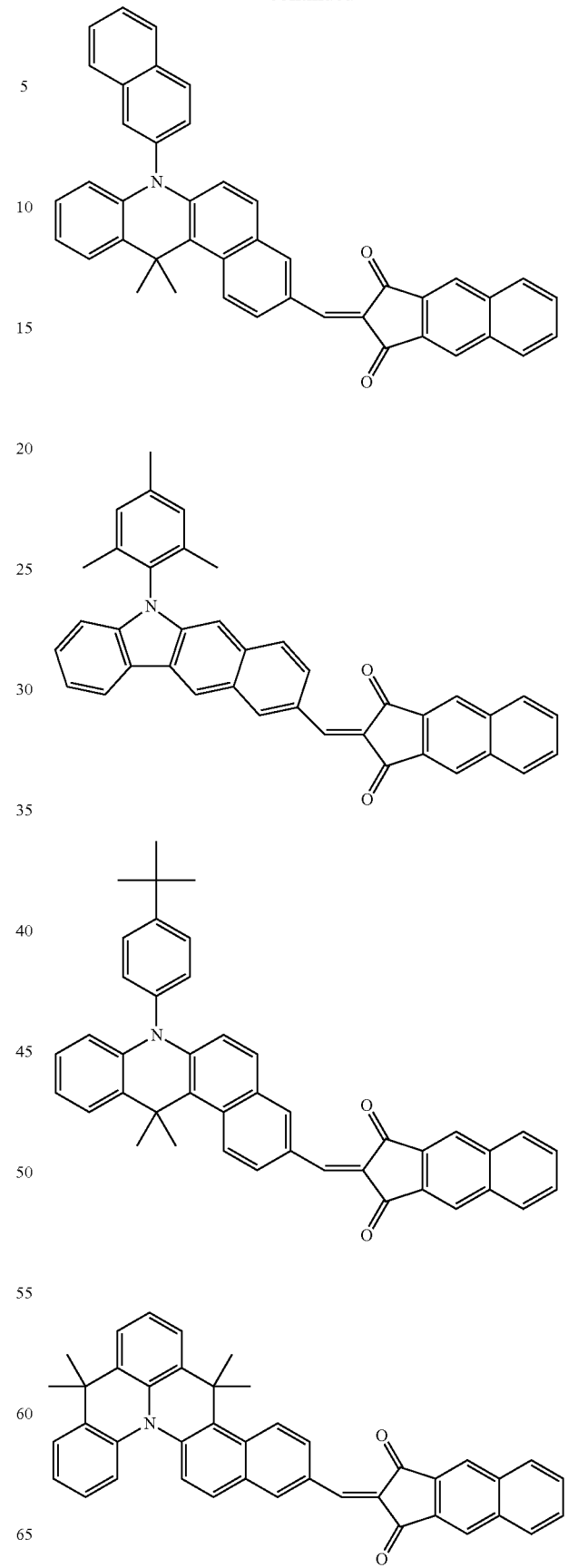

[Chem. 45]
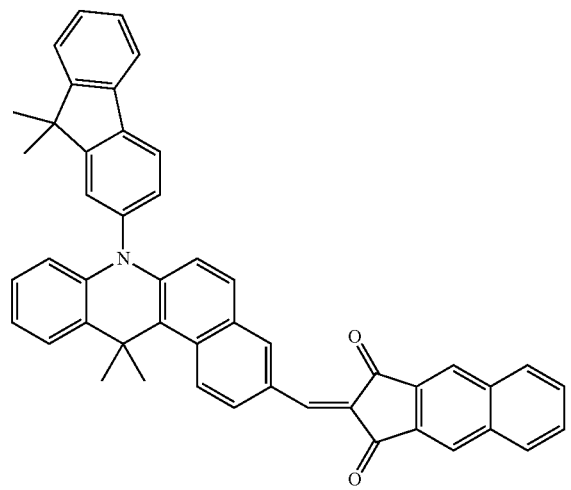
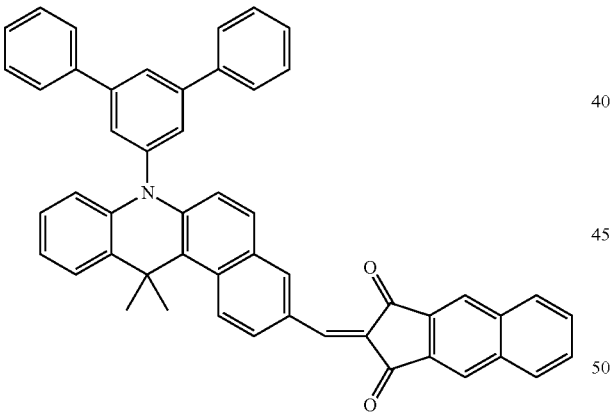
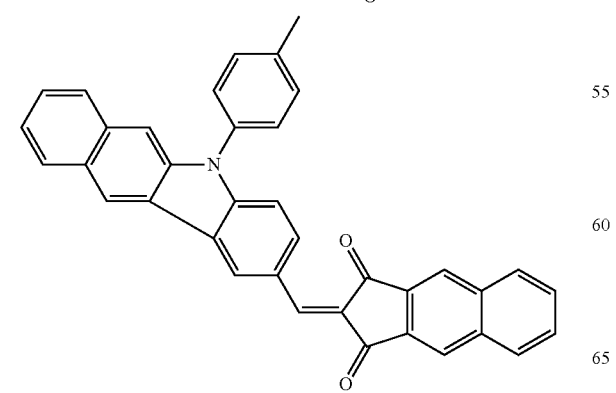
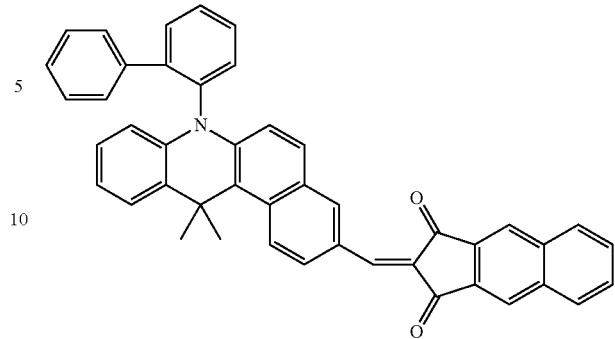
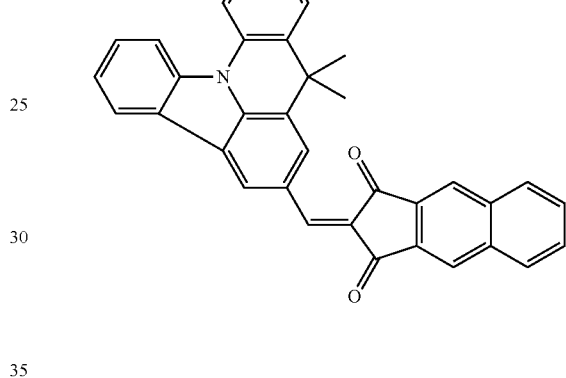
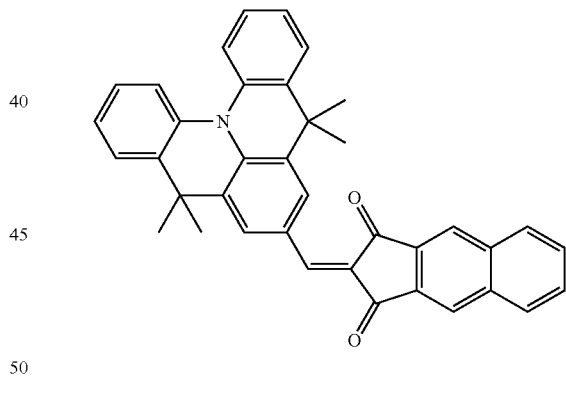
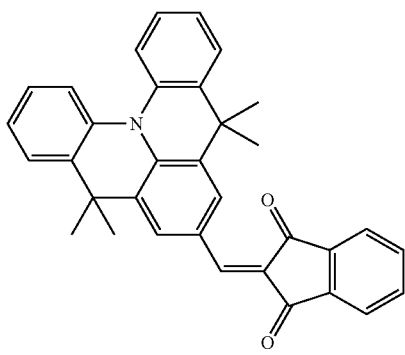

71
-continued
[Chem. 46]
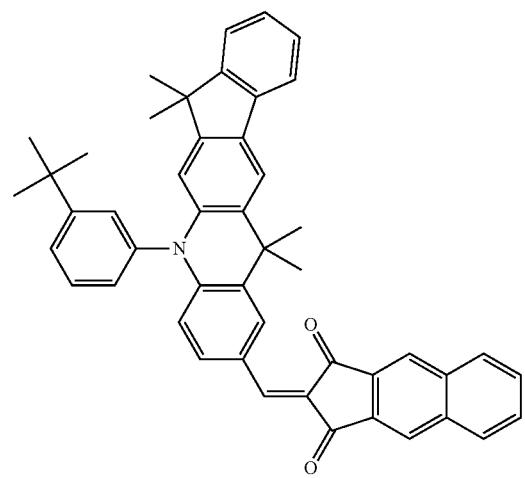
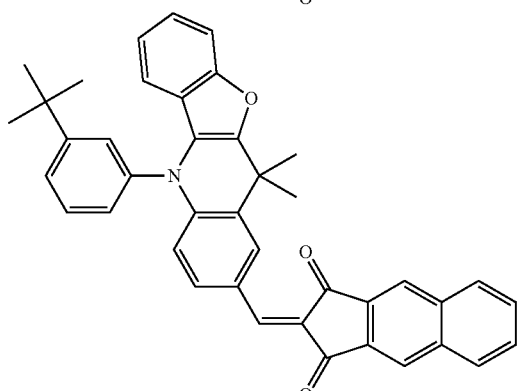
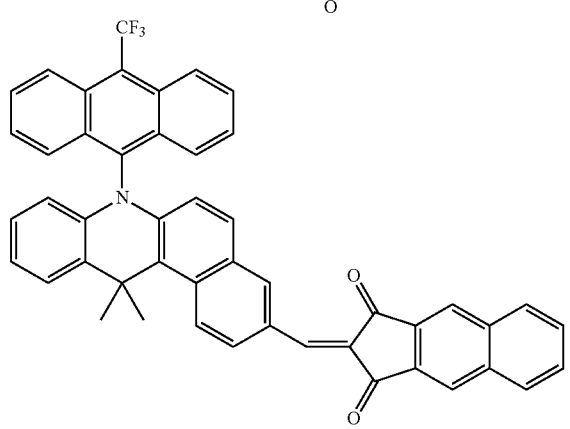
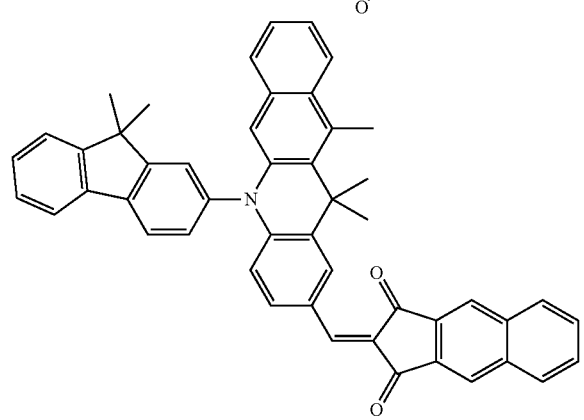
72
-continued
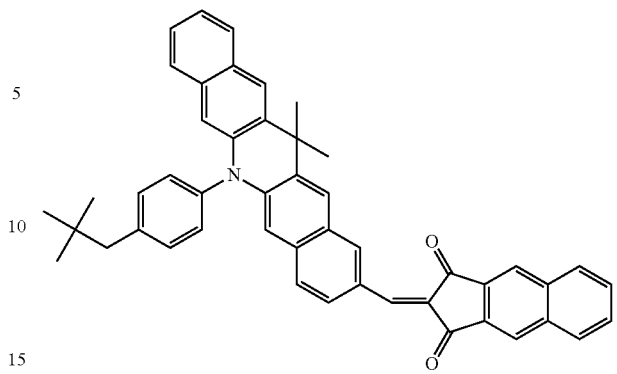
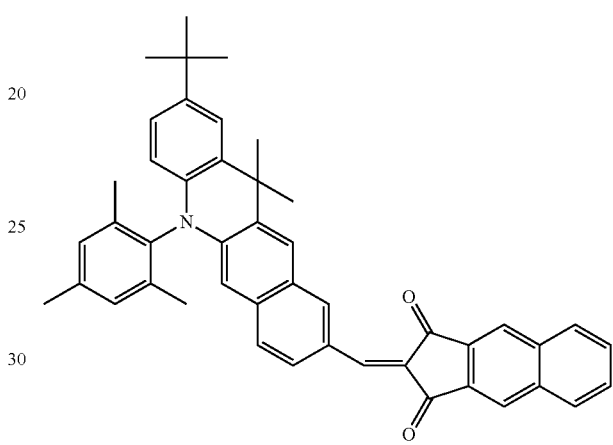
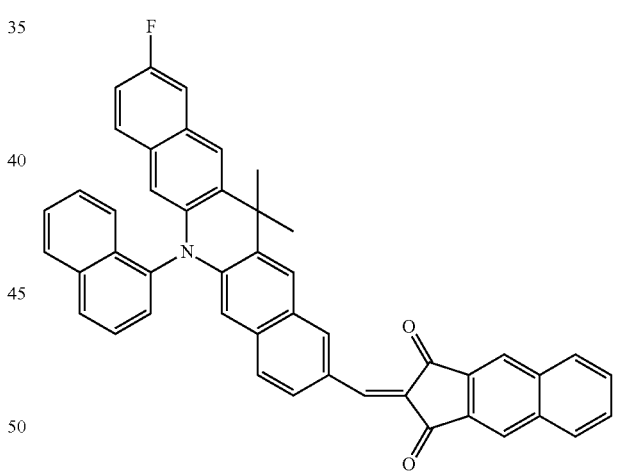
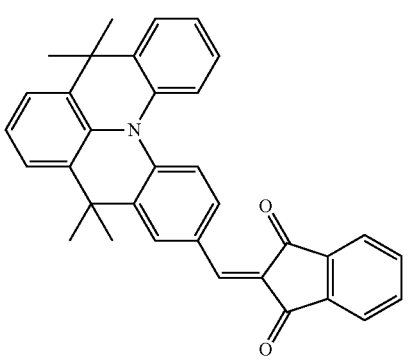

73
-continued
[Chem. 47]
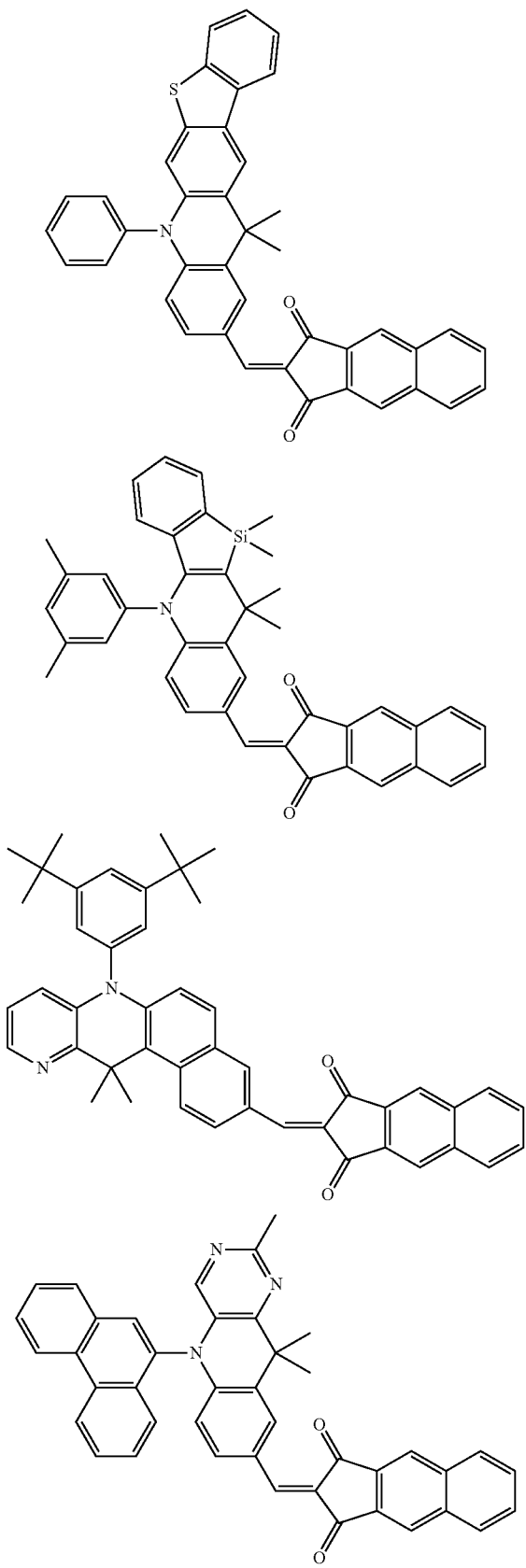
74
-continued
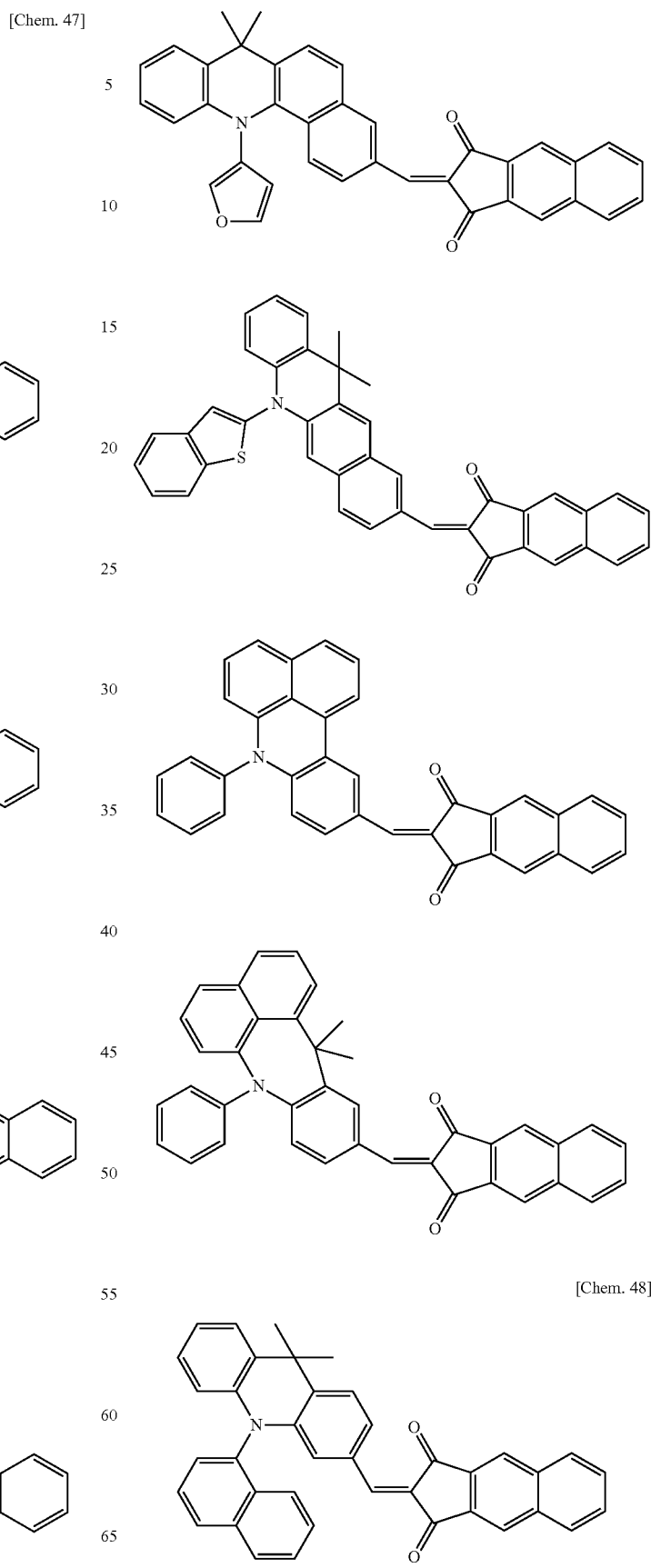
[Chem. 48]

75
-continued
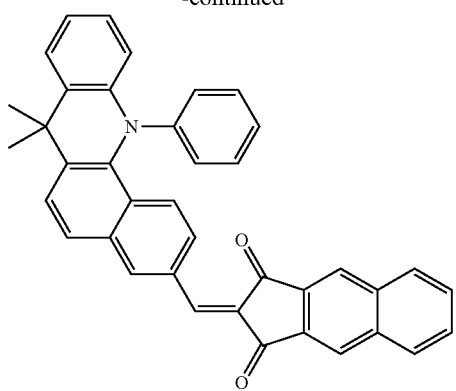
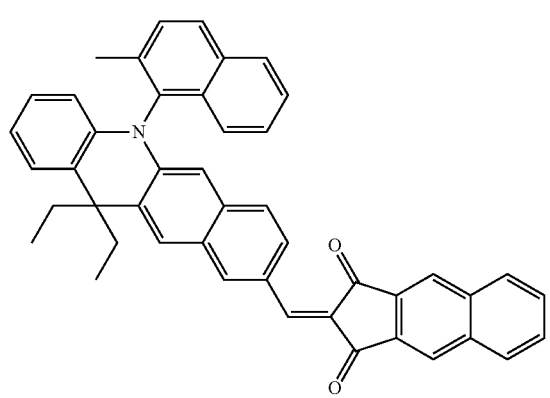
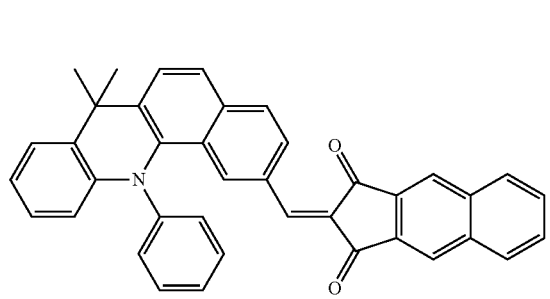
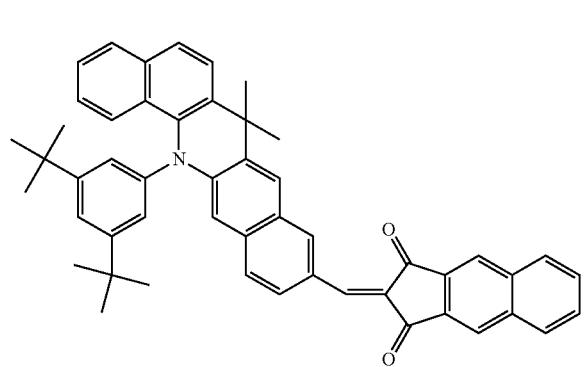
76
-continued
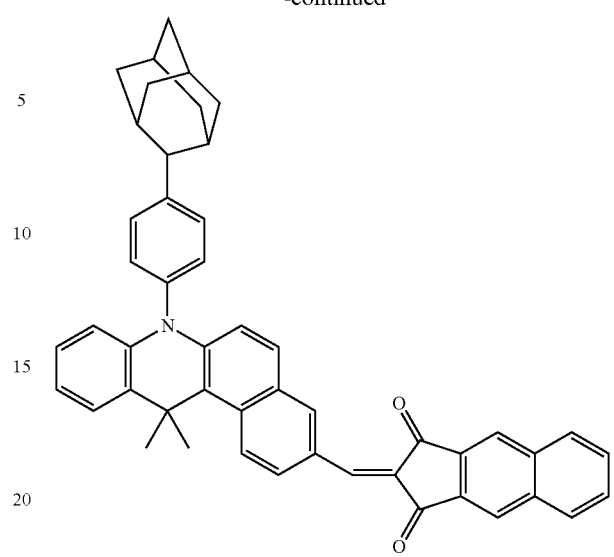
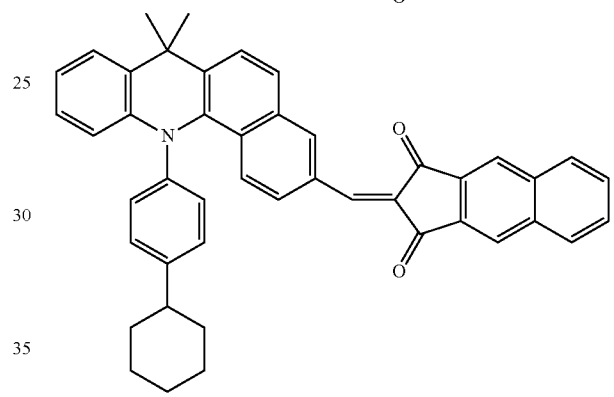
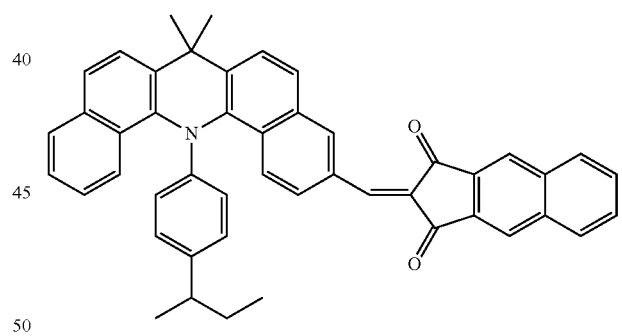
[Chem. 49]
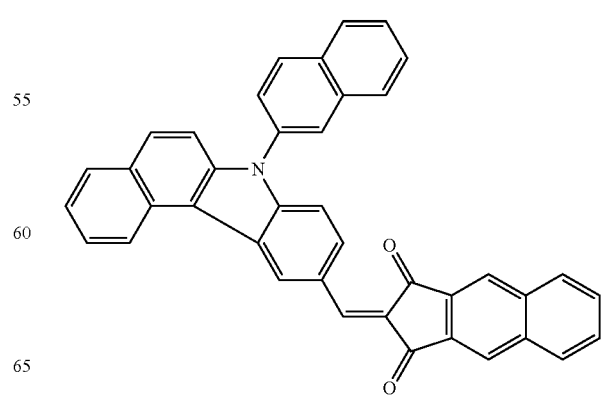

77
-continued
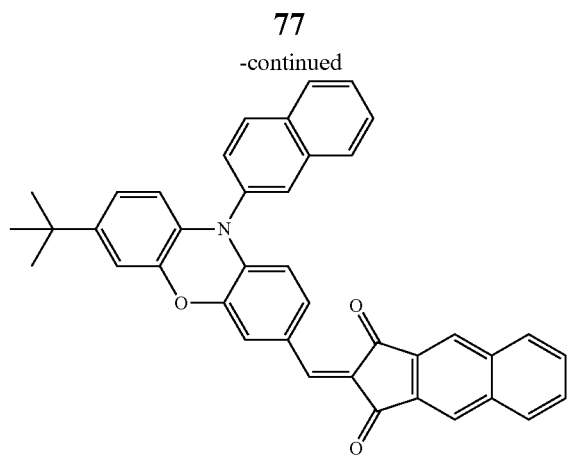
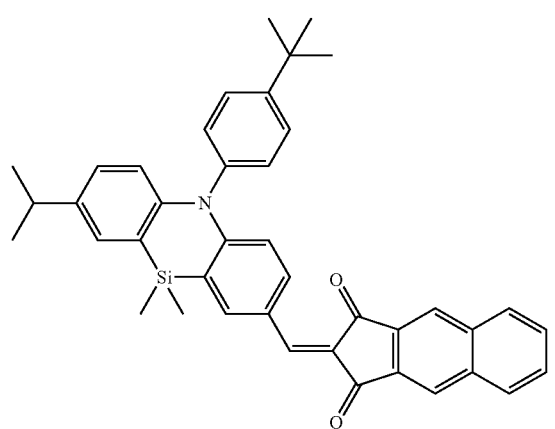
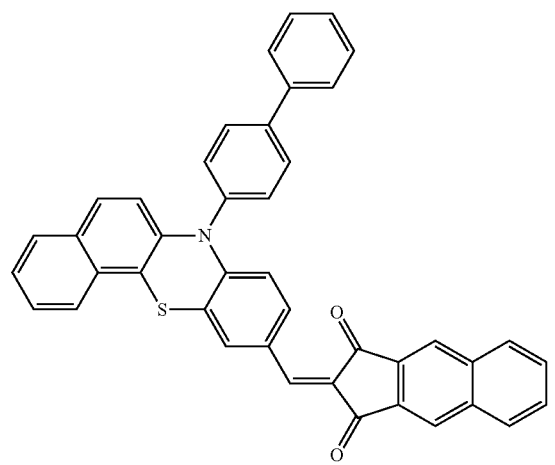
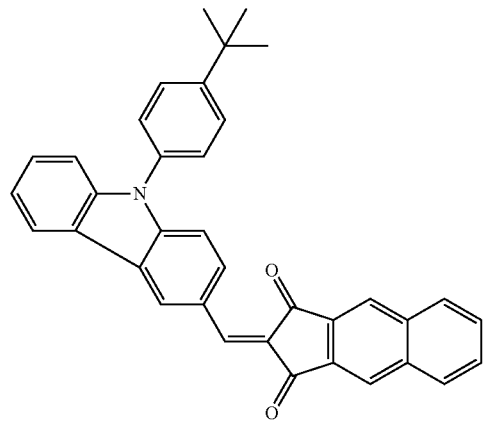
78
-continued
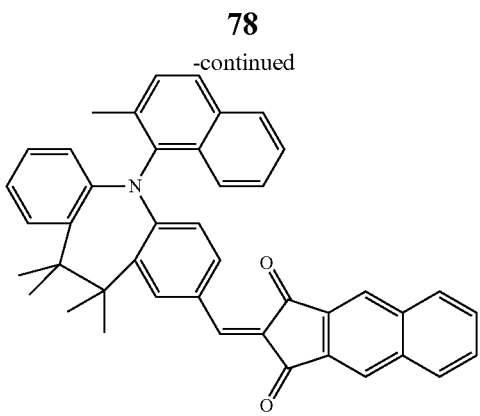
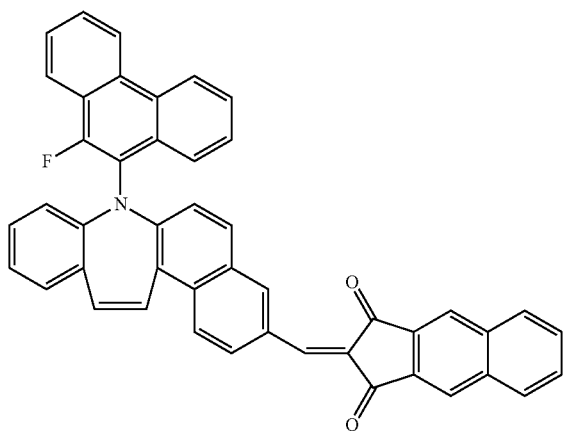
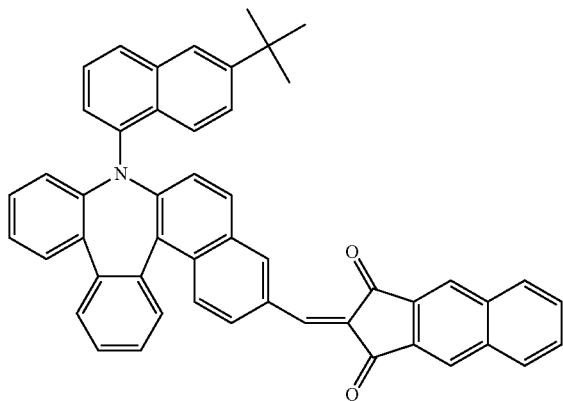
[Chem. 50]
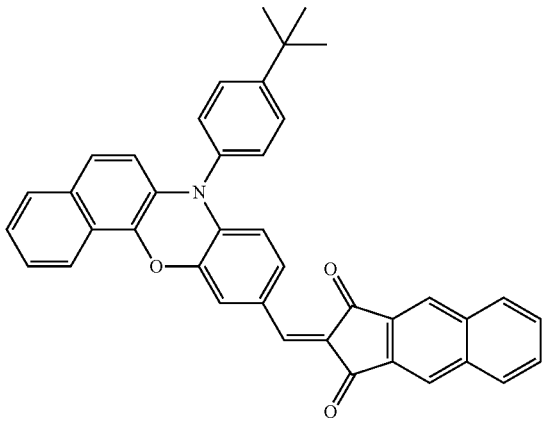

79
-continued
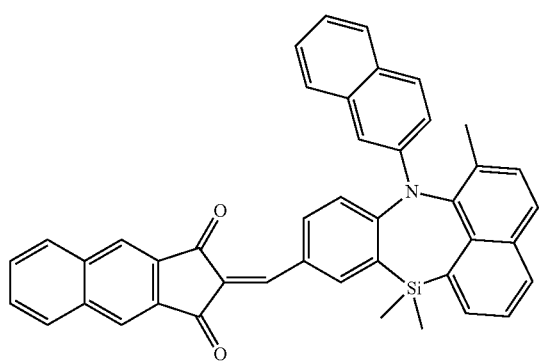
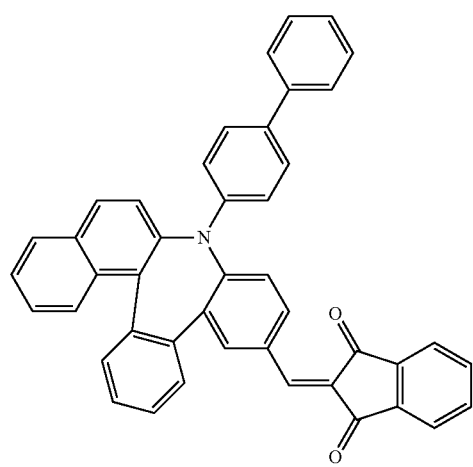
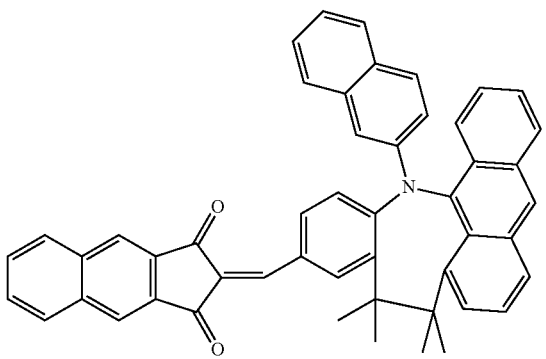
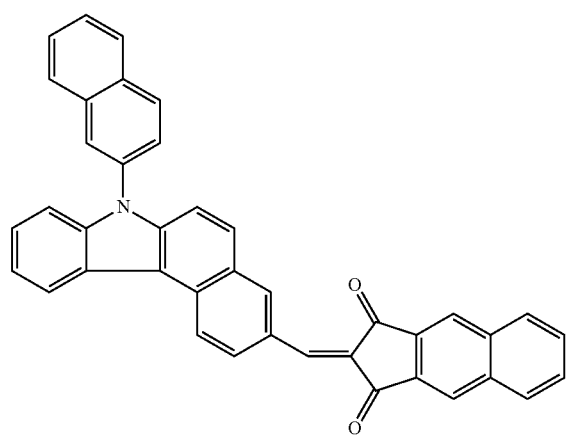
80
-continued
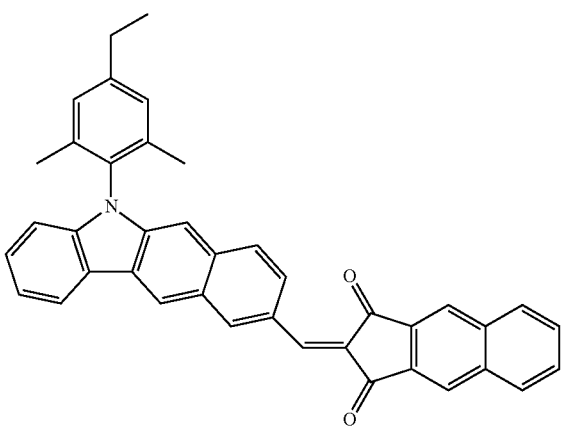
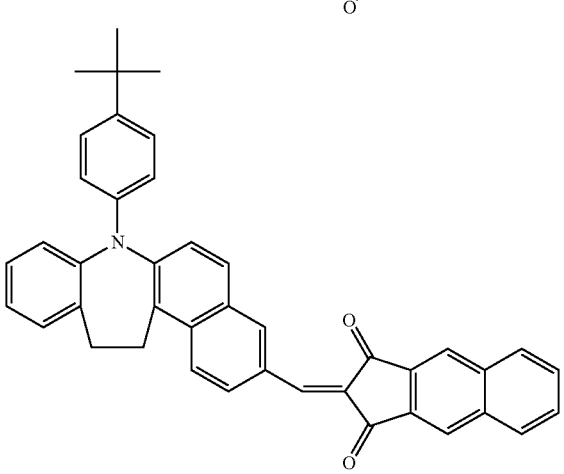
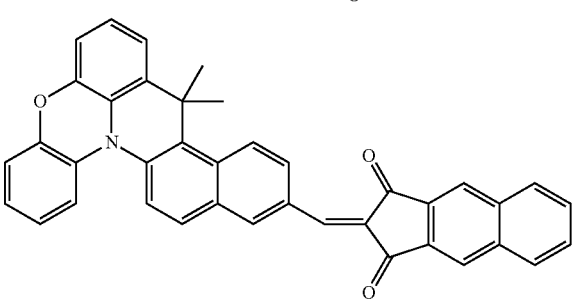
[Chem. 51]
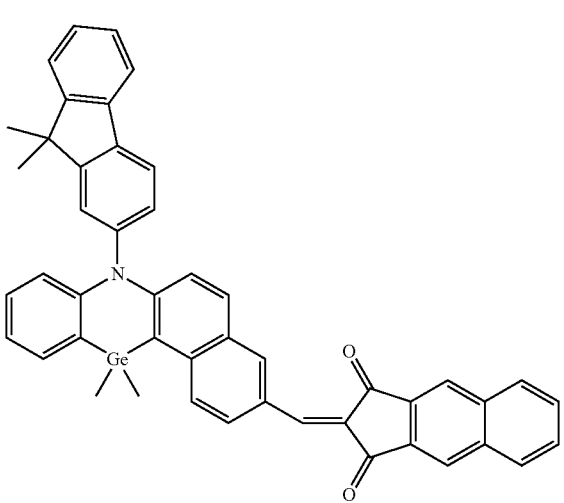

81
-continued
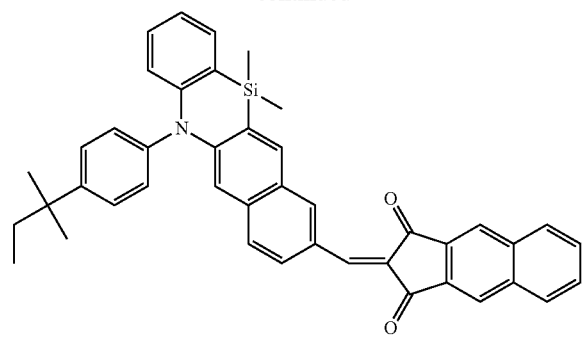
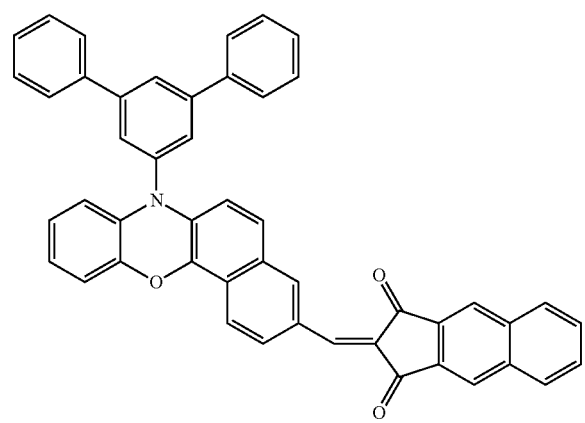
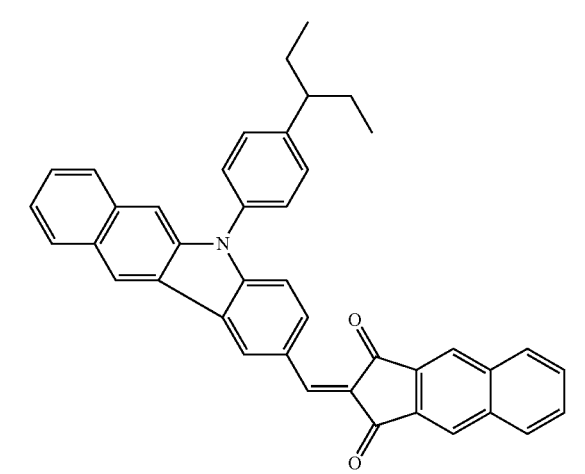
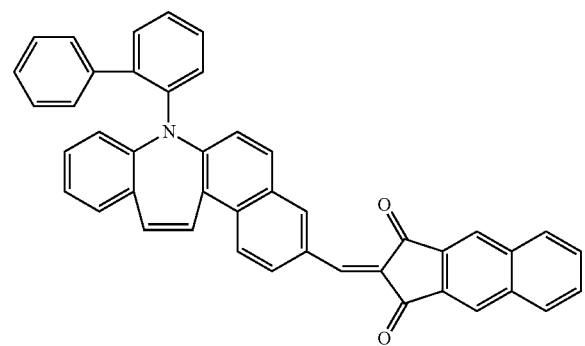
82
-continued
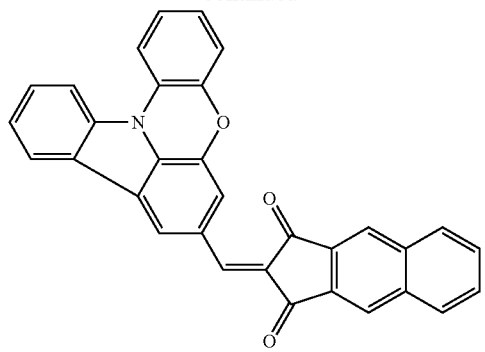
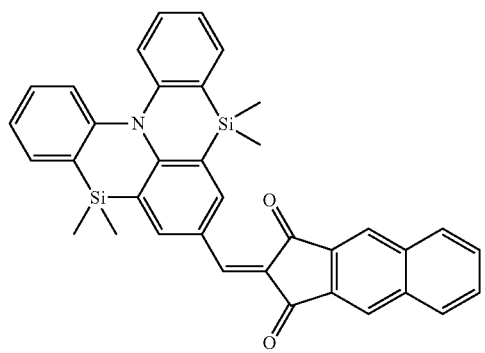
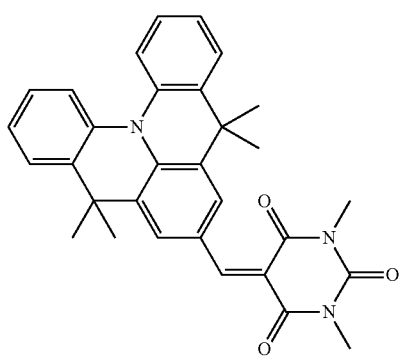
[Chem. 52]
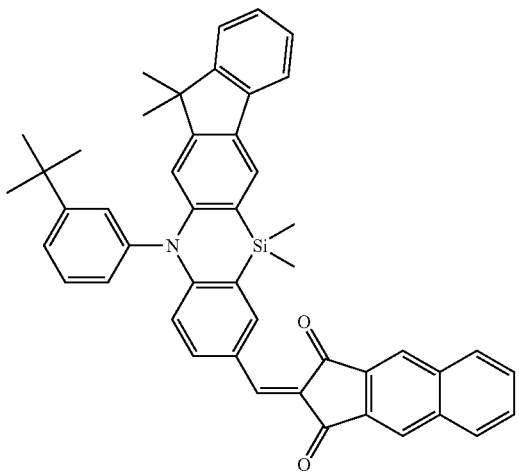

83
-continued
84
-continued
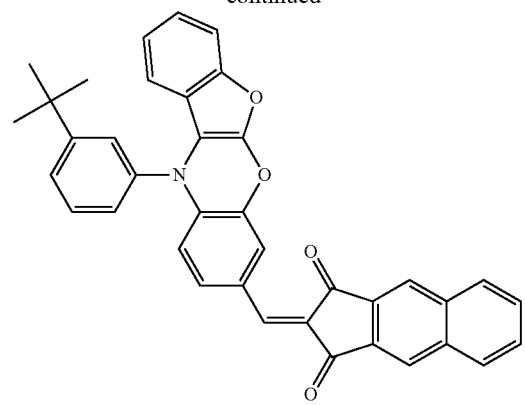
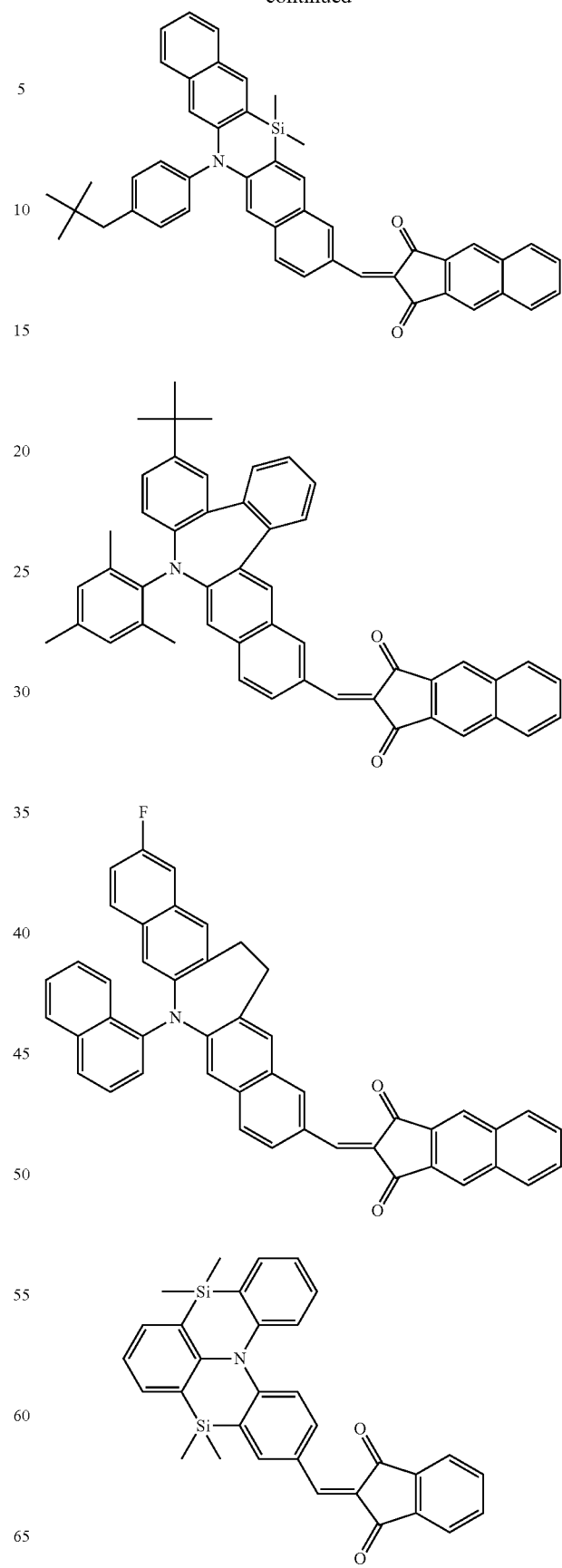

85
-continued
[Chem. 53]
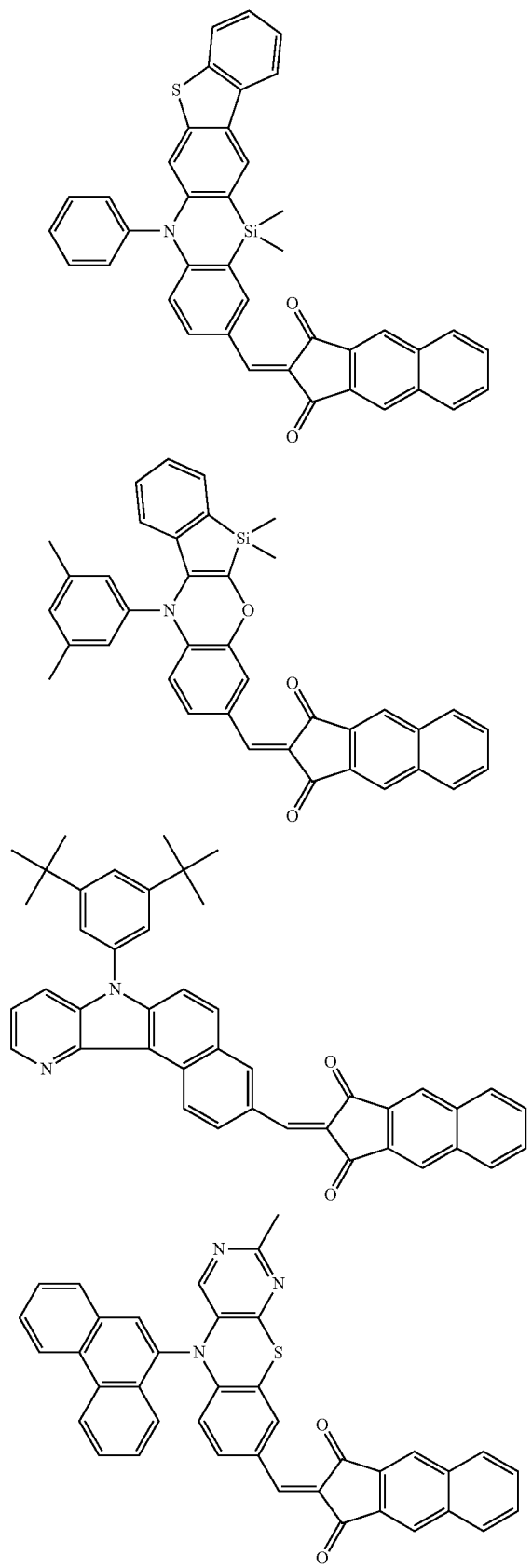
86
-continued
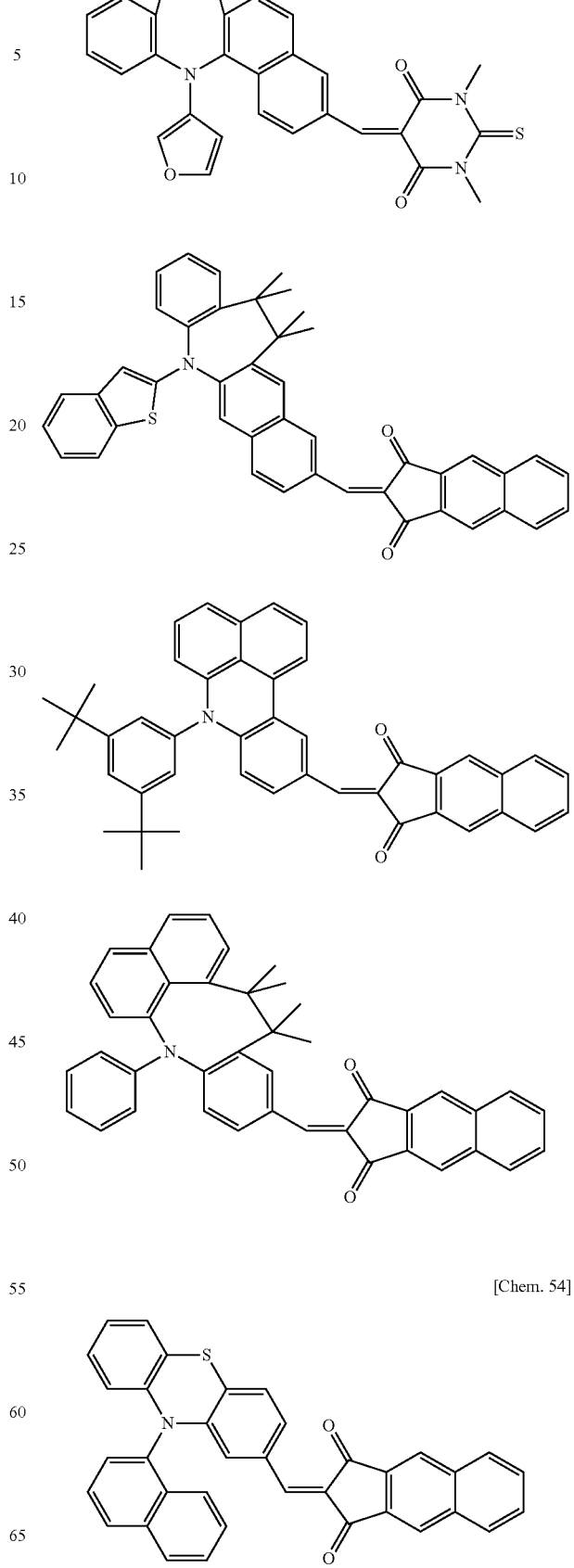
[Chem. 54]

87
-continued
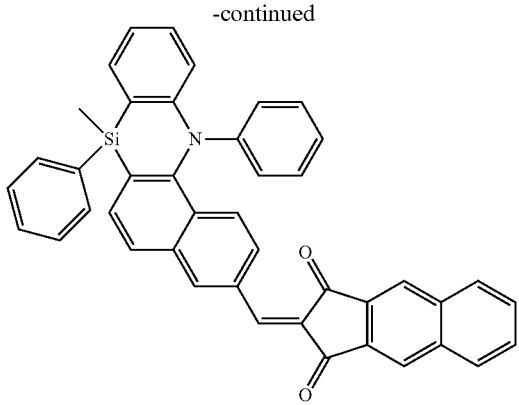
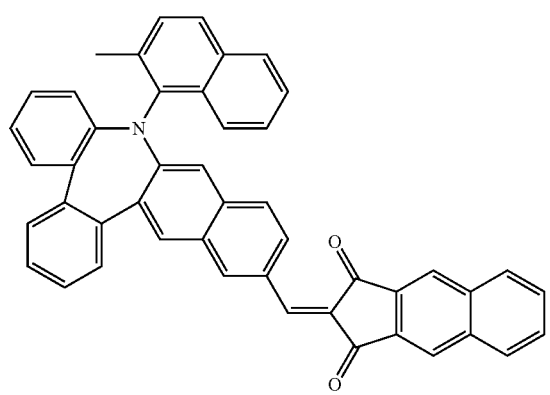
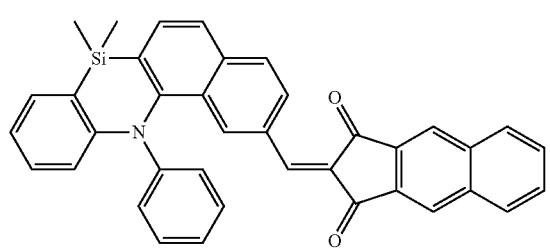
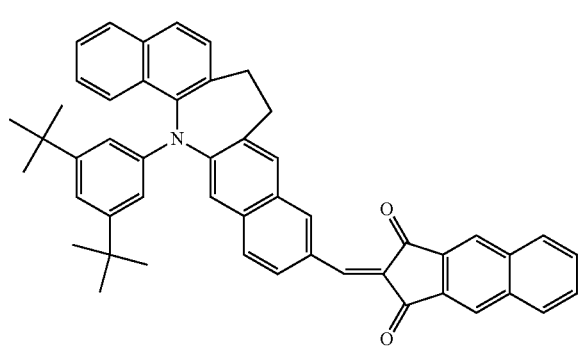
88
-continued
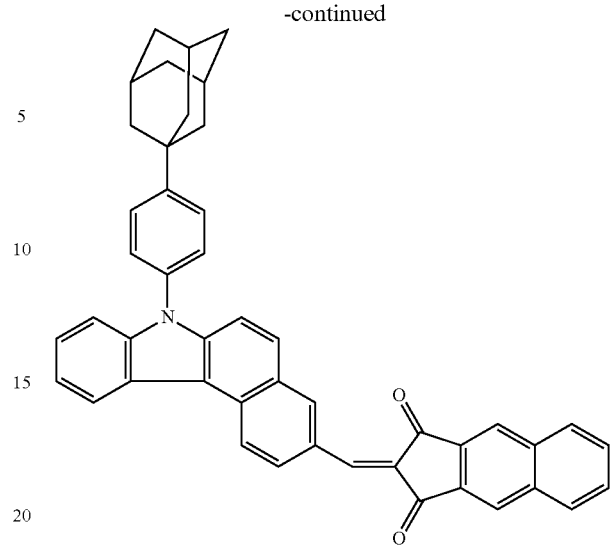
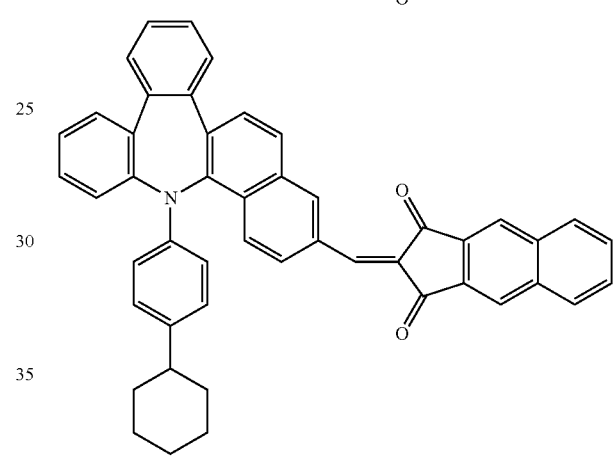
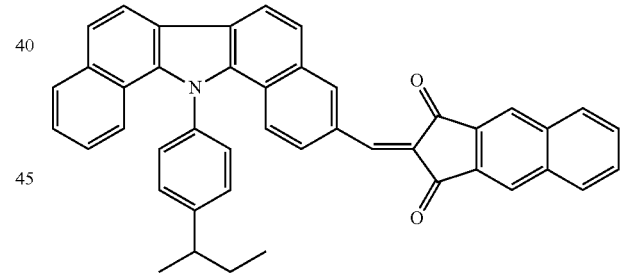
[Chem. 55]
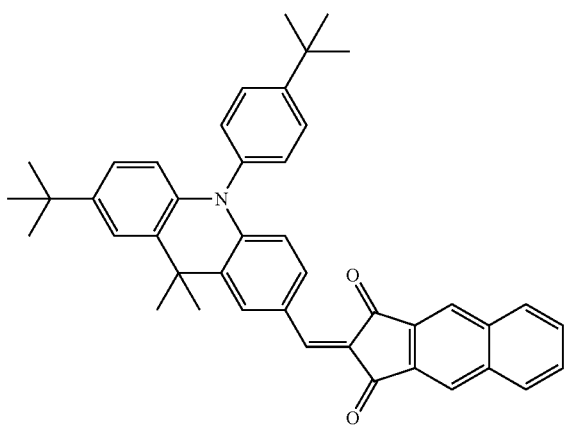

89
-continued
90
-continued
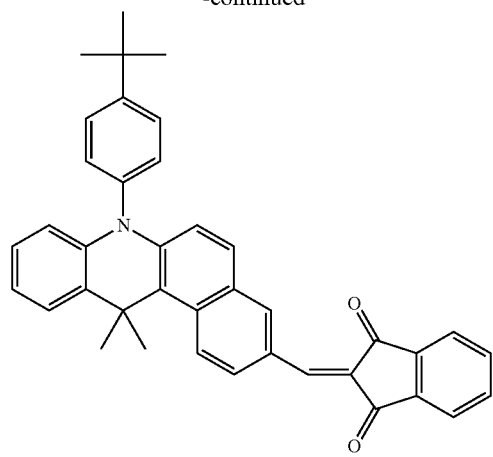
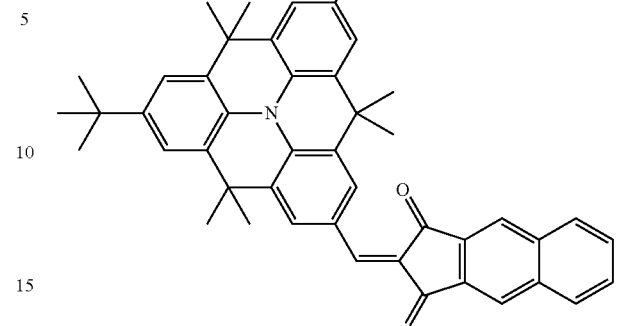
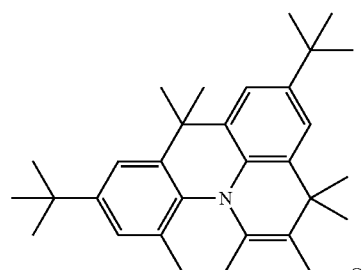
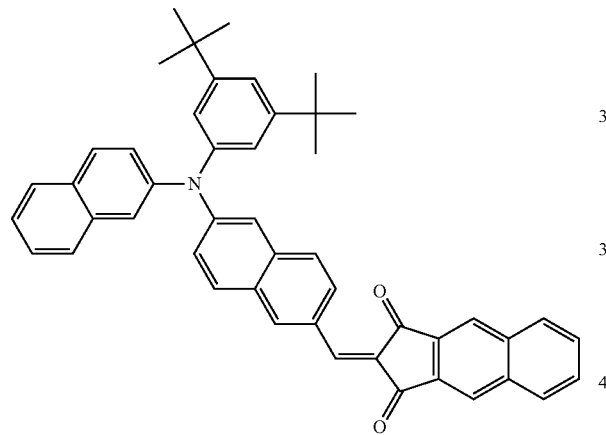
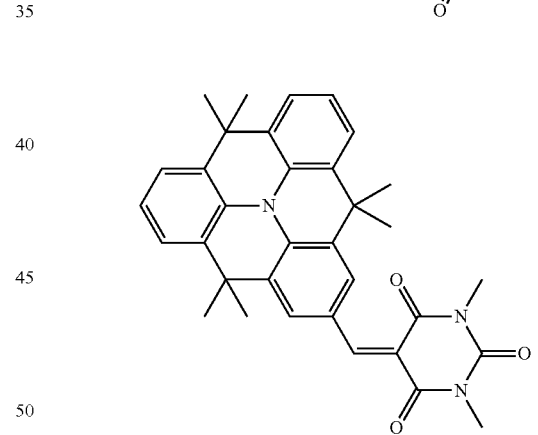
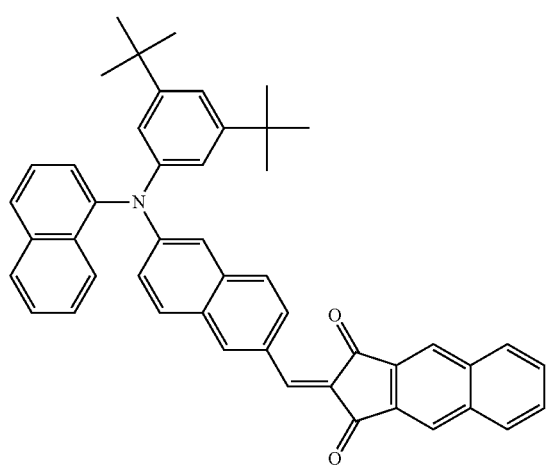
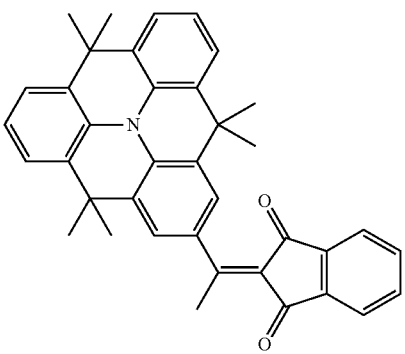

91
-continued
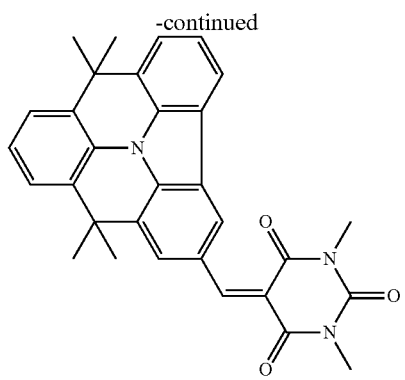
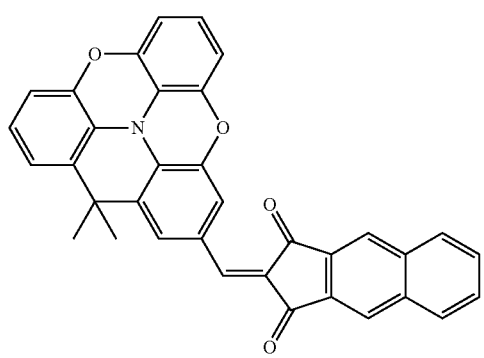
[Chem. 56]
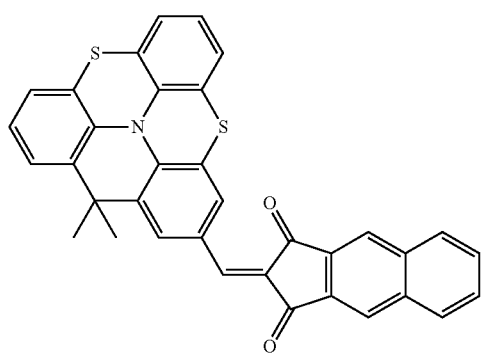
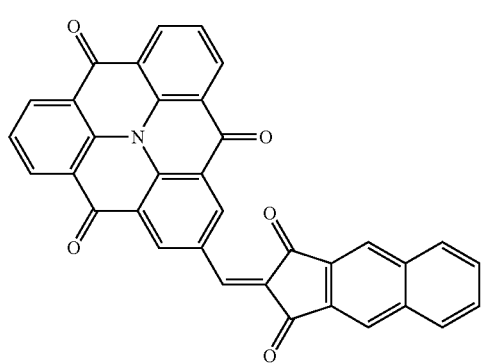
92
-continued
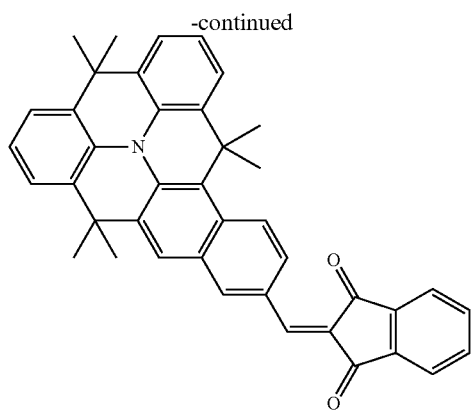
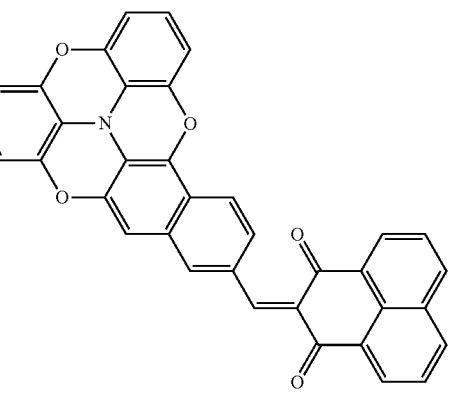

-continued

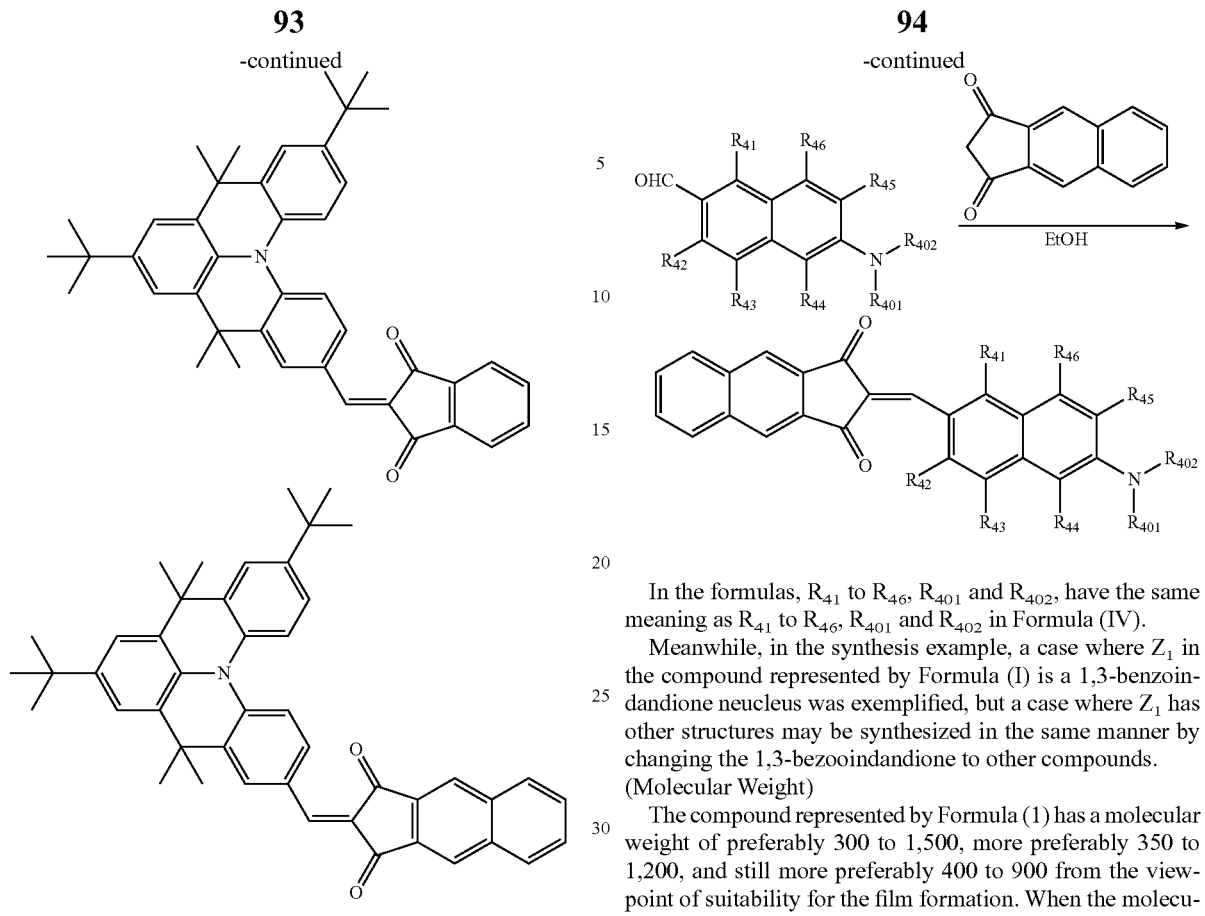

The compound represented by Formula (I) is useful particularly as a photoelectric conversion material used for photosensors or photocells. Further, as other uses, the compound may also be used as a coloring material, a liquid christal material, an organic semiconductor material, an organic luminescence device material, charge transporting material, a pharmaceuticals material, a fluorescent diagnostics material and the like.

Further, the compound represented by Formula (I) may be synthesized, for example, in accordance with the following reaction.

[Chem. 57]

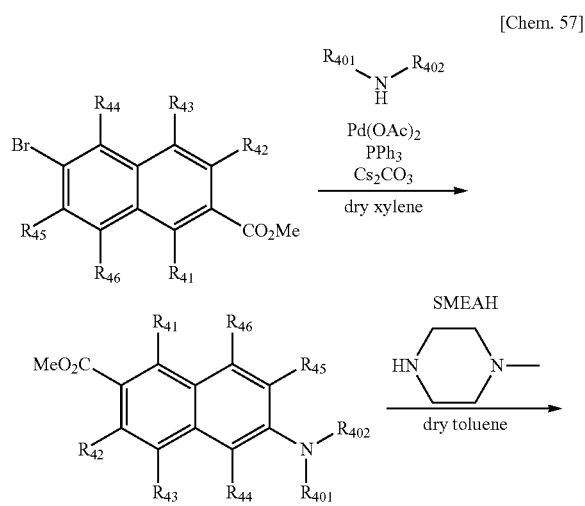

In the formulas, $R_{41}$ to $R_{46}$, $R_{401}$ and $R_{402}$, have the same meaning as $R_{41}$ to $R_{46}$, $R_{401}$ and $R_{402}$ in Formula (IV).

Meanwhile, in the synthesis example, a case where $Z_1$ in the compound represented by Formula (I) is a 1,3-benzoindandione neucleus was exemplified, but a case where $Z_1$ has other structures may be synthesized in the same manner by changing the 1,3-bezooindandione to other compounds.

(Molecular Weight)

The compound represented by Formula (1) has a molecular weight of preferably 300 to 1,500, more preferably 350 to 1,200, and still more preferably 400 to 900 from the viewpoint of suitability for the film formation. When the molecular weight is 300 or more, the film thickness of the formed photoelectric conversion film is hardly decreased due to volatilization, and when the molecular weight is 1,500 or less, it is easy to perform deposition, thereby facilitating the manufacture of the photoelectric conversion device.

The present invention also relates to a film containing the compound according to the present invention.

Further, the present invention also relates to a photoelectric conversion material containing the compound according to the present invention.

[Photoelectric Conversion Device]

The photoelectric conversion device of the present invention is a photoelectric conversion device containing a conductive film, an organic photoelectric conversion film and a transparent conductive film, in which the organic photoelectric conversion film contains the compound of the present invention and a fullerene or a fullerene derivative. In a preferred aspect of the photoelectric conversion device of the present invention, the conductive film, the organic photoelectric conversion film and the transparent conductive film are laminated in this order. The organic photoelectric conversion film includes at least a photoelectric conversion, and in addition to it, may include an electron blocking layer and a hole blocking layer.

Hereinafter, an appropriate embodiment of the photoelectric conversion device of the present invention will be described.

Figure 1B:
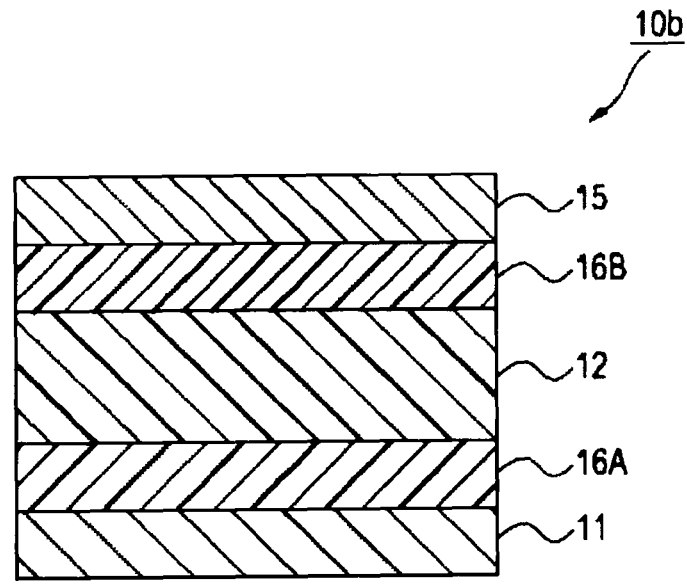

FIG. 1A and FIG. 1B illustrates a configuration example of the photoelectric conversion device according to the embodiment of the present invention.

A photoelectric conversion device 10a as illustrated in FIG. 1A has a configuration in which a conductive film (hereinafter, referred to as a lower electrode) 11 acting as a lower electrode, an electron blocking layer 16A formed on the lower electrode 11, a photoelectric conversion layer 12 formed on the electron blocking layer 16A, and a transparent conductive film (hereinafter, referred to as a upper electrode) 15 acting as a upper electrode are laminated in this order.

FIG. 1B illustrates a configuration example of another photoelectric conversion device. A photoelectric conversion device 10b as illustrated in FIG. 1B has a configuration in which an electron blocking layer 16A, a photoelectric conversion layer 12, a hole blocking layer 16B, and an upper electrode 15 are laminated on a lower electrode 11 in this order. Meanwhile, the lamination order of the electron blocking layer, the photoelectric conversion layer and the hole blocking layer of FIG. 1A and FIG. 1B may be reversed according to usage or properties.

In these configurations, it is preferred that light is incident to the organic photoelectric conversion film through the transparent conductive film.

In the case where the photoelectric conversion devices are used, an electric field may be applied. In this case, the conductive film and the transparent conductive film are used as a pair of electrodes, and an electric field of, for example, $1 \times 10^{-4}$ V/cm to $1 \times 10^{7}$ V/cm may be applied between the pair of electrodes.

Elements constituting the photoelectric conversion device according to the embodiment of the present invention will be described.

(Electrode)

The electrodes (the upper electrode (transparent conductive film) 15 and the lower electrode (conductive film) 11)) are composed of a conductive material. As the conductive material, for example, metals, alloys, metal oxides, an organic conductive compound, or a mixture thereof may be used.

Since light is incident from the upper electrode 15, the upper electrode 15 needs to be sufficiently transparent with respect to light to be detected. Specific examples include conductive metal oxides such as antimony or fluorine doped tin oxide (ATO, FTO), tin oxide, zinc oxide, indium oxide, indium tin oxide (ITO) and indium zinc oxide (IZO), metal thin films such as gold, silver, chromium and nickel, mixtures or laminates of the metals and the conductive metal oxides, inorganic conductive materials such as copper iodide and copper sulfide, organic conductive compounds such as polyaniline, polythiophene and polypyrrole, and laminates of the organic conductive compound and ITO. Among them, the transparent conductive metal oxides are preferred from the viewpoint of the high conductivity and transparency. Since the upper electrode 15 is formed on the photoelectric conversion layer 12, it is preferred that the upper electrode is formed by using a method that does not deteriorate the characteristics of the photoelectric conversion layer 12.

The lower electrode 11 includes a case of using a material whose transparency is imparted and, on the contrary, a case of using a material that reflects light without imparting transparency, depending on usage. Specific examples thereof include conductive metal oxides such as antimony or fluorine doped tin oxide (ATO, FTO), tin oxide, zinc oxide, indium oxide, indium tin oxide (ITO) and indium zinc oxide (IZO), metals such as gold, silver, chromium, nickel, titanium, tungsten and aluminum, and conductive compounds such as oxides or nitrides of the metals (for example, TiN), or mixtures or laminates of the metals and the conductive metal oxides, inorganic conductive compounds such as copper iodide and copper sulfide, organic conductive compounds such as polyaniline, polythiophene and polypyrrole, and laminates of the organic conductive compound and ITO or titanium nitride.

A method for forming the electrode is not particularly limited, but may be appropriately selected in consideration of suitability with the electrode material. In detail, the electrode may be formed by a wet method such as a printing method and a coating method, a physical method such as a vacuum deposition method, a sputtering method, and an ion plating method, and a chemical method such as CVD, and a plasma CVD method.

In the case where the material of the electrode is ITO, the electrode may be formed by a method such as an electron beam method, a sputtering method, a resistance heating deposition method, a chemical reaction method (sol-gel method) and coating of dispersion materials of indium tin oxide. Further, UV-ozone treatment and plasma treatment may be performed on the film manufactured by using ITO. In the case where the material of the electrode is TiN, various methods including a reactive sputtering method are used, and UV-ozone treatment and plasma treatment may be performed.

It is preferred that the upper electrode 15 is fabricated in a plasma-free state. By fabricating the upper electrode 15 in a plasma-free state, an influence of the plasma on the substrate may be decreased, thereby improving the characteristics of the photoelectric conversion. Herein, the plasma-free means a state where the plasma is not generated in formation of the upper electrode 15, or where a distance from a plasma generation source to the substrate is 2 cm or more, preferably 10 cm or more, and still more preferably 20 cm or more, and the plasma arrived at the substrate is reduced.

An apparatus where a plasma is not generated in formation of the upper electrode 15 includes, for example, an electron beam deposition apparatus (EB deposition apparatus) or a pulse laser deposition apparatus. With respect to the EB deposition apparatus or pulse laser deposition apparatus, the apparatuses disclosed in "New Development of Transparent Conductive Film" (published by CMC Publishing Co. Ltd., 1999) under the supervision of Sawada Yutaka, "New Development of Transparent Conductive Film II" (published by CMC Publishing Co. Ltd., 2002) under the supervision of Sawada Yutaka, "Technology of Transparent Conductive Film" (Ohmsha, Ltd., 1999) written by the Japan Society for the Promotion of Science (JSPS) and references added thereto may be used. Hereinafter, a method for forming a transparent electrode film by using the EB deposition apparatus is called an EB deposition method, and a method for forming a transparent electrode film by using the pulse laser deposition apparatus is called a pulse laser deposition method.

With respect to an apparatus for realizing a state where a distance from the plasma generation source to the substrate is 2 cm or more, and the plasma arrived at the substrate is reduced (hereinafter, referred to as a plasma-free film forming apparatus), for example, a facing target sputter apparatus or an arc plasma deposition method may be considered. With respect to those, the apparatuses disclosed in "New Development of Transparent Conductive Film" (published by CMC Publishing Co. Ltd., 1999) under the supervision of Sawada Yutaka, "New Development of Transparent Conductive Film II" (published by CMC Publishing Co. Ltd., 2002) under the supervision of Sawada Yutaka, "Technology of Transparent Conductive Film" (Ohmsha, Ltd., 1999) written by the Japan Society for the Promotion of Science (JSPS) and references added thereto may be used.

In the case where the transparent conductive film such as TCO is used as the upper electrode 15, DC short-circuiting or leakage current may be increased. One of these reasons is that fine cracks introduced into the photoelectric conversion layer 12 are covered by a dense film such as TCO, such that conduction with a first electrode film 11 placed at an opposite side is increased. Accordingly, in the case of the electrode made of Al having a relatively poor film quality, it is difficult to increase leakage current. The increase in the leakage current may be largely suppressed by controlling the film thickness of the upper electrode 15 with respect to the film thickness of the photoelectric conversion layer 12 (that is, a depth of crack). The thickness of the upper electrode 15 is required to be ⅕ or less, and preferably ⅒ or less of the thickness of the photoelectric conversion layer 12.

In general, if the conductive film is formed thinner than a predetermined range, a resistance value is rapidly increased, but in the solid-state imaging device into which the photoelectric conversion device according to the present embodiment is inserted, a sheet resistance value may preferably be 100Ω/□ to 10,000Ω/□, and the degree of freedom of the film thickness range utilized in film thinning is large. Further, as the thickness of the upper electrode (transparent conductive film) 15 is decreased, a quantity of absorbed light is decreased, such that the light transmittance is generally increased. The increase in the light transmittance is preferred in that light absorption in the photoelectric conversion layer 12 is increased, and thus, the photoelectric conversion ability is increased. In consideration of suppression of the leakage current, the increase in thin film resistance and the increase in transmittance accompanied by the film thinning, the film thickness of the upper electrode 15 is required to be preferably 5 nm to 100 nm, and more preferably 5 nm to 20 nm.

It is preferred for the photoelectric conversion device that a transparent conductive thin film is formed directly on the organic photoelectric conversion film.

(Photoelectric Conversion Layer)

The photoelectric conversion layer in the photoelectric conversion device of the present invention includes a compound having an absorption maximum at 400 nm or more and less than 720 nm in a UV-visible absorption spectrum, wherein a molar extinction coefficient is 10,000 mol$^{-1}$·l·cm$^{-1}$ or more at the absorption maximum wavelength, and a difference between a melting point and a deposition temperature (a melting point–a deposition temperature) is 31° C. or more. This compound may be exemplified by the compound of the present invention as described above. It is preferred that this compound functions as a p-type semiconductor.

[n-Type Organic Semiconductor]

It is preferred that the organic photoelectric conversion film further contains an n-type organic semiconductor in addition to the compound represented by Formula (I). Preferably, the n-type organic semiconductor, together with the compound represented by Formula (I), may be contained in the photoelectric conversion layer 12.

The n-type organic semiconductor is an acceptor organic semiconductor, represented by an electron transporting organic compound, and an organic compound having a property of easily accepting electrons. More particularly, the n-type organic semiconductor is an organic compound having higher electron affinity when two organic compounds are used in contact. Accordingly, the acceptor organic compound may be any organic compound as long as the organic compound has an electron accepting property. Example thereof include fullerene or a fullerene derivative, a condensed aromatic carbocyclic compound (a naphthalene derivative, an anthracene derivative, a phenanthrene derivative, a tetracene derivative, a pyrene derivative, a perylene derivative, a fluoranthene derivative), a 5- to 7-membered heterocyclic compound containing a nitrogen atom, an oxygen atom or a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyrrolidine, pyrrolopyridine, thiadiazolopyridine, dibenzazepine, tribenzazepine and the like), a polyarylene compound, a fluorine compound, a cyclopentadiene compound, a silyl compound, a metal complex having a nitrogen-containing heterocyclic compound as a ligand.

The n-type semiconductor is preferably fullerene or a fullerene derivative.

The fullerene refers to fullerene $C_{60}$, fullerene $C_{70}$, fullerene $C_{76}$, fullerene $C_{78}$, fullerene $C_{80}$, fullerene $C_{82}$, fullerene $C_{84}$, fullerene $C_{90}$, fullerene $C_{96}$, fullerene $C_{240}$, fullerene$_{540}$, mixed fullerene, a fullerene nanotube, and the fullerene derivative represents a compound in which a substituent is added thereto. The substituent is preferably an alkyl group, an aryl group or a heterocyclic group.

The fullerene derivative is preferably a compound as described in Japanese Patent Application Laid-Open No. 2007-123707.

As fullerene and fullerene derivatives, the compounds as described in Scientific Review Quarterly edited by the Chemical Society of Japan No. 43 (1999), Japanese Patent Application Laid-Open No. H10-167994, Japanese Patent Application Laid-Open No. H11-255508, Japanese Patent Application Laid-Open No. H11-255509, Japanese Patent Application Laid-Open No. 2002-241323 and Japanese Patent Application Laid-Open No. 2003-196881 may be used.

Among the fullerene and fullerene derivatives, fullerene is preferred, and fullerene $C_{60}$ is particularly preferred.

It is preferred that the organic photoelectric conversion film has a bulk hetero structure formed by the compound represented by Formula (1) and fullerene or fullerene derivatives in a mixed state. The bulk hetero structure is a film in which the p-type organic semiconductor (the compound represented by Formula (1)) and the n-type organic semiconductor are mixed and dispersed in the photoelectric conversion layer, and may be formed, for example, by a co-deposition method. The photoelectric conversion efficiency of the photoelectric conversion layer may be improved by containing the heterojunction structure such that a disadvantage in that a carrier diffusion length of the photoelectric conversion layer is short is compensated. Meanwhile, the bulk heterojunction structure is described in detail in paragraphs [0013] and [0014] of Japanese Patent Application Laid-Open No. 2005-303266.

The molar ratio of fullerene or a fullerene derivative to the compound represented by Formula (I) (fullerene or a fullerene derivative/the compound represented by Formula (1)) is preferably 0.5 or more, more preferably 1 or more, and still more preferably 3 or more. Further, it is more preferred to be 1 to 10 (molar ratio), and it is still more preferred to be 3 to 7 (molar ratio).

(Non-Luminescent Film)

In the organic photoelectric conversion film, the film in which the compound represented by Formula (I) and the n-type organic semiconductor are mixed is a non-luminescent film, and has different characteristics from organic light emitting diodes. The non-luminescent film refers to a case of film having a luminescence quantum efficiency of 1% or less, more preferably 0.5% or less, and still more preferably 0.1% or less.

The organic photoelectric conversion film may be formed by a dry film forming method or a wet film forming method. Specific examples of the dry film forming method include a physical vapor growth method such as a vacuum deposition method, a sputtering method, an ion plating method and a MBE method or a CVD method such as plasma polymerization. As the wet film forming method, a cast method, a spin coat method, a dipping method and a LB method are used. The dry film forming method is preferred, and the vacuum deposition method is more preferred. In the case where the layer is formed by the vacuum deposition method, manufacturing conditions such as a degree of vacuum and a deposition temperature may be determined according to a general method.

The thickness of the photoelectric conversion layer is preferably 10 to 1,000 nm, more preferably 50 to 800 nm, and particularly preferably 100 to 500 nm. By setting the thickness to 10 nm or more, a suitable dark current suppression effect can be obtained, and by setting the thickness to 1000 nm or less, a suitable photoelectric conversion efficiency can be obtained.

[Electric Charge Blocking Layer: Electron Blocking Layer, Hole Blocking Layer]

(Electron Blocking Layer)

An electron donating organic material may be used in the electron blocking layer. Particularly, for low molecular weight materials, aromatic diamine compounds such as N,N-bis(3-methylphenyl)-(1,1'-biphenyl)-4,4'-diamine (TPD) or 4,4'-bis[N-(naphthyl)-N-phenyl-amino]biphenyl (α-NPD), oxazole, oxadiazole, triazole, imidazole, imidazolone, a stilbene derivative, a pyrazoline derivative, tetrahydroimidazole, polyarylalkane, butadiene, 4,4',4"-tris(N-(3-methylphenyl)N-phenylamino)triphenylamine (m-MTDATA), porphyrin compounds such as porphine, copper tetraphenylporphine, phthalocyanine, copper phthalocyanine and titanium phthalocyanine oxide, a triazole derivative, an oxadiazole derivative, an imidazole derivative, a polyarylalkane derivative, a pyrazoline derivative, a pyrazolone derivative, a phenylenediamine derivative, an anylamine derivative, an amino-substituted chalcone derivative, an oxazole derivative, a styrylanthracene derivative, a fluorenone derivative, a hydrazone derivative, a silazane derivative and the like may be used, and for high molecular weight materials, polymers such as phenylenevinylene, fluorene, carbazole, indole, pyrene, pyrrole, picoline, thiophene, acetylene and diacetylene, or derivatives thereof may be used. Other than the electron donating compound, any compound may be used as long as the compound has a sufficient hole transportability.

Particularly, the compounds as described in [0083] to [0089] of Japanese Patent Application Laid-Open No. 2008-72090.

It is also preferred that the electron blocking layer contains a compound represented by Formula (F-1).

(F-1)

[Chem. 58]

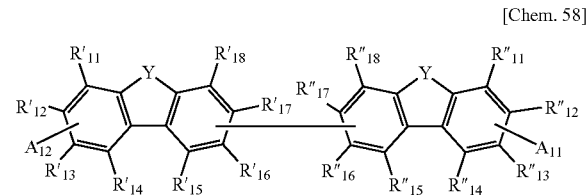

In Formula (F-1), each of $R''_{11}$ to $R''_{18}$ and $R'_{11}$ to $R'_{18}$ independently represents a hydrogen atom, a halogen atom, an alkyl group, an aryl group, a heterocyclic group, a hydroxyl group, an amino group or a mercapto group, and these may further have a substituent. Any one of $R''_{15}$ to $R''_{18}$ is linked to any one of $R'_{15}$ to $R'_{18}$ to form a single bond. Each of $A_{11}$ and $A_{12}$ independently represents a group represented by the following Formula (A-1), and is substituted as any one of $R''_{11}$ to $R''_{14}$ and $R'_{11}$ to $R'_{14}$. Each Y independently represents a carbon atom, a nitrogen atom, an oxygen atom, a sulfur atom or a silicon atom, and these may further have a substituent.

Formula (A-1)

[Chem. 59]

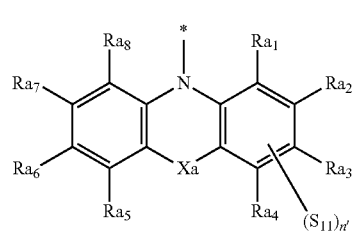

In Formula (A-1), each of $Ra_1$ to $Ra_8$ independently represents a hydrogen atom, a halogen atom, an alkyl group, an aryl group or a heterocyclic group, and these may further have a substituent. * represents a bonding position. Xa represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent. Each $S_{11}$ independently represents the following Substituent ($S_{11}$), and substituted into any one of $Ra_1$ to $Ra_8$. n' represents an integer of 0 to 4.

Substituent ($S_{11}$)

[Chem. 60]

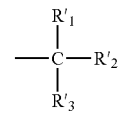

(Each of $R'_1$ to $R'_3$ independently represents a hydrogen atom or an alkyl group.)

In Formula (F-1), each of $R''_{11}$ to $R''_{18}$ and $R'_{11}$ to $R'_{18}$ independently represents a hydrogen atom, a halogen atom, an alkyl group, an aryl group, a heterocyclic group, a hydroxyl group, an amino group or a mercapto group, and these may further have a substituent. Specific examples of the further substituent may be exemplified by Substituent W as described above, and include preferably a halogen atom, an alkyl group, an aryl group, a heterocyclic group, a hydroxyl group, an amino group or a mercapto group, more preferably a halogen atom, an alkyl group, an aryl group or a heterocyclic group, still more preferably a fluorine atom, an alkyl group or an aryl group, particularly preferably an alkyl group or an aryl group, and most preferably an alkyl group.

$R''_{11}$ to $R''_{18}$ and $R'_{11}$ to $R'_{18}$ are preferably a hydrogen atom, an alkyl group which may have a substituent, an aryl group or a heterocyclic group, more preferably a hydrogen atom, an alkyl group having 1 to 18 carbon atoms which may have a substituent, an aryl group having 6 to 18 carbon atoms or a heterocyclic group having 4 to 16 carbon atoms. Among them, it is preferred that each of $R''_{12}$ and $R'_{12}$ is independently substituted by the substituent represented by Formula (A-1), it is more preferred that each of $R''_{12}$ and $R'_{12}$ is independently substituted by the substituent represented by Formula (A-1), and $R''_{11}$, $R''_{13}$ to $R''_{18}$, $R'_{11}$ and $R'_{13}$ to $R'_{18}$ are a hydrogen atom or an alkyl group having 1 to 18 carbon atoms which may have a substituent, and it is particularly preferred that each of R"$_{12}$ and R'$_{12}$ is independently substituted by the substituent represented by Formula (A-1), and R"$_{11}$, R"$_{13}$ to R"$_{18}$, R'$_{11}$ and R'$_{13}$ to R'$_{18}$ are a hydrogen atom.

Each Y independently represents a carbon atom, a nitrogen atom, an oxygen atom, a sulfur atom or a silicon atom, and these may further have a substituent. That is, Y represents a divalent linking group containing a carbon atom, a nitrogen atom, an oxygen atom, a sulfur atom or a silicon atom. Among them, —C(R'$_{21}$)(R'$_{22}$)—, —Si(R'$_{23}$)(R'$_{24}$)— and —N(R'$_{20}$)— are preferred, —C(R'$_{21}$)(R'$_{22}$)— and —N(R'$_{20}$)— are more preferred, and —C(R'$_{21}$)(R'$_{22}$)— is particularly preferred.

In —C(R'$_{21}$)(R'$_{22}$)—, each of R'$_{21}$ and R'$_{22}$ independently represents a hydrogen atom, a halogen atom, an alkyl group which may have a substituent, an aryl group or a heterocyclic group, a hydroxyl group, an amino group or a mercapto group. Specific examples of the further substituent may be exemplified by Substituent W. R'$_{21}$ and R'$_{22}$ are preferably a hydrogen atom, an alkyl group which may have a substituent, an aryl group or a heterocyclic group, more preferably a hydrogen atom, an alkyl group having 1 to 18 carbon atoms which may have a substituent, an aryl group having 6 to 18 carbon atoms or a heterocyclic group having 4 to 16 carbon atoms, still more preferably a hydrogen atom or an alkyl group having 1 to 18 carbon atoms which may have a substituent, and particularly preferably an alkyl group having 1 to 18 carbon atoms.

In —Si(R'$_{23}$)(R'$_{24}$)—, each of R'$_{23}$ and R'$_{24}$ independently represents a hydrogen atom, a halogen atom, an alkyl group which may have a substituent, aryl group or a heterocyclic group, a hydroxyl group, an amino group or a mercapto group. Specific examples of the further substituent may be exemplified by Substituent W. R'$_{23}$ and R'$_{24}$ are preferably a hydrogen atom, an alkyl group which may have a substituent, an aryl group or a heterocyclic group, more preferably a hydrogen atom, an alkyl group having 1 to 18 carbon atoms which may have a substituent, an aryl group having 6 to 18 carbon atoms or a heterocyclic group having 4 to 16 carbon atoms, still more preferably a hydrogen atom, an alkyl group having 1 to 18 carbon atoms which may have a substituent, and particularly preferably an alkyl group having 1 to 18 carbon atoms.

In —N(R'$_{20}$)—, R'$_{20}$ represents an alkyl group which may have a substituent, an aryl group or a heterocyclic group. Specific examples of the further substituent may be exemplified by Substituent W. R'$_{20}$ is more preferably a hydrogen atom, an alkyl group having 1 to 18 carbon atoms which may have a substituent, an aryl group having 6 to 18 carbon atoms or a heterocyclic group having 4 to 16 carbon atoms, still more preferably a hydrogen atom, an alkyl group having 1 to 18 carbon atoms which may have a substituent, and particularly preferably an alkyl group having 1 to 18 carbon atoms.

Each of Ra$_1$ to Ra$_8$ in Formula (A-1) independently represents a hydrogen atom, a halogen atom, an alkyl group which may have a substituent, an aryl group or a heterocyclic group, a hydroxyl group, an amino group or a mercapto group. Specific examples of the further substituent may be exemplified by Substituent W. Further, a plurality of substitutents described above may be bound to each other to form a ring.

Ra$_1$ to Ra$_8$ are preferably a hydrogen atom, a halogen atom, an alkyl group having 1 to 18 carbon atoms, an aryl group having 6 to 18 carbon atoms or a heterocyclic group having 4 to 16 carbon atoms, more preferably a hydrogen atom, an alkyl group having 1 to 12 carbon atoms or an aryl group having 6 to 14 carbon atoms, and still more preferably a hydrogen atom, an alkyl group having 1 to 6 carbon atoms or an aryl group having 6 to 10 carbon atoms. The alkyl group may be branched.

Preferred specific examples may include a hydrogen atom, a methyl group, an ethyl group, a propyl group, a butyl group, a hexyl group, a cyclohexyl group, a phenyl group and a naphthyl group.

Further, it is particularly preferred that Ra$_1$ and Ra$_6$ are a hydrogen atom or an alkyl group having 1 to 6 carbon atoms, and Ra$_1$, Ra$_2$, Ra$_4$, Ra$_5$, Ra$_7$ and Ra$_8$ are a hydrogen atom.

Xa represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent.

Xa is preferably a single bond, an alkylene group having 1 to 12 carbon atoms, an alkenylene group having 2 to 12 carbon atoms, an arylene group having 6 to 14 carbon atoms, a heterocyclic group having 4 to 13 carbon atoms, an oxygen atom, a sulfur atom, an imino group having a hydrocarbon group (preferably an aryl group or an alkyl group) having 1 to 12 carbon atoms (for example, a phenylimino group, a methylimino group or a t-butylimino group) or a silylene group, more preferably a single bond, an oxygen atom, an alkylene group having 1 to 6 carbon atoms (for example, a methylene group, a 1,2-ethylene group or a 1,1-dimethylmethylene group), an alkenylene group having 2 carbon atoms (for example, —CH$_2$=CH$_2$—), an arylene group having 6 to 10 carbon atoms (for example, a 1,2-phenylene group or a 2,3-naphthylene group) or a silylene group, and still more preferably a single bond, an oxygen atom or an alkylene group having 1 to 6 carbon atoms (for example, a methylene group, a 1,2-ethylene group or a 1,1-dimethylmethylene group). These substituents may further have Substituent W as described below.

Specific examples of the group represented by Formula (A-1) may include groups exemplified by the following N-1 to N-11. However, the group is not limited thereto. Preferably, the group represented by Formula (A-1) is more preferably N-1 to N-7, more preferably N-1 to N-6, still more preferably N-1 to N-3, particularly preferably N-1 to N-2, and most preferably N-1.

[Chem. 61]

N-1

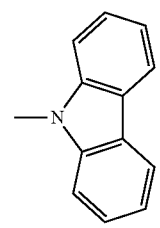

N-2

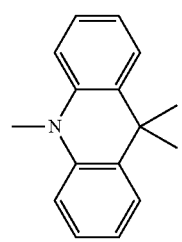

N-3 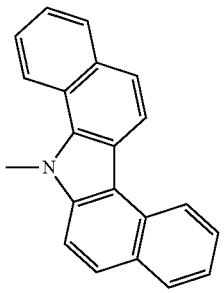

N-4 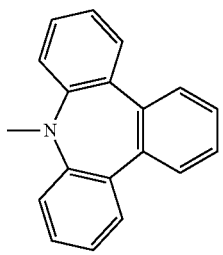

N-5 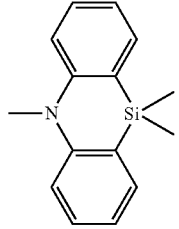

N-6 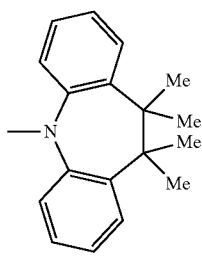

N-7 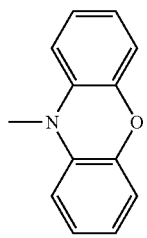

N-8 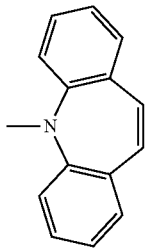

N-9 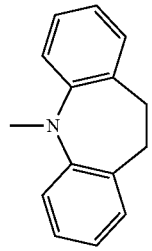

N-10 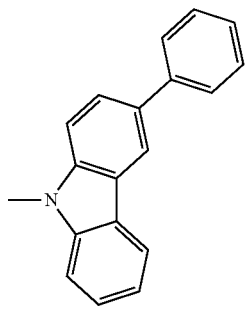

N-11 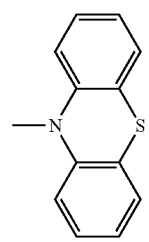

In Substituent ($S_{11}$), $R'_1$, represents a hydrogen atom or an alkyl group. $R'_1$ is preferably a methyl group, an ethyl group, a propyl group, an iso-propyl group, a butyl group or a tert-butyl group, more preferably a methyl group, an ethyl group, a propyl group, an iso-propyl group or a tert-butyl group, still more preferably a methyl group, an ethyl group, an iso-propyl group or a tert-butyl group, and particularly preferably a methyl group, an ethyl group or a tert-butyl group.

$R'_2$ represents a hydrogen atom or an alkyl group. $R'_2$ is preferably a hydrogen atom, a methyl group, an ethyl group, a propyl group, an iso-propyl group, a butyl group or a tert-butyl group, still more preferably a hydrogen atom, a methyl group, an ethyl group or a propyl group, more preferably a hydrogen atom or a methyl group, and particularly preferably a methyl group.

$R'_3$ represents a hydrogen atom or an alkyl group. $R'_3$ is preferably a hydrogen atom or a methyl group, and more preferably a methyl group.

Further, each of $R'_1$ to $R'_3$ may be bound to each other to form a ring. When forming a ring, the number of ring members is not particularly limited, but a 5- or 6-membered ring is preferred, and a 6-membered ring is more preferred.

$S_{11}$ represents Substituent ($S_{11}$), and is substituted by any one of $Ra_1$ to $Ra_8$. It is preferred that at least one of $Ra_1$ and $Ra_6$ in Formula (A-1) independently represents Substituent ($S_{11}$).

Substituent ($S_{11}$) may be exemplified by preferably the following (a) to (x), more preferably (a) to (j), still more preferably (a) to (h), particularly preferably (a) to (f), still yet more preferably (a) to (c), and most preferably (a).

[Chem. 62]
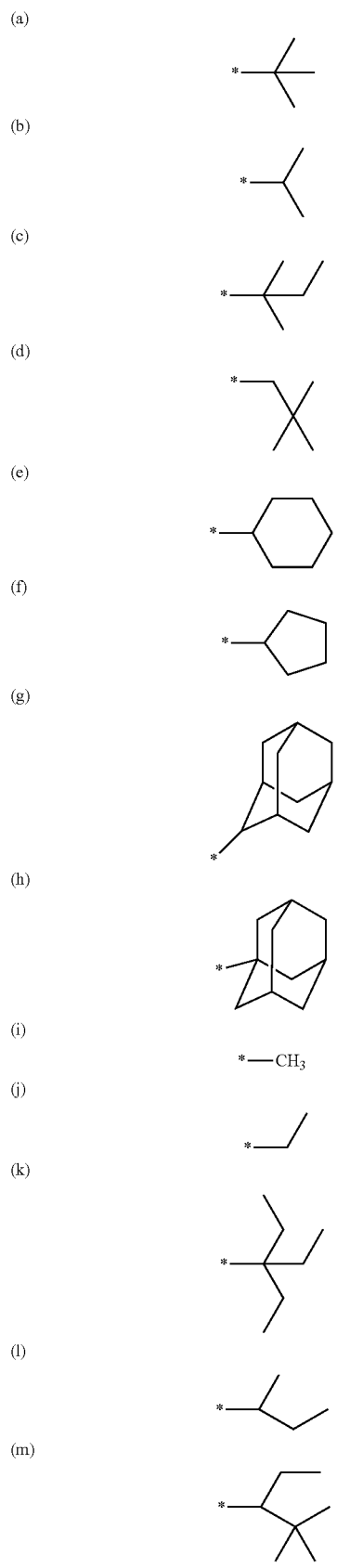
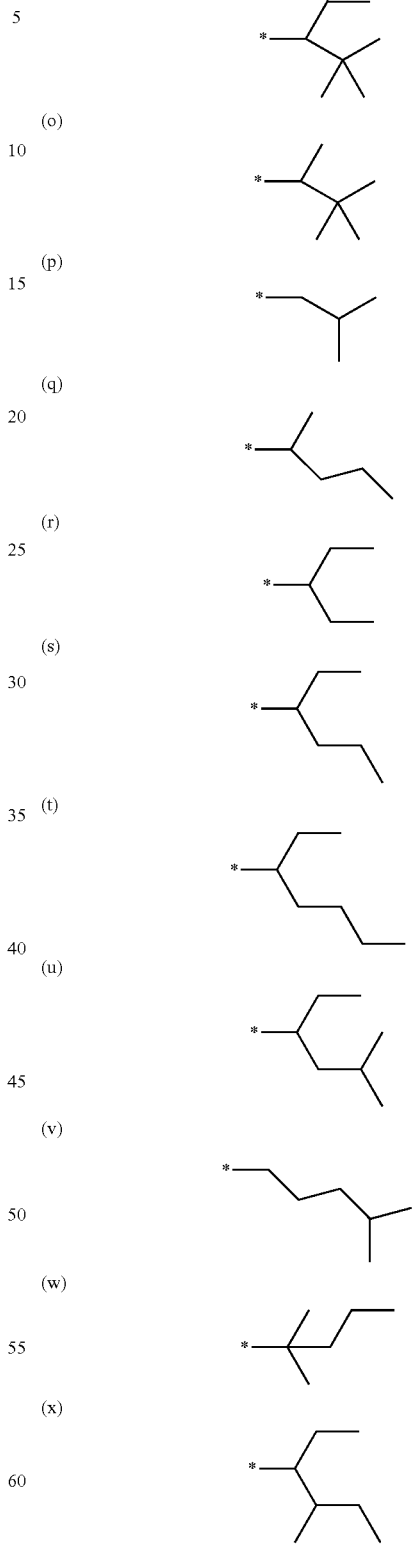
each n' independently represents an integer of 0 to 4, preferably 0 to 3, more preferably 0 to 2, still more preferably 1 to 2, and particularly preferably 2.

Formula (A-1) may be a group represented by the following Formula (A-3), a group represented by the following Formula (A-4) or a group represented by the following Formula (A-5).

[Chem. 63]

(A-3)
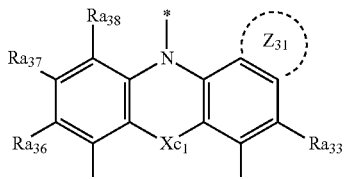

(A-4)
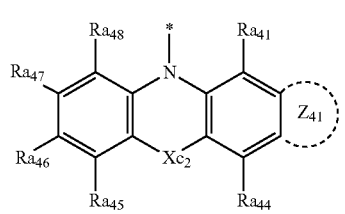

(A-5)
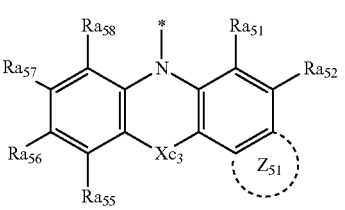

In Formula (A-3) to (A-5), each of $Ra_{33}$ to $Ra_{38}$, $Ra_{41}$, $Ra_{44}$ to $Ra_{48}$, $Ra_{51}$, $Ra_{52}$ and $Ra_{55}$ to $Ra_{58}$ independently represents a hydrogen atom, a halogen atom or an alkyl group, and these may further have a substituent. * represents a bonding position. Each of $Xc_1$, $Xc_2$ and $Xc_3$ independently represents a single bond, an oxygen atom, a sulfur atom, an alkylene group, a silylene group, an alkenylene group, a cycloalkylene group, a cycloalkenylene group, an arylene group, a divalent heterocyclic group or an imino group, and these may further have a substituent. Each of $Z_{31}$, $Z_{41}$ and $Z_{51}$ independently represents a cycloalkyl ring, an aromatic hydrocarbon ring or an aromatic heterocyclic ring, and these may further have a substituent.

In Formula (A-3) to (A-5), each of $Ra_{33}$ to $Ra_{38}$, $Ra_{41}$, $Ra_{44}$ to $Ra_{48}$, $Ra_{51}$, $Ra_{52}$ and $Ra_{55}$ to $Ra_{58}$ independently represents a hydrogen atom, a halogen atom (preferably a fluorine atom, a chlorine atom, a bromine atom or an iodine atom) or an alkyl group. For the reason that a substituent having a low polarity is advantageous in to hole transportation, a hydrogen atom or an alkyl group is preferred, and a hydrogen atom is more preferred.

When $Ra_{33}$ to $Ra_{38}$, $Ra_{41}$, $Ra_{44}$ to $Ra_{48}$, $Ra_{51}$, $Ra_{52}$ and $Ra_{55}$ to $Ra_{58}$ represent an alkyl group, the alkyl group is preferably an alkyl group having 1 to 18 carbon atoms, more preferably an alkyl group having 1 to 12 carbon atoms, and still more preferably an alkyl group having 1 to 6 carbon atoms. Specifically, a methyl group, an ethyl group, a propyl group, a butyl group, a hexyl group or a cyclohexyl group is preferred.

In Formulas (A-3) to (A-5), any adjacent groups of $Ra_{33}$ to $Ra_{38}$, $Ra_{41}$, $Ra_{44}$ to $Ra_{48}$, $Ra_{51}$, $Ra_{52}$ and $Ra_{55}$ to $Ra_{58}$ may be bound to each other to form a ring. The ring may be exemplified by Ring R as described below. This ring is preferably a benzene ring, a naphthalene ring, an anthracene ring, a pyridine ring, a pyrimidine ring or the like.

Each of $Xc_1$, $Xc_2$ and $Xc_3$ independently represents a single bond, an oxygen atom, a sulfur atom, an alkylene group, a silylene group, an alkenylene group, a cycloalkylene group, a cycloalkenylene group, an arylene group, a divalent heterocyclic group or an imino group. When $Xc_1$, $Xc_2$ and $Xc_3$ represent an alkylene group, a silylene group, an alkenylene group, a cycloalkylene group, a cycloalkenylene group, an arylene group, a divalent heterocyclic group or an imino group, these may further have a substituent. The further substituent may be exemplified by Substituent W as described below.

$Xc_1$, $Xc_2$ and $Xc_3$ are preferably a single bond, an alkylene group having 1 to 12 carbon atoms, an alkenylene group having 2 to 12 carbon atoms, an arylene group having 6 to 14 carbon atoms, a heterocyclic group having 4 to 13 carbon atoms, an oxygen atom, a sulfur atom, an imino group having a hydrocarbon group (preferably an aryl group or an alkyl group) having 1 to 12 carbon atoms (for example, a phenylimino group, a methylimino group and a t-butylimino group), and more preferably a single bond, an alkylene group having 1 to 6 carbon atoms (for example, a methylene group, a 1,2-ethylene group and a 1,1-dimethylmethylene group), an alkenylene group having 2 carbon atoms (for example, $—CH_2=CH_2—$), an arylene group having 6 to 10 carbon atoms (for example, a 1,2-phenylene group and a 2,3-naphthylene group).

Each of $Z_{31}$, $Z_{41}$ and $Z_{51}$ independently represents a cycloalkyl ring, an aromatic hydrocarbon ring or an aromatic heterocyclic ring. In Formulas (A-3) to (A-5), $Z_{31}$, $Z_{41}$ and $Z_{51}$ are condensed with a benzene ring. For the reason that a high heat resistance and a high hole transportability can be expected, $Z_{31}$, $Z_{41}$ and $Z_{51}$ are preferably an aromatic hydrocarbon ring.

Meanwhile, the electron blocking layer may be constituted in plural.

An inorganic material may be used in the electron blocking layer. In general, since inorganic materials have higher permittivity than organic materials, when used in the electron blocking layer, a great quantity of voltage is applied to the photoelectric conversion layer, thereby increasing the photoelectric conversion efficiency. Examples of the material that may be the electron blocking layer include calcium oxide, chromium oxide, chromium copper oxide, manganese oxide, cobalt oxide, nickel oxide, copper oxide, gallium copper oxide, strontium copper oxide, niobium oxide, molybdenum oxide, indium copper oxide, indium silver oxide, iridium oxide and the like. In the case where the electron blocking layer is a single layer, the layer may be formed of an inorganic material, and in the case where the charge blocking layer is a multi-layer, one or more layers may be formed of an inorganic material.

(Hole Blocking Layer)

An electron accepting organic material may be used in the hole blocking layer.

As the electron accepting material, an oxadiazole derivative such as 1,3-bis(4-tert-butylphenyl-1,3,4-oxadiazolyl)phenylene (OXD-7), an anthraquinodimethane derivative, a diphenylquinone derivative, bathocuproine, bathophenanthroline and a derivative thereof, a triazole compound, a tris(8-hydroxyquinolinate)aluminum complex, a bis(4-methyl-8-quinolinate)aluminum complex, a distyrylarylene derivative, a sylol compound, and the like may be used. Further, other than the electron accepting organic material, any materials may be used as long as the material has a sufficient electron transportability. A porphyrin-based compound, a styryl-based compound such as DCM (4-dicyanomethylene-2-methyl-6-(4-(dimethylaminostyryl))-4H pyran) and a 4H pyran-based compound may be used. Specifically, compounds as disclosed in paragraphs [0073] to [0078] of Japanese Patent Application Laid-Open No. 2008-72090 are preferred.

The thickness of the electron blocking layer and the hole blocking layer is preferably 10 nm to 200 nm, respectively, still more preferably 30 nm to 150 nm, and particularly preferably 50 nm to 100 nm. If this thickness is too thin, the dark current suppression effect is deteriorated, and if too thick, the photoelectric conversion efficiency is deteriorated. Further, when the photoelectric conversion device includes an electric charge blocking layer, it is more preferred to include an electron blocking layer.

[Photosensor]

The photoelectric conversion device may be largely categorized into a photocell and a photosensor, and the photoelectric conversion device of the present invention is suitable for a photosensor. The photosensor may include a form in which the photoelectric conversion device is used alone, or a form of a line sensor in which the photoelectric conversion device is arranged in a straight line form or a two dimensional sensor in which the photoelectric conversion device is arranged in a plane. The photoelectric conversion device of the present invention acts as an imaging device by converting light imaging information into an electric signal by using an optical system and a driving part as in a scanner in the case of a line sensor and by imaging the light imaging information on the sensor using an optical system as in an imaging module and converting light imaging information into an electric signal in the case of a two-dimensional sensor.

Since a photocell is a power generating apparatus, efficiency for converting light energy into electric energy is an important performance, but a dark current that is a current in a dark place is not considered as problematic in terms of a function. Furthermore, a heating process at a rear end is not required in installation of a color filter. Since an important performance of the photosensor is to convert a light-dark signal into an electric signal with a high precision, efficiency for converting a light quantity into current is an important performance. However, if the signal is outputted from a dark place, the signal becomes a noise. Therefore, low dark current is required. In addition, resistance to the process at the rear end is also important.

[Imaging Device]

Subsequently, a configuration example of an imaging device having a photoelectric conversion device 10a will be described. Meanwhile, in the configuration examples as described below, like reference numerals designate like elements in the drawings with respect to the member having the same configuration or operation as previously described members, so that a description thereof is simplified or omitted.

The imaging device is a device for converting light information of an image into an electric signal, in which a plurality of photoelectric conversion devices are arranged on a matrix in the same plane form, the light signal is converted into the electric signal in each of the photoelectric conversion devices (pixel), and the electric signal per pixel is outputted sequentially to the outside of the imaging device. Accordingly, one photoelectric conversion device and one or more transistors are constituted per pixel.

Figure 2:
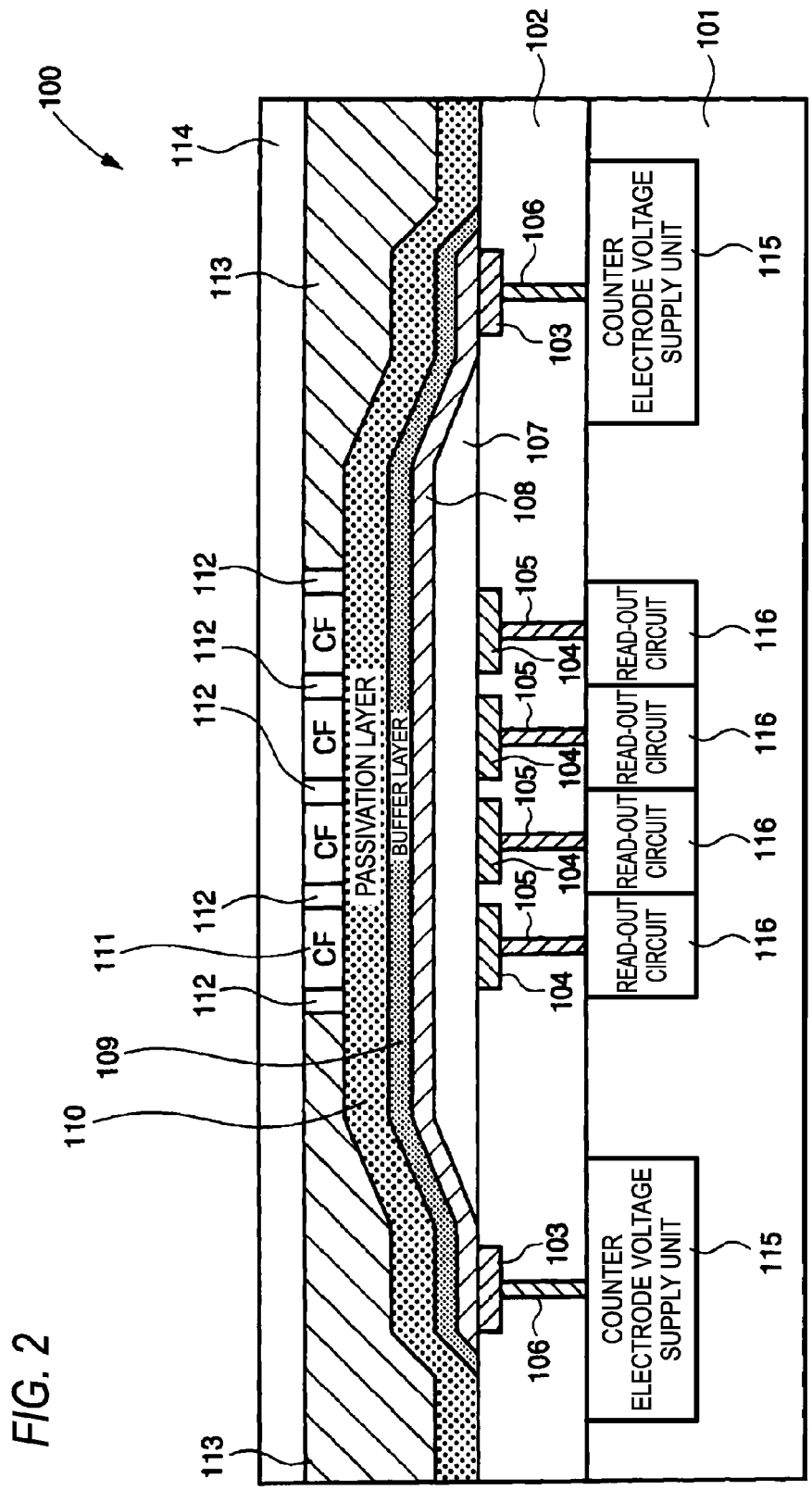
FIG. 2 is a cross-sectional schematic diagram of one pixel of an imaging device according to the present invention.

FIG. 2 is a schematic cross-sectional view illustrating a schematic configuration of an imaging device in order to describe an embodiment of the present invention. This imaging device is mounted and used in an imaging apparatus such as a digital camera and a digital video camera, an imaging module such as an electronic endoscope and a mobile phone, and the like.

This imaging device has a plurality of photoelectric conversion devices having the same configuration as shown in FIG. 1A and FIG. 1B, and a circuit board on which a read-out circuit that reads out signal according to the electric charge generated in the photoelectric conversion layer of each of the photoelectric conversion devices is formed, in which a plurality of photoelectric conversion devices are arranged in a one-dimensional or two-dimensional form on the same surface at the upper side of the circuit substrate.

An imaging device 100 as illustrated in FIG. 2 is provided with a substrate 101, an insulating layer 102, a connection electrode 103, a pixel electrode (lower electrode) 104, a connection portion 105, a connection portion 106, a photoelectric conversion layer 107, a counter electrode (upper electrode) 108, a buffer layer 109, a passivation layer 110, a color filter (CF) 111, a partitioning wall 112, a light shielding layer 113, a protective layer 114, a counter electrode voltage supply unit 115 and a read-out circuit 116.

The pixel electrode 104 has the same function as the electrode 11 of the photoelectric conversion device 10a as illustrated in FIG. 1A and FIG. 1B. The counter electrode 108 has the same function as the electrode 15 of the photoelectric conversion device 10a as illustrated in FIG. 1A and FIG. 1B. The photoelectric conversion layer 107 has the same configuration as a layer formed between the electrode 11 and the electrode 15 of the photoelectric conversion device 10a as illustrated in FIG. 1A and FIG. 1B.

The substrate 101 is a glass substrate or a semiconductor substrate such as Si. The insulating layer 102 is formed on the substrate 101. A plurality of pixel electrodes 104 and a plurality of connection electrodes 103 are formed on the surface of the insulating layer 102.

The photoelectric conversion layer 107 is a common layer to all the photoelectric conversion devices formed by covering a plurality of pixel electrodes 104 therewith.

The counter electrode 108, which is installed on the photoelectric conversion layer 107, is a common electrode to all the photoelectric conversion devices. The counter electrode 108 is formed to reach above the connection electrode 103 disposed at the outer side than the photoelectric conversion layer 107, and electrically connected to the connection electrode 103.

The connection portion 106 is buried in the insulating layer 102, and functions as a plug for electrically connecting the connection electrode 103 and the counter electrode voltage supply unit 115. The counter electrode voltage supply unit 115 is formed on the substrate 101, and applies a predetermined voltage to the counter electrode 108 through the connection portion 106 and connection electrode 103. In the case where the voltage applied to the counter electrode 108 is higher than a power source voltage of the imaging device, the predetermined voltage is supplied by boosting a power source voltage by using a voltage boosting circuit such as a charge pump.

The read-out circuit 116 is installed on the substrate 101 to correspond to each of a plurality of pixel electrodes 104, and reads out the signal according to the electric charge collected in the corresponding pixel electrode 104. The read-out circuit 116 is constituted by, for example, CCD, a CMOS circuit or a TFT circuit, and is shielded from light by a light shielding layer, which is not shown, disposed in the insulating layer 102. The read-out circuits 116 are electrically connected through the corresponding pixel electrode 104 and the corresponding connection portion 105.

The buffer layer 109 is formed on the counter electrode 108 so as to cover the counter electrode 108. The passivation layer 110 is formed on the buffer layer 109 so as to cover the buffer layer 109. The color filter 111 is formed at a position facing each of the pixel electrodes 104 on the passivation layer 110. The partition wall 112 is installed between the color filters 111, and improves light transmittance efficiency of the color filter 111.

The light shielding layer 113 is formed in a region other than a region in which the color filter 111 and the partition wall 112 are installed on the passivation layer 110, and prevents light from being incident to the photoelectric conversion layer 107 formed in a region other than an efficient pixel region. The protective layer 114 is formed on the color filter 111, the partition wall 112 and the light shielding layer 113, and protects the entire imaging device 100.

In the imaging device 100 constituted as described above, when light is incident, the light is incident to the photoelectric conversion layer 107, such that an electric charge is generated therefrom. The hole of the generated electric charge is collected in the pixel electrode 104, and the voltage signal according to the quantity thereof is outputted to the outside of the imaging device 100 by the read-out circuit 116.

The method for manufacturing the imaging device 100 is described below.

On the circuit substrate on which the counter electrode voltage supply unit 115 and the read-out circuit 116 are formed, the connection portions 105 and 106, a plurality of connection electrodes 103, a plurality of pixel electrodes 104 and the insulating layer 102 are formed. A plurality of pixel electrodes 104 are arranged on the surface of the insulating layer 102, for example, in a square lattice form.

Subsequently, the photoelectric conversion layer 107 is formed on the plurality of pixel electrodes 104, for example, by using a vacuum heating deposition method. Subsequently, the counter electrode 108 is formed on the photoelectric conversion layer 107, for example, by using a sputter method under vacuum. Next, the buffer layer 109 and the passivation layer 110 are sequentially formed on the counter electrode 108, for example, by using the vacuum heating deposition method. Subsequently, after the color filter 111, the partition wall 112 and the light shielding layer 113 are formed, the protective layer 114 is formed, thereby completing the manufacturing of the imaging device 100.

In the manufacturing method of the imaging device 100, although a process of placing the imaging device 100 under non-vacuum during the manufacturing is added between a process of forming the photoelectric conversion layer included in the photoelectric conversion layer 107 and a process of forming the passivation layer 110, performance deterioration of a plurality of photoelectric conversion devices can be prevented. The performance deterioration of the imaging device 100 may be prevented and a manufacturing cost may be suppressed by adding this process.

Hereinafter, the passivation layer 110, which is a configuration element of the imaging device 100 described above, will be described in detail.

[Passivation Layer]

The following requirements are needed for the passivation layer 110.

First, in each manufacturing process of the device, the photoelectric conversion layer should be protected by preventing invasion of a factor degrading the organic photoelectric conversion material contained in a solution, a plasma and the like.

Second, after the device is manufactured, degradation of the photoelectric conversion layer 107 should be prevented during preservation and use for a long period of time by preventing invasion of the factor degrading the organic photoelectric conversion material such as water molecules.

Third, when the passivation layer 110 is formed, the previously formed photoelectric conversion layer should not be degraded.

Fourth, since incident light reaches the photoelectric conversion layer 107 through the passivation layer 110, the passivation layer 110 should be transparent with respect to light of a wavelength detected in the photoelectric conversion layer 107.

The passivation layer 110 may be constituted by a thin film made of a single material, but effects such as relieving of total stress of the passivation layer 110, suppression of generation of defects such as cracks and pinholes by occurrence of dust during the manufacturing process, and easy optimization of material development can be expected by constituting the passivation layer with a multilayered structure so that different functions are provided to each of the layers. For example, the passivation layer 110 may have a double layer structure having a layer that achieves its original purpose of preventing permeation of a degradation factor such as water molecules and, on the layer, a "passivation auxiliary layer" that has a function that is difficult to be achieved in the layer. A configuration of three or more layers can be feasible, but in consideration of the manufacturing cost, it is more preferred that the number of layers is as small as possible.

[Formation of the Passivation Layer 110 by the Atom Layer Deposition Method (ALD Method)]

The performance of the photoelectric conversion material is largely degraded due to the degradation factor such as water molecules. Accordingly, it is required to cover and seal the entire photoelectric conversion layer by ceramics such as dense metal oxide.metal nitride.metal nitroxide or diamond-like carbon (DLC) that does not permeate water molecules. Conventionally, the passivation layer has been formed by aluminum oxide, silicon oxide, silicon nitride, silicon nitroxide, a laminate configuration thereof, or a laminate configuration of these ceramics and an organic polymer using various vacuum film manufacturing technologies. However, in the conventional passivation layer, since it is difficult to grow a thin film in steps due to a structure on the surface of the substrate, fine defects on the surface of the substrate, and particles attached to the surface of the substrate (because the step becomes a shadow), the film thickness is remarkably decreased as compared to a flat portion. Accordingly, the step portion becomes a path through which the degradation factor invades. In order to completely cover the step by the passivation layer, it is preferred to make the entire passivation layer thick by forming the film having a film thickness of 1 $\mu$m or more in the flat portion.

In the imaging device 100 having a pixel dimension of less than 2 $\mu$m, and particularly about 1 $\mu$m, if the distance between the color filter 111 and the photoelectric conversion layer, that is, the film thickness of the passivation layer 110 is large, incident light is diffracted or diverged in the passivation layer 110, causing color mixing. Accordingly, it is preferred that the imaging device 100 having a pixel dimension of about 1 $\mu$m is manufactured by using a passivation layer material/manufacturing method that does not degrade device performance even though the total film thickness of the passivation layer 110 is decreased.

The atomic layer deposition (ALD) method is a kind of CVD method and a technology for forming a thin film by alternately repeating adsorption/reaction of an organic metal compound molecule, a metal halogenated molecule, and a metal hydrogenated molecule, which are thin film materials, to the surface of the substrate, and decomposition of unreacted groups contained therein. When the thin film material approaches the surface of the substrate, the film material is in a low molecular state. Therefore, if there is a very small space into which low molecules can enter, it is possible to grow a thin film. Accordingly, the step portion that is problematic in the conventional thin film forming method is completely covered (the thickness of the thin film grown in the step portion is the same as the thickness of the thin film grown in the flat portion), resulting in an excellent step covering property. Accordingly, since the step caused by a structure on the surface of the substrate, fine defects on the surface of the substrate, and particles attached to the surface of the substrate may be completely covered, the step portion does not become an invasion path of the degradation factor of the photoelectric conversion material. In the case where the passivation layer 110 is formed by the atomic layer deposition method, it is possible to more efficiently decrease the required film thickness of the passivation layer as compared to the conventional technology.

In the case where the passivation layer 110 is formed by the atomic layer deposition method, the material corresponding to the preferable ceramics for the aforementioned passivation layer 110 may be appropriately selected. However, since the photoelectric conversion layer according to the embodiment of the present invention uses the photoelectric conversion material, the photoelectric conversion layer is limited to the material which can grow a thin film at a relatively low temperature at which the photoelectric conversion material is not degraded. By the atomic layer deposition method using alkylaluminum or halogenated aluminum as the material, a dense thin aluminum oxide film may be formed at a temperature of less than 200° C. at which the photoelectric conversion material is not degraded. Particularly, trimethylaluminum is preferably used because a thin aluminum oxide film may be formed at about 100° C. Silicon oxide or titanium oxide is also preferably used because a dense thin film may be formed at a temperature of less than 200° C. similarly to aluminum oxide by appropriately selecting materials.

EXAMPLE (Synthesis of Exemplary Compound (A-1))

Compound (A-1) in which $D_1$ in Formula (I) is a compound represented by Formula (III) may be prepared by the following reaction scheme.

[Chem. 64]

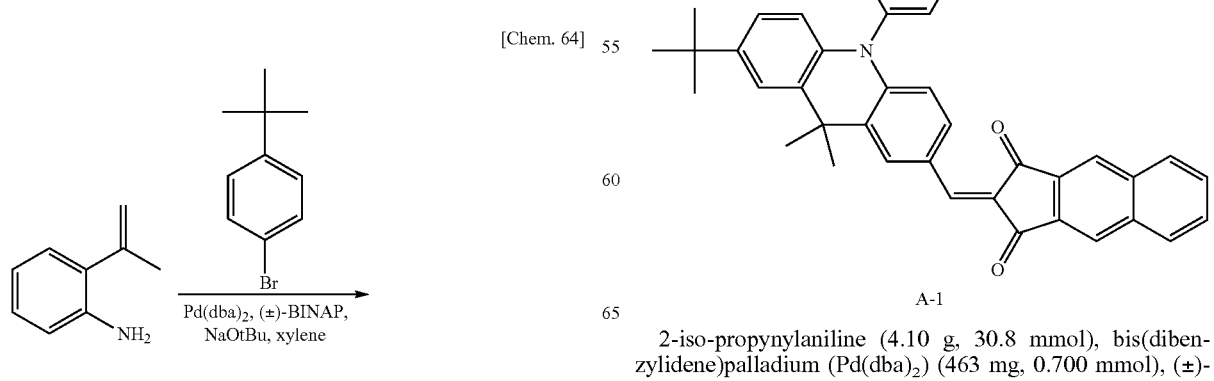

2-iso-propynylaniline (4.10 g, 30.8 mmol), bis(dibenzylidene)palladium (Pd(dba)$_2$) (463 mg, 0.700 mmol), (±)-

BINAP (2,2'-bis(diphenylphosphino)-1,1'-binaphthyl) (653 mg, 1.05 mmol), sodium-tert-butoxide (4.03 g, 42.0 mmol) and 1-bromo-4-tert-butylbenzene (5.97 g, 28.0 mmol) were dissolved in 50 ml of xylene, and reacted by boiling under reflux for 6 hours under a nitrogen atmosphere to obtain Compound 1 in 90% yield. Compound 1 (6.70 g, 25.2 mmol) was added to a mixed solvent of 37 ml of acetic acid and 7.5 ml of hydrochloric acid, and followed by stirring at 60° C. for 30 minutes to obtain Compound 2 in 82% yield. Compound 2 (1.30 g, 4.90 mmol), palladium acetate ((Pd(OAc)$_2$)) (55.0 mg, 0.245 mmol), tri(t-butyl)phosphine (149 mg, 7.35 mmol), cesium carbonate (3.19 g, 9.80 mmol) and 1-bromo-4-tert-butylbenzene (1.15 g, 5.39 mmol) were dissolved in 15 ml of xylene, and reacted by boiling under reflux for 6 hours under a nitrogen atmosphere to obtain Compound 3 in 70% yield. Compound 3 (1.36 g, 3.43 mmol) was added to 25 ml of DMF (N,N-dimethylformamide) with stirring under a nitrogen atmosphere, and phosphoryl bromide (1.97 g, 6.86 mmol) was added in small portions. Stirring was performed at 100° C. for 1 hour to obtain Compound 4 in 68% yield. Compound 4 (750 mg, 1.76 mmol) and benzindandione (380 mg, 1.94 mmol) were added to 9 ml of acetic acid under a nitrogen atmosphere, and refluxed for 3 hours. After allowing to cool, suction filtration was performed, and recrystallization was performed with N,N-dimethylacetamide. Suction filtration was performed to obtain Compound (A-1) in 57% yield. The compound was identified by $^1$H-NMR.

$^1$H-NMR (400 M Hz, in DMSO-d$_6$): δ (ppm)=1.29 (s, 9H), 1.43 (s, 9H), 1.80 (s, 6H), 6.11 (d, J=8.6 Hz, 1H), 6.20 (d, J=8.7 Hz, 1H), 7.09 (dd, J=8.7, 1.8 Hz, 1H), 7.36 (d, J=8.8 Hz, 2H), 7.58 (s, 1H), 7.74-7.78 (m, 4H), 7.84 (s, 1H), 8.13-8.17 (m, 1H), 8.28-8.31 (m, 2H), 8.56 (d, J=15.4 Hz, 2H), 36 (s, 1H). m.p.=341° C., $\lambda_{max}$ 549 nm (in CHCl$_3$) (ε=66000 mol$^{-1}$·l·cm$^{-1}$)

(Synthesis of Exemplary Compound (A-2))

Compound (A-2) in which D$_1$ in Formula (I) is a compound represented by Formula (III) may be prepared by the following reaction scheme.

[Chem. 65]

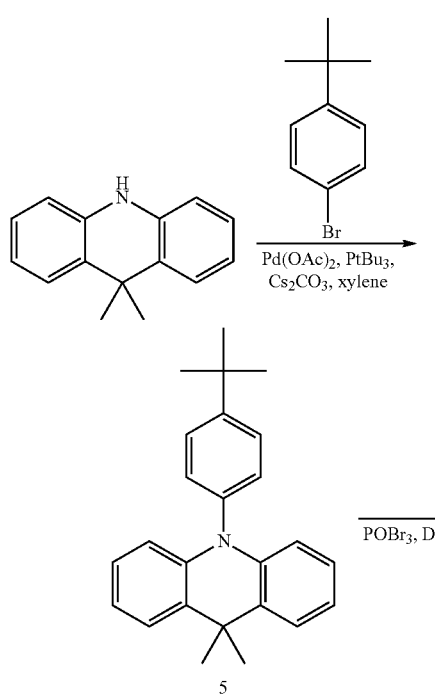

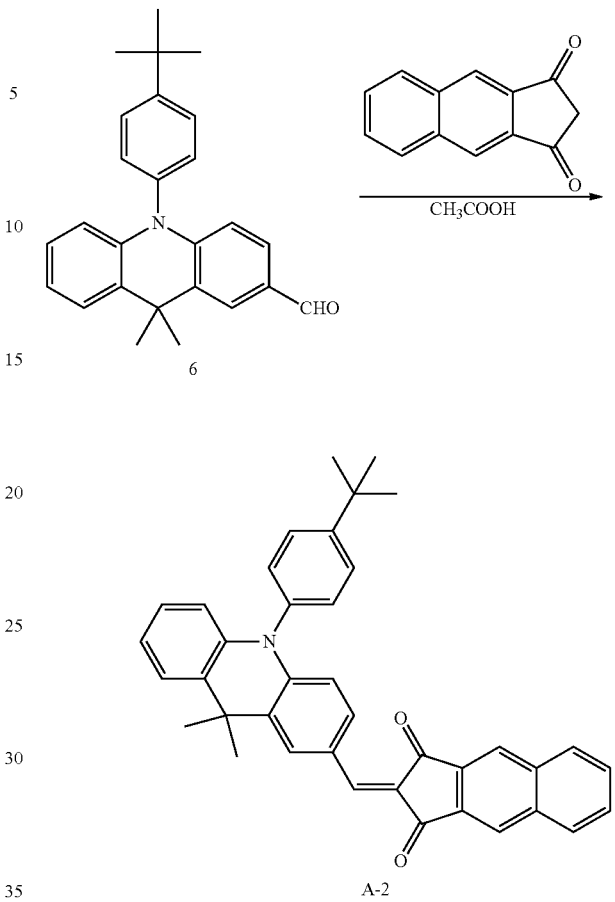

10-hydro-9,9-dimethylacridine (1.00 g, 478 mmol), palladium acetate (107 mg, 0.478 mmol), tri(t-butyl)phosphine (290 mg, 1.43 mmol), cesium carbonate (3.9 g, 12.0 mmol) and 1-bromo-4-tert-butylbenzene (1.12 g, 5.26 mmol) were dissolved in 15 ml of xylene, and reacted by boiling under reflux for 6 hours under a nitrogen atmosphere to obtain Compound 5 in 74% yield. Compound 5 (1.20 g, 3.52 mmol) was added to 18 ml of DMF with stirring under a nitrogen atmosphere, and phosphoryl bromide (1.51 g, 52.8 mmol) was added in small portions. Stirring was performed at 100° C. for 1 hour to obtain Compound 6 in 77% yield. Compound 6 (500 mg, 1.35 mmol) and benzindandione (292 mg, 1.49 mmol) were added to 6 ml of acetic acid under a nitrogen atmosphere, and refluxed for 3 hours. After allowing to cool, suction filtration was performed, and recrystallization was performed with N,N-dimethylacetamide. Suction filtration was performed to obtain Compound (A-2) in 45% yield. The compound was identified by $^1$H-NMR.

$^1$H-NMR (400 M Hz, in CDCl$_3$): δ (ppm)=1.45 (s, 9H), 1.85 (s, 6H), 6.33-6.37 (m, 2H), 7.00-7.06 (m, 2H), 7.24 (s, 1H), 7.52-7.55 (m, 1H), 7.65-7.68 (m, 4H), 7.90 (s, 1H), 8.04-8.09 (m, 3H), 8.46 (d, J=9.0 Hz, 2H), 9.22 (s, 1H). m.p.=330° C., $\lambda_{max}$=534 nm (in CHCl$_3$) (ε=73000 mol$^{-1}$·l·cm$^{-1}$)

(Synthesis of Exemplary Compound (A-3))

Compound (A-3) in which D$_1$ in Formula (I) is a compound represented by Formula (III) may be prepared by the following reaction scheme.

[Chem. 66]

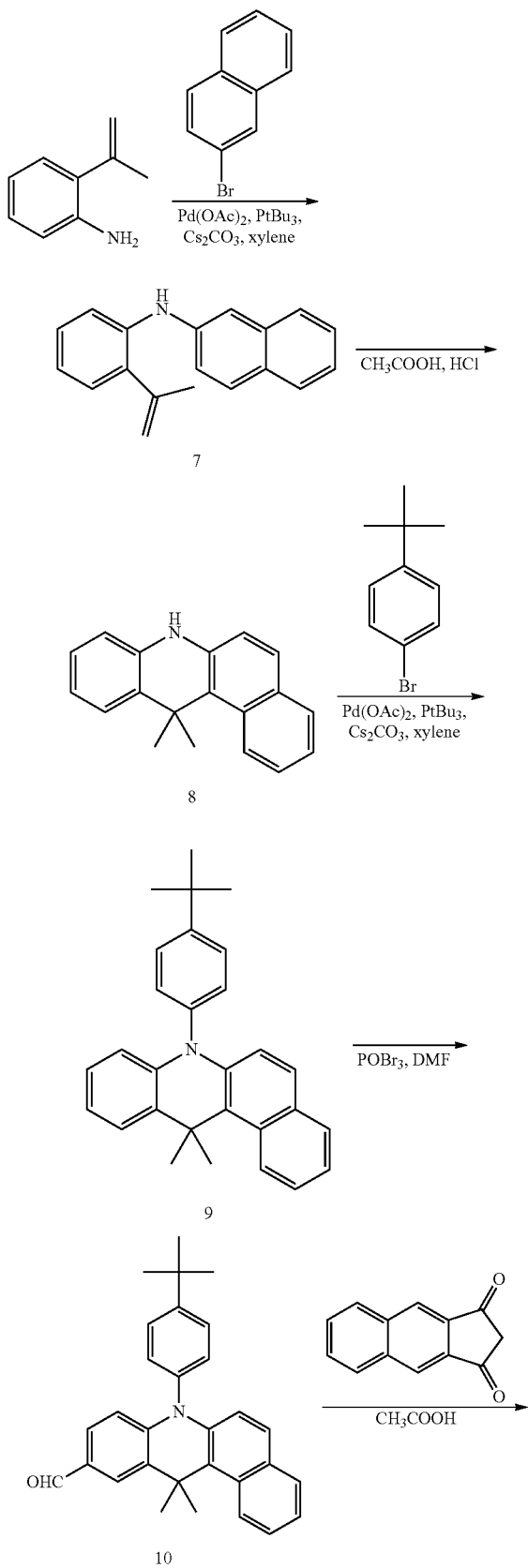

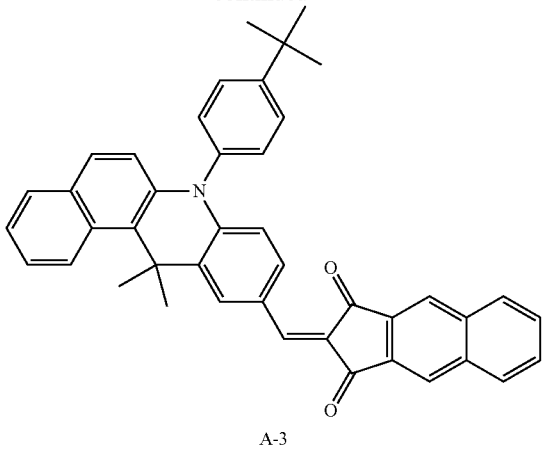 [SMILES: CC(C)(C)c1ccc(N2c3ccc(C=C4C(=O)c5cc6ccccc6cc5C4=O)cc3C(C)(C)c3c2ccc2ccccc32)cc1 ; "A-3"]

A-3

2-iso-propynylaniline (4.10 g, 30.8 mmol), palladium acetate (254 mg, 1.04 mmol), tri(t-butyl)phosphine (631 mg, 3.12 mmol), cesium carbonate (20.1 g, 61.6 mmol) and 2-bromonaphthalene (7.02 g, 33.9 mmol) were dissolved in 50 ml of xylene, and reacted by boiling under reflux for 6 hours under a nitrogen atmosphere to obtain Compound 7 in 78% yield. Compound 7 (6.22 g, 24.0 mmol) was added to a mixed solvent of 35 ml of acetic acid and 7 ml of hydrochloric acid, and followed by stirring at 60° C. for 30 minutes to obtain Compound 8 in 71% yield. Compound 8 (1.10 g, 4.24 mmol), palladium acetate (95.2 mg, 0.424 mmol), tri(t-butyl)phosphine (257 mg, 1.27 mmol), cesium carbonate (2.76 g, 8.48 mmol) and 1-bromo-4-tert-butylbenzene (994 mg, 4.66 mmol) were dissolved in 17 ml of xylene, and reacted by boiling under reflux for 7 hours under a nitrogen atmosphere to obtain Compound 9 in 75% yield. Compound 9 (1.25 g, 3.18 mmol) was added to 24 ml of DMF with stirring under a nitrogen atmosphere, and phosphoryl bromide (1.82 g, 6.36 mmol) was added in small portions. Stirring was performed at 100° C. for 1 hour to obtain Compound 10 in 64% yield. Compound 10 (700 mg, 1.67 mmol) and benzindandione (361 mg, 1.84 mmol) were added to 9 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-3) in 62% yield. The compound was identified by $^1$H-NMR.

$^1$H-NMR (400 M Hz, in CDCl$_3$): δ (ppm)=1.48 (s, 9H), 2.45 (s, 6H), 6.19 (d, J=8.8 Hz, 1H), 6.54 (d, J=8.9 Hz, 1H), 7.22-7.30 (m, 4H), 7.41-7.50 (m, 2H), 7.65-7.69 (m, 4H), 7.89 (s, 1H). 8.00-8.10 (m, 3H), 8.46 (d, J=7.6 Hz, 2H), 8.59 (d, J=11.5 Hz, 1H), 9.29 (s, 1H). m.p.=355° C., $\lambda_{max}$=559 nm (in CHCl$_3$) ($\epsilon$=61000 mol$^{-1}$·l·cm$^{-1}$)

(Synthesis of Exemplary Compound (A-4))

Compound (A-4) in which D$_1$ in Formula (I) is a compound represented by Formula (III) may be prepared by the following reaction scheme.

[Chem. 67]

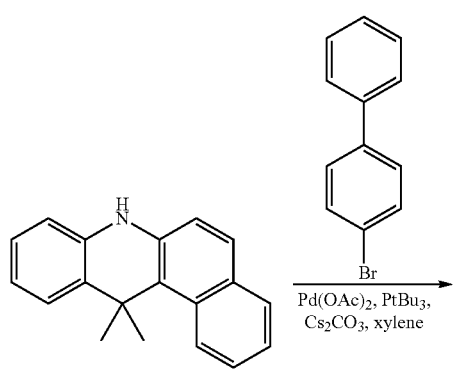

8

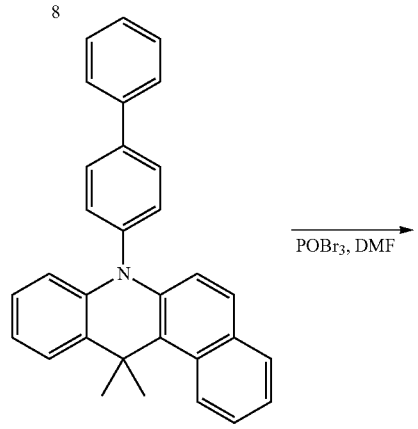

11

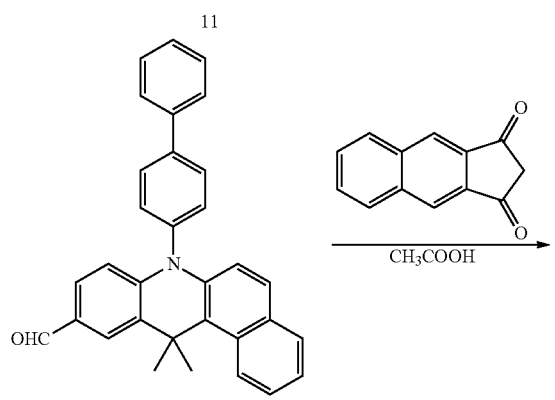

12

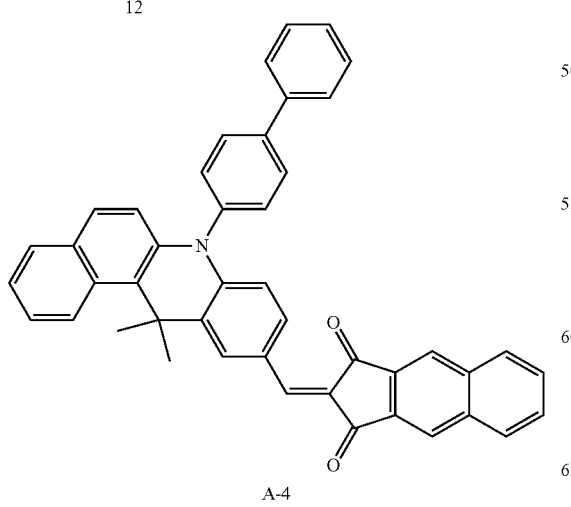

A-4

Compound 8 (1.10 g, 4.24 mmol), palladium acetate (95.2 mg, 0.424 mmol), tri(t-butyl)phosphine (257 mg, 1.27 mmol), cesium carbonate (2.76 g, 8.48 mmol) and 4-bromobiphenyl (1.09 g, 4.66 mmol) were dissolved in 17 ml of xylene, and reacted by boiling under reflux for 7 hours under a nitrogen atmosphere to obtain Compound 11 in 68% yield. Compound 11 (1.19 g, 2.88 mmol) was added to 22 ml of DMF with stirring under a nitrogen atmosphere, and phosphoryl bromide (2.06 g, mmol) was added in small portions. Stirring was performed at 100° C. for 1 hour to obtain Compound 12 in 55% yield. Compound 12 (600 mg, 1.37 mmol) and benzindandione (294 mg, 1.50 mmol) were added to 9 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-4) in 57% yield. The compound was identified by $^1$H-NMR.

$^1$H-NMR (400 M Hz, in DMSO-d$_6$): δ (ppm)=2.38 (s, 6H), 6.20 (d, J=8.8 Hz, 1H), 6.57 (d, J=9.1 Hz, 1H), 7.35 (t, J=7.4 Hz, 1H), 7.40-7.46 (m, 1H), 7.52-7.59 (m, 5H), 7.63 (d, J=9.2 Hz, 1H), 7.77-7.80 (m, 3H), 7.85-7.88 (m, 3H), 8.07 (d, J=8.4 Hz, 2H), 8.15-8.17 (m, 1H), 8.28-8.31 (m, 2H), 8.158-8.69 (m, 3H), 9.35 (s, 1H). m.p.=340° C., λ$_{max}$=554 nm (in CHCl$_3$) (ε=63000 mol$^{-1}$·l·cm$^{-1}$)

(Synthesis of Exemplary Compound (A-5))

Compound (A-5) in which D$_1$ in Formula (I) is a compound represented by Formula (III) may be prepared by the following reaction scheme.

[Chem. 68]

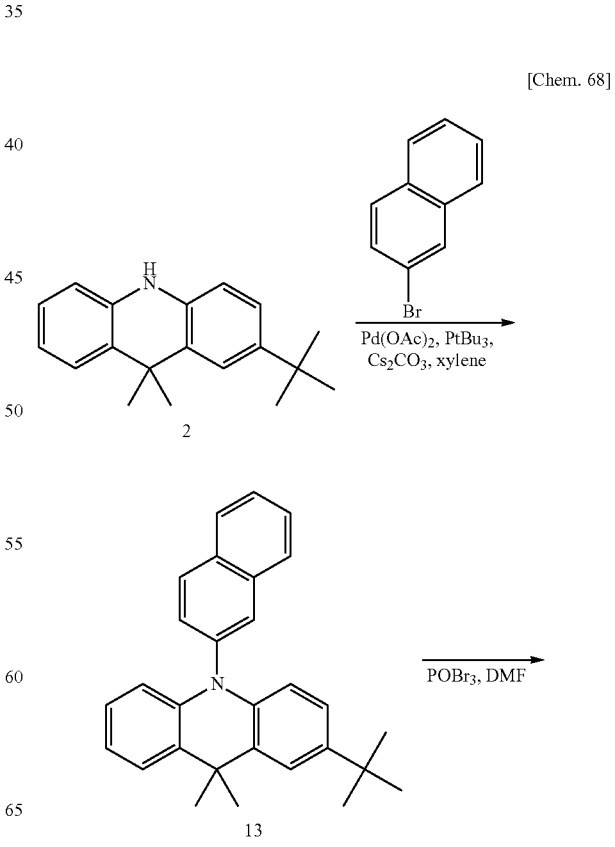

2

13

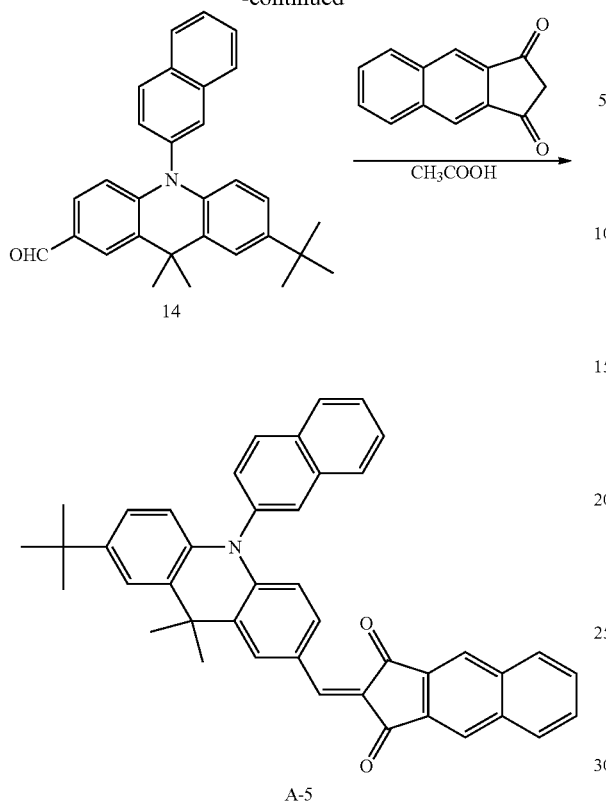

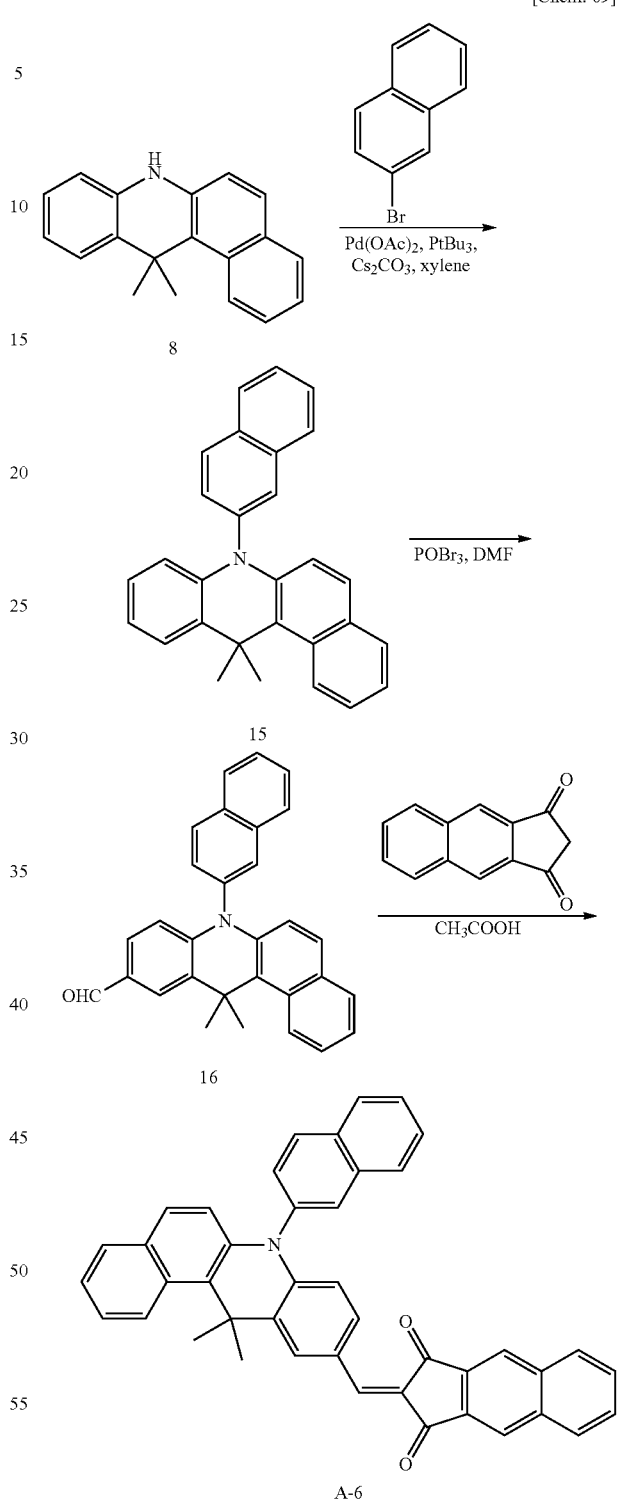

Compound 2 (1.30 g, 4.90 mmol), palladium acetate (55.0 mg, 0.245 mmol), tri(t-butyl)phosphine (149 mg, 7.35 mmol), cesium carbonate (3.19 g, 9.80 mmol) and 2-bromonaphthalene (1.12 g, 5.39 mmol) were dissolved in 15 ml of xylene, and reacted by boiling under reflux for 6 hours under a nitrogen atmosphere to obtain Compound 13 in 40% yield. Compound 13 (760 mg, 1.94 mmol) was added to 14 ml of DMF with stirring under a nitrogen atmosphere, and phosphoryl bromide (1.18 g, 4.12 mmol) was added in small portions. Stirring was performed at 100° C. for 1 hour to obtain Compound 14 in 73% yield. Compound 14 (600 mg, 1.43 mmol) and benzindandione (309 mg, 1.57 mmol) were added to 6 ml of acetic acid under a nitrogen atmosphere, and refluxed for 3 hours. After allowing to cool, suction filtration was performed, and recrystallization was performed with N,N-dimethylacetamide. Suction filtration was performed to obtain Compound (A-5) in 52% yield. The compound was identified by $^1$H-NMR.

$^1$H-NMR (400 M Hz, in CDCl$_3$): δ (ppm)=1.33 (s, 9H), 1.91 (s, 6H), 6.27 (d, J=8.6 Hz, 1H), 6.36 (d, J=8.7 Hz, 1H), 7.00 (dd, J=8.4, 1.8 Hz, 1H), 7.40 (dd, J=8.4, 1.7 Hz, 1H), 7.58-7.67 (m, 5H), 7.87-7.91 (m, 3H), 7.96-8.02 (m, 2H), 8.06-8.08 (m, 2H), 8.15 (d, J=8.5 Hz, 1H), 8.46 (d, J=11.9 Hz, 2H), 9.29 (s, 1H). m.p.=303° C., λ$_{max}$=541 nm (in CHCl$_3$) (ε=68000 mol$^{-1}$·l·cm$^{-1}$)

(Synthesis of Exemplary Compound (A-6))

Compound (A-6) in which D$_1$ in Formula (I) is a compound represented by Formula (III) may be prepared by the following reaction scheme.

Compound 8 (1.10 g, 4.24 mmol), palladium acetate (95.2 mg, 0.424 mmol), tri(t-butyl)phosphine (257 mg, 1.27 mmol), cesium carbonate (2.76 g, 8.48 mmol) and 2-bromonaphthalene (966 mg, 4.66 mmol) were dissolved in 17 ml of xylene, and reacted by boiling under reflux for 7 hours under a nitrogen atmosphere to obtain Compound 15 in 65% yield. Compound 15 (1.06 g, 2.76 mmol) was added to 20 ml of DMF with stirring under a nitrogen atmosphere, and phosphoryl bromide (1.97 g, 6.90 mmol) was added in small portions. Stirring was performed at 100° C. for 1 hour to obtain Compound 16 in 58% yield. Compound 16 (400 mg, 0.967 mmol) and benzindandione (209 mg, 1.06 mmol) were added to a mixed solvent of 8 ml of toluene and 8 ml of iso-propyl alcohol under a nitrogen atmosphere, and refluxed for 3 hours. After allowing to cool, suction filtration was performed, and recrystallization was performed with N,N-dimethylacetamide. Suction filtration was performed to obtain Compound (A-6) in 61% yield. The compound was identified by $^1$H-NMR.

$^1$H-NMR (400 MHz, in CDCl$_3$): δ (ppm)=2.48 (s, 6H), 6.21 (d, J=8.8 Hz, 1H), 6.54 (d, J=9.1 Hz, 1H), 7.31 (t, J=7.7 Hz, 1H), 7.38-7.43 (m, 2H), 7.48-7.52 (m, 1H), 7.60-7.69 (m, 5H), 7.88-7.94 (m, 4H), 8.03 (d, J=8.6 Hz, 1H), 8.07-8.10 (m, 2H), 8.18 (d, J=8.6 Hz, 1H), 8.47 (d, J=10.5 Hz, 2H), 8.62 (d, J=9.0 Hz, 1H), 9.31 (s, 1H). m.p.=335° C., λ$_{max}$=555 nm (in CHCl$_3$) (ε=65000 mol$^{-1}$·l·cm$^{-1}$)

(Synthesis of Exemplary Compound (A-7))

Compound (A-7) in which D$_1$ in Formula (I) is a compound represented by Formula (III) may be prepared by the following reaction scheme.

[Chem. 70]

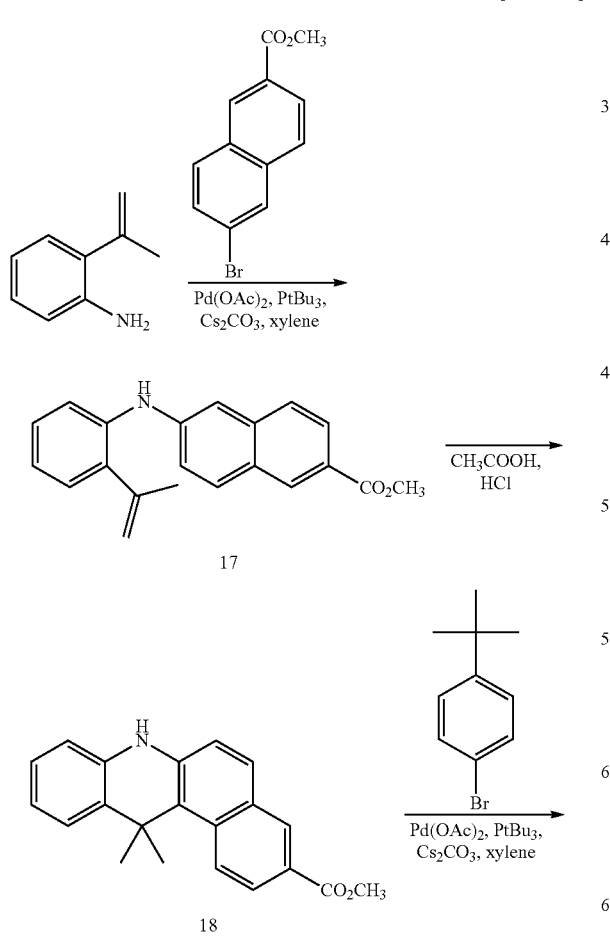

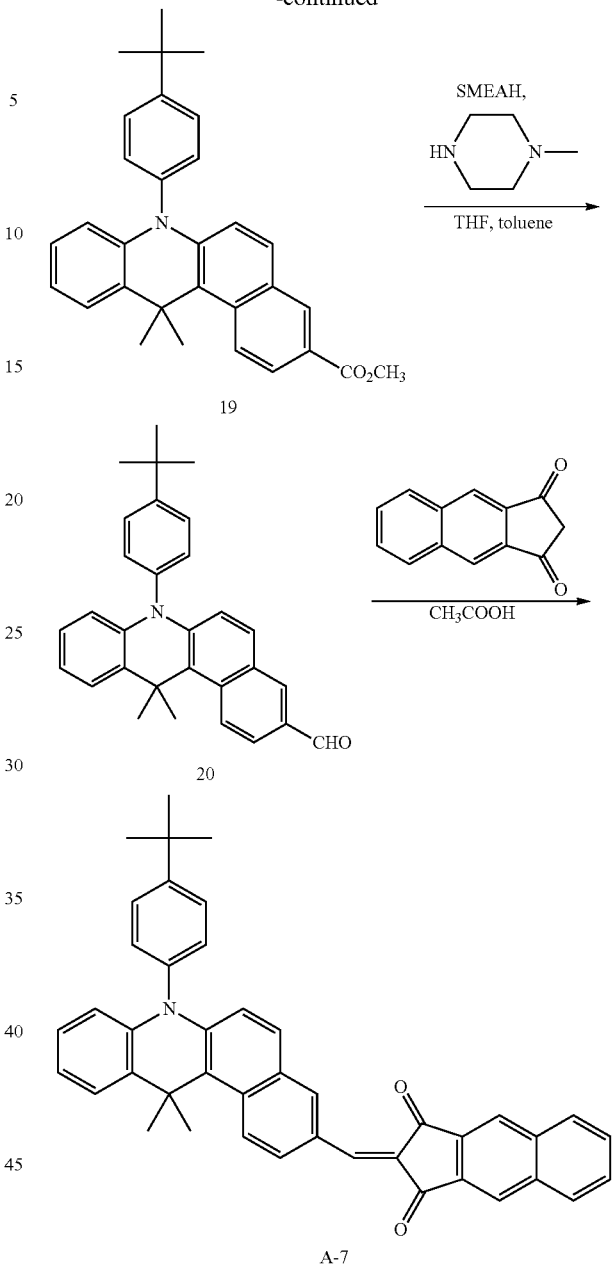

2-iso-propynylaniline (4.20 g, 31.5 mmol), palladium acetate (210 mg, 0.95 mmol), tri(t-butyl)phosphine (570 mg, 2.80 mmol), cesium carbonate (20.5 g, 62.9 mmol) and methyl 6-bromo-2-naphthoate (8.35 g, 31.5 mmol) were dissolved in 50 ml of xylene, and reacted by boiling under reflux for 5 hours under a nitrogen atmosphere to obtain Compound 17 in 78% yield. Compound 17 (7.80 g, 24.6 mmol) was added to a mixed solvent of 40 ml of acetic acid and 8 ml of hydrochloric acid, and followed by stirring at 60° C. for 30 minutes to obtain Compound 18 in 82% yield. Compound 18 (1.00 g, 3.15 mmol), palladium acetate (70.7 mg, 0.315 mmol), tri(t-butyl)phosphine (191 mg, 0.945 mmol), cesium carbonate (2.05 g, 6.30 mmol) and 1-bromo-4-tert-butylbenzene (671 mg, 3.15 mmol) were dissolved in 15 ml of xylene, and reacted by boiling under reflux for 7 hours under a nitrogen atmosphere to obtain Compound 19 in 95% yield. A 70% solution of sodium bis(2-methoxyethoxy)aluminum dihydride in toluene (5.37 ml, 18.6 mmol) was added to 13 ml of THF under a nitrogen atmosphere, and cooled to 0° C. N-methylpiperazine (2.01 g, 20.1 mmol) was added dropwise, and stirred for 30 minutes to adjust a reducing agent solution. The reducing agent solution was added dropwise to 20 ml of a solution of Compound 19 (1.35 g, 3.00 mmol) in THF at −40° C. under a nitrogen atmosphere. The reaction solution was stirred at −20° C. for 4 hours, and the reaction was then stopped with diluted hydrochloric acid to obtain Compound 20 in 81% yield. Compound 20 (700 mg, 1.67 mmol) and benzindandione (361 mg, 1.84 mmol) were added to 9 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-7) in 51% yield. The compound was identified by $^1$H-NMR.

$^1$H-NMR (400 M Hz, in CDCl$_3$): δ (ppm)=1.45 (s, 9H), 2.31 (s, 6H), 6.09 (d, J=8.6 Hz, 1H), 6.53 (d, J=8.7 Hz, 1H), 6.89-6.98 (m, 2H), 7.22 (d, J=8.7 Hz, 2H), 7.48-7.56 (m, 2H), 7.63-7.72 (m, 4H), 8.04-8.12 (m, 3H), 8.47-8.57 (m, 3H), 8.69-8.73 (m, 1H), 8.79 (s, 1H). m.p.=335° C., λ$_{max}$=568 nm (in CHCl$_3$) (ε=53000 mol$^{-1}$·cm$^{-1}$)

(Synthesis of Exemplary Compound (A-8))

Compound (A-8) in which D$_1$ in Formula (I) is a compound represented by Formula (III) may be prepared by the following reaction scheme.

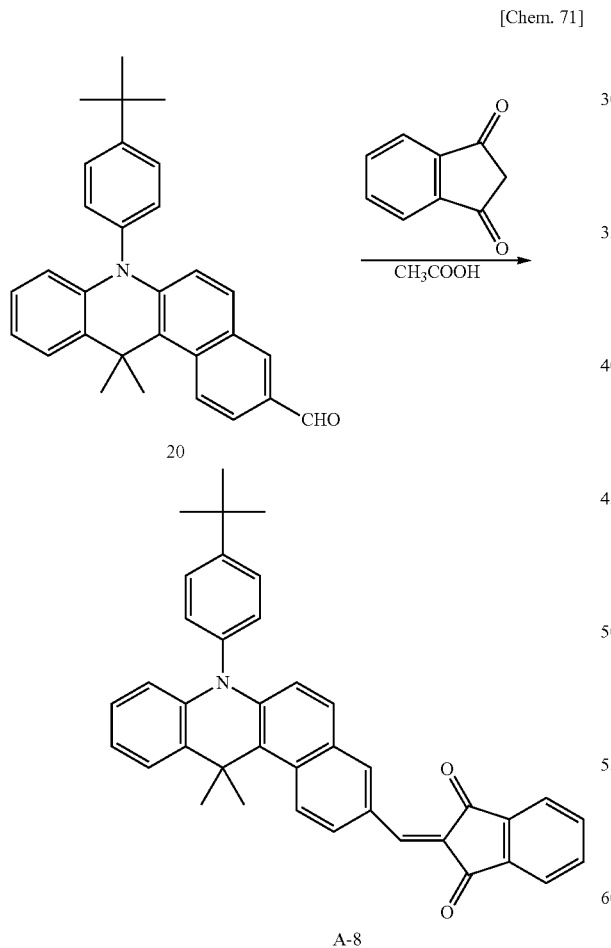

Compound 20 (700 mg, 1.67 mmol) and indandione (361 mg, 1.84 mmol) were added to 5 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-8) in 53% yield. The compound was identified by $^1$H-NMR.

$^1$H-NMR (400 M Hz, in CDCl$_3$): δ (ppm)=1.45 (s, 9H), 2.32 (s, 6H), 6.10 (d, J=8.6 Hz, 1H), 6.53 (d, J=8.7 Hz, 1H), 6.89-6.98 (m, 2H), 7.21 (d, J=8.7 Hz, 2H), 7.48-7.55 (m, 2H), 7.65 (d, J=8.6 Hz, 2H), 7.77-7.81 (m, 2H), 7.95-8.04 (m, 3H), 8.53 (d, J=8.6 Hz, 1H), 8.62-8.67 (m, 1H), 8.70 (s, 1H). m.p.=319° C., λ$_{max}$=536 nm (in CHCl$_3$) (ε=44000 mol$^{-1}$·cm$^{-1}$)

(Synthesis of Exemplary Compound (A-9))

Compound (A-9) in which D$_1$ in Formula (I) is a compound represented by Formula (III) may be prepared by the following reaction scheme.

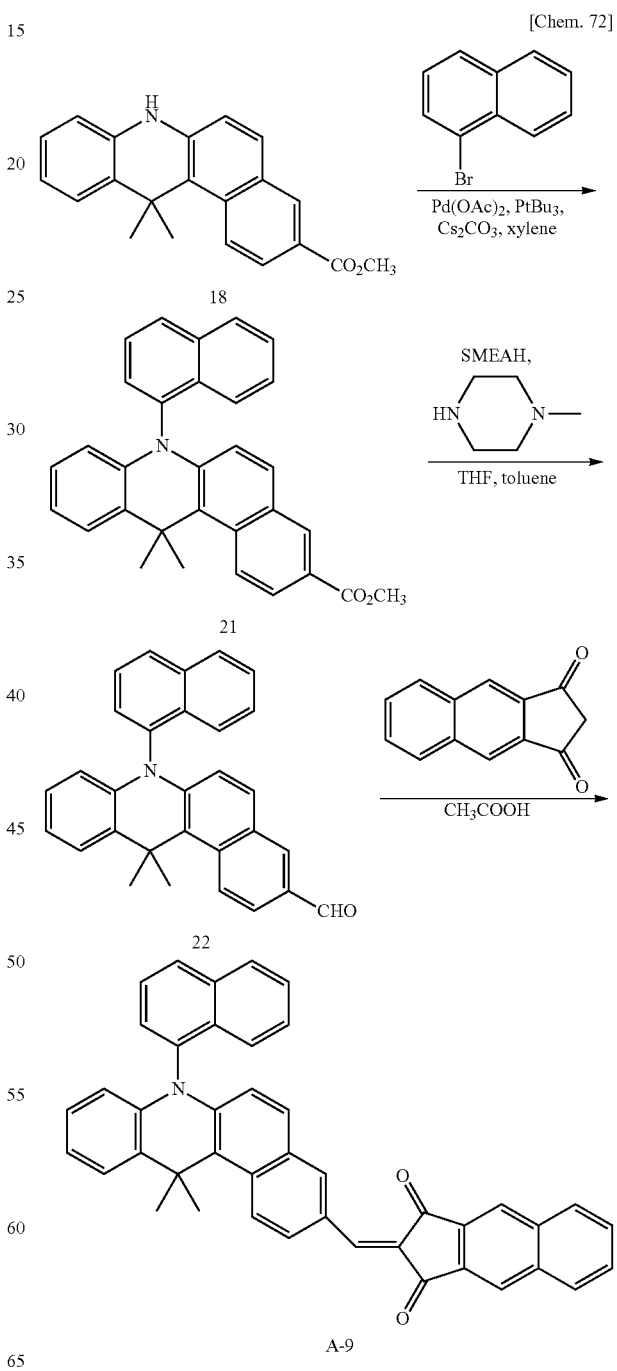

Compound 18 (1.00 g, 3.15 mmol), palladium acetate (70.7 mg, 0.315 mmol), tri(t-butyl)phosphine (191 mg, 0.945 mmol), cesium carbonate (2.05 g, 6.30 mmol) and 1-bromonaphthalene (717 mg, 3.47 mmol) were dissolved in 15 ml of xylene, and reacted by boiling under reflux for 7 hours under a nitrogen atmosphere to obtain Compound 21 in 97% yield. A 70% solution of sodium bis(2-methoxyethoxy)aluminum dihydride (SMEAH) in toluene (5.37 ml, 18.6 mmol) was added to 13 ml of THF under a nitrogen atmosphere, and cooled to 0° C. N-methylpiperazine (2.01 g, 20.1 mmol) was added dropwise, and stirred for 30 minutes to adjust a reducing agent solution. The reducing agent solution was added dropwise to 20 ml of a solution of Compound 21 (1.33 g, 3.00 mmol) in THF at −40° C. under a nitrogen atmosphere. The reaction solution was stirred at −20° C. for 4 hours, and the reaction was then stopped with diluted hydrochloric acid to obtain Compound 22 in 59% yield. Compound 22 (500 mg, 1.21 mmol) and benzindandione (260 mg, 1.33 mmol) were added to 9 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-9) in 41% yield. The compound was identified by $^1$H-NMR.

$^1$H-NMR (400 M Hz, in CDCl$_3$): δ (ppm)=1.55 (s, 9H), 2.40 (s, 3H), 2.43 (s, 3H), 5.91 (d, J=8.8 Hz, 1H), 6.37 (d, J=8.9 Hz, 1H), 6.69 (t, J=8.8 Hz, 1H), 6.95 (t, J=8.6 Hz, 1H), 7.40-7.48 (m, 2H), 7.52-7.59 (m, 3H), 7.66-7.79 (m, 4H), 8.00-8.11 (m, 5H), 8.50 (s, 2H), 8.60 (d, J=8.9 Hz, 1H), 8.72 (d, J=8.9 Hz, 1H), 8.77 (s, 1H). m.p.=356° C., λ$_{max}$=560 nm (in CHCl$_3$) (ε=48000 mol$^{-1}$·l·cm$^{-1}$)

(Synthesis of Exemplary Compound (A-13))

Compound (A-13) in which D$_1$ in Formula (I) is a compound represented by Formula (III) may be prepared by the following reaction scheme.

[Chem. 73]

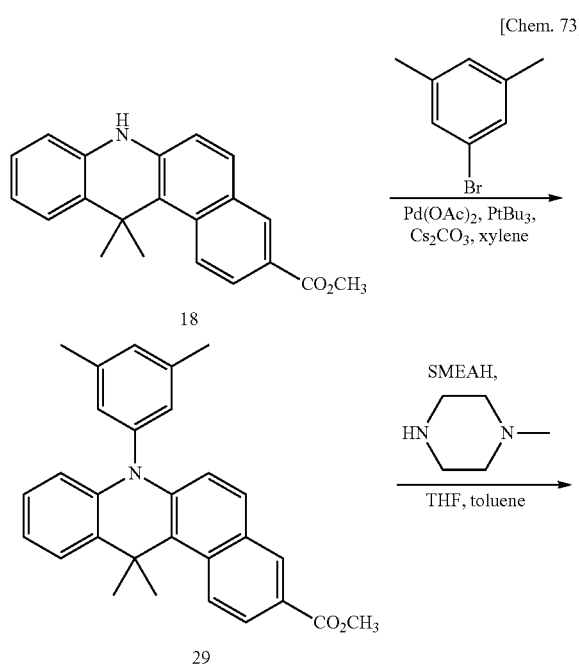

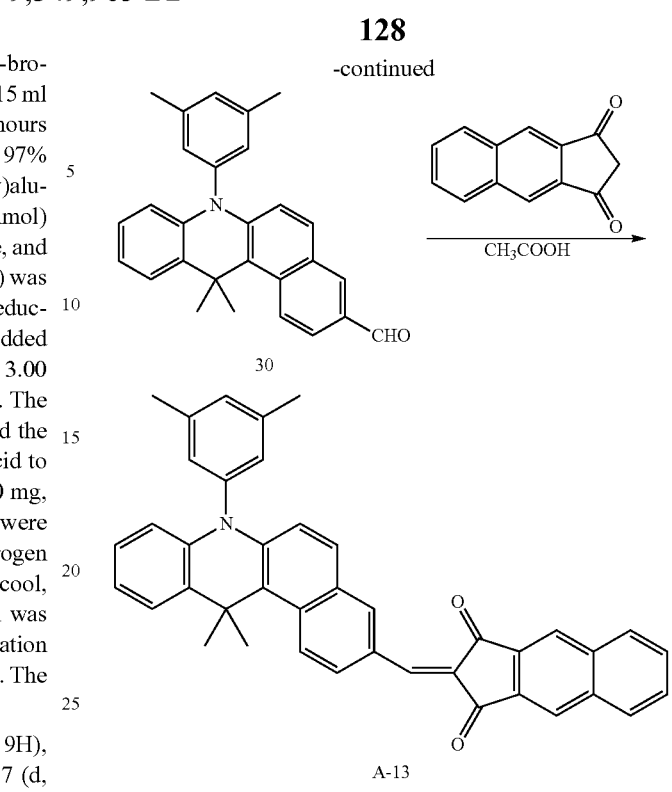

A-13

Compound 18 (1.00 g, 3.15 mmol), palladium acetate (70.7 mg, 0.315 mmol), tri(t-butyl)phosphine (191 mg, 0.945 mmol), cesium carbonate (2.05 g, 6.30 mmol) and 5-bromo-m-xylene (642 mg, 3.47 mmol) were dissolved in 15 ml of xylene, and reacted by boiling under reflux for 7 hours under a nitrogen atmosphere to obtain Compound 29 in 96% yield. A 70% solution of sodium bis(2-methoxyethoxy)aluminum dihydride (SMEAH) in toluene (5.37 ml, 18.6 mmol) was added to 13 ml of THF under a nitrogen atmosphere, and cooled to 0° C. N-methylpiperazine (2.01 g, 20.1 mmol) was added dropwise, and stirred for 30 minutes to adjust a reducing agent solution. The reducing agent solution was added dropwise to 20 ml of a solution of Compound 29 (1.26 g, 3.00 mmol) in THF at −40° C. under a nitrogen atmosphere. The reaction solution was stirred at −20° C. for 4 hours, and the reaction was then stopped with diluted hydrochloric acid to obtain Compound 30 in 65% yield. Compound 30 (763 mg, 1.95 mmol) and benzindandione (421 mg, 2.15 mmol) were added to 9 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-13) in 42% yield. The compound was identified by $^1$H-NMR.

$^1$H-NMR (400 M Hz, in CDCl$_3$): δ (ppm)=1.58 (s, 6H), 2.30 (s, 3H), 2.41 (s, 3H), 6.14 (d, J=8.8 Hz, 1H), 6.59 (d, J=9.8 Hz, 1H), 6.90-6.99 (m, 4H), 7.18 (s, 1H), 7.45-7.51 (m, 1H), 7.56 (d, J=9.5 Hz, 1H), 7.68-7.72 (m, 2H) 8.07 (s, 1H), 8.10-8.15 (m, 2H), 8.50 (s, 2H), 8.55 (d, J=8.7 Hz, 1H), 8.68-8.71 (m, 1H), 8.82 (s, 1H). m.p.=331° C., λ$_{max}$=569 nm (in CHCl$_3$) (ε=52000 mol$^{-1}$·l·cm$^{-1}$)

(Synthesis of Exemplary Compound (A-14))

Compound (A-14) in which D$_1$ in Formula (I) is a compound represented by Formula (III) may be prepared by the following reaction scheme.

[Chem. 74]

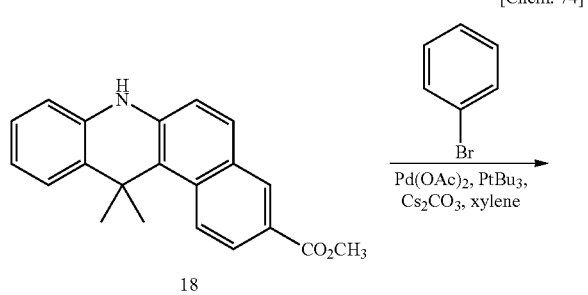

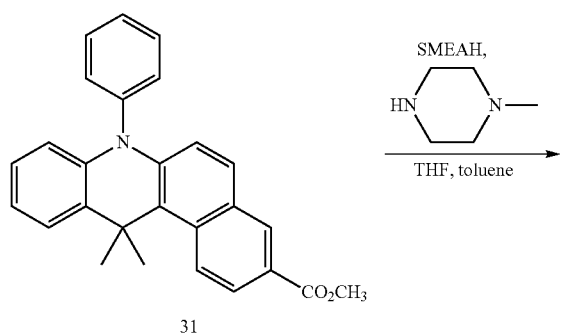

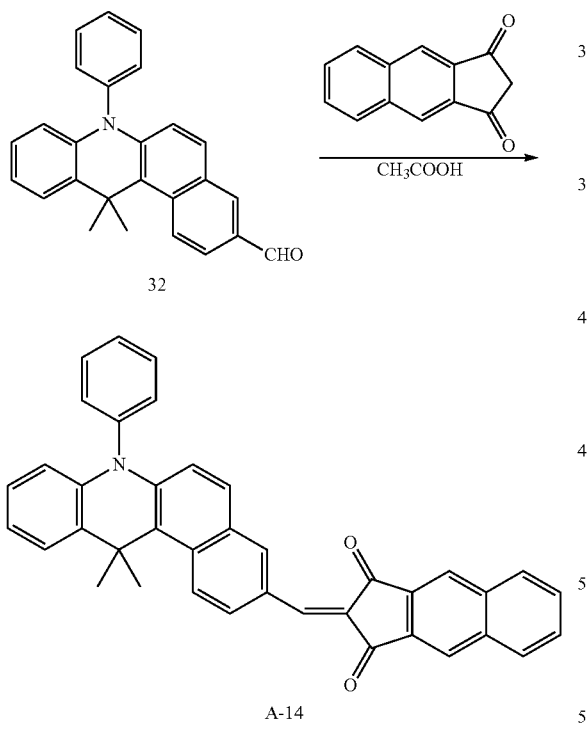

Compound 18 (1.00 g, 3.15 mmol), palladium acetate (70.7 mg, 0.315 mmol), tri(t-butyl)phosphine (191 mg, 0.945 mmol), cesium carbonate (2.05 g, 6.30 mmol) and bromobenzene (645 mg, 3.47 mmol) were dissolved in 15 ml of xylene, and reacted by boiling under reflux for 7 hours under a nitrogen atmosphere to obtain Compound 31 in 89% yield. A 70% solution of sodium bis(2-methoxyethoxy)aluminum dihydride (SMEAH) in toluene (5.01 ml, 17.4 mmol) was added to 12 ml of THF under a nitrogen atmosphere, and cooled to 0° C. N-methylpiperazine (1.88 g, 18.8 mmol) was added dropwise, and stirred for 30 minutes to adjust a reducing agent solution. The reducing agent solution was added dropwise to 19 ml of a solution of Compound 31 (1.18 g, 2.80 mmol) in THF at −40° C. under a nitrogen atmosphere. The reaction solution was stirred at −20° C. for 4 hours, and the reaction was then stopped with diluted hydrochloric acid to obtain Compound 32 in 70% yield. Compound 32 (712 mg, 1.96 mmol) and benzindandione (423 mg, 2.16 mmol) were added to 15 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-14) in 55% yield. The compound was identified by $^1$H-NMR.

$^1$H-NMR (400 M Hz, in CDCl$_3$): δ (ppm)=2.34 (s, 6H), 6.10 (d, J=8.6 Hz, 1H), 6.52 (d, J=9.6 Hz, 1H), 6.89-7.00 (m, 4H), 7.32 (d, J=8.5 Hz, 2H), 7.48-7.59 (m, 3H), 7.64-7.70 (m, 4H), 8.07 (s, 1H), 8.08-8.13 (m, 2H), 8.51 (s, 2H), 8.56 (d, J=8.5 Hz, 1H), 8.68-8.71 (m, 1H), 8.80 (s, 1H). m.p.=328° C., $\lambda_{max}$=563 nm (in CHCl$_3$) (ϵ=56000

(Synthesis of Exemplary Compound (A-15))

Compound (A-15) in which D$_1$ in Formula (I) is a compound represented by Formula (III) may be prepared by the following reaction scheme.

[Chem. 75]

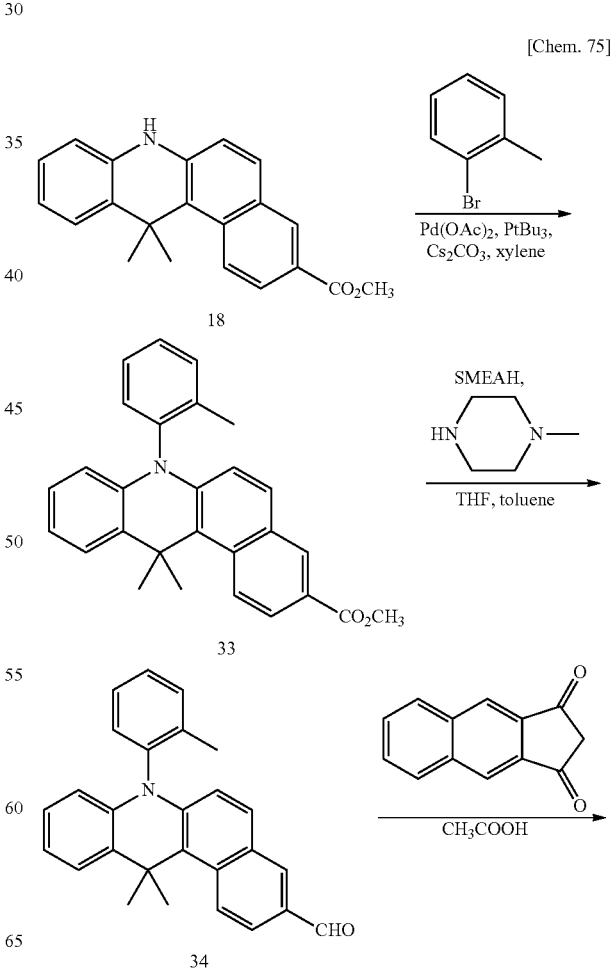

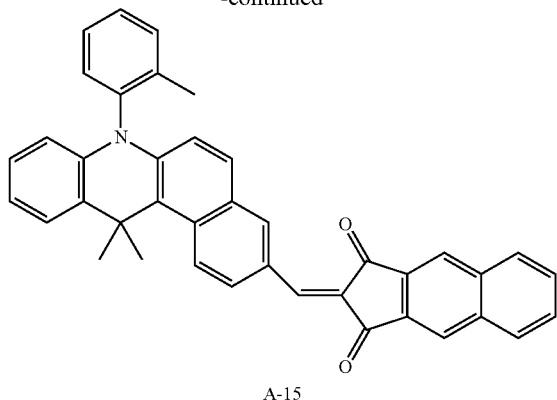

A-15

Compound 18 (1.00 g, 3.15 mmol), palladium acetate (70.7 mg, 0.315 mmol), tri(t-butyl)phosphine (191 mg, 0.945 mmol), cesium carbonate (2.05 g, 6.30 mmol) and o-bromotoluene (593 mg, 3.47 mmol) were dissolved in 15 ml of xylene, and reacted by boiling under reflux for 7 hours under a nitrogen atmosphere to obtain Compound 33 in 72% yield. A 70% solution of sodium bis(2-methoxyethoxy)aluminum dihydride (SMEAH) in toluene (4.06 ml, 14.1 mmol) was added to 10 ml of THF under a nitrogen atmosphere, and cooled to 0° C. N-methylpiperazine (1.52 g, 15.2 mmol) was added dropwise, and stirred for 30 minutes to adjust a reducing agent solution. The reducing agent solution was added dropwise to 15 ml of a solution of Compound 33 (924 mg, 2.27 mmol) in THF at −40° C. under a nitrogen atmosphere. The reaction solution was stirred at −20° C. for 4 hours, and the reaction was then stopped with diluted hydrochloric acid to obtain Compound 34 in 63% yield. Compound 34 (540 mg, 1.43 mmol) and benzindandione (308 mg, 1.57 mmol) were added to 10 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-15) in 40% yield. The compound was identified by $^1$H-NMR.

$^1$H-NMR (400 M Hz, in CDCl$_3$): δ (ppm)=2.10 (s, 3H), 2.30 (s, 3H), 2.34 (s, 3H), 6.00 (d, J=8.5 Hz, 1H), 6.46 (d, J=8.7 Hz, 1H), 6.89-6.99 (m, 2H), 7.23-7.26 (m, 1H), 7.45-7.53 (m, 4H), 7.57 (d, J=8.8 Hz, 1H), 7.68-7.71 (m, 2H), 8.06 (s, 1H), 8.09-8.13 (m, 2H), 8.50 (s, 2H), 8.58 (d, J=8.9 Hz, 1H), 8.70 (m, 1H), 8.82 (s, 1H). m.p.=286° C., λ$_{max}$=564 nm (in CHCl$_3$) (ε=53000 mol$^{-1}$·L·cm$^{-1}$)

(Synthesis of Exemplary Compound (A-16))

Compound (A-16) in which D$_1$ in Formula (I) is a compound represented by Formula (III) may be prepared by the following reaction scheme.

[Chem. 76]

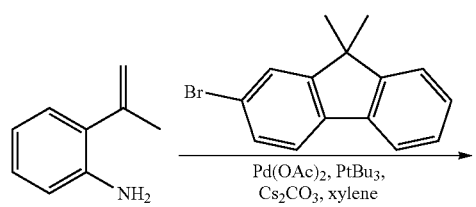

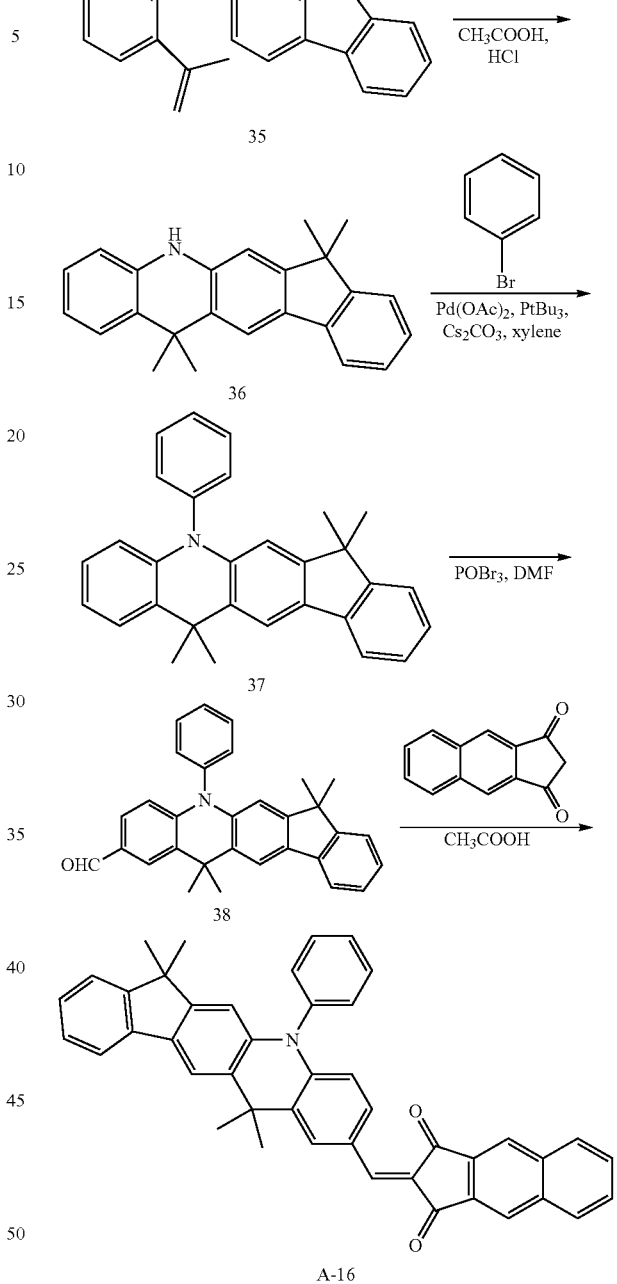

2-iso-propynylaniline (4.20 g, 31.5 mmol), palladium acetate (210 mg, 0.95 mmol), tri(t-butyl)phosphine (570 mg, 2.80 mmol), cesium carbonate (20.5 g, 62.9 mmol) and 2-bromo-9,9-dimethylfluorene (11.1 g, 31.5 mmol) were dissolved in 50 ml of xylene, and reacted by boiling under reflux for 5 hours under a nitrogen atmosphere to obtain Compound 35 in 73% yield. Compound 35 (7.48 g, 23.0 mmol) was added to a mixed solvent of 35 ml of acetic acid and 7 ml of hydrochloric acid, and followed by stirring at 60° C. for 30 minutes to obtain Compound 36 in 81% yield. Compound 36 (3.25 g, 10.0 mmol), palladium acetate (112 mg, 0.500 mmol), tri(t-butyl)phosphine (303 mg, 1.50 mmol), cesium carbonate (6.52 g, 20.0 mmol) and bromobenzene (1.73 g, 11.0 mmol) were dissolved in 40 ml of xylene, and reacted by boiling under reflux for 7 hours under a nitrogen atmosphere to obtain Compound 37 in 75% yield. Compound 37 (2.01 g, 5.00 mmol) was added to 38 ml of DMF with stirring under a nitrogen atmosphere, and phosphoryl bromide (3.58 g, 12.5 mmol) was added in small portions. Stirring was performed at 100° C. for 1 hour to obtain Compound 38 in 66% yield. Compound 38 (1.42 g, 3.30 mmol) and benzindandione (712 mg, 3.63 mmol) were added to 18 ml of an acetic acid solvent under a nitrogen atmosphere, and refluxed for 3 hours. After allowing to cool, suction filtration was performed, and recrystallization was performed with N,N-dimethylacetamide. Suction filtration was performed to obtain Compound (A-16) in 65% yield. The compound was identified by $^1$H-NMR.

$^1$H-NMR (400 M Hz, in CDCl$_3$): δ (ppm)=1.29 (s, 6H), 1.94 (s, 6H), 6.32 (s, 1H), 6.36 (d, J=8.4 Hz, 1H), 7.23-7.26 (m, 1H), 7.31-7.42 (m, 4H), 7.61-7.76 (m, 6H), 7.89 (d, J=14.0 Hz, 2H), 8.04-8.10 (m, 3H), 8.47 (d, J=13.9 Hz, 2H), 9.28 (s, 1H). m.p.=332° C., λ$_{max}$=553 nm (in CHCl$_3$) (ε=62000 mol$^{-1}$·l·cm$^{-1}$)

(Synthesis of Exemplary Compound (A-17))

Compound (A-17) in which D$_1$ in Formula (I) is a compound represented by Formula (III) may be prepared by the following reaction scheme.

[Chem. 77]

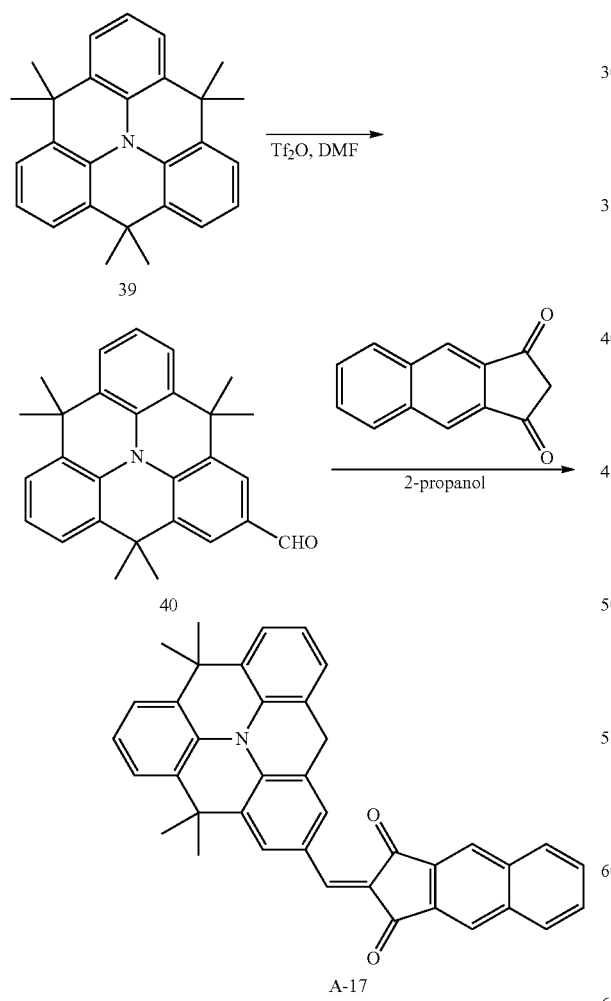

Compound 39 was synthesized by the method described in Org. Lett. 2009, 11, 1-4. Compound 39 (400 mg, 1.09 mmol) was dissolved in dehydrated N,N-dimethylformamide (4 ml), and trifluoromethanesulfonic anhydride (0.3 ml) was added dropwise thereto. The reaction solution was heated to 90° C. under a nitrogen atmosphere, and followed by stirring for 1 hour to obtain Compound 40 in 94% yield. Compound 40 (400 mg, 1.02 mmol) and benzindandione (220 mg, 1.12 mmol) were added to a solvent of 2-propanol (7 ml) under a nitrogen atmosphere, and refluxed for 3 hours. After allowing to cool, suction filtration was performed, and recrystallization was performed with tetrahydrofuran. Suction filtration was performed to obtain Compound (A-17) in 43% yield. The compound was identified by $^1$H-NMR.

$^1$H-NMR (400 M Hz, in CDCl$_3$): δ (ppm)=1.70 (s, 6H), 1.76 (s, 1H), 7.24 (t, J=11 Hz, 4H), 7.43-7.49 (m, 4H), 7.67-7.70 (m, 2H), 8.00 (s, 1H), 8.08-8.12 (m, 2H), 8.51 (d, J=15.0 Hz, 2H), 8.82 (s, 2H). m.p.=283° C., λ$_{max}$=569 nm (in CHCl$_3$) (ε=58000 mol$^{-1}$·l·cm$^{-1}$)

(Synthesis of Exemplary Compound (A-18))

Compound (A-18) was synthesized in the same manner as the synthesis of Compound (A-17), except that benzindandione in the synthesis of Compound (A-17) was changed to indandione. The compound was identified by $^1$H-NMR.

$^1$H-NMR (400 M Hz, in CDCl$_3$): δ (ppm)=1.68 (s, 6H), 1.74 (s, 12H), 7.24 (t, J=12 Hz, 2H), 7.43-7.48 (m, 4H), 7.78-7.81 (m, 2H), 7.90 (s, 1H), 7.97-8.06 (m, 2H), 8.72 (s, 2H). m.p.=248° C., λ$_{max}$=536 nm (in CHCl$_3$) (ε=49000 mol$^{-1}$·l·cm$^{-1}$)

(Synthesis of Exemplary Compound (A-19))

Compound (A-19) in which D$_1$ in Formula (I) is a compound represented by Formula (III) may be prepared by the following reaction scheme.

[Chem. 78]

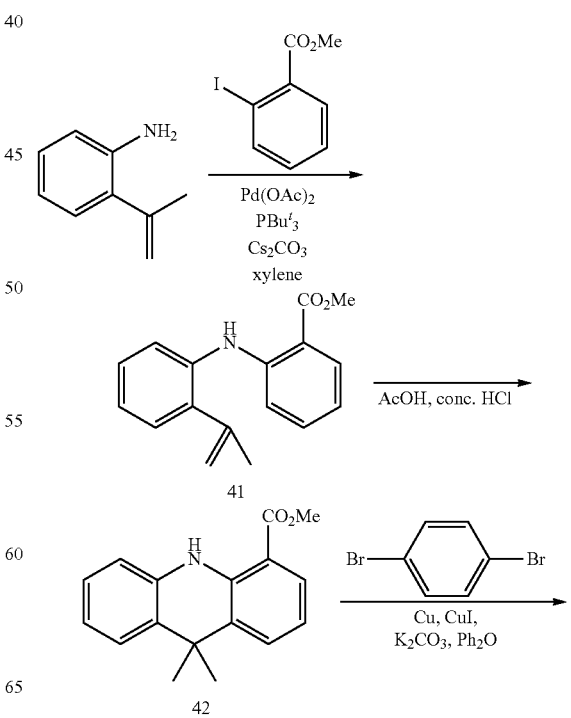

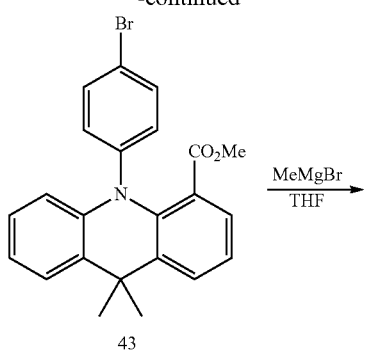

43

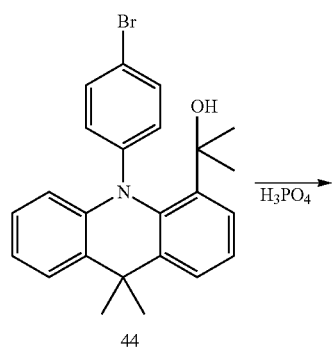

44

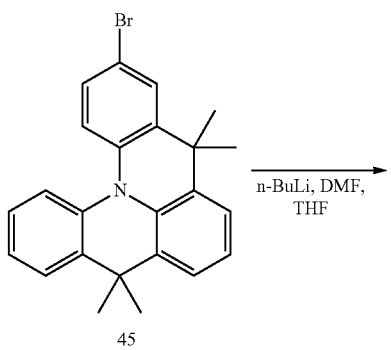

45

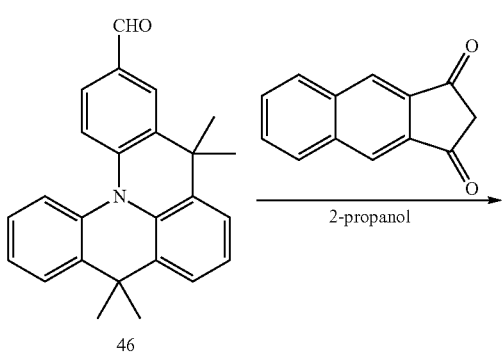

46

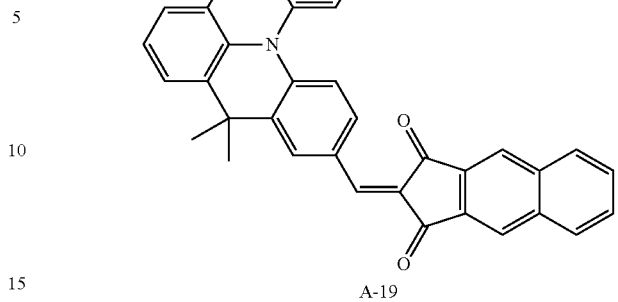

A-19

Isopropenylaniline, methyl ortho-iodobenzoate, palladium acetate, tri(t-butyl)phosphine and cesium carbonate were dissolved in 50 ml of xylene, and reacted under reflux for 5 hours under a nitrogen atmosphere to obtain Compound 41 in 78% yield. Compound 41 was added to a mixed solvent of acetic acid and concentrated hydrochloric acid, and followed by stirring at 60° C. for 1 hour to obtain Compound 42 in 82% yield. Compound 42, para-dibromobenzene, copper powder, copper iodide and calcium carbonate were added to diphenyl ether, and refluxed for 5 hours to obtain Compound 43 in 76% yield. Compound 43 was dissolved in dehydrated tetrahydrofuran, and a 3 M methyl Grignard reagent (ethyl ether solution) was added dripwise. After that, the reaction solution was heated to a reflux temperature, and followed by stirring for 1 hour to obtain Compound 44 in 95% yield. Compound 44 was added to phosphoric acid, and followed by stirring at 90° C. for 2 hours to obtain Compound 45 in 45% yield. Compound 45 was dissolved in dehydrated tetrahydrofuran, cooled to −40° C. by using a dry ice bath, and then, n-butyllithium (1.6 M in hexane) was added dropwise, and followed by stirring for 15 minutes. Dehydrated N,N-dimethylformamide was added dropwise thereto, and the dry ice bath was removed. 1 M diluted hydrochloric acid was added to obtain Compound 46 in 68% yield. Compound 46 and benzindandione were added to a 2-propanol solvent under a nitrogen atmosphere, and refluxed for 3 hours. After allowing to cool, suction filtration was performed, and recrystallization was performed with tetrahydrofuran. Suction filtration was performed to obtain Compound (A-19). The compound was identified by $^1$H-NMR.

$^1$H-NMR (400 M Hz, in CDCl$_3$): δ (ppm)=1.25 (s, 3H), 1.33 (s, 3H), 1.95 (s, 3H), 2.15 (s, 3H), 7.20-7.30 (m, 2H), 7.38-7.46 (m, 2H), 7.56-7.72 (m, 6H), 8.02 (s, 1H), 8.10-8.15 (m, 2H), 8.37 (d, J=15.0 Hz, 1H), 8.52 (d, J=15.0 Hz, 2H), 9.17 (s, 1H).

(Synthesis of Exemplary Compound (A-20))

Compound (A-20) was synthesized in the same manner as the synthesis of Compound (A-19), except that benzindandione in the synthesis of Compound (A-19) was changed to indandione.

(Synthesis of Exemplary Compound (A-21))

Compound (A-21) in which D$_1$ in Formula (I) is a compound represented by Formula (III) may be prepared by the following reaction scheme.

[Chem. 79]

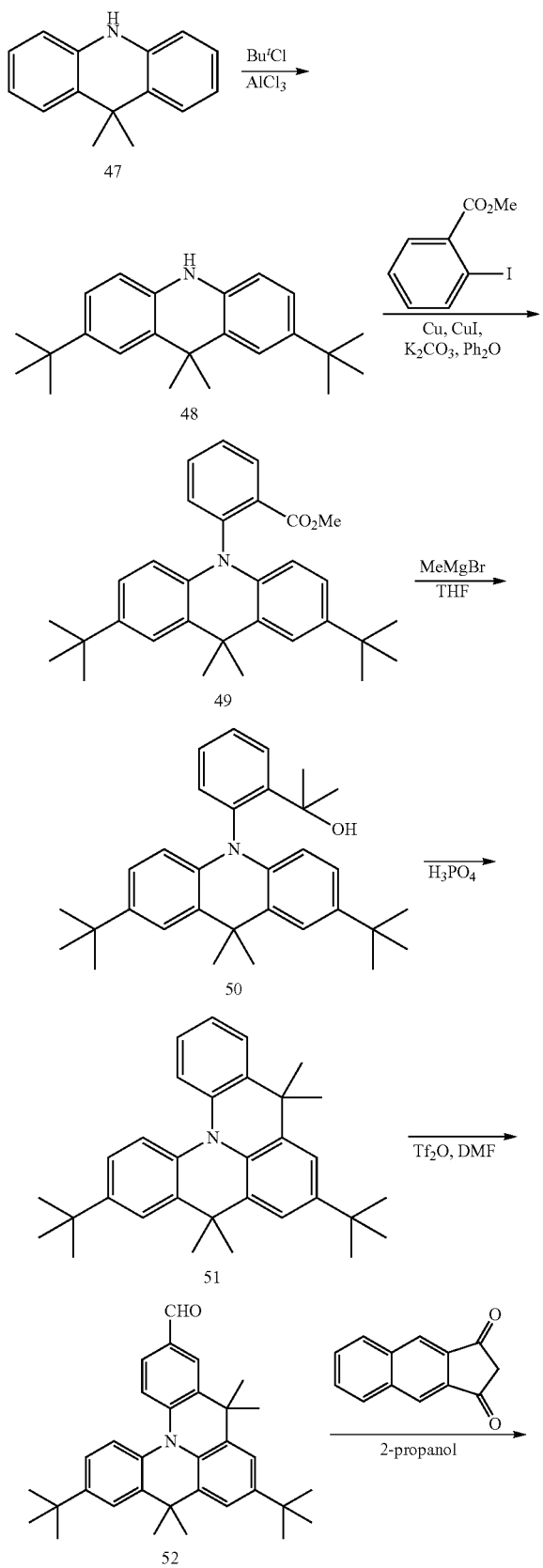

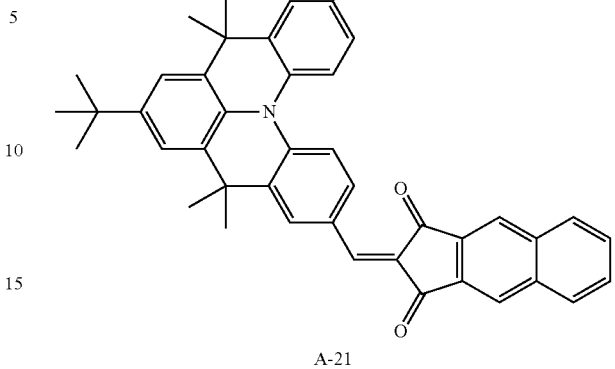

A-21

Compound 47 was synthesized by the method described in Chemishe Berichte 1980, 113, 358-384. Compound 47 was dissolved in 1,2-dichloroethane, cooled in an ice bath, and then, aluminum chloride and t-butyl chloride were added. This reaction solution was heated to 60° C., and followed by stirring for 1 hour to obtain Compound 48 in 80% yield. Compound 48 and methyl ortho-iodobenzoate were dissolved in diphenyl ether, and copper powder, copper iodide and calcium carbonate were added, overheated to 180° C. under a nitrogen atmosphere, and followed by stirring for 4.5 hours to obtain Compound 49 in 86% yield. Compound 49 was dissolved in dehydrated tetrahydrofuran, and a 3 M methyl Grignard reagent (ethyl ether solution) was added dripwise thereto. After that, the reaction solution was heated to a reflux temperature, and followed by stirring for 1 hour to obtain Compound 50 in 95% yield. Compound 50 was added to phosphoric acid, and followed by stirring at 90° C. for 2 hours to obtain Compound 51 in 40% yield. Compound 51 was dissolved in dehydrated N,N-dimethylformamide, and trifluoromethanesulfonic anhydride was added dropwise thereto. The reaction solution was heated to 90° C. under a nitrogen atmosphere, and followed by stirring for 1 hour to obtain Compound 52 in 80% yield. Compound 52 and benzindandione were added to a 2-propanol solvent under a nitrogen atmosphere, and refluxed for 3 hours. After allowing to cool, suction filtration was performed, and recrystallization was performed with tetrahydrofuran. Suction filtration was performed to obtain Compound (A-21) in 45% yield. The compound was identified by $^1$H-NMR.

$^1$H-NMR (400 M Hz, in CDCl$_3$): δ (ppm)=1.25 (s, 3H), 1.30 (s, 3H), 1.40 (s, 18H), 1.97 (s, 3H), 2.14 (s, 3H), 7.25-7.30 (m, 2H), 7.42 (d, J=16.0 Hz, 2H), 7.49 (d, J=15.0 Hz, 1H), 7.57 (m, 1H), 7.64-7.72 (m, 3H), 8.00 (s, 1H), 8.07-8.13 (m, 2H), 8.37 (d, J=15.0 Hz, 1H), 8.50 (d, J=15.0 Hz, 2H), 9.15 (s, 1H).

(Synthesis of Exemplary Compound (A-22))

Compound (A-22) was synthesized in the same manner as the synthesis of Compound (A-21), except that benzindandione in the synthesis of Compound (A-21) was changed to indandione.

(Synthesis of Exemplary Compound (A-23))

Compound (A-23) in which $D_1$ in Formula (I) is a compound represented by Formula (III) may be prepared by the following reaction scheme.

[Chem. 80]

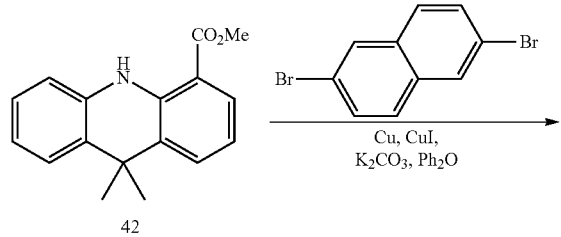

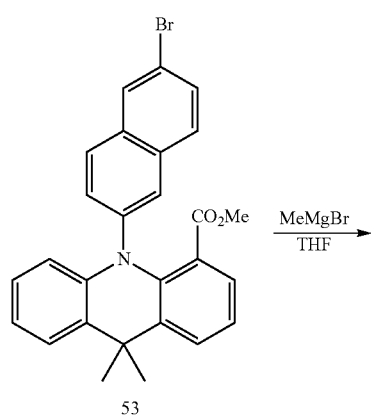

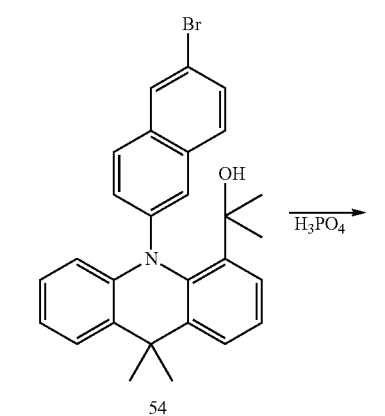

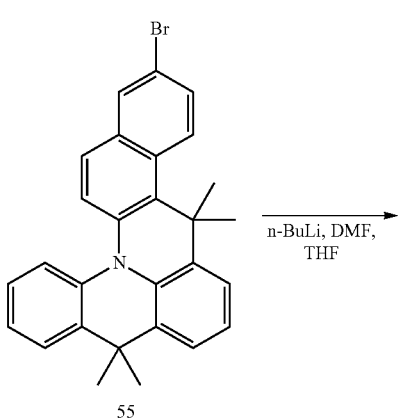

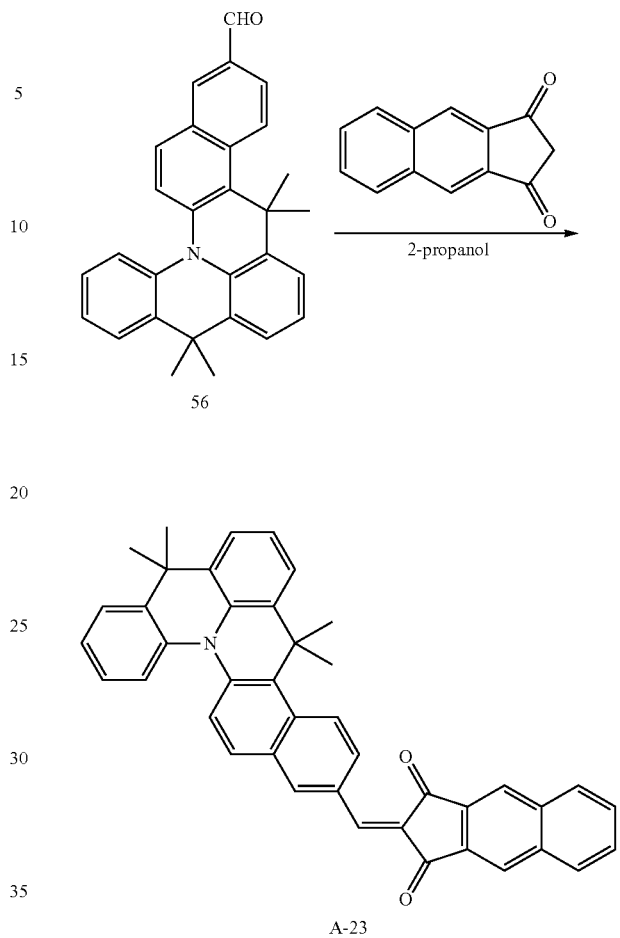

Compound 42, 2,6-dibromonaphthalene, copper powder, copper iodide and calcium carbonate were added to diphenyl ether, and refluxed for 5 hours to obtain Compound 53 in 67% yield. Compound 53 was dissolved in dehydrated tetrahydrofuran, and a 3 M methyl Grignard reagent (ethyl ether solution) was added dripwise. After that, the reaction solution was heated to a reflux temperature, and followed by stirring for 1 hour to obtain Compound 54 in 90% yield. Compound 54 was added to phosphoric acid, and followed by stirring at 90° C. for 2 hours to obtain Compound 55 in 60% yield. Compound 55 was dissolved in dehydrated tetrahydrofuran, cooled to −40° C. by using a dry ice bath, and then, n-butyllithium (1.6 M in hexane) was added dropwise, and followed by stirring for 15 minutes. Dry N,N-dimethylformamide was added dropwise thereto, and the dry ice bath was removed. 1 M diluted hydrochloric acid was added to obtain Compound 56 in 71% yield. Compound 56 and benzindandione were added to a 2-propanol solvent under a nitrogen atmosphere, and refluxed for 3 hours. After allowing to cool, suction filtration was performed, and recrystallization was performed with tetrahydrofuran. Suction filtration was performed to obtain Compound (A-23) in 53% yield. The compound was identified by $^1$H-NMR.

(Synthesis of Exemplary Compound (A-24))

Compound (A-24) in which $D_1$ in Formula (I) is a compound represented by Formula (III) may be prepared by the following reaction scheme.

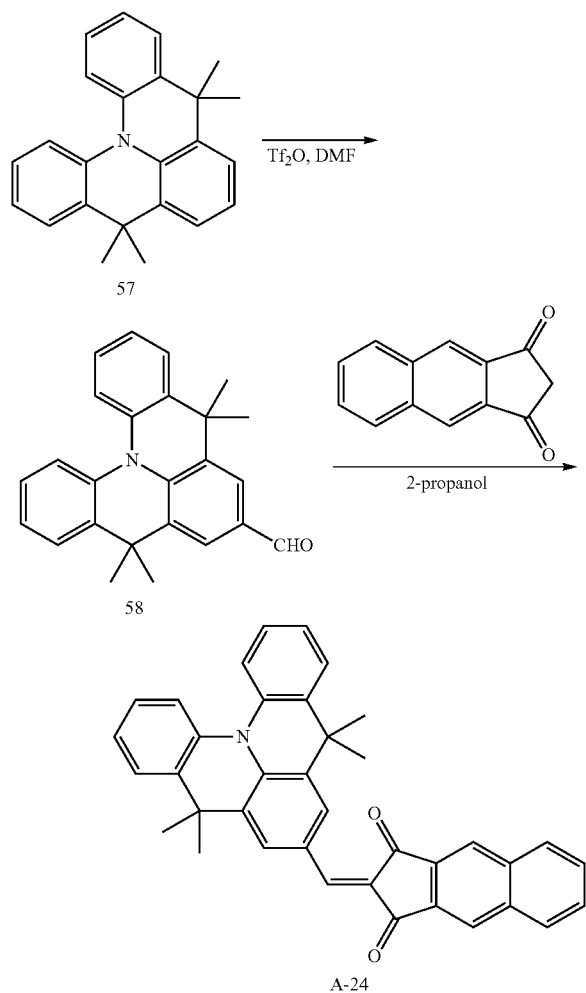

Compound 57 was synthesized by the method described in Org. Lett. 2009, 11, 1-4. Compound (A-24) was synthesized in the same manner as the synthesis of Compound (A-17).

<Measurement of Melting Point>

The melting point (m.p.) of Compound (A-1) was 341° C., as measured using TG/DTA AST-2 manufactured by SII Nano Technology Inc.

The melting points of other compounds were measured in the same manner. The results are shown in Table 1.

<Measurement of Deposition Temperature>

The deposition temperature of Compound (A-1) was defined as a temperature at which the deposition speed reaches 0.4 Å/s ($0.4 \times 10^{-10}$ m/s) when heating a crucible in a degree of vacuum of $4 \times 10^{-4}$ Pa or less. During deposition, the distance between an opening of a crucible and a substrate was set to 30 cm, and Thermoball Cell (bottom of crucible: 15 mmΦ) manufactured by Choshu Industry was used as a crucible.

The deposition temperatures of other compounds were measured in the same manner. The results are shown in Table 1.

<Measurement of UV-Visible Absorption Spectrum and Molar Extinction Coefficient>

The absorption spectrum (chloroform solution) of the compound (A-1) was measured using UV-2550 manufactured by Shimadzu Corporation, and the peak wavelength (UV/vis absorption maximum wavelength, $\lambda_{max}$) was 549 nm, and the molar extinction coefficient (ε) was 66,000 $mol^{-1} \cdot l \cdot cm^{-1}$.

The maximum absorption wavelengths and the molar extinction coefficients of other compounds were measured in the same manner. The results are shown in Table 1.

TABLE 1

| Compound | Melting point (° C.) | Deposition temperature (° C.) | Melting point – Deposition temperature (° C.) | UV/vis absorption maximum wavelength (nm) | Molar extinction coefficient ($mol^{-1} \cdot l \cdot cm^{-1}$) | Remarks |
|---|---|---|---|---|---|---|
| A-1 | 341 | 240 | 101 | 549 | 66000 | Example |
| A-2 | 330 | 236 | 94 | 534 | 73000 | Example |
| A-3 | 355 | 265 | 90 | 559 | 61000 | Example |
| A-4 | 340 | 281 | 59 | 554 | 63000 | Example |
| A-5 | 303 | 251 | 52 | 541 | 68000 | Example |
| A-6 | 335 | 275 | 60 | 555 | 65000 | Example |
| A-7 | 335 | 264 | 71 | 568 | 53000 | Example |
| A-8 | 319 | 236 | 83 | 536 | 44000 | Example |
| A-9 | 356 | 280 | 76 | 560 | 48000 | Example |
| A-13 | 331 | 255 | 76 | 569 | 52000 | Example |
| A-14 | 328 | 252 | 76 | 563 | 56000 | Example |
| A-15 | 286 | 242 | 44 | 564 | 53000 | Example |
| A-16 | 332 | 255 | 77 | 553 | 62000 | Example |
| A-17 | 283 | 230 | 53 | 569 | 58000 | Example |
| A-18 | 248 | 200 | 48 | 536 | 49000 | Example |
| A-19 | 285 | 220 | 65 | 560 | 54000 | Example |
| A-20 | 262 | 198 | 64 | 532 | 48000 | Example |
| A-21 | 310 | 243 | 67 | 560 | 59000 | Example |
| A-22 | 280 | 215 | 65 | 541 | 49000 | Example |
| A-23 | 338 | 260 | 78 | 570 | 54000 | Example |
| A-24 | 310 | 245 | 65 | 558 | 56000 | Example |

TABLE 1-continued

| Compound | Melting point (° C.) | Deposition temperature (° C.) | Melting point – Deposition temperature (° C.) | UV/vis absorption maximum wavelength (nm) | Molar extinction coefficient $(mol^{-1} \cdot l \cdot cm^{-1})$ | Remarks |
|---|---|---|---|---|---|---|
| C-1 | 257 | 252 | 5 | 550 | 53000 | Comparative Example |
| C-2 | 300 | 270 | 30 | 539 | 49000 | Comparative Example |
| C-3 | 264 | 260 | 4 | 551 | 64000 | Comparative Example |

Fabrication of Photoelectric Conversion Device

Example 1-1

A solid-state imaging device including a photoelectric conversion device having a configuration as, illustrated in FIG. 2 was fabricated. Here, the photoelectric conversion device was constituted with a lower electrode (104), a photoelectric conversion film (107) and an upper electrode (108), and an organic photoelectric conversion film including a photoelectric conversion layer and an electron blocking layer was formed as the photoelectric conversion film (107). That is, amorphous ITO of 30 nm was formed on a glass substrate by a sputtering method to fabricate a lower electrode. Compound (B-1) of 100 nm was formed by a vacuum heating deposition method to form an electron blocking layer. Further, thereon, a layer, which was formed by co-depositing Compound (A-1) and fullerene ($C_{60}$) so as to be 100 nm and 300 nm, respectively, in terms of a single layer, was formed by a vacuum heating deposition in a state where the temperature of the substrate was controlled to 25° C. to form a photoelectric conversion layer (about 2.5 in terms of molar ratio). Further, as an upper electrode, amorphous ITO of 10 nm was formed by a sputtering method to fabricate a transparent electrode (upper electrode), thereby fabricating a solid-state imaging device. On the upper electrode, a SiO film was formed as a passivation layer by heating deposition and then, an aluminum oxide layer was formed thereon by an ALD method (1st batch). After the device of the 1st batch was fabricated, a 2nd batch having the same device configuration and thickness as those of the 1st batch were fabricated without changing materials (electron blocking layer material, Compound (A-1) and $C_{60}$) in the crucible. After the 2nd batch was fabricated, Compound (A-1) remained in the crucible was dissolved in THF (tetrahydrofuran), and the purity was measured by HPLC (high performance liquid chromatography) (crucible remaining purity). The vacuum deposition of both of the electron blocking layer and the photoelectric conversion layer was performed in a degree of vacuum of $4 \times 10^{-4}$ Pa. The deposition temperature is defined as a temperature at which the deposition speed reaches 0.4 Å/s ($0.4 \times 10^{-10}$ m/s) when heating in a degree of vacuum of $4 \times 10^{-4}$ Pa or less.

Examples 1-2 to 1-26 and Comparative Examples 1-1 to 1-6

Photoelectric conversion devices were fabricated in the same manner as in Example 1-1, except that, and compounds (B-1) and (A-1) used in the electron blocking layer and the photoelectric conversion material were changed as shown in Table 2.

[Evaluation]

Each of the devices obtained was checked whether it functions as a photoelectric conversion device. It is confirmed that, when voltage is applied to the lower electrode and the upper electrode of each of the devices obtained so as to be an electric field strength of $2.5 \times 10^5$ V/cm, any devices show a dark current of 100 nA/cm$^2$ or less in a dark place, but show a current of 10 μA/cm$^2$ or more in a bright place, thereby functioning as a photoelectric conversion device.

The relative response speed (a vertical rise time with a signal strength of from 0% to 90%) (a relative value when the 1st batch in Example 1-1 is counted as 1) when an electric filed of $2 \times 10^5$ V/cm was applied to the photoelectric conversion devices in the solid-state imaging device of Examples 1-1 to 1-26 and Comparative Examples 1-1 to 1-6, is shown in Table 2. Meanwhile, in the case of measuring the photoelectric conversion performance of each device, light is incident to the upper electrode (transparent conductive film).

The evaluation results are shown in Table 2 below.

TABLE 2

| | Electron blocking material | Photoelectric conversion material | Melting point (° C.) | Deposition temperature (° C.) | Melting point – Deposition temperature (° C.) | Crucible remaining purity (LC %) | Vertical rise time with a signal strength of from 0% to 90% (Response speed) (Relative value) | |
|---|---|---|---|---|---|---|---|---|
| | | | | | | | 1st batch | 2nd batch |
| Ex. 1-1 | B-1 | $C_{60}$/A-1 | 341 | 240 | 101 | 100 | 1.0 | 1.03 |
| Ex. 1-2 | B-1 | $C_{60}$/A-2 | 330 | 236 | 94 | 99.6 | 0.9 | 0.91 |

TABLE 2-continued

| | Electron blocking material | Photoelectric conversion material | Melting point (° C.) | Deposition temperature (° C.) | Melting point – Deposition temperature (° C.) | Crucible remaining purity (LC %) | Vertical rise time with a signal strength of from 0% to 90% (Response speed) (Relative value) 1st batch | 2nd batch |
|---|---|---|---|---|---|---|---|---|
| Ex. 1-3 | B-1 | $C_{60}$/A-3 | 355 | 265 | 90 | 100 | 0.27 | 0.27 |
| Ex. 1-4 | B-1 | $C_{60}$/A-4 | 340 | 281 | 59 | 99.2 | 1.67 | 1.65 |
| Ex. 1-5 | B-1 | $C_{60}$/A-5 | 303 | 251 | 52 | 99.1 | 4.82 | 4.80 |
| Ex. 1-6 | B-1 | $C_{60}$/A-6 | 335 | 275 | 60 | 100 | 6.38 | 6.20 |
| Ex. 1-7 | B-1 | $C_{60}$/A-7 | 335 | 264 | 71 | 98.9 | 0.21 | 0.21 |
| Ex. 1-8 | B-1 | $C_{60}$/A-8 | 319 | 236 | 83 | 99.7 | 0.18 | 0.17 |
| Ex. 1-9 | B-1 | $C_{60}$/A-9 | 356 | 280 | 76 | 99.0 | 0.17 | 0.17 |
| Ex. 1-10 | B-1 | $C_{60}$/A-13 | 331 | 255 | 76 | 99.8 | 0.17 | 0.18 |
| Ex. 1-11 | B-1 | $C_{60}$/A-14 | 328 | 252 | 76 | 99.5 | 0.18 | 0.18 |
| Ex. 1-12 | B-1 | $C_{60}$/A-15 | 286 | 242 | 44 | 98.9 | 0.19 | 0.19 |
| Ex. 1-13 | B-1 | $C_{60}$/A-16 | 332 | 255 | 77 | 99.3 | 0.21 | 0.22 |
| Ex. 1-14 | B-1 | $C_{60}$/A-17 | 283 | 230 | 53 | 99.4 | 0.15 | 0.15 |
| Ex. 1-15 | B-1 | $C_{60}$/A-18 | 248 | 200 | 48 | 99.1 | 0.15 | 0.14 |
| Ex. 1-16 | B-1 | $C_{60}$/A-19 | 285 | 220 | 65 | 99.6 | 0.17 | 0.17 |
| Ex. 1-17 | B-1 | $C_{60}$/A-20 | 262 | 198 | 64 | 99.5. | 0.15 | 0.15 |
| Ex. 1-18 | B-1 | $C_{60}$/A-21 | 310 | 243 | 67 | 99.8 | 0.20 | 0.19 |
| Ex. 1-19 | B-1 | $C_{60}$/A-22 | 280 | 215 | 65 | 99.8 | 0.17 | 0.17 |
| Ex. 1-20 | B-1 | $C_{60}$/A-23 | 338 | 260 | 78 | 99.7 | 0.18 | 0.19 |
| Ex. 1-21 | B-1 | $C_{60}$/A-24 | 310 | 245 | 65 | 99.7 | 0.17 | 0.17 |
| Ex. 1-22 | B-2 | $C_{60}$/A-1 | 341 | 240 | 101 | 99.9 | 1.03 | 1.04 |
| Ex. 1-23 | B-2 | $C_{60}$/A-7 | 335 | 264 | 71 | 99.3 | 0.21 | 0.22 |
| Ex. 1-24 | B-2 | $C_{60}$/A-8 | 319 | 236 | 83 | 99.6 | 0.17 | 0.17 |
| Ex. 1-25 | B-2 | $C_{60}$/A-12 | 310 | 250 | 60 | 100 | 0.25 | 0.25 |
| Ex. 1-26 | B-2 | $C_{60}$/A-15 | 286 | 242 | 44 | 99.3 | 0.18 | 0.18 |
| Comparative Ex 1-1 | B-1 | $C_{60}$/C-1 | 257 | 252 | 5 | 96.9 | 0.34 | 0.71 |
| Comparative Ex 1-2 | B-1 | $C_{60}$/C-2 | 300 | 270 | 30 | 94.6 | 0.15 | 0.62 |
| Comparative Ex 1-3 | B-1 | $C_{60}$/C-3 | 264 | 260 | 4 | 97.2 | 0.17 | 0.58 |
| Comparative Ex 1-4 | B-2 | $C_{60}$/C-1 | 257 | 252 | 5 | 96.7 | 0.35 | 0.77 |
| Comparative Ex 1-5 | B-2 | $C_{60}$/C-2 | 300 | 270 | 30 | 94.9 | 0.17 | 0.69 |
| Comparative Ex 1-6 | B-2 | $C_{60}$/C-3 | 264 | 260 | 4 | 96.2 | 0.16 | 0.60 |

In Table 2, "LC %", the unit of the crucible remaining purity, indicates "area % by liquid chromatography".

As clearly seen from Table 2, since Examples 1-1 to 1-26 has a very small change in response speed between batches and a high crucible remaining purity, compared to Comparative Examples 1-1 to 1-6, the photoelectric conversion material is hardly decomposed, and thus it is possible to fabricate a device suitable for manufacturing (which is able to withstand heating deposition for a long period of time).

Furthermore, an imaging device having a configuration as illustrated in FIG. 2 was fabricated. That is, amorphous ITO of 30 nm was formed on a CMOS substrate by a sputtering method, and then was patterned such that pixels are located for each photodiode (PD) on the CMOS substrate by photolithography, thereby using it as a lower electrode, and, after the film formation of the electron blocking material, was fabricated in the same manner as in Examples 1-1 to 1-26 and Comparative Examples 1-1 to 1-6. The evaluation was performed in the same manner, and the results were obtained as shown in Table 2, indicating that, even for imaging devices, the device based on the example of the present invention has a small dark current after heating and a high heat resistance.

Example 2-1

A solid-state imaging device including a photoelectric conversion device having a configuration as illustrated in FIG. 2 was fabricated. Here, the photoelectric conversion device was constituted with a lower electrode (104), a photoelectric conversion film (107) and an upper electrode (108), and an organic photoelectric conversion film including a photoelectric conversion layer and an electron blocking layer was formed as the photoelectric conversion film (107). That is, amorphous ITO of 30 nm was formed on a glass substrate by a sputtering method to fabricate a lower electrode. Compound (B-1) of 100 nm was formed by a vacuum heating deposition method to form an electron blocking layer. Further, thereon, a layer, which was formed by co-depositing Compound (A-1) and fullerene ($C_{60}$) so as to be 100 nm and 300 nm, respectively, in terms of a single layer, was formed by a vacuum heating deposition in a state where the temperature of the substrate was controlled to 25° C. to form a photoelectric conversion layer. Further, as an upper electrode, amorphous ITO of 10 nm was formed by a sputtering method to fabricate a transparent electrode (upper electrode), thereby fabricating a solid-state imaging device. On the upper electrode, a SiO film was formed as a passivation layer by heating deposition and then, an aluminum oxide $Al_2O_3$ layer was formed thereon by an ALCVD method.

Example 2-2 to 2-25 and Comparative Example 2-1 to 2-6

Photoelectric conversion devices were fabricated in the same manner as in Example 2-1, except that, and compounds (B-1) and (A-1) used in the electron blocking layer and the photoelectric conversion material were changed as shown in Table 3.

[Evaluation]

Each of the devices obtained was checked whether it functions as a photoelectric conversion device. It is confirmed that, when voltage is applied to the lower electrode and the upper electrode of each of the devices obtained so as to be an electric field strength of $2.5 \times 10^5$ V/cm, any devices show a dark current of 100 $nA/cm^2$ or less in a dark place, but show a current of 10 $\mu A/cm^2$ or more in a bright place, thereby functioning as a photoelectric conversion device.

The sensitivity in a region having a wavelength of 500 nm to 750 nm (a relative value counting Example 2-1 as 100) when an electric filed of $2 \times 10^5$ V/cm was applied to the photoelectric conversion devices in the solid-state imaging device of Examples 1-1 to 1-26 and Comparative Examples 1-1 to 1-6, is shown in Table 3. Meanwhile, in the case of measuring the photoelectric conversion performance of each device, light is incident to the upper electrode (transparent conductive film). The sensitivity was measured by an IPCE measurement apparatus.

Further, the fluorescent maximum wavelength and the fluorescence intensity were measured with respect to Compounds (A-1) to (A-9), (A-13) to (A-24) and (C-1) to (C-3), which were used as a photoelectric conversion material. The fluorescent maximum wavelength and the fluorescence intensity were measured using FP-6300 manufactured by JASCO Corporation.

The evaluation results are shown in Table 3 below.

TABLE 3

| | Electron blocking material | Photoelectric conversion material | UV/vis absorption maximum wavelength (nm) | Molar extinction coefficient $(mol^{-1}cm^{-1})$ | Fluorescent maximum wavelength (nm) | Fluorescence intensity | Sensitivity in a region of 500 nm to 750 nm (Relative value) |
|---|---|---|---|---|---|---|---|
| Ex 2-1 | B-1 | $C_{60}$/A-1 | 549 | 66000 | 637 | 60000 | 100 |
| Ex 2-2 | B-1 | $C_{60}$/A-2 | 534 | 73000 | 615 | 69000 | 102 |
| Ex 2-3 | B-1 | $C_{60}$/A-3 | 559 | 61000 | 646 | 41000 | 108 |
| Ex 2-4 | B-1 | $C_{60}$/A-4 | 554 | 63000 | 641 | 55000 | 104 |
| Ex 2-5 | B-1 | $C_{60}$/A-5 | 541 | 68000 | 628 | 67000 | 98 |
| Ex 2-6 | B-1 | $C_{60}$/A-6 | 555 | 65000 | 641 | 58000 | 101 |
| Ex 2-7 | B-1 | $C_{60}$/A-7 | 568 | 53000 | 586 | 39000 | 115 |
| Ex 2-8 | B-1 | $C_{60}$/A-8 | 536 | 44000 | 653 | 93000 | 109 |
| Ex 2-9 | B-1 | $C_{60}$/A-9 | 560 | 48000 | 673 | 50000 | 118 |
| Ex 2-10 | B-1 | $C_{60}$/A-13 | 569 | 52000 | 687 | 34000 | 123 |
| Ex 2-11 | B-1 | $C_{60}$/A-14 | 563 | 55000 | 678 | 49000 | 119 |
| Ex 2-12 | B-1 | $C_{60}$/A-15 | 564 | 53000 | 679 | 46000 | 115 |
| Ex 2-13 | B-1 | $C_{60}$/A-16 | 553 | 62000 | 654 | 28000 | 109 |
| Ex 2-14 | B-1 | $C_{60}$/A-17 | 569 | 58000 | 669 | 37000 | 119 |
| Ex 2-15 | B-1 | $C_{60}$/A-18 | 536 | 49000 | 637 | >100000 | 110 |
| Ex 2-16 | B-1 | $C_{60}$/A-19 | 560 | 54000 | 661 | 41000 | 115 |
| Ex 2-17 | B-1 | $C_{60}$/A-20 | 532 | 48000 | 630 | 72000 | 108 |
| Ex 2-18 | B-1 | $C_{60}$/A-21 | 560 | 59000 | 672 | 29000 | 118 |
| Ex 2-19 | B-1 | $C_{60}$/A-22 | 541 | 49000 | 643 | 55000 | 110 |
| Ex 2-20 | B-1 | $C_{60}$/A-23 | 570 | 54000 | 670 | 48000 | 118 |
| Ex 2-21 | B-1 | $C_{60}$/A-24 | 558 | 56000 | 655 | 38000 | 110 |
| Ex 2-22 | B-2 | $C_{60}$/A-1 | 549 | 66000 | 637 | 60000 | 101 |
| Ex 2-23 | B-2 | $C_{60}$/A-7 | 568 | 53000 | 586 | 39000 | 115 |
| Ex 2-24 | B-2 | $C_{60}$/A-8 | 536 | 44000 | 653 | 93000 | 110 |
| Ex 2-25 | B-2 | $C_{60}$/A-15 | 564 | 53000 | 679 | 46000 | 118 |
| Comparative Ex 2-1 | B-1 | $C_{60}$/C-1 | 550 | 53000 | 686 | 9785 | 90 |
| Comparative Ex 2-2 | B-1 | $C_{60}$/C-2 | 539 | 49000 | 669 | 6076 | 83 |
| Comparative Ex 2-3 | B-1 | $C_{60}$/C-3 | 551 | 64000 | 672 | 25690 | 91 |
| Comparative Ex 2-4 | B-2 | $C_{60}$/C-1 | 550 | 53000 | 686 | 9785 | 91 |
| Comparative Ex 2-5 | B-2 | $C_{60}$/C-2 | 539 | 49000 | 669 | 6076 | 83 |
| Comparative Ex 2-6 | B-2 | $C_{60}$/C-3 | 551 | 64000 | 672 | 25690 | 90 |

As clearly seen from Table 3, Examples 2-1 to 2-25 have a high sensitivity in a region of 500 nm to 750 nm (red), compared to Comparative Examples 2-1 to 2-6.

The compounds used in Examples and Comparative Examples are shown below.

[Chem. 82]
A-1
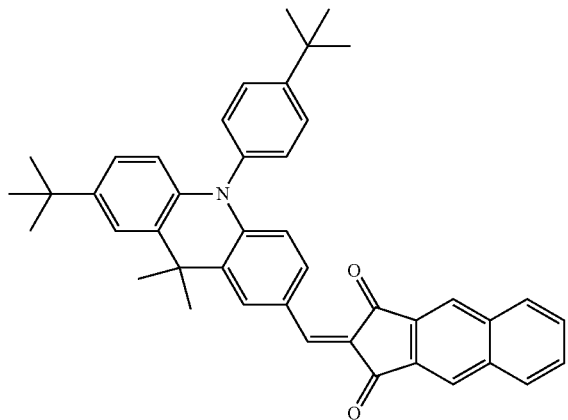
A-2
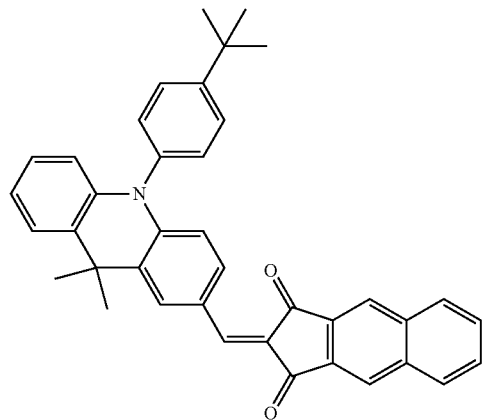
A-3
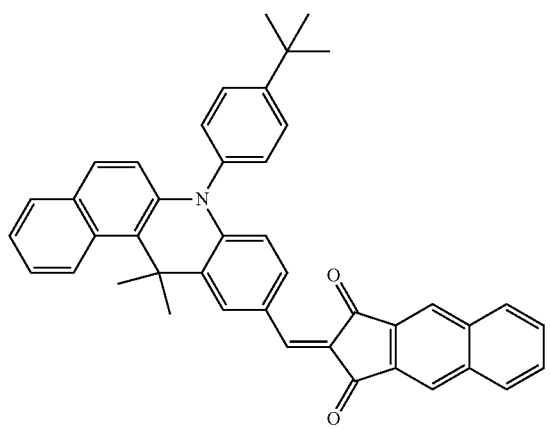
A-4
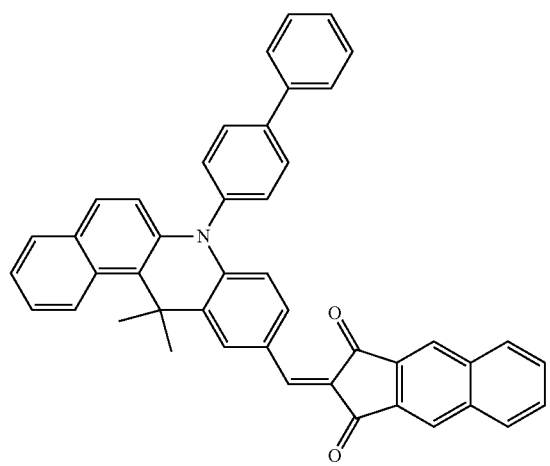
A-5
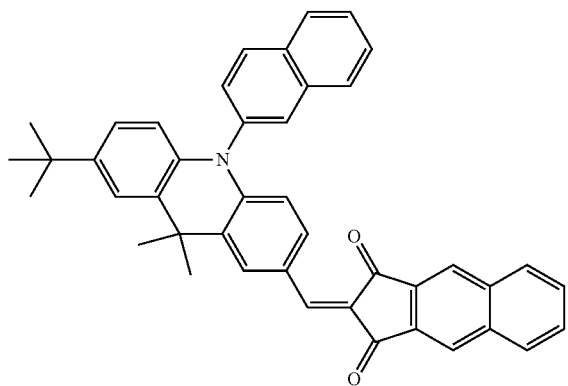
A-6
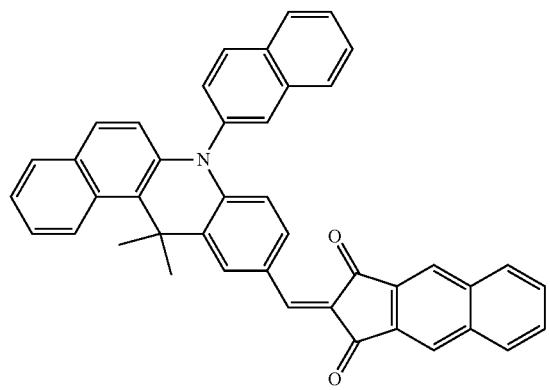

-continued
A-7
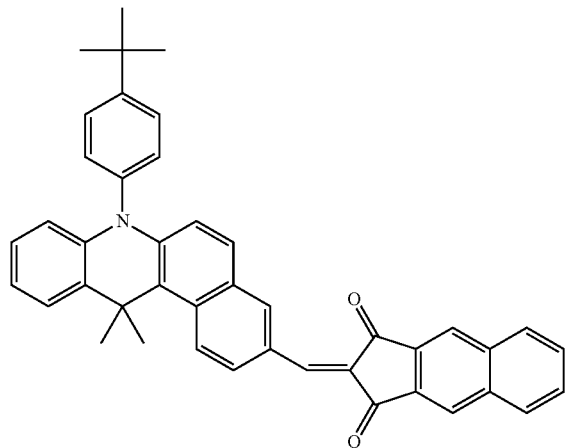
A-8
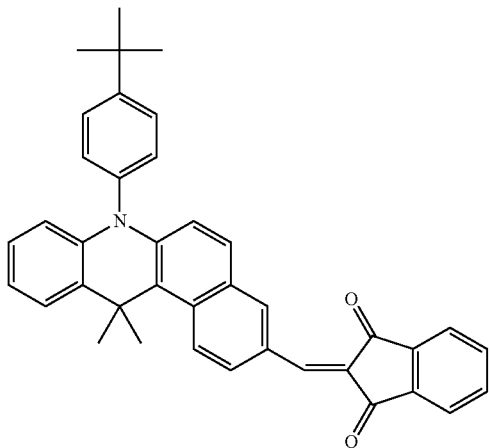
[Chem. 83]
A-9
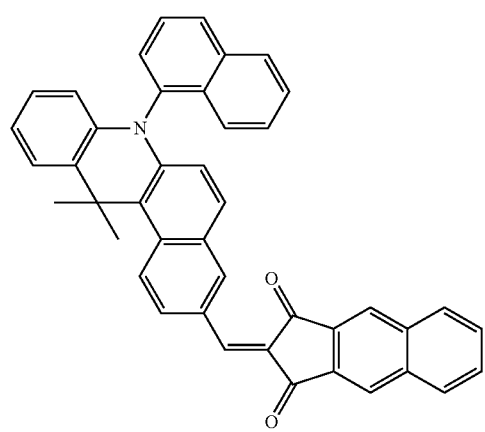
[Chem. 84]
A-13
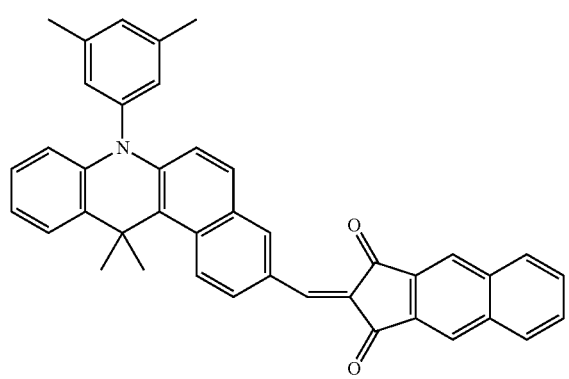
A-14
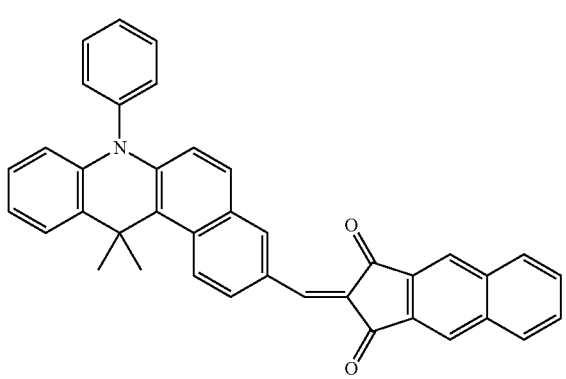

-continued
A-15
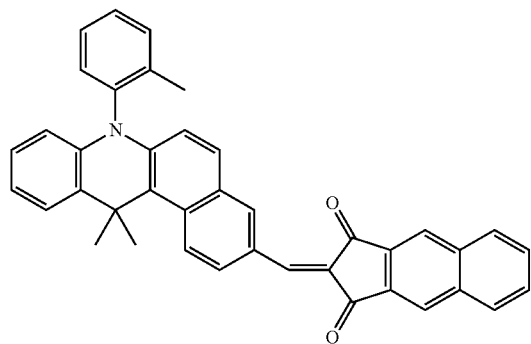
A-16
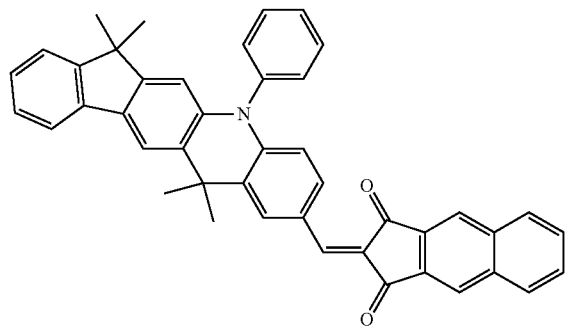
A-17
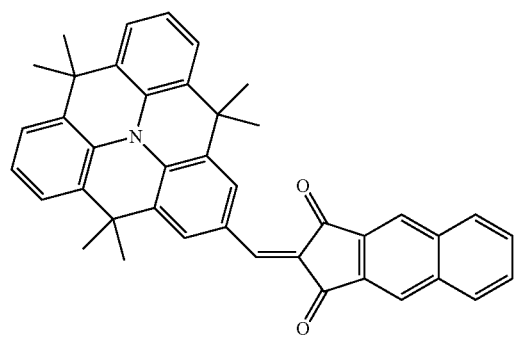
A-18
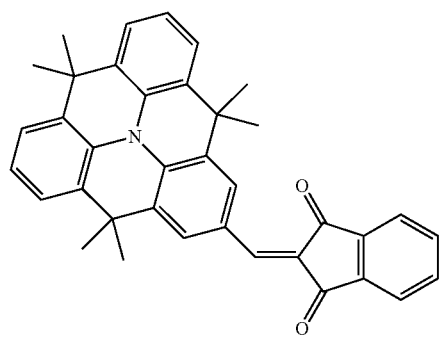
A-19
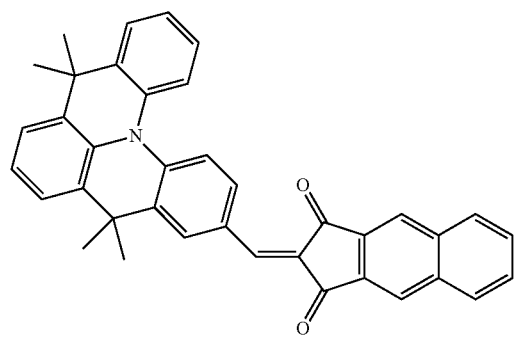
A-20
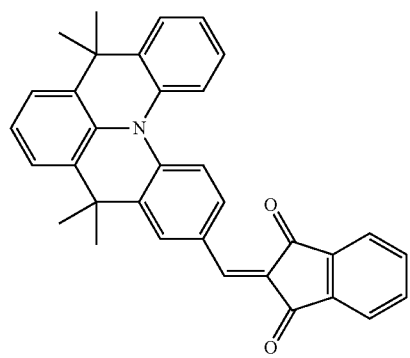
[Chem. 85]
A-21
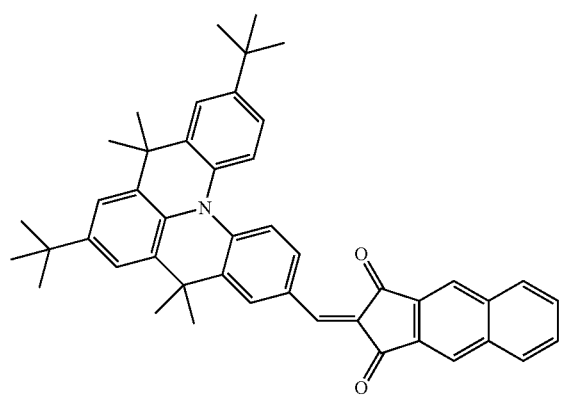
A-22
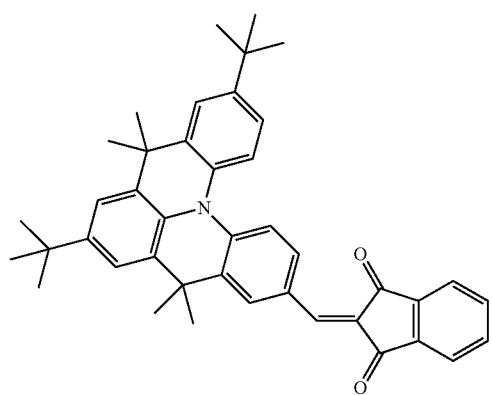

-continued
A-23
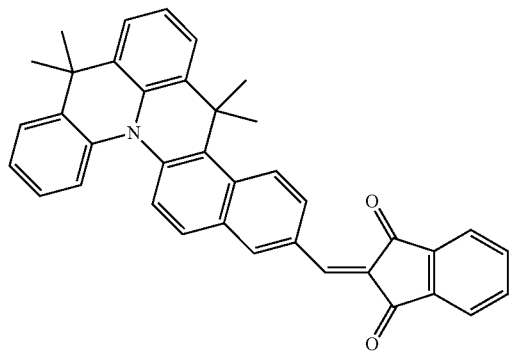
A-24
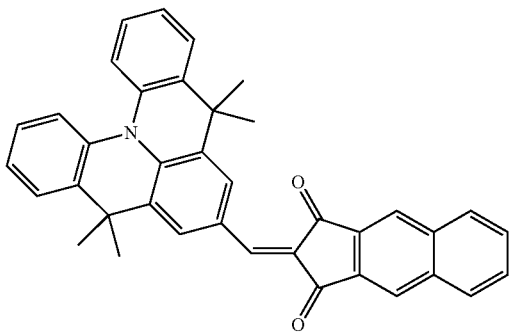
[Chem. 86]
B-1
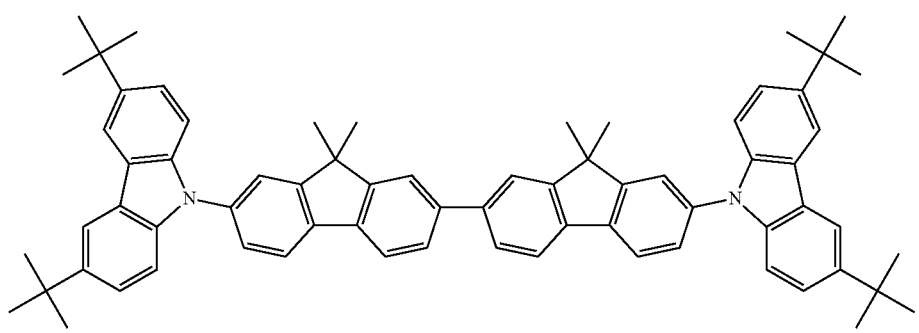
B-2
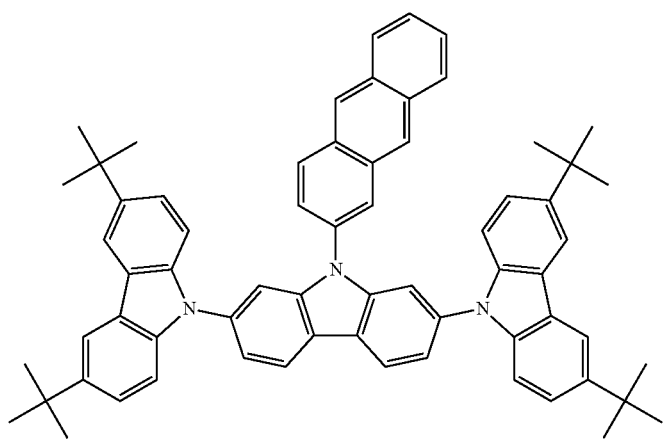
[Chem. 87]
C-1
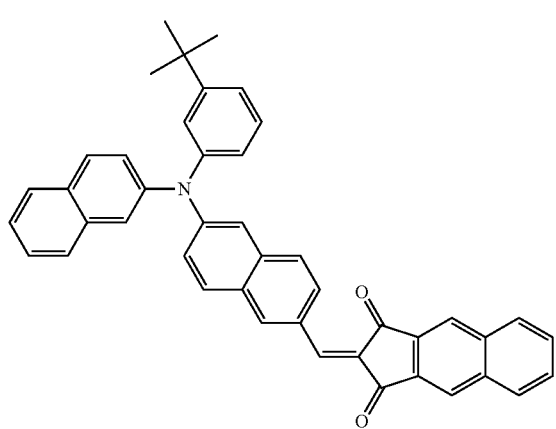
C-2
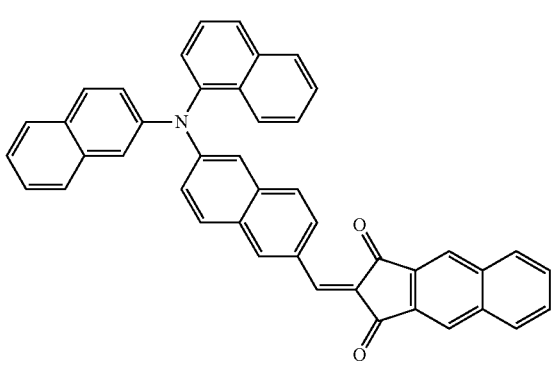

-continued

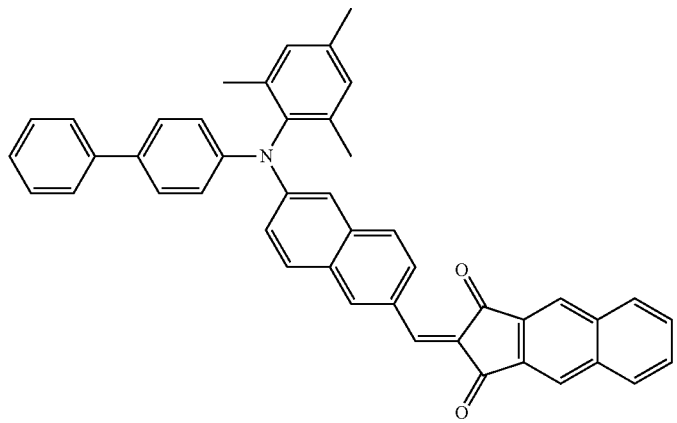

INDUSTRIAL APPLICABILITY

According to the present invention, a film can be formed by deposition at a high temperature without causing materials to be decomposed, and thus, it is possible to provide a compound capable of providing a photoelectric conversion device having a high charge collection efficiency, a high speed response property, a low dark current property and a high heat resistance, and suitable for manufacturing (able to endure thermal evaporation for a long period of time). Further, it is possible to provide the photoelectric conversion device and an imaging device including the photoelectric conversion device.

Although the present invention has been described with reference to detailed and specific embodiments thereof, it is obvious to those skilled in the art that various changes or modifications may be made without departing from the spirit and scope of the present invention.

The present application is based on Japanese Patent Application (Patent Application No. 2010-201491) filed on Sep. 8, 2010 and Japanese Patent Application (Patent Application No. 2011-084012) filed on Apr. 5, 2011, the contents of which are herein incorporated by reference.

EXPLANATION OF REFERENCE NUMERALS AND SYMBOLS 10a, 10b: Photoelectric conversion device
11: Lower electrode (Conductive film)
12: Photoelectric conversion layer (Photoelectric conversion film)
15: Upper electrode (Transparent conductive film)
16A: Electron blocking layer
16B: Hole blocking layer
100: Imaging device
101: Substrate
102: Insulating layer
103: Connection electrode
104: Pixel electrode (Lower electrode)
105: Connection portion
106: Connection portion
107: Photoelectric conversion layer
108: Counter electrode (Upper electrode)
109: Buffer layer
110: Passivation layer
111: Color filter (CF)
112: Partitioning wall
113: Light shielding layer
114: Protective layer
115: Counter electrode voltage supply unit
116: Read-out circuit

What is claimed is:

1. A photoelectric conversion device containing:
a conductive film,
an organic photoelectric conversion film, and
a transparent conductive film,
wherein the organic photoelectric conversion film contains a compound represented by the following Formula (IV-a), which has an absorption maximum at 400 nm or more and less than 720 nm in a UV-visible absorption spectrum,
wherein a molar extinction coefficient is 10,000 $mol^{-1} \cdot l \cdot cm^{-1}$ or more at the absorption maximum wavelength, and a difference between a melting point and a deposition temperature (a melting point—a deposition temperature) is 31° C. or more:

Formula (IV-a)

in Formula (IV-a), each of $L_1$, $L_2$ and $L_3$ independently represents an unsubstituted methine group,
n represents an integer of 0 or more,
m represents 1,
each of $R_{41}$ to $R_{46}$ independently represent a hydrogen atom or an alkyl group,
each of $R_{42}$ and $R_{43}$, $R_{43}$ and $R_{44}$, $R_{45}$ and $R_{46}$, and $R_{41}$ and $R_{46}$ may be bound to each other to form a ring,
each of $R_{47}$ to $R_{49}$ independently represent a hydrogen atom, an alkyl group having 1 to 6 carbon atoms or an aryl group having 6 to 10 carbon atoms,
each of $R_{410}$ to $R_{415}$ independently represent a hydrogen atom, an alkyl group having 1 to 6 carbon atoms or an aryl group having 6 to 10 carbon atoms, Xa represents an alkylene group, and is linked as one of $R_{44}$ or $R_{45}$, $Z_1$ is and an oxygen atom is represented by the following Formula (VIII) or the following Formula (IX):

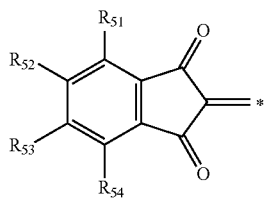

Formula (VIII)

in Formula (VIII), each of $R_{51}$ to $R_{54}$ independently represents a hydrogen atom or an alkyl group, any adjacent two of $R_{51}$ to $R_{54}$ may be bound to each other to form a ring, and

* represents a bonding position to $L_1$:

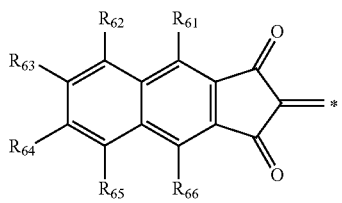

Formula (IX)

in Formula (IX), each of $R_{61}$ to $R_{66}$ independently represents a hydrogen atom or an alkyl group, any adjacent two of $R_{61}$ to $R_{66}$ may be bound to each other to form a ring, and

* represents a bonding position to $L_1$ wherein the photoelectric conversion film contains a fullerene selected from the group consisting of fullerene $C_{60}$, fullerene $C_{70}$, fullerene $C_{76}$, fullerene $C_{78}$, fullerene $C_{80}$, fullerene $C_{82}$, fullerene $C_{84}$, fullerene $C_{90}$, fullerene $C_{96}$, fullerene $C_{240}$, and fullerene $C_{540}$.

2. The photoelectric conversion device according to claim 1, which contains the conductive film, the organic photoelectric conversion film and the transparent conductive film in this order.

3. The photoelectric conversion device according to claim 1, wherein the fullerene is $C_{60}$.

4. The photoelectric conversion device according to claim 1, wherein the organic photoelectric conversion film has a bulk hetero structure formed in the state where a compound and the fullerene are mixed.

5. The photoelectric conversion device according to claim 4, wherein a molar ratio of the fullerene to the compound is 0.5 or more.

6. An imaging device which contains:

the photoelectric conversion device according to claim 1.

* * * * *